United States Patent
Colosi et al.

(10) Patent No.: US 11,406,690 B2
(45) Date of Patent: *Aug. 9, 2022

(54) ADENO-ASSOCIATED VIRUS FACTOR VIII VECTORS

(71) Applicants: BIOMARIN PHARMACEUTICAL INC., Novato, CA (US); UCL BUSINESS PLC, London (GB); ST. JUDE CHILDREN'S RESEARCH HOSPITAL, Memphis, TN (US)

(72) Inventors: Peter Cameron Colosi, Novato, CA (US); Amit Nathwani, London (GB); Jenny McIntosh, London (GB); Edward Tuddenham, London (GB); Andrew Davidoff, Memphis, TN (US)

(73) Assignees: BIOMARIN PHARMACEUTICAL INC., Novato, CA (US); UCL BUSINESS LTD, London (GB); ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 54 days.

This patent is subject to a terminal disclaimer.

(21) Appl. No.: 16/588,130

(22) Filed: Sep. 30, 2019

(65) Prior Publication Data
US 2020/0101140 A1  Apr. 2, 2020

Related U.S. Application Data

(63) Continuation of application No. 15/294,310, filed on Oct. 14, 2016, now Pat. No. 10,463,718, which is a continuation of application No. 14/482,648, filed on Sep. 10, 2014, now Pat. No. 9,504,762.

(60) Provisional application No. 61/877,042, filed on Sep. 12, 2013.

(51) Int. Cl.
| | | |
|---|---|---|
| A01N 63/00 | (2020.01) | |
| A61K 38/37 | (2006.01) | |
| A61K 48/00 | (2006.01) | |
| C12N 7/00 | (2006.01) | |
| C07K 14/755 | (2006.01) | |
| C12N 15/86 | (2006.01) | |

(52) U.S. Cl.
CPC .......... *A61K 38/37* (2013.01); *A61K 48/0058* (2013.01); *A61K 48/0066* (2013.01); *C07K 14/755* (2013.01); *C12N 7/00* (2013.01); *C12N 15/86* (2013.01); *C12N 2750/14132* (2013.01); *C12N 2750/14142* (2013.01); *C12N 2750/14143* (2013.01); *C12N 2750/14151* (2013.01); *C12N 2800/22* (2013.01); *C12N 2830/008* (2013.01)

(58) Field of Classification Search
CPC .......... A61K 38/37; C12N 15/86; C12N 2750/14132; C12N 2800/22; C12N 2830/008

USPC ........................................................ 424/93.2
See application file for complete search history.

(56) References Cited

U.S. PATENT DOCUMENTS

| | | | |
|---|---|---|---|
| 6,200,560 B1 | 3/2001 | Couto et al. | |
| 6,221,349 B1 | 4/2001 | Couto et al. | |
| 6,383,794 B1* | 5/2002 | Mountz ................. | C12N 15/86 |
| | | | 435/235.1 |
| 7,351,577 B2 | 4/2008 | Couto et al. | |
| 8,030,065 B2 | 10/2011 | Gray | |
| 9,393,323 B2 | 7/2016 | Nathwani et al. | |
| 2003/0096787 A1 | 5/2003 | Perricaudet et al. | |
| 2007/0042462 A1 | 2/2007 | Hildinger | |
| 2008/0131403 A1* | 6/2008 | Wang ................. | C12N 15/1137 |
| | | | 424/93.6 |
| 2013/0024960 A1 | 1/2013 | Nathwani et al. | |
| 2017/0095538 A1 | 4/2017 | Colosi et al. | |
| 2018/0161403 A1 | 6/2018 | Nathwani et al. | |

FOREIGN PATENT DOCUMENTS

| | | |
|---|---|---|
| RU | 2001125671 A | 8/2003 |
| RU | 2219241 C2 | 12/2003 |
| WO | WO-2007/003582 A2 | 1/2007 |
| WO | 2011005968 A1 † | 1/2011 |
| WO | WO 2011/005968 * | 1/2011 |
| WO | WO-2011/005968 A1 | 1/2011 |

OTHER PUBLICATIONS

Edelstein (Journal Gene Med., 2004, vol. 6, p. 597-602).*
Wu (Mol. Therapy, 2008, vol. 16, No. 2, p. 280-289).*
Lu (Human Gene Therapy, Jun. 2008, vol. 19, No. 6, p. 648-654).*
Ishiwata (J. Gene Med., 2009, vol. 11, p. 1020-1029).*
McIntosh (Blood Apr. 2013, vol. 121, No. 17, p. 3335-3344).*
Rogers (Front Biosci., 2015, vol. 20, p. 556-603).*

(Continued)

*Primary Examiner* — Michael C Wilson
(74) *Attorney, Agent, or Firm* — Marshall, Gerstein & Borun LLP

(57) ABSTRACT

The present disclosure provides methods of generating multiplexed genetically modified animals, for example, porcine endogenous retrovirus (PERV)-inactivated pigs. The disclosure also provides methods of improving the birth rate of multiplexed genetically modified animals. In some embodiments, the present closure is concerned with the generation and utilization of porcine cells in which porcine endogenous retroviral (PERV) elements have been inactivated. In sonic embodiments, the PERV-free or PERV-reduced porcine cells are cloned to produce porcine embryos. In some embodiments, the PERV-free or PERV-reduced embryos may be grown into adult swine from which organs and/or tissues may be extracted and used for such purposes as xenotransplantation into non-porcine animals such as humans.

5 Claims, 21 Drawing Sheets

Specification includes a Sequence Listing.

(56) References Cited

OTHER PUBLICATIONS

Burton et al., Coexpression of factor VIII heavy and light chain adeno-associated viral vectors produces biologically active protein, Proc. Natl. Acad. Sci. USA, 96(22):12725-30 (Oct. 1999).
Chao et al., Sustained expression of human factor VIII in mice using a parvovirus-based vector, Blood, 95(5):1594-9 (Mar. 2000).
De Simone et al., Cis- and trans-acting elements responsible for the cell-specific expression of the human alpha 1-antitrypsin gene, EMBO J., 6(9):2759-66 (1987).
Edelstein et al., Gene therapy clinical trials worldwide 1989-2004-an overview, J. Gene Med., 6(6):597-602 (2004).
European Patent Application No. 14771729.2, Third Party Observations Communication Pursuant to Rule 114(2) EPC, dated Feb. 18, 2019.
Ghosh et al., Expanding adeno-associated viral vector capacity: a tale of two vectors, Biotechnol. Genet. Eng. Rev., 24:165-77 (2007).
Gnatenko et al., Human factor VIII can be packaged and functionally expressed in an adeno-associated virus background: applicability to haemophilia A gene therapy, Br. J. Haematol., 104(1):27-36 (Jan. 1999).
Hirsch et al., Little vector, big gene transduction: fragmented genome reassembly of adeno-associated virus, Mol. Ther., 18(1):6-8 (2010).
International Preliminary Report on Patentability, International Application No. PCT/US2014/054960, dated Mar. 15, 2016.
International Search Report and Written Opinion, International Application No. PCT/US2014/054960, dated Dec. 22, 2014.
Ishiwata et al., Liver-restricted expression of the canine factor VIII gene facilitates prevention of inhibitor formation in factor VIII-deficient mice, J. Gene Med., 11 (11): 1020-9 (2009).
Japanese Patent Application No. 2016-542067, Notice of Reasons for Rejection, dated Feb. 14, 2019.
Japanese Patent Application No. 2016-542067, Notice of Reasons for Rejection, dated Jul. 4, 2018.
Lu et al., Complete correction of hemophilia A with adeno-associated viral vectors containing a full-size expression cassette, Hum. Gene Ther., 19(6):648-54 (2008).
McIntosh et al., Therapeutic levels of FVIII following a single peripheral vein administration of rAAV vector encoding a novel human factor VIII variant, Blood, 121(17):3335-44 (2013).
Nathwani et al., Adenovirus-associated virus vector-mediated gene transfer in hemophilia B, N. Engl. J. Med., 365(25):2357-65 (2011).
Rogers et al., Gene therapy for hemophilia, Front Biosci (Landmark Ed.), 20:556-603 (2015).
Sarkar et al., A single adeno-associated virus (AAV)-murine factor VIII vector partially corrects the hemophilia A phenotype, J. Thromb. Haemost., 1(2):220-6 (2003).
Ward et al., Codon optimization of human factor VIII cDNAs leads to high-level expression, Blood, 117(3):798-807 (2011).
Wu et al., Optimization of self-complementary AAV vectors for liver-directed expression results in sustained correction of hemophilia B at low vector dose, Mol. Ther., 16(2):280-9 (2008).
Yan et al., Inverted terminal repeat sequences are important for intermolecular recombination and circularization of adeno-associated virus genomes, J. Virol., 79(1):364-79 (2005).
Youjin et al., The treatment of hemophilia A: from protein replacement to AAV-mediated gene therapy, Biotechnol. Lett., 31(3):321-8 (Mar. 2009).

\* cited by examiner
† cited by third party

Schematic of Proto 1

Schematic of Proto 1S

Schematic of Proto 2S

Schematic of Protos 3S

Schematic of Proto 4

Schematic of Proto 5

Schematic of Proto 6

Insert ApoE/C1 enhancer (forward orientation) into FVIII intron

Schematic of Proto 7

Insert ApoE/C1 enhancer (reverse orientation) into FVIII intron

ADENO-ASSOCIATED VIRUS FACTOR VIII VECTORS

This application is a continuation of U.S. patent application Ser. No. 15/294,310, now U.S. Pat. No. 10,463,718 filed Oct. 14, 2016, and U.S. patent application Ser. No. 14/842,648 now U.S. Pat. No. 9,504,762, filed Sep. 10, 2014, which claim priority to the U.S. Provisional Patent Application Ser. No. 61/877,042, filed Sep. 12, 2013, which are incorporated by reference herein their entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII. The invention also relates to methods of making the herein described AAV FVIII vectors and associated therapeutic uses of thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., New Engl. J. Med. 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., Blood, 117:798-807, 2011, and McIntosh et al., Blood 121:3335-3344, 2013).

While AAV vectors have been reported in the literature having AAV genomes of >5.0 kb, in many of these cases the 5' or 3' ends of the encoded genes appear to be truncated (see Hirsch et al., Molec. Ther. 18-6-8, 2010, and Ghosh et al., Biotech. Genet. Engin. Rev. 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein useful in gene therapy approaches for the treatment of hemophilia A. As such, the present invention relates to AAV vectors that encode functionally active FVIII such that either the AAV virions encapsidate the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. Moreover, to avoid capsid directed immune response, AAV vectors should have the highest possible transduction/expression activity of the target protein per capsid particle. This invention also relates to the production of completely packaged AAV FVIII vectors with high expression activity. Finally, the present invention relates to methods for producing the herein described AAV Factor VIII vectors and associated methods for using the same.

SUMMARY OF INVENTION

The present invention provides AAV vectors encoding functionally active FVIII (referred to herein as "AAV FVIII vectors"). The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, allowing for blood coagulation to occur and decreasing the time that it takes for blood to clot in a subject suffering from Hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa.

As used herein, an "AAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements, i.e., one or more promoters and/or enhancers, and a polyadenylation sequence, and, optionally, one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., J. Virol. 79(1):364-379 (2005) which is herein incorporated by reference in its entirety.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII having the B domain replaced by the 14 amino acid SQ sequence, i.e., encoding FVIII SQ. The SQ sequence is disclosed in Ward et al., Blood, 117:798-807, 2011, and McIntosh et al., Blood 121:3335-3344, 2013. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121: 3335-3344, 2013). This sequence is referred herein as the "UCL SQ FVIII."

In a first aspect, the AAV vector of the invention comprises Proto 1, which is depicted schematically in FIG. 2A, and comprises the nucleic acid sequence set forth in SEQ ID NO: 1.

In a second aspect, the AAV vector of the invention comprises Proto 1S, which is depicted schematically in FIG. 2B, and comprises the nucleic acid sequence set forth in SEQ ID NO: 2.

In a third aspect, the AAV vector of the invention comprises Proto 2S, which is depicted schematically in FIG. 2C, and comprises the nucleic acid sequence set forth in SEQ ID NO: 3.

In a fourth aspect, the AAV vector of the invention comprises Proto 3S, which is depicted schematically in FIG. 2D, and comprises the nucleic acid sequence set forth in SEQ ID NO: 4.

In another embodiment, the AAV vector of the invention comprises a nucleic acid encoding FVIII lacking the entire B domain, including the SQ sequence, and the a3 domain, which is located just N-terminal to the light chain or C domain. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121:3335-3344, 2013).

In a first aspect, the AAV vector of the invention comprises Proto 4, which is depicted schematically in FIG. 3A, and comprises the nucleic acid sequence set forth in SEQ ID NO: 5.

In a second aspect, the AAV vector of the invention comprises Proto 5, which is depicted schematically in FIG. 3B, and comprises the nucleic acid sequence set forth in SEQ ID NO: 6.

In a third aspect, the AAV vector of the invention comprises Proto 6, which is depicted schematically in FIG. 3C, and comprises the nucleic acid sequence set forth in SEQ ID NO: 7.

In a fourth aspect, the AAV vector of the invention comprises Proto 7, which is depicted schematically in FIG. 3D, and comprises the nucleic acid sequence set forth in SEQ ID NO: 8.

In another embodiment, the AAV vector of the invention comprises a nucleic acid comprising an AAV2 5' inverted terminal repeat (ITR), a liver-specific transcription regulatory region, a codon-optimized functionally active FVIII coding region, optionally one or more introns, a polyadenylation sequence, and an AAV2 3' ITR. In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding regions encodes the FVIII SQ variant. In another preferred embodiment, the liver specific transcription regulatory region comprises a a1 microglobulin enhancer sequence and the 186 base human alpha anti-trypsin (AAT) proximal promoter.

In a first aspect, the AAV vector of the invention comprises Construct 100ATG comprising the nucleic acid sequence forth in SEQ ID NO: 9.

In a second aspect, the AAV vector of the invention comprises Construct 100ATG bGH poly A comprising the nucleic acid sequence set forth in SEQ ID NO: 10.

In a third aspect, the AAV vector of the invention comprises Construct 100ATG short bGH polyA sequence set forth in SEQ ID NO: 11.

In a fourth aspect, the AAV vector of the invention comprises Construct 103ATG comprising the nucleic acid sequence forth in SEQ ID NO: 12.

In a fifth aspect, the AAV vector of the invention comprises Construct 103ATG short bGH poly A comprising the nucleic acid sequence set forth in SEQ ID NO: 13.

In a sixth aspect, the AAV vector of the invention comprises Construct 105ATG bGH poly A comprising the nucleic acid sequence set forth in SEQ ID NO: 14.

In a seventh aspect, the AAV vector of the invention comprises Construct DC172ATG FVIII comprising the nucleic acid sequence set forth in SEQ ID NO: 15.

In an eighth aspect, the AAV vector of the invention comprises Construct DC172ATG FVIII hAAT comprising the nucleic acid sequence set forth in SEQ ID NO: 16.

In a ninth aspect, the AAV vector of the invention comprises Construct DC172 2×HCR ATG FVIII comprising the nucleic acid sequence set forth in SEQ ID NO: 17.

In a tenth aspect, the AAV vector of the invention comprises Construct DC172 2×HCR ATG FVIII hAAT comprising the nucleic acid sequence set forth in SEQ ID NO: 18.

In an eleventh aspect, the AAV vector of the invention comprises Construct 2× SerpinA hAAT ATG FVIII comprising the nucleic acid sequence set forth in SEQ ID NO: 19.

In a twelfth aspect, the AAV vector of the invention comprises Construct 2× SerpinA hAAT ATG FVIII 2× μ-globulin enhancer comprising the nucleic acid sequence set forth in SEQ ID NO: 20.

In a thirteenth aspect, the AAV vector of the invention Construct 100ATG short polyA 2× μ-globulin enhancer comprising the nucleic acid sequence set forth in SEQ ID NO: 21.

In a fourteenth aspect, the AAV vector of the invention comprises Construct Factor VIII-BMN001 comprising the nucleic acid sequence set forth in SEQ ID NO: 22.

In a fifteenth aspect, the AAV vector of the invention comprises Construct Factor VIII-BMN002 sequence set forth in SEQ ID NO: 23.

In a sixteenth aspect, the AAV vector of the invention comprises Construct 99 comprising the nucleic acid sequence set forth in SEQ ID NO: 24.

In a seventeenth aspect, the AAV vector of the invention comprises Construct 100 comprising the nucleic acid sequence set forth in SEQ ID NO: 25.

In an eighteenth aspect, the AAV vector of the invention comprises Construct 100 reverse orientation comprising the nucleic acid sequence set forth in SEQ ID NO: 26.

In a nineteenth aspect, the AAV vector of the invention Construct 100AT comprising the nucleic acid sequence set forth in SEQ ID NO: 27.

In a twentieth aspect, the AAV vector of the invention Construct 100AT 2× MG comprising the nucleic acid sequence set forth in SEQ ID NO: 28.

In a twenty-first aspect, the AAV vector of the invention comprises Construct 100AT 2× MG bGH polyA comprising the nucleic acid sequence set forth in SEQ ID NO: 29.

In a twenty-second aspect, the AAV vector of the invention comprises Construct 100AT 2× MG (reverse) bGH polyA comprising the nucleic acid sequence set forth in SEQ ID NO: 30.

In a twenty-third aspect, the AAV vector of the invention comprises Construct 100 bGH polyA comprising the nucleic acid sequence set forth in SEQ ID NO: 31.

In a twenty-fourth aspect, the AAV vector of the invention comprises Construct 100-400 comprising the nucleic acid sequence set forth in SEQ ID NO: 32.

In a twenty-fifth aspect, the AAV vector of the invention comprises Construct 101 comprising the nucleic acid sequence set forth in SEQ ID NO: 33.

In a twenty-sixth aspect, the AAV vector of the invention comprises Construct 102 sequence comprising the nucleic acid sequence set forth in SEQ ID NO: 34.

In a twenty-seventh aspect, the AAV vector of the invention comprises Construct 103 comprising the nucleic acid sequence set forth in SEQ ID NO: 35.

In a twenty-ninth aspect, the AAV vector of the invention comprises Construct 103 reverse orientation comprising the nucleic acid sequence set forth in SEQ ID NO: 36.

In a thirtieth aspect, the AAV vector of the invention comprises Construct 103AT comprising the nucleic acid sequence set forth in SEQ ID NO: 37.

In a thirty-first aspect, the AAV vector of the invention comprises Construct 103AT 2× MG comprising the nucleic acid sequence set forth in SEQ ID NO: 38.

In a thirty-second aspect, the AAV vector of the invention comprises Construct 103AT 2× MG bGH polyA comprising the nucleic acid sequence set forth in SEQ ID NO: 39.

In a thirty-third aspect, the AAV vector of the invention comprises the Construct 103 bGH polyA comprising the nucleic acid sequence set forth in SEQ ID NO: 40.

In a thirty-fourth aspect, the AAV vector of the invention comprises Construct 104 comprising the nucleic acid comprising the nucleic acid sequence set forth in SEQ ID NO: 41.

In a thirty-fifth aspect, the AAV vector of the invention comprises Construct 105 comprising the nucleic acid sequence set forth in SEQ ID NO: 42.

In a thirty-sixth aspect, the AAV vector of the invention comprises Construct 106 comprising the nucleic acid sequence set forth in SEQ ID NO: 43.

In a thirty-seventh aspect, the AAV vector of the invention comprises Construct 106AT comprising the nucleic acid sequence set forth in SEQ ID NO: 44.

In a thirty-eighth aspect, the AAV vector of the invention comprises Construct 2× SerpinA hAAT comprising the nucleic acid sequence set forth in SEQ ID NO: 45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation.

The AAV vectors of the invention in single strand is less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand ranges from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particle comprising any of the AAV vectors of the invention. The methods comprise the steps of culturing a cell that has been transfected with any of the AAV vectors of the invention and recovering recombinant AAV from the supernatant of the transfected cell.

The cells of the invention are any cell type are susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NS0, SP2/0, PER.C6, Vero, RD, BHK, HT 1080, A549, Cos-7, ARPE-19 and MRC-5 cells, and including mammalian cells such as HEK293, HeLa, CHO, NS0, SP2/0, PER.C6, Vero, RD, BHK, HT 1080, A549, Cos-7, ARPE-19 and MRC-5 cells.

The invention also provides for a viral particle comprising any of the AAV vectors of the invention or any viral particle produced by the forgoing methods of the invention.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient an effective amount of any of the AAV vectors of the invention, or a viral particle of the invention or a viral particles produced by a method of the invention.

In a further embodiment, the invention provides for a use of any of the AAV vectors of the invention for preparation of a medicament for the treatment of hemophilia A. In one aspect, the medicament comprises an amount of AAV vector that expresses human FVIII in an amount effective to treat hemophilia A.

In another embodiment, the invention provides for a composition comprising any of the AAV vectors of the invention for the treatment of hemophilia A. In one aspect, the composition comprises an amount of AAV vector that expresses human FVIII in an amount effective to treat hemophilia A.

In another embodiment, the AAV vectors of the invention are used to produce AAV viral particles that are useful to treat a patient suffering from Hemophilia A.

DESCRIPTION OF DRAWINGS

FIG. 2A provides a schematic of the Proto 1 vector. Starting from the UCL SQ vector (see FIG. 1), the extraneous wild-type AAV2 viral sequences were deleted, and sequences corresponding to restriction sites between the human AAT 5' UTR and the human FVIII coding region, and between the human FVIII termination codon and the synthetic polyadenylation sequence, were removed. FIG. 2B provides a schematic of the Proto 1S vector. Starting from the Proto 1 vector, 10 bases at the 3' end of the AAV2 5'ITR and 10 bases at the 5' end of the 3' ITR were deleted. FIG. 2C provides a schematic of the Proto 2S vector. Starting from the Proto 1S vector, the human ApoE/C1 enhancer and human AAT promoter distal X region were moved into a 100 base synthetic intron that was inserted between exons 1 and 2 of the human FVIII sequence. As indicated by the arrows, the orientation of the human ApoE/C1 enhancer and human AAT promoter distal X region are reversed compared to their orientation in Proto 1S. FIG. 2D provides a schematic of the Proto 3S vector. Starting from Proto 2S, the human AAT promoter distal X region is replaced by a second copy of the human ApoE/C1 enhancer in the reverse orientation.

FIG. 3A provides a schematic of the Proto 4 vector. Starting from the Proto 1 vector, the SQ sequence and a3 domain were deleted. FIG. 3B provides a schematic of the Proto 5 vector. Starting from the Proto 4 vector, a 129 base FVIII intron was inserted between exons 1 and 2 of the human Factor VIII sequence. FIG. 3C provides a schematic of the Proto 6 vector. Starting from the Proto 5 vector, a second copy of the human ApoE/C1 enhancer was inserted in the forward orientation into the FVIII intron. FIG. 3R provides a schematic of the Proto 7 vector. Starting from the Proto 5 vector, a second copy of the human ApoE/C1 enhancer was inserted in the reverse orientation into the FVIII intron.

FIG. 4A provides a schematic of Construct 100ATG. FIG. 4B provides a schematic of Construct 100ATG bGH polyA. FIG. 4C provides a schematic of Construct 100ATG short bGH poly A. FIG. 4D provides a schematic of Construct 103ATG. FIG. 4E provides a schematic of Construct 103ATG short bGH poly A. FIG. 4F provides a schematic of Construct 105ATG bGH polyA. FIG. 4G provides a schematic of Construct DC172ATG FVIII. FIG. 4H provides a schematic of Construct DC172ATG FVIII hAAT. FIG. 4I provides a schematic of Construct DC172 2×HCR ATG FVIII. FIG. 4J provides a schematic of Construct DC172 2×HCR ATG FVIII hAAT. FIG. 4K provides a schematic of Construct 2× SerpinA hAAT ATG FVIII. FIG. 4AA provides a schematic of Construct 103. FIG. 4BB provides a schematic of Construct 103 reverse orientation. FIG. 4CC provides a schematic of Construct 103AT. FIG. 4DD provides a schematic of Construct 103AT 2× MG. FIG. 4EE provides a schematic of Construct 103AT 2× MG bGH poly A. FIG. 4FF provides a schematic of 103 sbGH poly A. FIG. 4GG provides a schematic of Construct 104. FIG. 4HH provides a schematic of Construct 105. FIG. 4II provides a schematic of Construct 106. FIG. 4JJ provides a schematic of Construct 106AT. FIG. 4KK provides a schematic of Construct 2× SerpinA hAAT.

DETAILED DESCRIPTION

Oversized AAV vectors are randomly truncated at the 5' ends and lack a 5' AAV ITR. Because AAV is a single-stranded DNA virus, and packages either the sense or antisense strand, the sense strand in oversized AAV vectors lacks the 5' AAV ITR and possibly portions of the 5' end of the target protein-coding gene, and the antisense strand in oversized AAV vectors lacks the 3' ITR and possibly portions of the 3' end of the target protein-coding gene. A functional transgene is produced in oversized AAV vector infected cells by annealing of the sense and antisense truncated genomes within the target cell.

The invention provides for AAV vectors encoding functionally active FVIII, i.e., completely packaged AAV FVIII vectors or AAV FVIII vectors with high expression activity. The AAV FVIII vectors of the invention have improved expression/particle, as well as improved AAV virus production yield and simplified purification. Introducing one or more introns into the FVIII protein-coding region enhances expression. Reconfiguring the number and positioning of enhancers also enhances expression.

UCL SQ Vector

Figure 1:
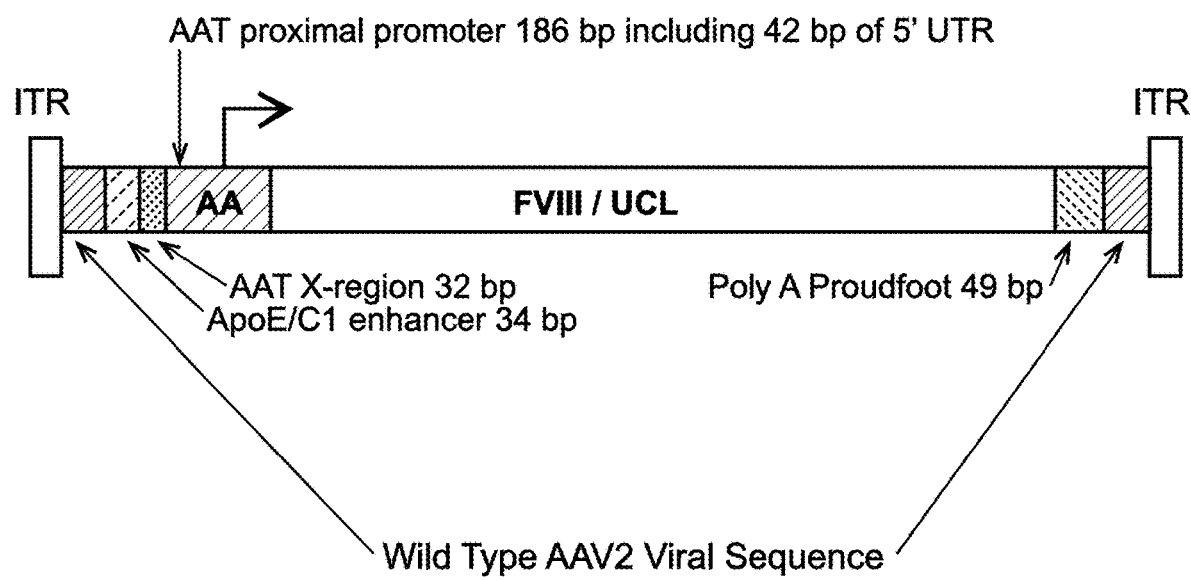
FIG. 1 provides a schematic of the UCL SQ vector. From left to right, the UCL SQ vector comprises the AAV2 5' ITR, wild-type AAV2 viral sequence, the 34 base human ApoE/C1 enhancer, the 32 base human AAT promoter distal X region, the 186 base human AAT promoter, including 42 bases of 5' UTR sequence, the codon-optimized human FVIII SQ sequence (see Nathwani et al., US Pat. App. Pub. No. 2013/0024960A1, published Jan. 24, 2013, which is incorporated herein by reference in its entirety, and McIntosh et al., Blood 121:3335-3344, 2013), the 49 bases synthetic polyadenylation sequence, wild-type AAV2 viral sequence, and the AAV2 3'ITR. The UCL SQ vector is 5081 bases in length.

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

As shown in Nathwani et al., US Pat. App. Pub. No. 2013/0024960A1, published Jan. 24, 2013, and McIntosh et al., Blood 121:3335-3344, 2013, the UCL SQ vector expresses functionally active FVIII in vitro and in vivo.

Proto 1, Proto 1S, Proto 2S and Proto 3S Vectors

To avoid the problem of over-sized AAV vectors and/or to increase the expression of the AAV vectors, the invention provides completely packaged, smaller, i.e., less than 5.0 kb, AAV vectors encoding the FVIII SQ variant. The 4970 bp nucleotide sequence of sequence of Proto 1 is set forth in SEQ ID NO: 1.

To generate the AAV vector Proto 1, sequences that appear to be unnecessary for production of functionally active FVIII were deleted as compared to the UCL SQ vector. As shown in Example 1, 110 bases of extraneous DNA were removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector is 4970 bases in length. When designed, it was unknown whether the Proto 1 vector would be capable of expressing functional FVIII polypeptide, either in vitro or in vivo.

To generate the AAV vector Proto 1S, 10 bases at the 3' end of the AAV2 5'ITR, and 10 bases at the 5' end of the AAV32 3'ITR, were removed from the Proto 1 vector. The resultant Proto 1S vector is 4950 bases in length. The nucleotide sequence of sequence of Proto 1S is set forth in SEQ ID NO: 2.

To generate the AAV vector Proto 2S, a synthetic 100 base intron was inserted between exons 1 and 2 of the codon-optimized FVIII SQ sequence in the Proto 1S vector. The 34 bases ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO: 3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO: 4.

Proto 4, Proto S, Proto 6 and Proto 7 Vectors

To reduce the size of AAV vectors and/or increase the expression of the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO: 5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO: 6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO: 7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO: 8.

Additional AAV FVIII Vectors with Improved Promoter/Enhancer Sequences

Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the µ-globulin enhancer or fragments thereof, the human alpha 1 antitrypsin promoter (hAAT) or fragments thereof, Serpin A enhancer or fragments thereof, the LP1 promoter enhancer or fragments thereof or macro-globulin enhancer or fragment thereof. These constructs comprise a polyadenylation sequence such as the bGH poly A sequence or the synthetic rabbit β-globin poly A sequence.

In some embodiment, the constructs comprise an intron or fragments of an intron such as a hAAT intron or a human β-globin intron.

Construct 100ATG is 5511 bases in length. This construct is set forth in SEQ ID NO: 9 in which bases 1-145 are the 5'AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5352 are a synthetic rabbit β-globin poly A and bases 5367-5511 are the 3' AAV2 ITR.

Construct 100ATG bGH poly A is 5688 bases in length. This construct is set forth in SEQ ID NO: 10 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5529 are a bGH poly A and bases 5544-5688 are the 3' AAV2 ITR.

Construct 100ATG short bGH poly A is 5613 bases in length. This construct is set forth in SEQ ID NO: 11 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5454 are a short bGH poly A and bases 5469-5613 are the 3' AAV2 ITR.

Construct 103ATG is 5362 bases in length. This construct is set forth in SEQ ID NO: 12 in which bases 1-145 are the 5' AAV2 ITR, bases 169-344 are four copies (4×) of a 44bp ApoE repeat, bases 360-577 are a hAAT promoter, bases 578-761 are a modified human β-globin $2^{nd}$ intron, bases 774-5147 are a codon optimized SQ FVIII, bases 5156-5203 are a synthetic rabbit β-globin poly A and bases 5218-5362 are the 3' AAV2 ITR.

Construct 103ATG short bGH poly A is 5464 bases in length. This construct is set forth in SEQ ID NO: 13 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5305 are a bGH short poly A and bases 5320-5464 are the 3' AAV2 ITR.

Construct 105ATG bGH polyA is 6354 bases in length. This construct is set forth in SEQ ID NO: 14 in which bases 1-145 are the 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are a codon optimized SQ FVIII, bases 5315-5539 are a bGH poly A, bases 5546-6195 are two copies (2×) of a 325 bp ApoE HCR and bases 6210-6354 are the 3' AAV2 ITR.

Construct DC172ATG FVIII is 6308 bases in length. This construct is set forth in SEQ ID NO: 15 in which bases 1-145 are the 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are a codon optimized SQ FVIII, bases 5926-6149 are a bGH poly A and bases 6164-6308 are the 3' AAV2 ITR.

Construct DC172ATG FVIII hAAT is 5635 bases in length, This construct is set forth as SEQ ID NO: 16 in which bases 1-145 are the 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are a codon optimized SQ FVIII, bases 5253-5476 are a bGH poly A and bases 5490-5635 are the 3' AAV2 ITR.

Construct DC172 2×HCR ATG FVIII is 6962 bases in length. This construct is set forth in SEQ ID NO: 17 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are a codon optimized SQ FVIII, bases 6580-6803 are a bGH poly A and bases 6818-6962 are the 3' AAV2 ITR.

Construct DC172 2×HCR ATG FVIII hAAT is 6289 bases in length. This construct is set forth in SEQ ID NO: 18 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are a codon optimized SQ FVIII, bases 5907-6130 are a bGH poly A and bases 6245-6289 are the 3' AAV2 ITR.

Construct 2× SerpinA hAAT ATG FVIII is 5430 bases in length. This construct is set forth in SEQ ID NO: 19 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, and bases 5286-5430 are the 3'AAV2 ITR.

Construct 2× SerpinA hAAT ATG FVIII 2× μ-globulin enhancer is 5779 bases in length. This construct is set forth in SEQ ID NO: 20 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, bases 5279-5618 are two copies (2×) of a 170 bp μ-globulin enhancer and bases 5635-5779 are the 3' AAV2 ITR.

Construct 100ATG short bGH poly A 2× μ-globulin enhancer is 5962 bases in length. This construct is set forth in SEQ ID NO: 21 in which bases 1-145 are the 5' AAV2 ITR, bases 160-502 are an ApoE HCR, bases 509-726 are a hAAT promoter, bases 727-910 are a modified human β-globin $2^{nd}$ intron, bases 923-5296 are a codon optimized SQ FVIII, bases 5305-5454 are a short bGH poly A, bases 5462-5801 are two copies (2×) of a 170 bp microglobulin enhancer and bases 5818-5962 are the 3' AAV2 ITR.

Construct Factor VIII-BMN001 is 5919 bases in length. This construct is set forth in SEQ ID NO: 22 in which bases 1-145 are the 5' AAV2 ITR, bases 160-480 are an ApoE HCR, bases 487-884 are a 398bp hAAT promoter, bases 885-1145 are a truncated hAAT intron, bases 1155-5528 are a codon optimized SQ FVIII, bases 5537-5760 are a bGH poly A and bases 5775-5919 are the 3' AAV2 ITR.

Construct FVIII-BMN002 is 5306 bases in length. This construct is set forth in SEQ ID NO: 23 in which bases 1-145 are the 5' AAV2 ITR, bases 175-705 are an LP1 promoter/enhancer, bases 718-5091 are a codon optimized SQ FVIII, bases 5100-5147 are a synthetic rabbit β-globin poly A and bases 5162-5306 are the 3' AAV2 ITR.

Construct 99 is 5461 bases in length. This construct is set forth in SEQ ID NO: 24 in which bases 1-145 are the 5' AAV2 ITR, bases 169-627 are an ApoE HCR/MAR, bases 634-866 are a hAAT promoter, bases 873-5246 are a codon optimized SQ FVIII, bases 5255-5302 are a synthetic rabbit β-globin poly A and bases 5317-5461 are the 3' AAV2 ITR.

Construct 100 is 5327 bases in length. This construct is set forth in SEQ ID NO: 25 in which bases 1-145 are the 5' AAV2 ITR, bases 169-493 are an ApoE HCR, bases 509-726 are a hAAT promoter, bases 739-5112 are a codon optimized SQ FVIII, bases 5121-5168 are a synthetic rabbit β-globin poly A and bases 5183-5327 are the 3' AAV2 ITR.

Construct 100 reverse orientation is 5309 bases in length. This construct is set forth in SEQ ID NO: 26 in which bases 1-145 are the 5' AAV2 ITR, bases 160-484 are an ApoE HCR in reverse orientation, bases 491-708 are a hAAT promoter, bases 721-5094 are a codon optimized SQ FVIII, bases 5103-5150 are a synthetic rabbit β-globin poly A and bases 5165-5309 are the 3' AAV2 ITR.

Construct 100AT is 5532 bases in length. This construct is set forth in SEQ ID NO: 27 in which bases 1-145 are the 5' AAV2 ITR, bases 169-493 are an ApoE HCR, bases 509-726 are a hAAT promoter, bases 727-931 are a hAAT intron, bases 944-5317 are a codon optimized SQ FVIII, bases 5326-5373 are a synthetic rabbit β-globin poly A and bases 5388-5532 are the 3' AAV2 ITR.

Construct 100AT 2× MG is 5877 bases in length. This construct is set forth in SEQ ID NO: 28 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5718 are a synthetic rabbit β-globin poly A and bases 5733-5877 are the 3' AAV2 ITR.

Construct 100AT 2× MG bGH poly A is 6054 bases in length. This construct is set forth in SEQ ID NO: 29 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100AT 2× MG (reverse) bGH poly A is 6054 bases in length. This construct is set forth in SEQ ID NO: 30 in which bases 1-145 are the 5' AAV2 ITR, bases 169-493 are an ApoE HCR, bases 508-847 are two copies (2×) of a 170 bp μ-globulin enhancer in reverse orientation, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100 bGH poly A is 5504 bases in length. This construct is set forth in SEQ ID NO: 31 in which bases 1-145 are the 5' AAV2 ITR, bases 169-493 are an ApoE HCR, bases 509-726 are a hAAT promoter, bases 739-5112 are a codon optimized SQ FVIII, base pairs 5121-5345 are a bGH poly A and bases 5360-5504 are the 3' AAV2 ITR.

Construct 100-400 is 5507 bases in length. This construct is set forth in SEQ ID NO: 32 in which bases 1-145 are the 5' AAV2 ITR, bases 169-493 are an ApoE HCR, bases 512-906 are a 398 bp hAAT promoter, bases 919-5292 are a codon optimized SQ FVIII, bases 5301-5348 are a synthetic rabbit β-globin poly A and bases 5363-5507 are the 3' AAV2 ITR.

Construct 101 is 5311 base in length. This construct is set forth in SEQ ID NO: 33 in which bases 1-145 are the 5' AAV2 ITR, bases 170-477 are two copies (2×) of a 154bp ApoE HCR, bases 493-710 are a hAAT promoter, bases 723-5096 are a codon optimized SQ FVIII, bases 5105-5152 are a synthetic rabbit β-globin poly A and bases 5167-5311 are the 3' AAV2 ITR.

Construct 102 is 5156 bases in length. This construct is set forth in SEQ ID NO: 34 in which bases 1-145 are the 5' AAV2 ITR, bases 169-322 are a 154bp ApoE HCR, bases 338-555 are a hAAT promoter, bases 568-4941 are a codon optimized SQ FVIII, bases 4950-4997 are a synthetic rabbit β-globin poly A and bases 5012-5156 are the 3' AAV2 ITR.

Construct 103 is 5178 bases in length. This construct is set forth in SEQ ID NO: 35 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5019 are a synthetic rabbit β-globin poly A and bases 5034-5178 are the 3' AAV2 ITR.

Construct 103 reverse orientation is 5160 bases in length. This construct is set forth in SEQ ID NO: 36 in which bases 1-145 are the 5' AAV2 ITR, bases 160-335 are four copies (4×) of a 44 bp ApoE HCR in reverse orientation, bases 342-559 are a hAAT promoter, bases 572-4945 are a codon optimized SQ FVIII, bases 4954-5001 are a synthetic rabbit β-globin poly A and bases 5016-5160 are the 3' AAV2 ITR.

Construct 103AT is 5383 bases in length. This construct is set forth in SEQ ID NO: 37 in which bases 1-145 are the 5' AAV2 ITR, bases 169-344 are four copies (4×) of a 44 bp ApoE HCR, bases 360-577 are a hAAT promoter, bases 578-782 are a hAAT intron, bases 795-4374 are a codon optimized SQ FVIII, bases 5177-5224 are a synthetic rabbit β-globin poly A and bases 5239-5383 are the 3' AAV2 ITR.

Construct 103AT 2× MG is 5728 bases in length. This construct is set forth in SEQ ID NO: 38 in which bases 1-145 are the 5' AAV2 ITR, bases 169-344 are four copies (4×) of a 44 bp ApoE HCR, bases 359-698 are two copies (2×) of a 170bp μ-globulin enhancer, bases 705-922 are a hAAT promoter, bases 923-1127 are a hAAT intron, bases 1140-5513 are a codon optimized SQ FVIII, bases 5522-5569 are a synthetic rabbit β-globin poly A and bases 5584-5728 are the 3' AAV2 ITR.

Construct 103AT 2× MG bGH poly A is 5905 bases in length. This construct is set forth in SEQ ID NO: 39 in which bases 1-145 are the 5' AAV2 ITR, bases 169-344 are four copies (4×) of a 44 bp ApoE HCR, bases 359-698 are two copies (2×) of a 170bp μ-globulin enhancer, bases 705-922 are a hAAT promoter, bases 923-1127 are a hAAT intron, bases 1140-5513 are a codon optimized SQ FVIII, bases 5522-5746 are a synthetic rabbit β-globin poly A and bases 5761-5905 are the 5' AAV2 ITR.

Construct 103 bGH poly A is 5355 bases in length. This construct is set forth in SEQ ID NO: 40 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5196 are a synthetic rabbit β-globin poly A and bases 5211-5355 are the 3' AAV2 ITR.

Construct 104 is 5618 bases in length. This construct is set forth in SEQ ID NO: 41 in which bases 1-145 are the 5' AAV2 ITR, bases 169-784 are four copies (4×) of a 154bp ApoE HCR, bases 800-1017 are a hAAT promoter, bases 1030-5403 are a codon optimized SQ FVIII, bases 5412-5459 are a synthetic rabbit β-globin poly A and bases 5474-5618 are the 3' AAV2 ITR.

Construct 105 is 5993 bases in length. This construct is set forth in SEQ ID NO: 42 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A, bases 5185-5834 are two copies (2×) of an ApoE HCR and bases 5849-5993 are the 3' AAV2 ITR.

Construct 106 is 5337 bases in length. This construct is set forth in SEQ ID NO: 43 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A and bases 5193-5337 are the 3' AAV2 ITR.

Construct 106AT is 5542 bases in length. This construct is set forth in SEQ ID NO: 44 in which bases 1-145 are the 5' AAV2 ITR, bases 173-512 are two copies (2×) of a 170 bp μ-globulin enhancer, bases 519-736 are a hAAT promoter, bases 737-941 are a hAAT intron, bases 954-5327 are a codon optimized SQ FVIII, bases 5336-5383 are a synthetic rabbit β-globin poly A and bases 5398-5542 are the 3' AAV2 ITR.

Construct 2× SerpinA hAAT is 5126 base. This construct is set forth in SEQ ID NO: 45 in which bases 1-145 are the 5' AAV2 ITR, bases 160-301 are an ApoE HCR, bases 308-525 are a hAAT promoter, bases 538-4911 are a codon optimized SQ FVIII, bases 4920-4967 are a synthetic rabbit β-globin poly A and bases 4982-5126 are the 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chlorini et al., J. Vir. 71: 6823-33(1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, NJ (1995); O'Reilly et al., BACULOVIRUS EXPRESSION VECTORS, A LABORATORY MANUAL, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kirnbauer et al., Vir. 219:37-44 (1996); Zhao et al., Vir. 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be redocued using any invertebrate cell type which allows for production of AAV or biologic products and which can be maintained in culture. For example, the insect cell line used can be from *Spodoptera frugiperda*, such as SF9, SF21, SF900+, drosophila cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (BmNPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the UCL SQ vector, and preferably 1.5-fold, 2-fold, 3-fold, 4-fold, or 5-fold or more expression and/or activity as compared to the UCL SQ vector.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the UCL SQ vector.

Other aspects and advantages of the present invention will be understood upon consideration of the following illustrative examples.

EXAMPLES

Example 1

Generation of Proto 1, Proto 1S, Proto 2S and Proto 3S Vectors

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

Figure 2A:
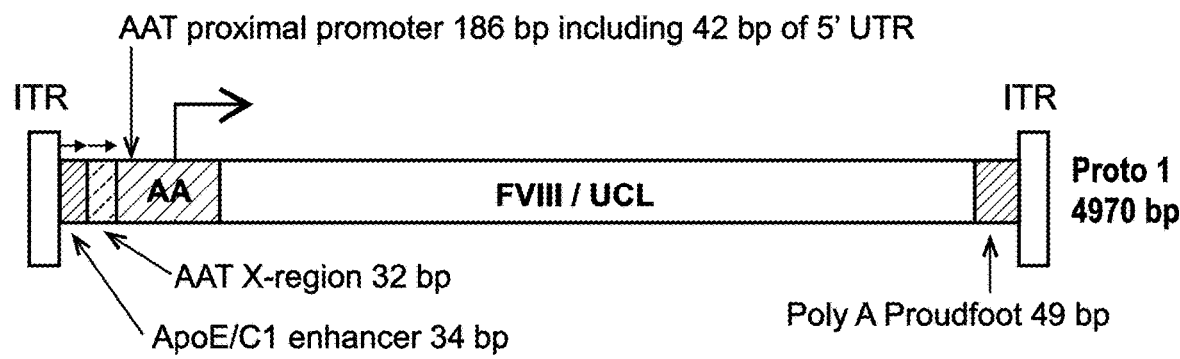
FIGS. 2A-2D provide schematics and sequences of the Proto 1, Proto 1S, Proto 2S and Proto 3S vectors.

To obtain a vector that is smaller than the UCL SQ vector, DNA sequences believed by the inventors herein to be unnecessary for FVIII expression and/or activity, or for AAV virion production, were removed from the UCL SQ vector sequence. Extraneous DNA sequence was removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector, which is 4970 bases in length, is shown in schematic form in FIG. 2A, and the sequence is set forth in SEQ ID NO: 1. Proto 1 produced infectious virus and encodes a functional Factor VIII polypeptide.

Figure 2B:
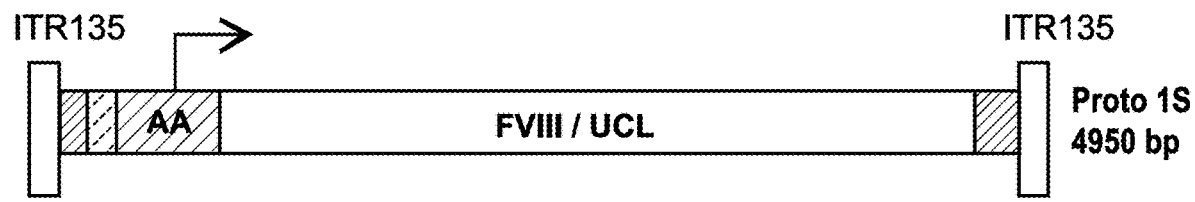

Sequences adjacent to the hairpin loop in the AAV2 ITR may also be dispensable in recombinant AAV vectors (see Srivastava et al., U.S. Pat. No. 6,521,225; Wang et al., J. Virol. 70:1668-1677, 1996; and Wang et al., J. Virol. 71:3077-3082, 1997). To further reduce the size of the Proto 1 vector, 10 bases of AAV2 sequence was removed directly 3' to the hairpin loop in the AAV2 5'ITR and 10 bases of AAV2 sequence was removed directly 5' to the hairpin loop in the AAV2 3'ITR. The resultant Proto 1S vector, which is 4950 bases in length, is shown in schematic form in FIG. 2B, and the sequence is set forth in SEQ ID NO: 2.

In an effort to increase the expression of the FVIII SQ variant in the Proto 1S vector, a 100 base synthetic intron was inserted between exons 1 and 2 in the codon-optimized FVIII sequence. It is known that insertion of an intron can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in Gray et al., U.S. Pat. No. 8,030,065 (FIX expression) and in Nathwani et al., US Pat. App. Pub. No. 2013/0024960 (FVIII expression), both of which are incorporated herein by reference in their entirety. The 32 base human AAT promoter distal X region, described in Di Simone et al., EMBO J. 6:2759-2766, 1987, is located within a regulatory domain that enhances expression of a heterologous promoter.

Figure 2C:
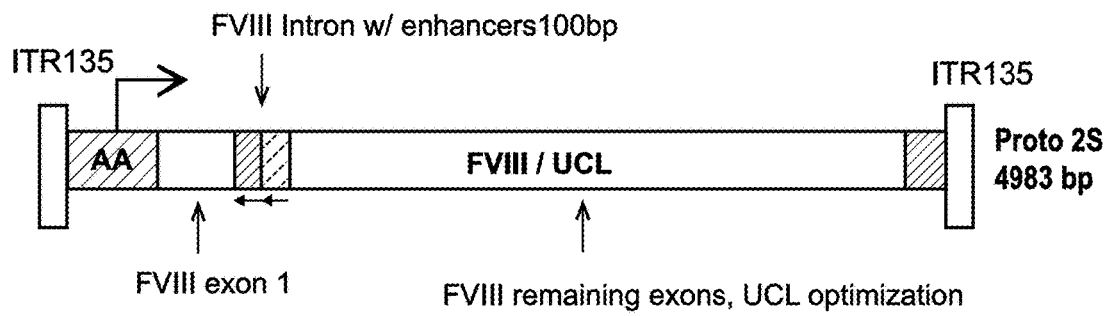

In another attempt to further increase the expression of the FVIII SQ variant in the Proto 1S vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 1S. The resultant Proto 2S vector, which is 4983 bases in length, is shown in schematic form in FIG. 2C, and the sequence set forth in SEQ ID NO: 3.

Figure 2D:
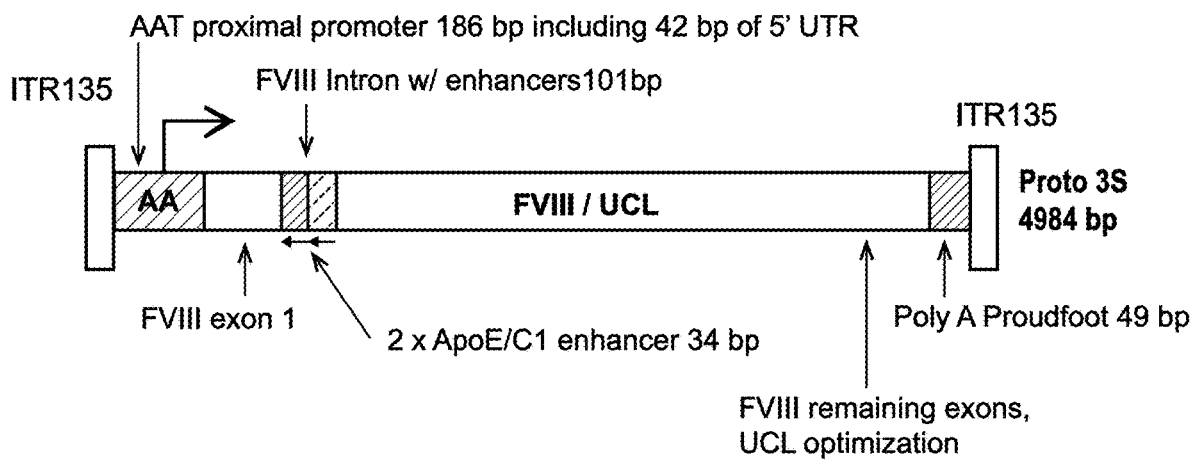

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO: 4.

The Proto 1, Proto 1S, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
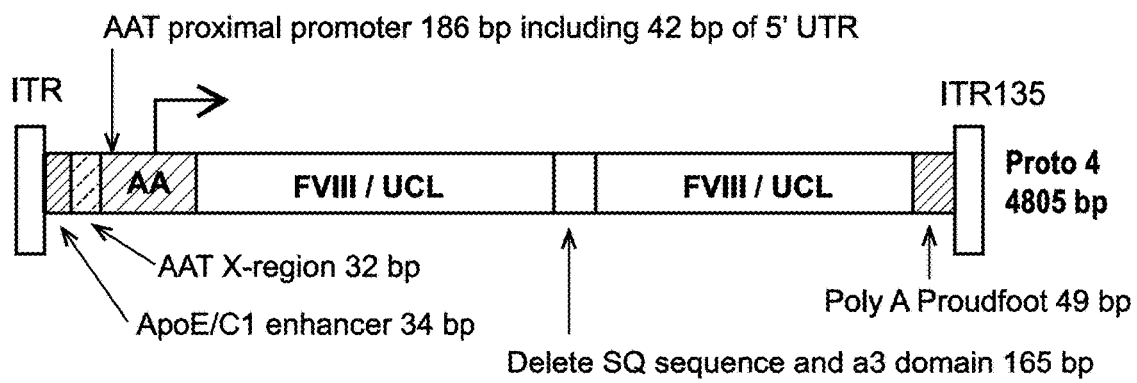
FIGS. 3A-3D provide schematics of the Proto 4, Proto 5, Proto 6 and Proto 7 vectors.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO: 5.

Figure 3B:
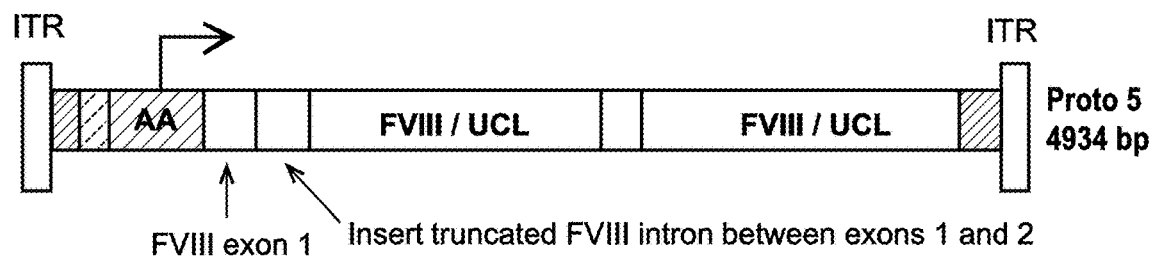

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO: 6.

Figure 3C:
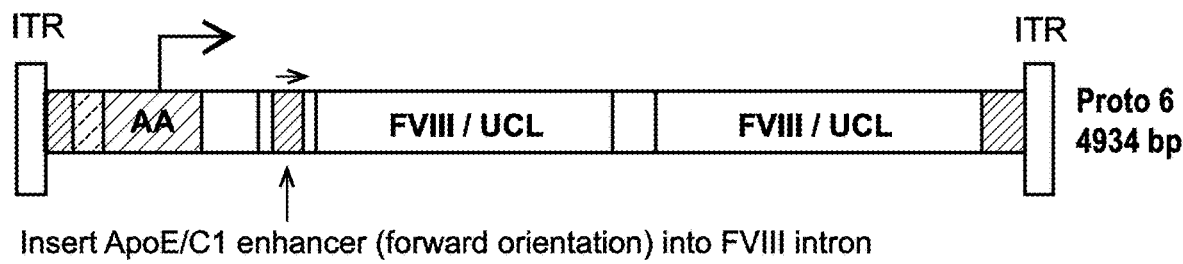

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO: 7.

Figure 3D:
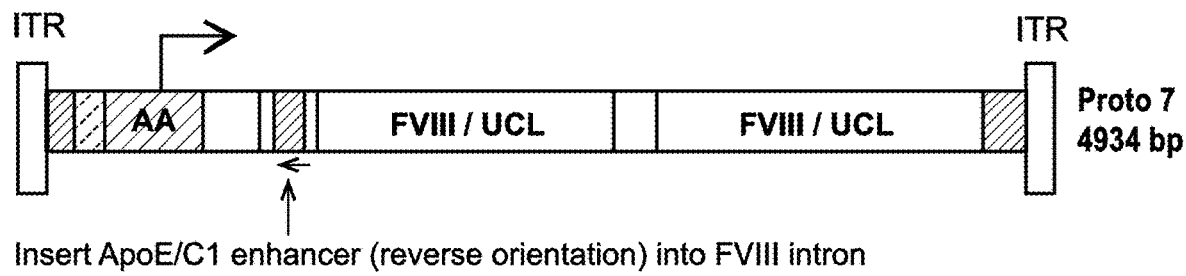
Figure 4A:
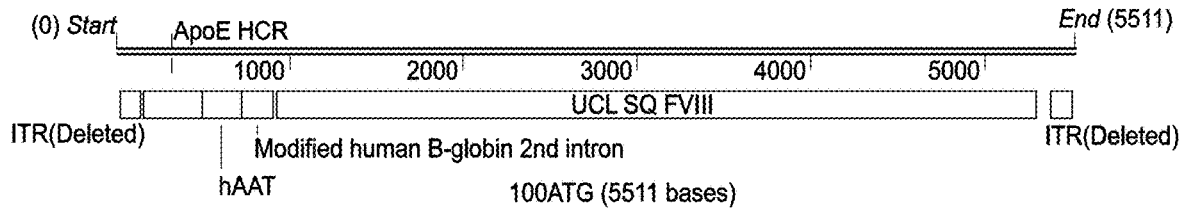
FIGS. 4A-4KK provide schematics of the AAV FVIII vectors with improved promoter/enhancer sequences.
Figure 4B:
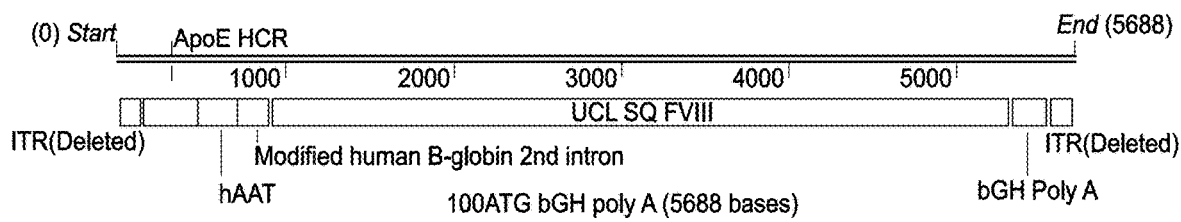
Figure 4C:
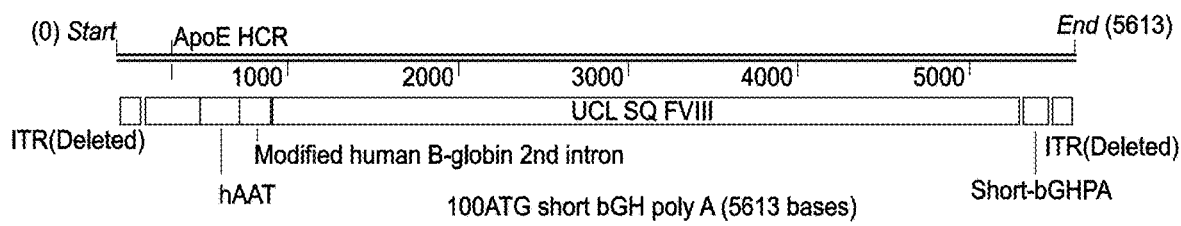
Figure 4D:
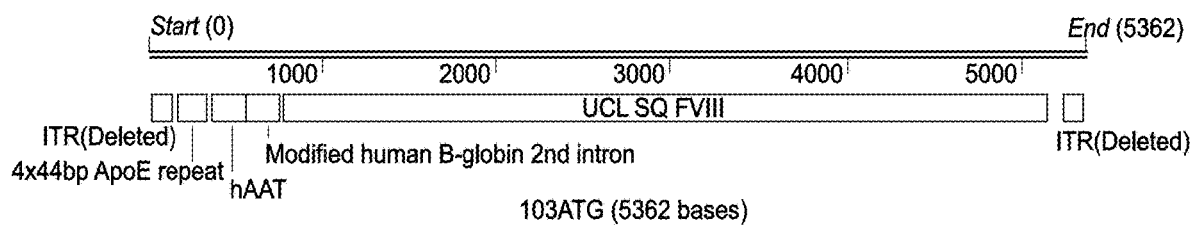
Figure 4E:
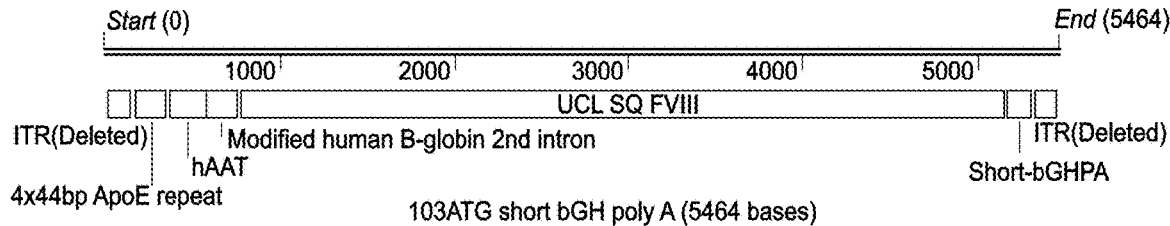
Figure 4F:
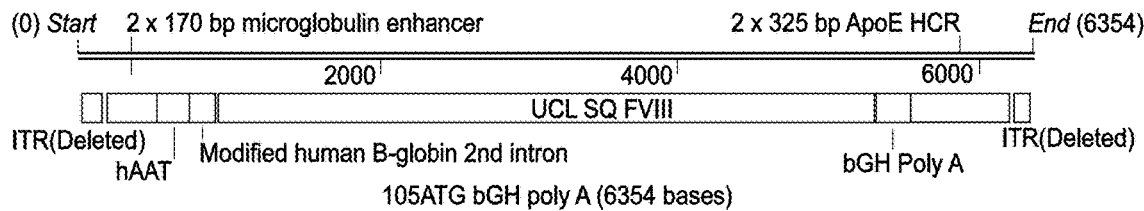
Figure 4G:
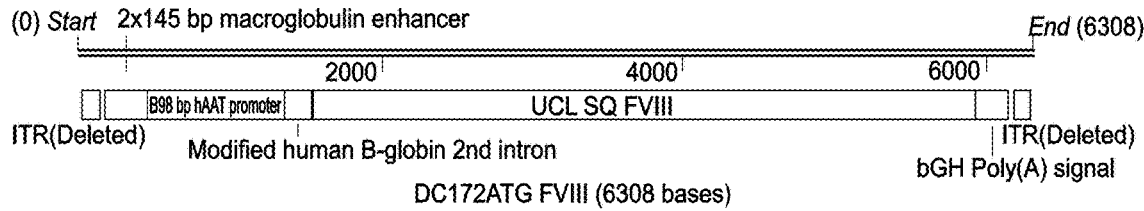
Figure 4H:
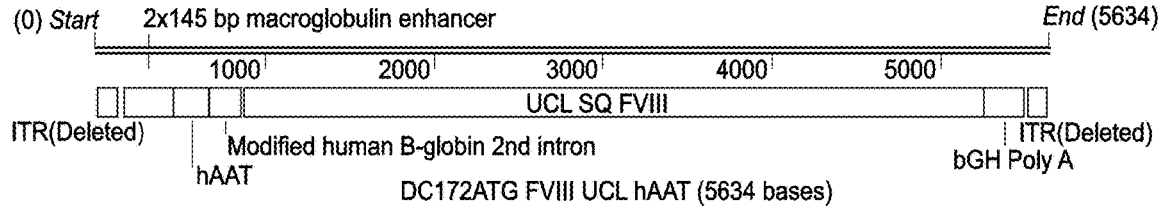
Figure 4I:
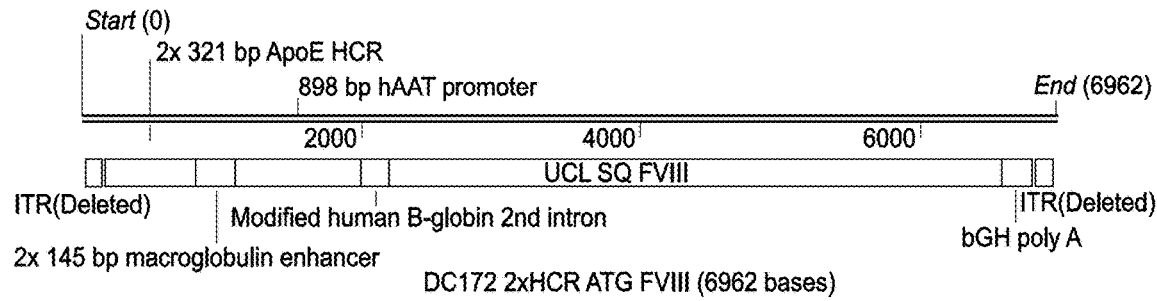
Figure 4J:
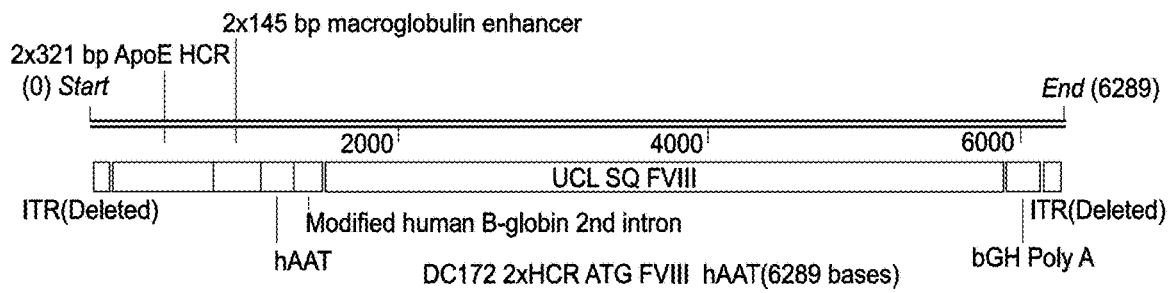
Figure 4K:
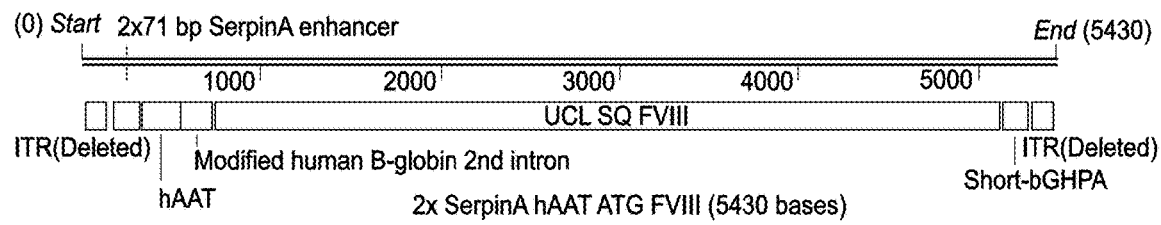
Figure 4L:
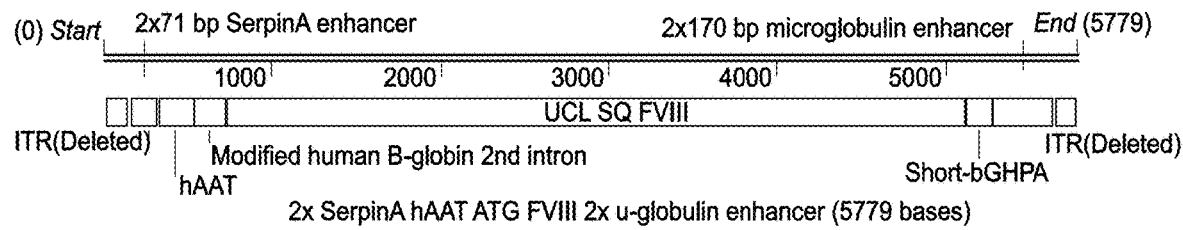
FIG. 4L provides a schematic of Construct 2× SerpinA hAAT ATG FVIII 2× µ-globulin enhancer.
Figure 4M:
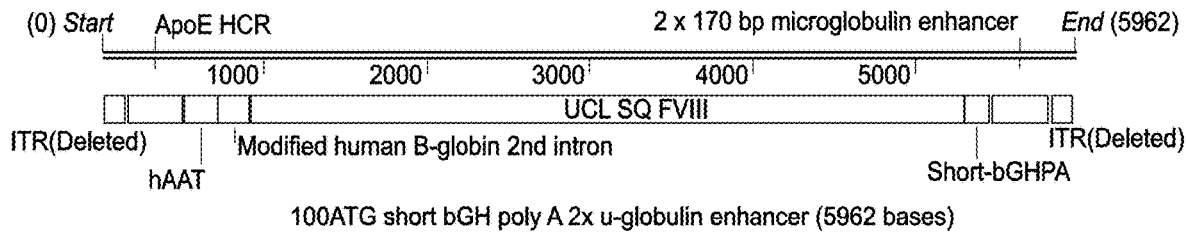
FIG. 4M provides a schematic of Construct 100ATG short bGH poly A 2× µ-globulin enhancer.
Figure 4N:
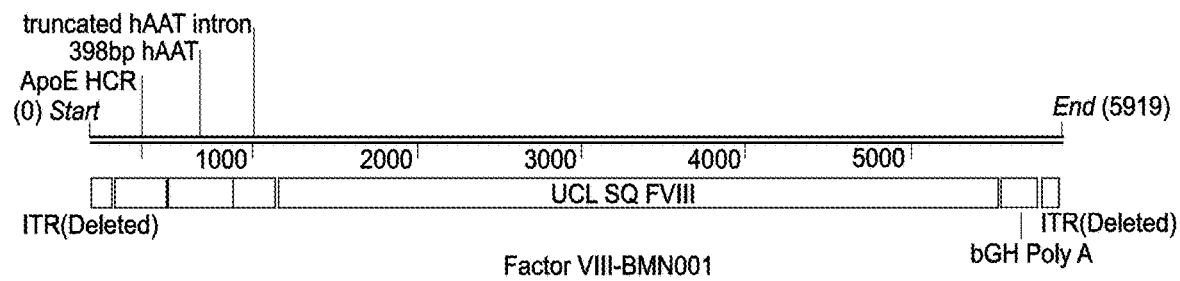
FIG. 4N provides a schematic of Construct Factor VIII-BMN001.
Figure 4O:
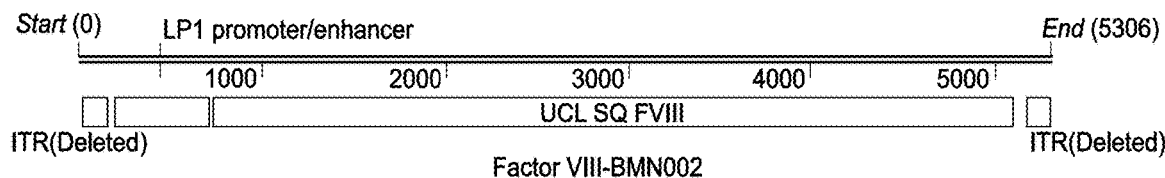
FIG. 4O provides a schematic of Construct FVIII-BMN002.
Figure 4P:
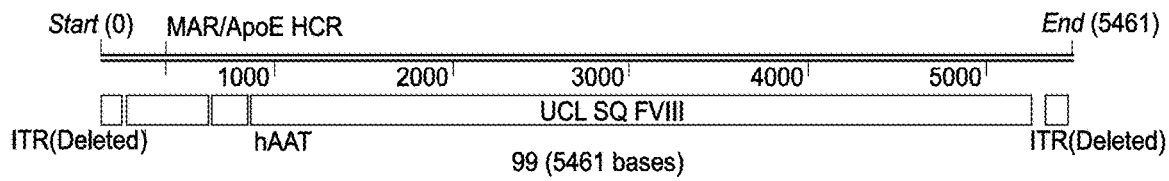
FIG. 4P provides a schematic of Construct 99.
Figure 4Q:
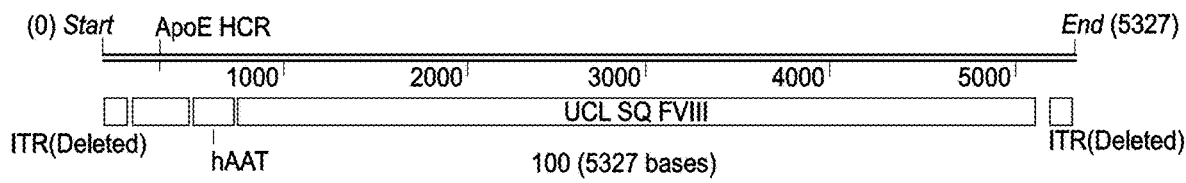
FIG. 4Q provides a schematic of Construct 100.
Figure 4R:
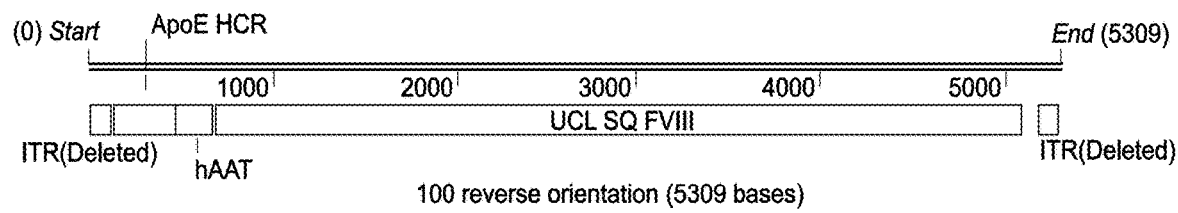
FIG. 4R provides a schematic of Construct 100 reverse orientation.
Figure 4S:
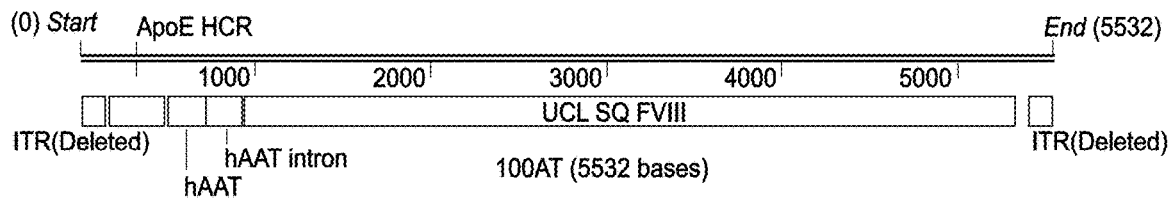
FIG. 4S provides a schematic of Construct 100AT.
Figure 4T:
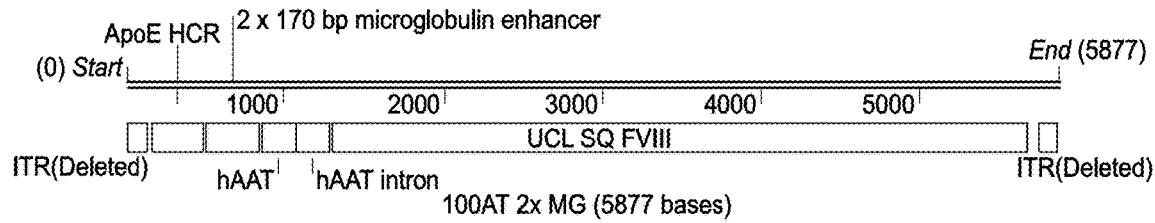
FIG. 4T provides a schematic of Construct 100AT 2× MG.
Figure 4U:
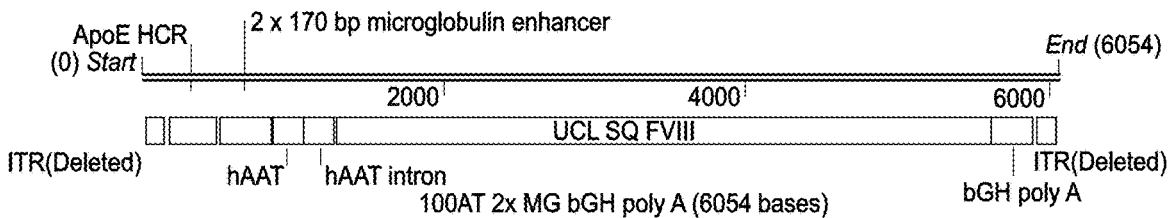
FIG. 4U provides a schematic of Construct 100AT 2× MG bGH polyA.
Figure 4V:
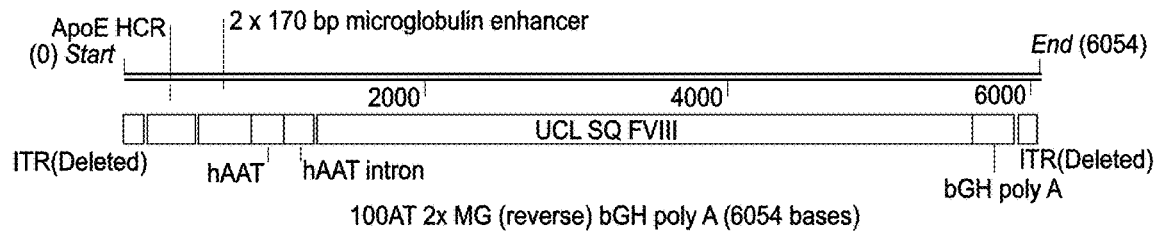
FIG. 4V provides a schematic of Construct 100AT 2× MG (reverse) bGH poly A.
Figure 4W:
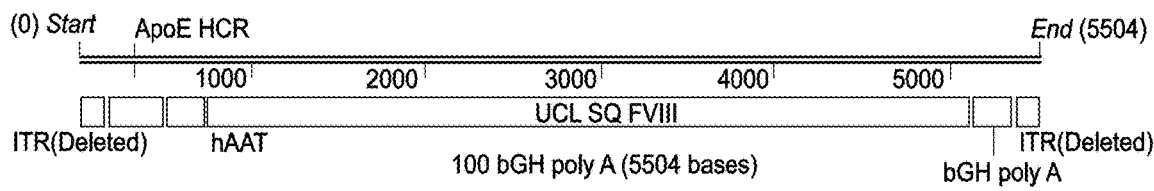
FIG. 4W provides a schematic of Construct 100 bGH poly A.
Figure 4X:
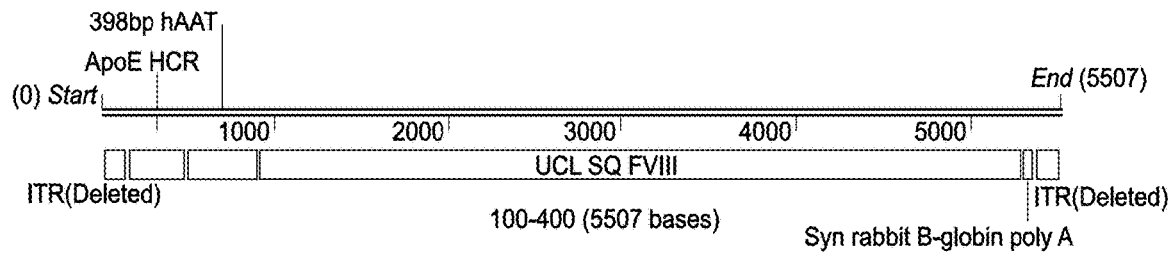
FIG. 4X provides a schematic of Construct 100-400.
Figure 4Y:
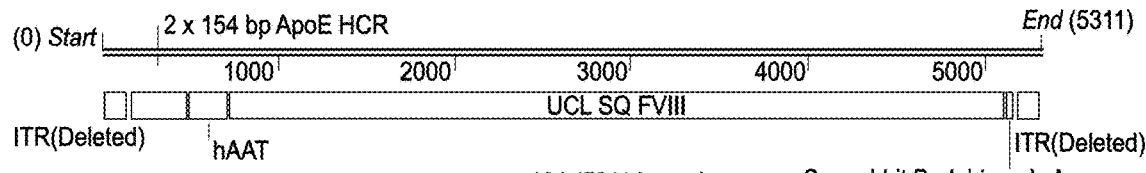
FIG. 4Y provides a schematic of Construct 101.
Figure 4Z:
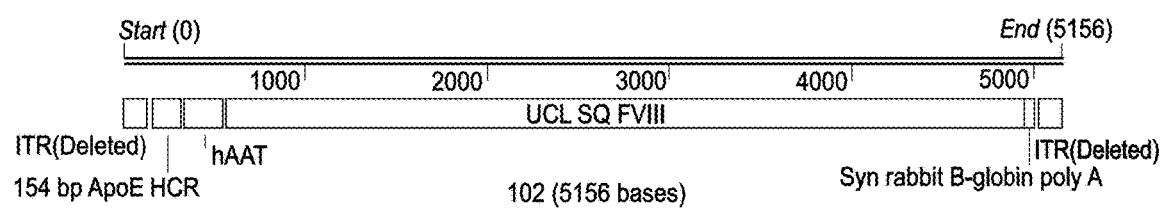
FIG. 4Z provides a schematic of Construct 102.
Figure 4A:
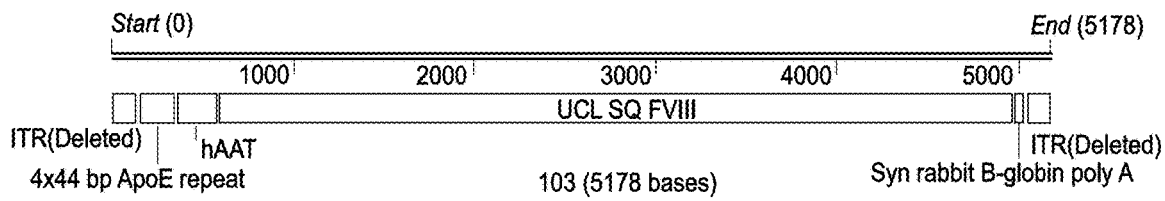
Figure 4B:
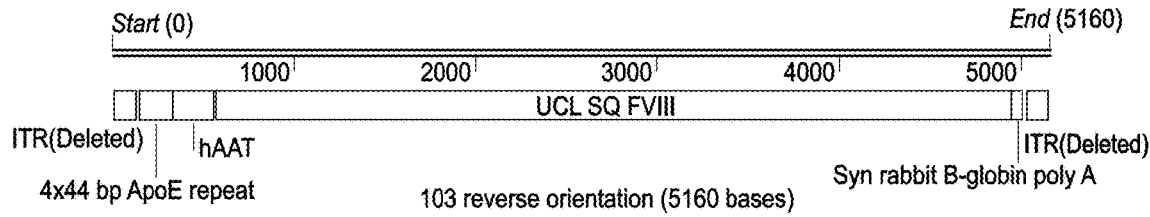
Figure 4C:
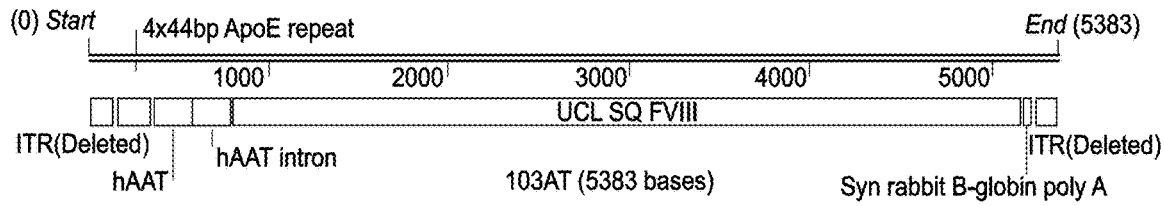
Figure 4D:
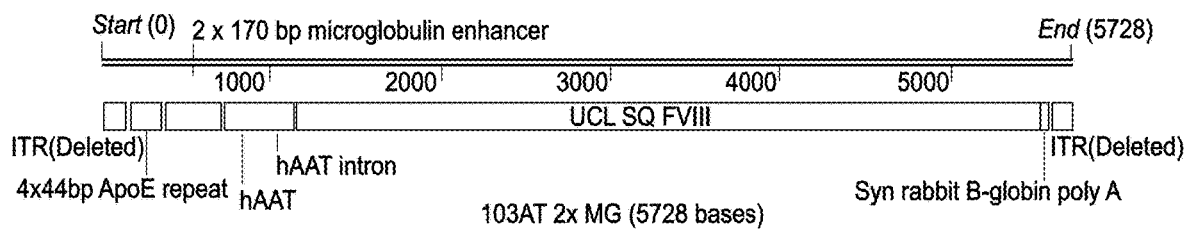
Figure 4E:
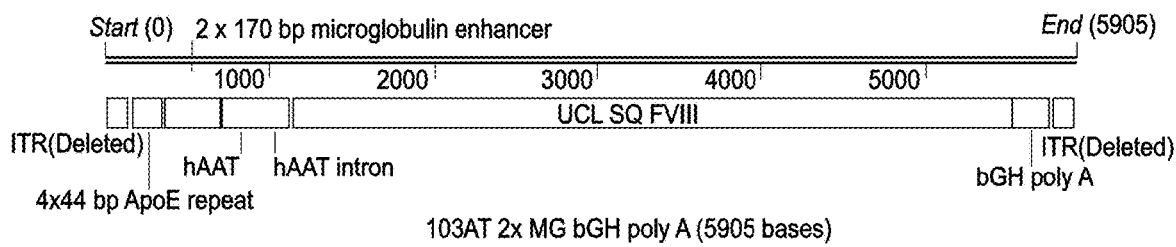
Figure 4F:
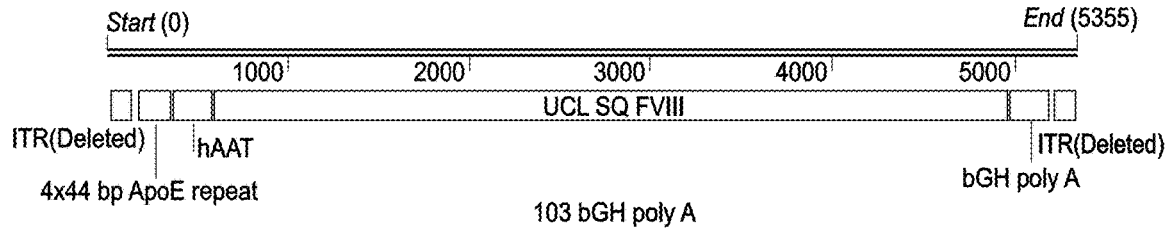
Figure 4G:
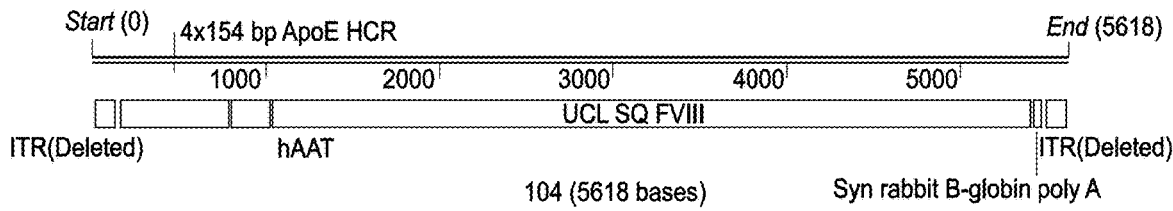
Figure 4H:
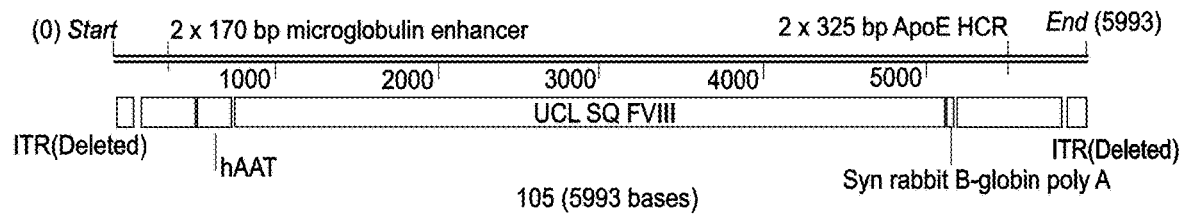
Figure 4I:
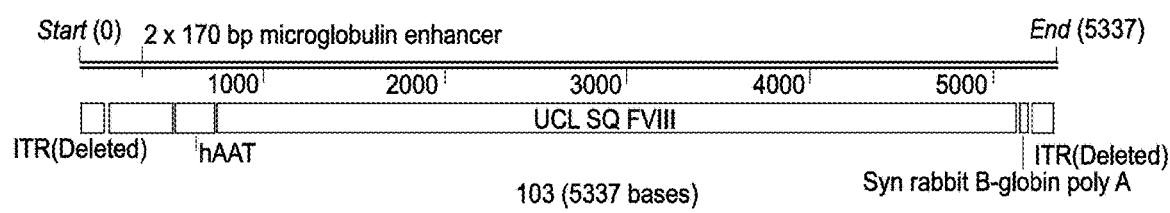
Figure 4J:
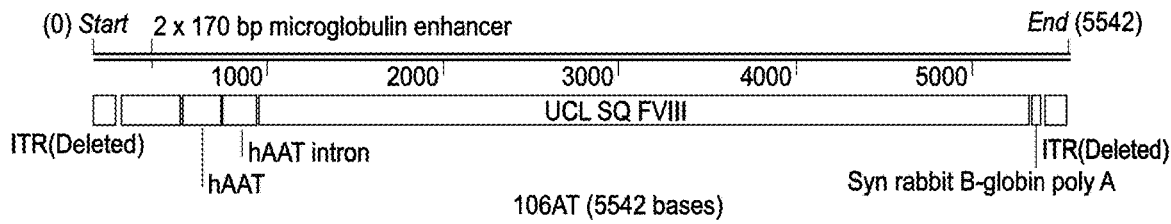
Figure 4K:
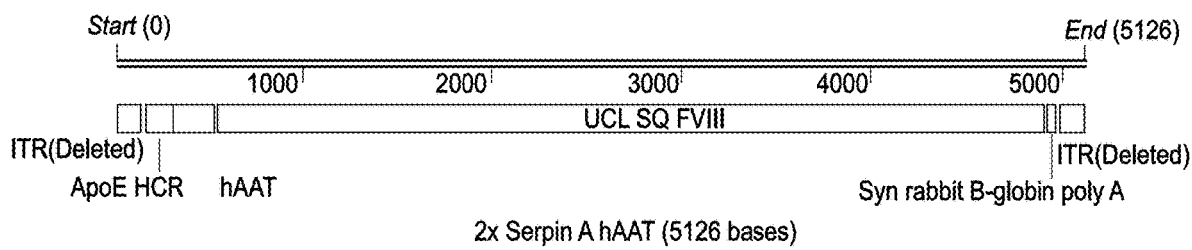

The resultant Proto 7 vector, which is 4934 bases in length and has the intronic ApoE/C1 enhancer in the reverse orientation, is shown in schematic form in FIG. 3D, and the sequence is set forth in SEQ ID NO: 8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays.

A preliminary in vitro assay is performed to compare the FVIII expression and activity from the AAV FVIII vectors of the present invention with that from the UCL SQ vector. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the UCL SQ vector, demonstrating that the Proto 1, Proto 1S and Proto 2S vectors were capable of expressing functional Factor VIII protein.

Production of AAV Virions in 293 Cells and Baculovirus-Infected Insect Cells.

To demonstrate that the AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses Adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5'ITR (sense strand) or 3'ITR (anti-sense strand).

Alternatively, a PCR assay is used to determine whether the AAV FVIII vectors nucleic acids have complete ends, i.e., terminate at the 5' end of the hairpin loop in the AAV2 5'ITR (sense strand) or 3'ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, given intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional AAV vectors with strong promoters that increase expression of functional FVIII, constructs were generated with modified enhancer and/or promoter sequences. In some embodiments, the constructs comprised shortened versions of the ApoE or the μ-globulin enhancers. These constructs were generated using standard DNA cloning techniques and the sequences thereof are shown in SEQ IS NOS: 9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described in Example 1. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1 \times 10^6$ cells/well in a 6-well plate (or $6 \times 10^6$ cells in a 10-cm plate or $1.7 \times 10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30-45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of Baculovirus (P1)

Sf9 cells were grown to approximately $4 \times 10^6$ cells/mL and diluted to approximately $2 \times 10^6$ cells/mL with fresh medium in shaking flasks. An amount of the Sf9 cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV Using P1 Recombinant Baculoviruses

Sf9 cells were grown to about $1 \times 10^7$ cells/mL and diluted to about $5 \times 10^6$ cells/mL. An amount of the diluted Sf9 cells were infected with Bac-vector (5 Moi) and Bac-helper (15 Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5 M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV genomes which comprise a codon optimized SQ FVIII-encoding gene sequence were generated using baculovirus and 293 cells using the UCL SQ, Proto 1, Proto 51, Proto S2 and Proto S3 constructs. The packaging limits are 4800bp for baculovirus and 4950 for 293 cells.

Figure 5:
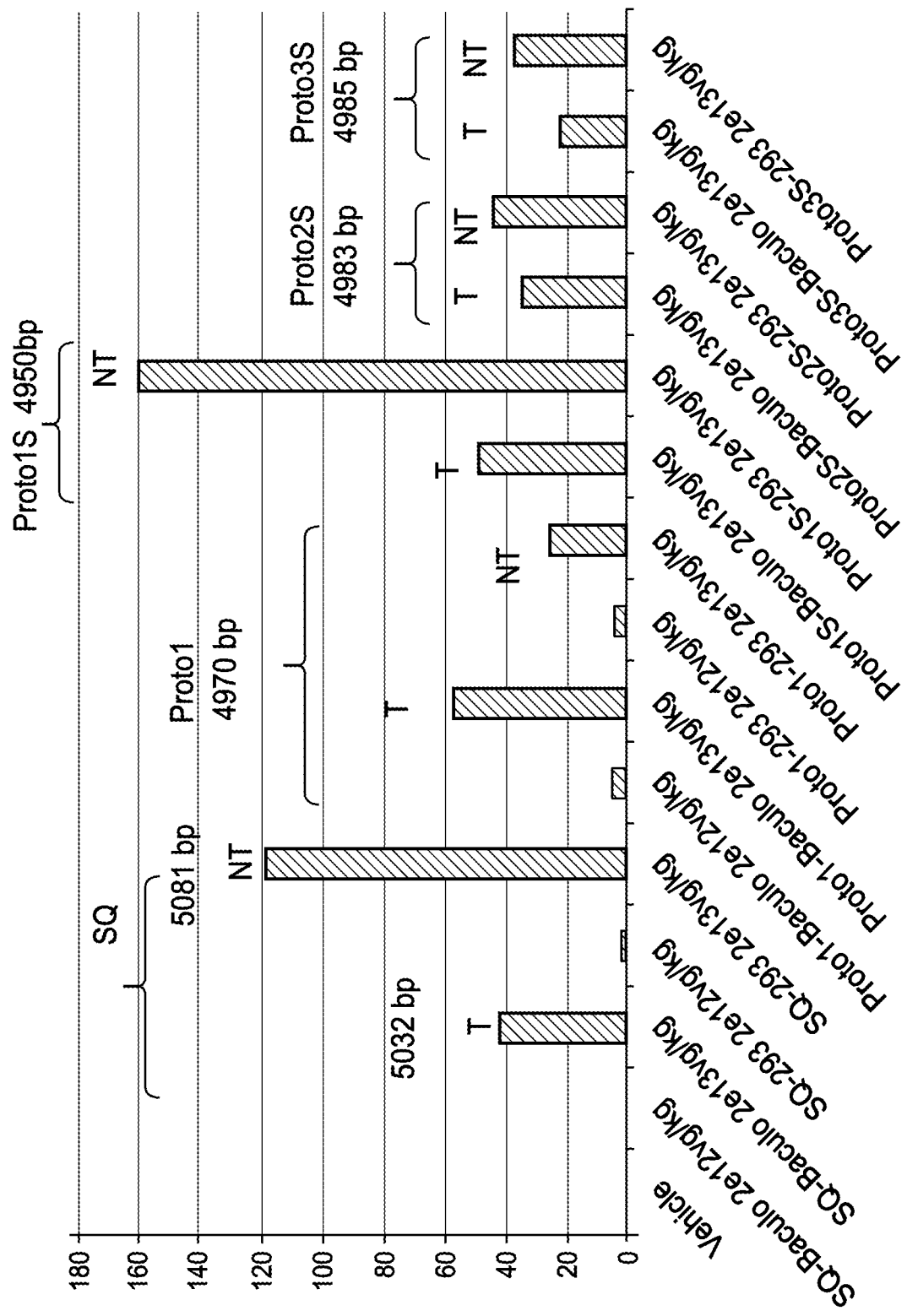
FIG. 5 provides the results of the evaluation of the Proto Constructs in Rag2 mice, and demonstrates Proto 1 transduces FVIII similarly to wild type.
Figure 6:
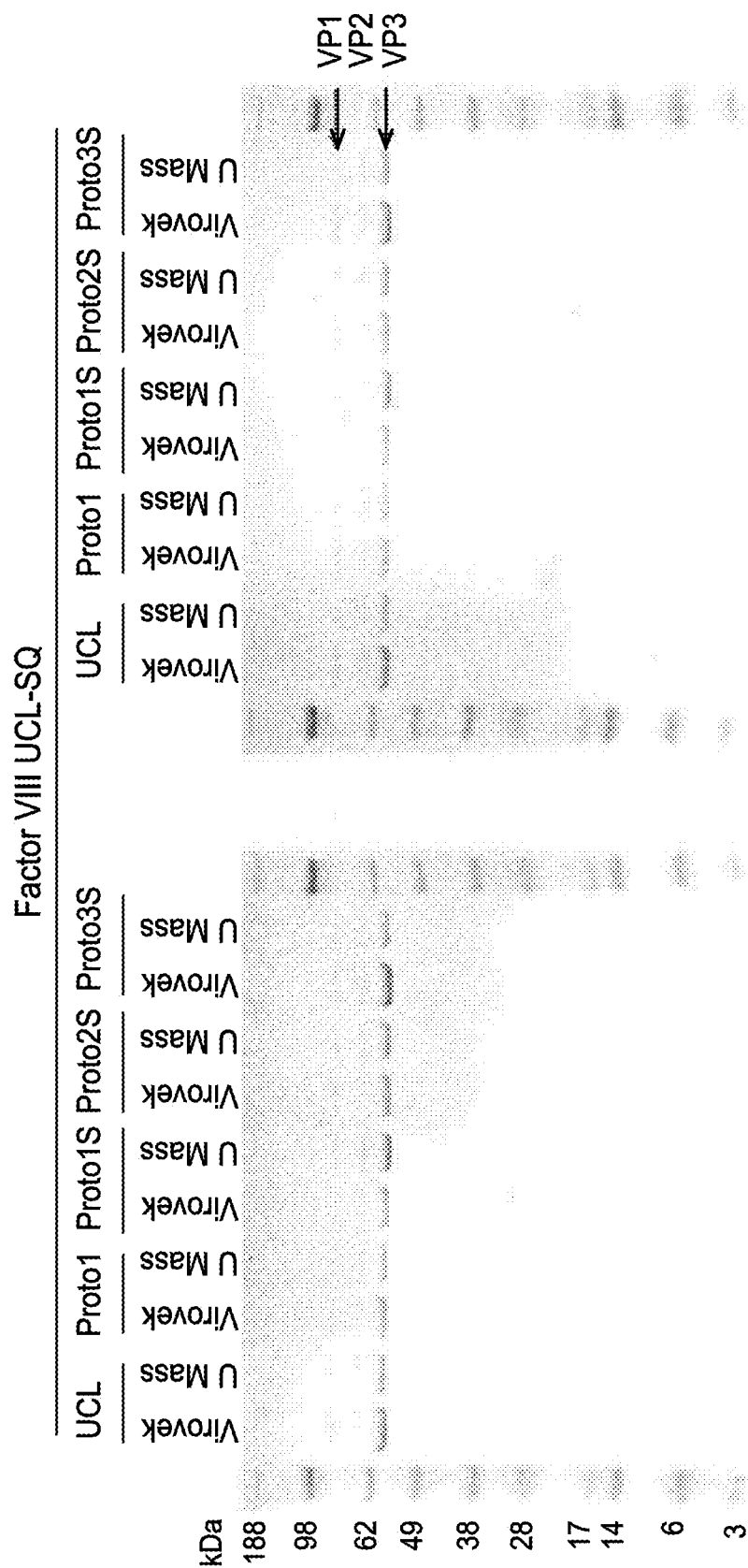
FIGS. 6 and 7 demonstrate that Proto 1, Proto 1S, Proto 2S and Proto 3S express the VP1, VP2 and VP3 protein (FIG. 5) and the VP1, VP2 and VP3 DNA (FIG. 6).
Figure 7:
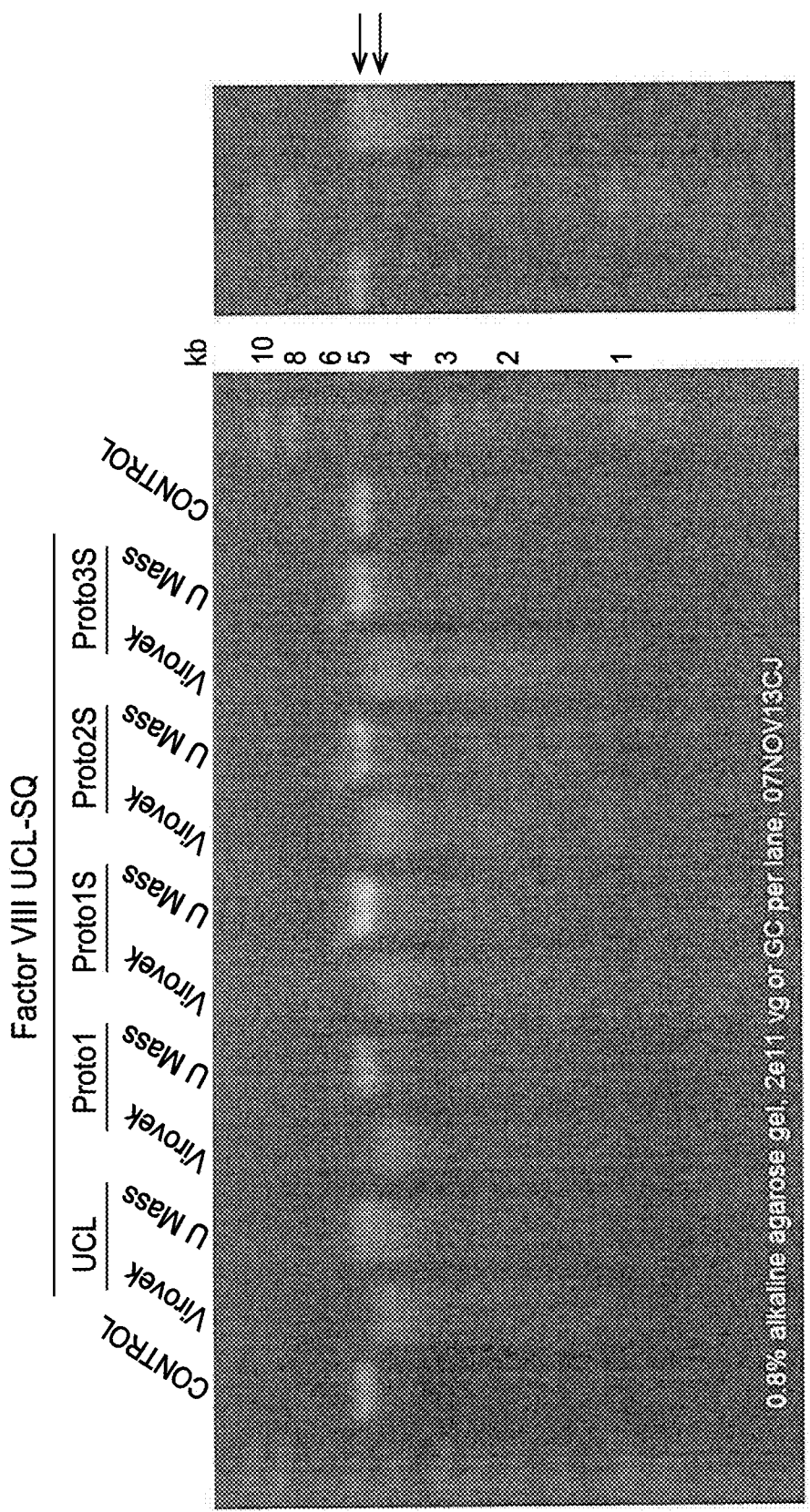

As shown in FIG. 5, Proto 1 with truncated or non-truncated genomes transduce FVIII similar to the UCL SQ construct. The AAV5.2 produced from baculovirus and 293T cell lysates as measured on a on 4-12% Bis-Tris Gel. Each samples expressed VP1, VP2 and VP3 protein, as shown in the FIG. 6. The genomic DNA from the AAV samples was run on 0.8% alkaline agarose gels, as shown in FIG. 7.

Transduction of Proto 1 was similar to the UCL SQ construct when these AAV were made by the baculovirus system. The inclusion of the intron containing Proto2S and 3S did not transduce better than Proto 1. The UCL SQ vector containing the AAV flanking sequences made in 293 cells were more potent than the UCL SQ lacking the AAV sequence made in baculovirus. As a result, additional enhancers were added to Proto 1, e.g. Construct 101, 102, 102 and 104, in an attempt to increase potency.

Example 6

Expression and Activity of AAV FVIII Vectors with Improved Promoters/Enhancer Sequences The expression and activity of AAV vectors comprising Constructs 99 to Construct 106 were tested using the hydrodynamic injection protocol. Hydrodynamic delivery is a rapid method to screen liver promoters in vivo. AAV plasmid DNA was generated using the method described in Example 5 and then diluted in TransIT-QR Hydrodynamic Delivery Solution. The plasmid DNA was injected into the tail vein of 5-6 week old C57Bl/6 mice (18-25 g) at a volume determined by (mouse weight (g)/10)=0.1 ml delivery solution). The injection time was less than 5 seconds. Plasma from each mouse was collected 48 hours after injection and the amount of FVIII antigen expressed was measured using an ELISA assay.

Increasing doses of Proto 1 plasmid (2.5, 5, 12.5 and 50 µg) were injected into the tail vein of mice. The amount of FVIII in the plasma of the injected mouse was measured using an ELISA test and recombinant FVIII (Xyntha SQ equivalents) was used as a standard for comparison.

Figure 8:
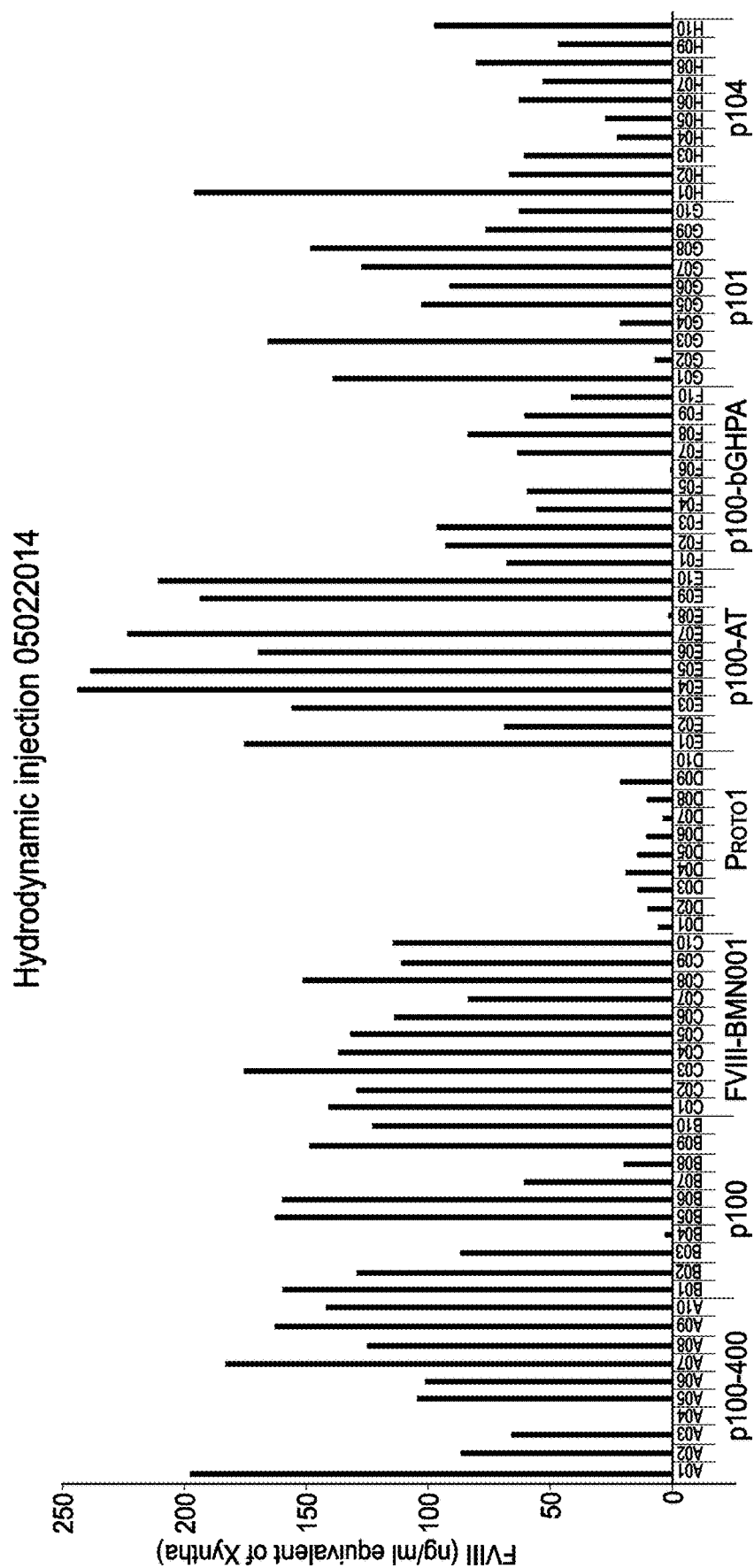
FIGS. 8-10 demonstrate that improved promoter constructs have increased expression of FVIII.

To investigate expression the improved promoter/enhancer elements of construct p100-400, Construct 100 (p100), Construct FVIII-BMN001 (pFVIII-BMN001), Proto1, Construct 100AT (p100-AT), Construct 100 bGH poly A (p100-bGHPA), Construct 101 (p101) and Construct 104 (p104). As shown in FIG. 8, all constructs produced functional FVIII at varying levels of efficiency.

Figure 9:
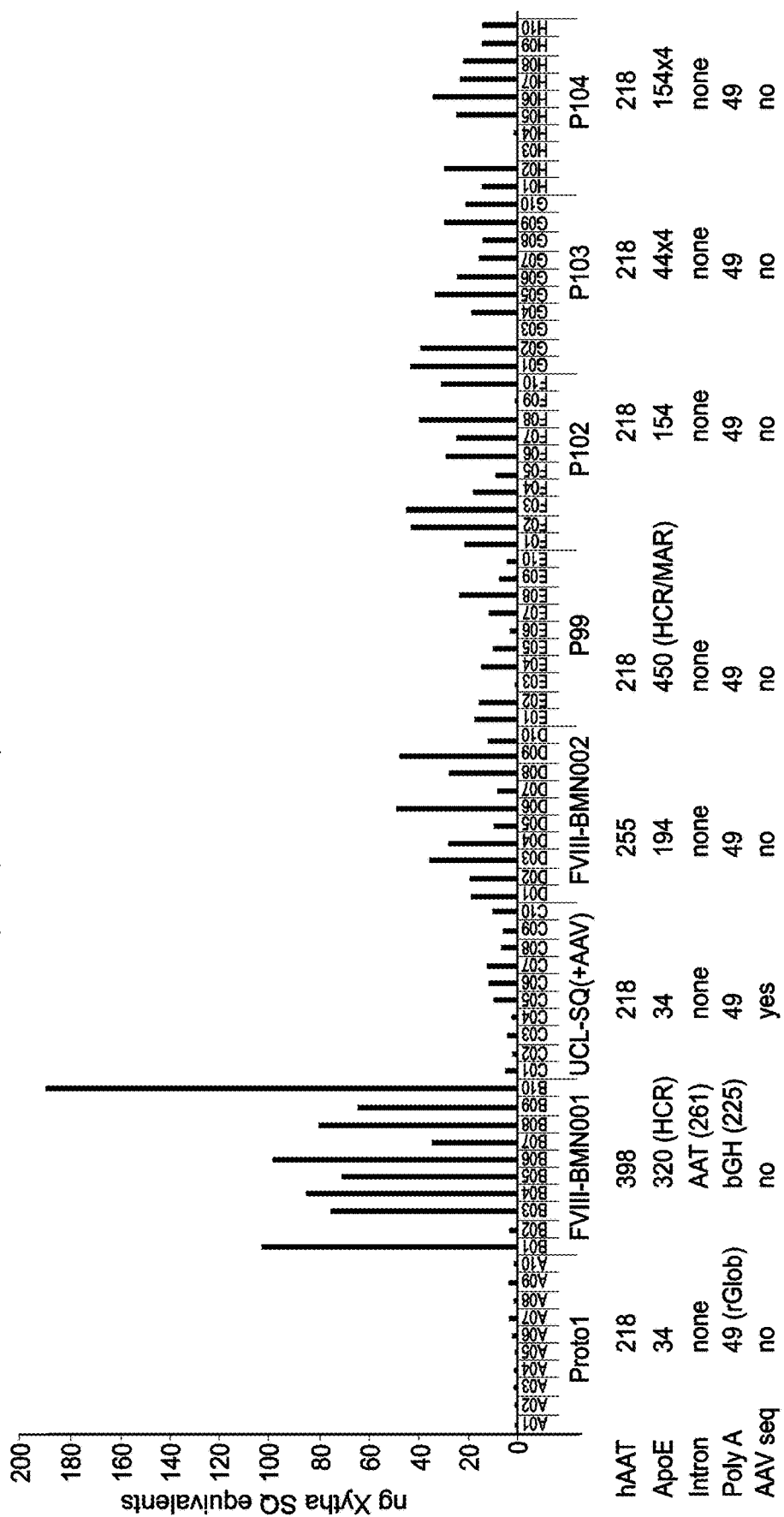
Figure 10:
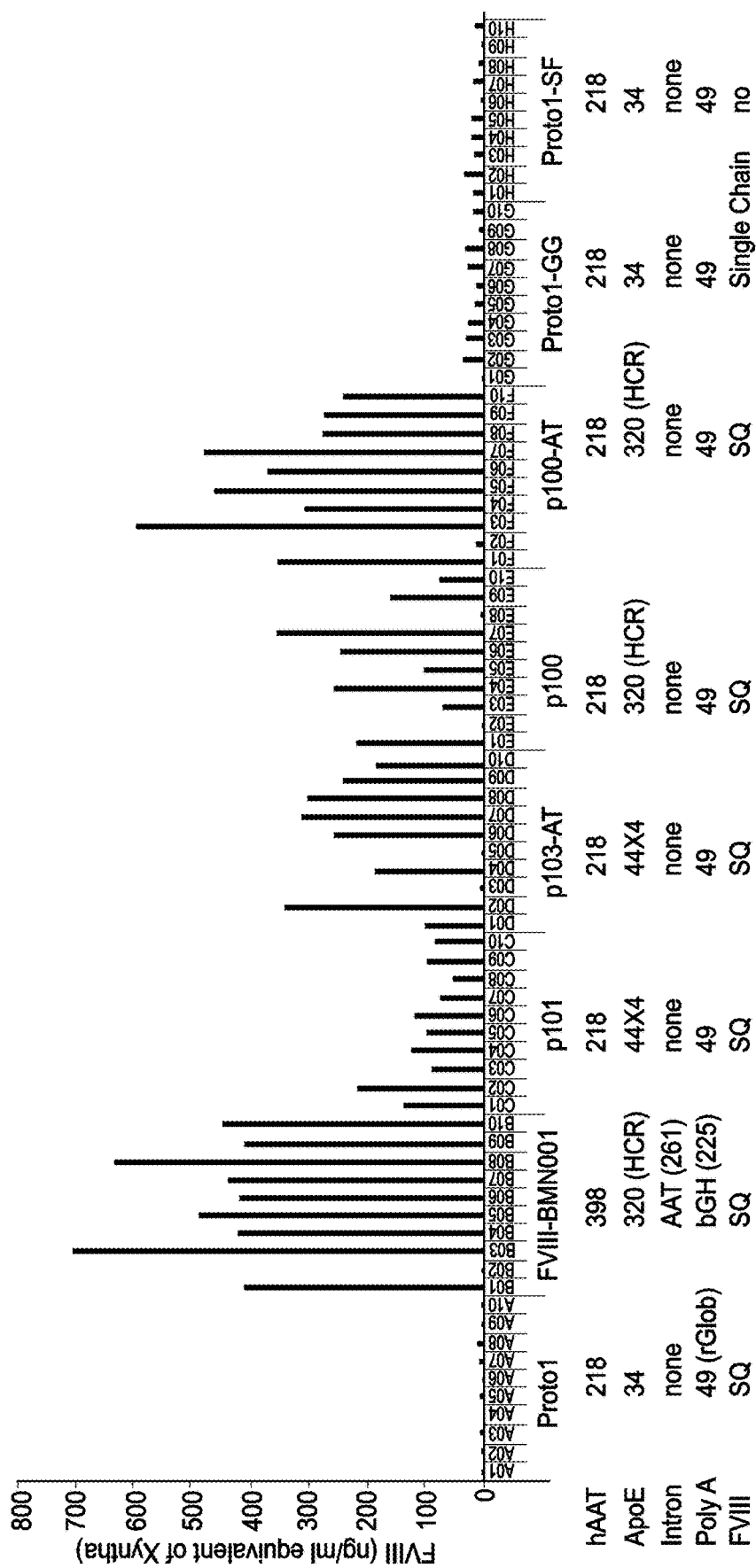

FIGS. 9 and 10 provide data for injection of 1 µg of plasmid of various constructs. As shown in FIG. 8, injection of Construct FVIII-BMN001, Constuct FVIII-BMN002, Construct 102 (p102), Construct 103 (p103) and Construct 104 (p104) resulted in expression of at least 20 ng of FVIII in 5 out of 10 mice. As shown in FIG. 9, injection of Construct FVIII-BMN001, Construct 103 (p103), Construct 103-AT (p103-AT; 398 bp hAAT promoter), Construct 100 (p100), Construct 100AT (p100-AT; 398 bp hAAT promoter) resulted in expression of at least 100 ng/ml of FVIII in 5 out of 10 mice.

What is claimed:

1. An adeno-associated virus (AAV) Factor VIII (FVIII) vector comprising a nucleic acid comprising an inverted terminal repeat (ITR), a liver-specific transcription regulatory region, and a functionally active FVIII coding region, wherein the functionally active FVIII coding region comprises nucleotides 923-5296 of SEQ ID NO: 9.

2. A method of producing a recombinant adeno-associated virus (AAV) particle comprising
   A) culturing a cell that has been transfected with a AAV vector of claim 1; and
   B) recovering recombinant AAV particle from the supernatant of the transfected cell.

3. A viral particle comprising the viral vector of claim 1.

4. An isolated cell comprising the viral vector of claim 1.

5. A method of treating a patient suffering from hemophilia A comprising intravenously administering to the patient an effective amount of an AAV FVIII vector of claim 1.

* * * * *

SEQUENCE LISTING

<160> NUMBER OF SEQ ID NOS: 45

<210> SEQ ID NO 1
<211> LENGTH: 4970
<212> TYPE: DNA
<213> ORGANISM: Adeno-Associated Virus

<400> SEQUENCE: 1

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240
gcccctgttt gctcctccga taactggggt gaccttggtt aatattcacc agcagcctcc     300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgaggttc tgcttctctg ccaccaggag atactacctg     480
ggggctgtgg agctgagctg ggactacatg cagtctgacc tggggagct gcctgtggat     540 gccaggttcc cccccagagt gcccaagagc ttccccttca cacctctgt ggtgtacaag     600 aagaccctgt ttgtggagtt cactgaccac ctgttcaaca ttgccaagcc caggcccccc     660
tggatgggcc tgctgggccc caccatccag ctgaggtgt atgacactgt ggtgatcacc     720
ctgaagaaca tggccagcca ccctgtgagc ctgcatgctg tgggggtgag ctactggaag     780
gcctctgagg gggctgagta tgatgaccag accagccaga gggagaagga ggatgacaag     840
gtgttccctg ggggcagcca cacctatgtg tggcaggtgc tgaaggagaa tggccccatg     900
gcctctgacc ccctgtgcct gacctacagc tacctgagcc atgtggacct ggtgaaggac     960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga gtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggat aagaacaatg aggaggctga ggactatgat    1500
gatgacctga ctgactctga gatggatgtg gtgaggtttg atgatgacaa cagccccagc    1560
ttcatccaga tcaggtctgt ggccaagaag cacccccaaga cctgggtgca ctacattgct    1620
gctgaggagg aggactggga ctatgccccc ctggtgctgg cccctgatga caggagctac    1680
aagagccagt acctgaacaa tggcccccag aggattggca ggaagtacaa gaaggtcagg    1740
ttcatggcct acactgatga accttcaag accaggggagg ccatccagca tgagtctggc    1800
atcctgggcc cctgctgta tgggaggtg ggggacaccc tgctgatcat cttcaagaac    1860
caggccagca ggccctacaa catctacccc catggcatca ctgatgtgag gcccctgtac    1920
agcaggaggc tgcccaaggg ggtgaagcac ctgaaggact cccccatcct gcctgggag    1980 atcttcaagt acaagtggac tgtgactgtg gaggatggcc ccaccaagtc tgaccccagg    2040
tgcctgacca gatactacag cagctttgtg aacatggaga gggacctggc ctctggcctg    2100
```

```
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
actgagaaca tccagaggtt cctgcccaac cctgctgggg tgcagctgga ggaccctgag    2280
ttccaggcca gcaacatcat gcacagcatc aatggctatg tgtttgacag cctgcagctg    2340
tctgtgtgcc tgcatgaggt ggcctactgg tacatcctga gcattggggc ccagactgac    2400
ttcctgtctg tgttcttctc tggctacacc ttcaagcaca agatggtgta tgaggacacc    2460
ctgaccctgt tccccttctc tggggagact gtgttcatga gcatggagaa ccctggcctg    2520
tggattctgg gctgccacaa ctctgacttc aggaacaggg gcatgactgc cctgctgaaa    2580
gtctccagct gtgacaagaa cactggggac tactatgagg acagctatga ggacatctct    2640
gcctacctgc tgagcaagaa caatgccatt gagcccagga gcttcagcca gaacccccca    2700
gtgctgaaga ggcaccagag ggagatcacc aggaccaccc tgcagtctga ccaggaggag    2760
attgactatg atgacaccat ctctgtggag atgaagaagg aggactttga catctacgac    2820
gaggacgaga accagagccc caggagcttc agaagaagac caggcactac cttcattgct    2880
gctgtggaga ggctgtggga ctatggcatg agcagcagcc cccatgtgct gaggaacagg    2940
gcccagtctg gctctgtgcc ccagttcaag aaggtggtgt tccaggagtt cactgatggc    3000
agcttcaccc agccctgta cagagggag ctgaatgagc acctgggcct gctgggcccc    3060
tacatcaggg ctgaggtgga ggacaacatc atggtgacct caggaaccag gccagcagg    3120 ccctacagct tctacagcag cctgatcagc tatgaggagg accagaggca ggggctgag    3180 cccaggaaga actttgtgaa gcccaatgaa accaagacct acttctggaa ggtgcagcac    3240
cacatggccc ccaccaagga tgagtttgac tgcaaggcct gggcctactt ctctgatgtg    3300
gacctggaga aggatgtgca ctctggcctg attggccccc tgctggtgtg ccacaccaac    3360
accctgaacc ctgcccatgg caggcaggtg actgtgcagg agtttgccct gttcttcacc    3420
atctttgatg aaaccaagag ctggtacttc actgagaaca tggagaggaa ctgcagggcc    3480
ccctgcaaca tccagatgga ggaccccacc ttcaaggaga actacaggtt ccatgccatc    3540
aatggctaca tcatggacac cctgcctggc ctggtgatgg cccaggacca ggatcagg    3600 tggtacctgc tgagcatggg cagcaatgag aacatccaca gcatccactt ctctggccat    3660
gtgttcactg tgaggaagaa ggaggagtac aagatggccc tgtacaacct gtaccctggg    3720
gtgtttgaga ctgtggagat gctgcccagc aaggctggca tctgggggt ggagtgcctg    3780 attggggagc acctgcatgc tggcatgagc accctgttcc tggtgtacag caacaagtgc    3840 cagaccccc tgggcatggc ctctggccac atcagggact tccagatcac tgcctctggc    3900
cagtatggcc agtgggcccc caagctggcc aggctgcact actctggcag catcaatgcc    3960
tggagcacca aggagccctt cagctggatc aaggtggacc tgctggcccc catgatcatc    4020
catggcatca gaccagggg ggccaggcag aagttcagca gcctgtacat cagccagttc    4080
atcatcatgt acagcctgga tggcaagaag tggcagacct acaggggcaa cagcactggc    4140
accctgatgg tgttctttgg caatgtggac agctctggca tcaagcacaa catcttcaac    4200
ccccccatca ttgccagata catcaggctg cacccccacc ctacagcat caggagcacc    4260 ctgaggatgg agctgatggg ctgtgacctg aacagctgca gcatgcccct gggcatggag    4320
agcaaggcca tctctgatgc ccagatcact gccagcagct acttcaccaa catgtttgcc    4380
acctggagcc ccagcaaggc caggctgcac ctgcagggca ggagcaatgc ctggaggccc    4440
```

```
caggtcaaca accccaagga gtggctgcag gtggacttcc agaagaccat gaaggtgact      4500
ggggtgacca cccaggggt gaagagcctg ctgaccagca tgtatgtgaa ggagttcctg       4560
atcagcagca gccaggatgg ccaccagtgg accctgttct tccagaatgg caaggtgaag      4620
gtgttccagg gcaaccagga cagcttcacc cctgtggtga acagcctgga cccccccctg     4680
ctgaccagat acctgaggat tcaccccag agctgggtgc accagattgc cctgaggatg      4740
gaggtgctgg gctgtgaggc ccaggacctg tactgaaata aagatctttt attttcatta    4800
gatctgtgtg ttggttttt gtgtgaggaa cccctagtga tggagttggc cactccctct      4860
ctgcgcgctc gctcgctcac tgaggccggg cgaccaaagg tcgcccgacg cccgggcttt     4920
gcccgggcgg cctcagtgag cgagcgagcg cgcagagagg gagtggccaa                  4970
```

<210> SEQ ID NO 2
<211> LENGTH: 4950
<212> TYPE: DNA
<213> ORGANISM: Adeno-Associated Virus

<400> SEQUENCE: 2

```
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg     120
gccaactcca tcactgtttg ctgcttgcaa tgtttgccca ttttagggtg gacacaggac     180
gctgtggttt ctgagccagg gggcgactca gatcccagcc agtggactta gcccctgttt    240
gctcctccga taactggggt gaccttggtt aatattcacc agcagcctcc ccgttgccc     300 ctctggatcc actgcttaaa tacgacgag acagggccc tgtctcctca gcttcaggca      360
ccaccactga cctgggacag tgaatcgcca ccatgcagat tgagctgagc acctgcttct    420
tcctgtgcct gctgaggttc tgcttctctg ccaccaggag atactacctg ggggctgtgg   480
agctgagctg ggactacatg cagtctgacc tgggggagct gcctgtggat gccaggttcc    540 ccccagagt gcccaagagc ttccccttca cacctctgt ggtgtacaag aagaccctgt    600 tgtggagtt cactgaccac ctgttcaaca ttgccaagcc caggcccccc tggatgggcc     660
tgctgggccc caccatccag gctgaggtgt atgacactgt ggtgatcacc ctgaagaaca    720
tggccagcca ccctgtgagc ctgcatgctg tgggggtgag ctactggaag gcctctgagg   780
gggctgagta tgatgaccag accagccaga gggagaagga ggatgacaag gtgttccctg    840
ggggcagcca cacctatgtg tggcaggtgc tgaaggagaa tggccccatg gcctctgacc    900
ccctgtgcct gacctacagc tacctgagcc atgtggacct ggtgaaggac ctgaactctg     960
gcctgattgg ggccctgctg gtgtgcaggg agggcagcct ggccaaggag aagacccaga   1020
ccctgcacaa gttcatcctg ctgtttgctg tgtttgatga gggcaagagc tggcactctg    1080
aaaccaagaa cagcctgatg caggacaggg atgctgcctc tgccagggcc tggcccaaga    1140
tgcacactgt gaatggctat gtgaacagga gcctgcctgg cctgattggc tgccacagga    1200
agtctgtgta ctggcatgtg attggcatgg gcaccacccc tgaggtgcac agcatcttcc    1260
tggagggcca caccttcctg gtcaggaacc acaggcaggc cagcctggag atcagcccca    1320
tcaccttcct gactgcccag acctgctgga tggacctggg ccagttcctg ctgttctgcc    1380
acatcagcag ccaccagcat gatggcatgg aggcctatgt gaaggtggac agctgccctg    1440 aggagccca gctgaggatg aagaacaatg aggaggctga ggactatgat gatgacctga    1500
ctgactctga gatggatgtg gtgaggtttg atgatgacaa cagccccagc ttcatccaga    1560
tcaggtctgt ggccaagaag caccccaaga cctgggtgca ctacattgct gctgaggagg    1620
```

```
aggactggga ctatgccccc ctggtgctgg cccctgatga caggagctac aagagccagt    1680
acctgaacaa tggcccccag aggattggca ggaagtacaa gaaggtcagg ttcatggcct    1740
acactgatga aaccttcaag accagggagg ccatccagca tgagtctggc atcctgggcc    1800
ccctgctgta tggggaggtg ggggacaccc tgctgatcat cttcaagaac caggccagca    1860
ggccctacaa catctacccc catggcatca ctgatgtgag cccctgtac agcaggaggc     1920 tgcccaaggg ggtgaagcac ctgaaggact tccccatcct gcctggggag atcttcaagt    1980
acaagtggac tgtgactgtg gaggatggcc ccaccaagtc tgaccccagg tgcctgacca    2040
gatactacag cagctttgtg aacatggaga gggacctggc ctctggcctg attggccccc    2100
tgctgatctg ctacaaggag tctgtggacc agaggggcaa ccagatcatg tctgacaaga    2160
ggaatgtgat cctgttctct gtgtttgatg agaacaggag ctggtacctg actgagaaca    2220
tccagaggtt cctgcccaac cctgctgggg tgcagctgga ggaccctgag ttccaggcca    2280
gcaacatcat gcacagcatc aatggctatg tgtttgacag cctgcagctg tctgtgtgcc    2340
tgcatgaggt ggcctactgg tacatcctga gcattgggc ccagactgac ttcctgtctg     2400
tgttcttctc tggctacacc ttcaagcaca agatggtgta tgaggacacc ctgaccctgt    2460
tccccttctc tggggagact gtgttcatga gcatggagaa ccctggcctg tggattctgg    2520
gctgccacaa ctctgacttc aggaacaggg gcatgactgc cctgctgaaa gtctccagct    2580
gtgacaagaa cactggggac tactatgagg acagctatga ggacatctct gcctacctgc    2640
tgagcaagaa caatgccatt gagcccagga gcttcagcca gaaccccca gtgctgaaga    2700 ggcaccagag ggagatcacc aggaccaccc tgcagtctga ccaggaggag attgactatg    2760
atgacaccat ctctgtggag atgaagaagg aggactttga catctacgac gaggacgaga    2820
accagagccc caggagcttc agaagaaga ccaggcacta cttcattgct gctgtggaga     2880
ggctgtggga ctatgcatg agcagcagcc ccatgtgct gaggaacagg gcccagtctg      2940
gctctgtgcc ccagttcaag aaggtggtgt tccaggagtt cactgatggc agcttcaccc    3000 agccctgta cagaggggag ctgaatgagc acctgggcct gctgggcccc tacatcaggg     3060
ctgaggtgga ggacaacatc atggtgacct tcaggaacca ggccagcagg ccctacagct    3120
tctacagcag cctgatcagc tatgaggagg accagaggca gggggctgag cccaggaaga    3180
actttgtgaa gcccaatgaa accaagacct acttctggaa ggtgcagcac cacatggccc    3240
ccaccaagga tgagtttgac tgcaaggcct gggcctactt ctctgatgtg gacctggaga    3300
aggatgtgca ctctggcctg attggccccc tgctggtgtg ccacaccaac accctgaacc    3360
ctgcccatgg caggcaggtg actgtgcagg agtttgccct gttcttcacc atctttgatg    3420
aaaccaagag ctggtacttc actgagaaca tggagaggaa ctgcagggcc cctgcaaca    3480 tccagatgga ggaccccacc ttcaaggaga actacaggtt ccatgccatc aatggctaca    3540
tcatggacac cctgcctggc ctggtgatgg cccaggacca gaggatcagg tggtacctgc    3600
tgagcatggg cagcaatgag aacatccaca gcatccactt ctctggccat gtgttcactg    3660
tgaggaagaa ggaggagtac aagatggccc tgtacaacct gtaccctggg gtgtttgaga    3720
ctgtggagat gctgcccagc aaggctggca tctggaggt ggagtgcctg attggggagc     3780
acctgcatgc tggcatgagc accctgttcc tggtgtacag caacaagtgc cagacccccc    3840
tgggcatggc ctctggccac atcagggact tccagatcac tgcctctggc cagtatggcc    3900
agtgggcccc caagctggcc aggctgcact actctggcag catcaatgcc tggagcacca    3960
```

```
aggagccctt cagctggatc aaggtggacc tgctggcccc catgatcatc catggcatca    4020
agacccaggg ggccaggcag aagttcagca gcctgtacat cagccagttc atcatcatgt    4080
acagcctgga tggcaagaag tggcagacct acaggggcaa cagcactggc accctgatgg    4140
tgttctttgg caatgtggac agctctggca tcaagcacaa catcttcaac cccccatca    4200
ttgccagata tcaggctg cacccacc actacagcat caggagcacc ctgaggatgg    4260
agctgatggg ctgtgacctg aacagctgca gcatgcccct gggcatggag agcaaggcca    4320
tctctgatgc ccagatcact gccagcagct acttcaccaa catgtttgcc acctggagcc    4380
ccagcaaggc caggctgcac ctgcagggca ggagcaatgc ctggaggccc caggtcaaca    4440
accccaagga gtggctgcag gtggacttcc agaagaccat gaaggtgact ggggtgacca    4500
cccagggggt gaagagcctg ctgaccagca tgtatgtgaa ggagttcctg atcagcagca    4560
gccaggatgg ccaccagtgg accctgttct tccagaatgg caaggtgaag gtgttccagg    4620
gcaaccagga cagcttcacc cctgtggtga cagcctgga ccccccctg ctgaccagat    4680
acctgaggat tcacccccag agctgggtgc accagattgc cctgaggatg gaggtgctgg    4740
gctgtgaggc ccaggacctg tactgaaata aagatctttt attttcatta gatctgtgtg    4800
ttggttttt gtgtgagtga tggagttggc cactccctct ctgcgcgctc gctcgctcac    4860
tgaggccggg cgaccaaagg tcgcccgacg cccgggcttt gcccgggcgg cctcagtgag    4920
cgagcgagcg cgcagagagg gagtggccaa                                    4950

<210> SEQ ID NO 3
<211> LENGTH: 4983
<212> TYPE: DNA
<213> ORGANISM: Adeno-Associated Virus

<400> SEQUENCE: 3
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctccccgt tgccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac aacctggctc agaaaccaca gcgtcctgtg    540
tccattctaa ttttcctttt cttcacgcag atttcctcct agagtgccaa atcttttcc    600
attcaacacc tcagtcgtgt acaaaaagac tctgtttgta gaattcacgg atcacctttt    660
caacatcgct aagcccaggc ccccctggat gggcctgctg ggccccacca tccaggctga    720
ggtgtatgac actgtggtga tcaccctgaa gaacatggcc agccacctg tgagcctgca    780
tgctgtgggg gtgagctact ggaaggcctc tgaggggct gagtatgatg accagaccag    840
ccagaggag aaggaggatg acaaggtgtt ccctgggggc agccacacct atgtgtggca    900
ggtgctgaag gagaatggcc ccatggcctc tgacccctg tgcctgacct acagctacct    960
gagccatgtg gacctggtga aggacctgaa ctctggcctg attggggccc tgctggtgtg    1020
cagggagggc agcctggcca aggagaagac ccagaccctc acaagttca tcctgctgtt    1080
tgctgtgttt gatgagggca gagagctggc actctgaaacc aagaacagcc tgatgcagga    1140
```

```
cagggatgct gcctctgcca gggcctggcc caagatgcac actgtgaatg gctatgtgaa    1200
caggagcctg cctggcctga ttggctgcca caggaagtct gtgtactggc atgtgattgg    1260
catgggcacc acccctgagg tgcacagcat cttcctggag ggccacacct tcctggtcag    1320
gaaccacagg caggccagcc tggagatcag ccccatcacc ttcctgactg cccagaccct    1380
gctgatggac ctgggccagt tcctgctgtt ctgccacatc agcagccacc agcatgatgg    1440
catggaggcc tatgtgaagg tggacagctg ccctgaggag ccccagctga ggatgaagaa    1500
caatgaggag gctgaggact atgatgatga cctgactgac tctgagatgg atgtggtgag    1560
gtttgatgat gacaacagcc ccagcttcat ccagatcagg tctgtggcca agaagcaccc    1620
caagacctgg gtgcactaca ttgctgctga ggaggaggac tgggactatg cccccctggt    1680
gctgccccct gatgacagga gctacaagag ccagtacctg aacaatggcc cccagaggat    1740
tggcaggaag tacaagaagg tcaggttcat ggcctacact gatgaaacct tcaagaccag    1800
ggaggccatc cagcatgagt ctggcatcct gggccccctg ctgtatgggg aggtggggga    1860
caccctgctg atcatcttca agaaccaggc cagcaggccc tacaacatct acccccatgg    1920
catcactgat gtgaggcccc tgtacagcag gaggctgccc aaggggggtga agcacctgaa    1980 ggacttcccc atcctgcctg ggagatcttt caagtacaag tggactgtga ctgtggagga    2040
tggccccacc aagtctgacc ccaggtgcct gaccagatac tacagcagct tgtgaacat    2100 ggagagggac ctggcctctg gcctgattgg ccccctgctg atctgctaca aggagtctgt    2160
ggaccagagg ggcaaccaga tcatgtctga caagaggaat gtgatcctgt tctctgtgtt    2220
tgatgagaac aggagctggt acctgactga gaacatccag aggttcctgc ccaaccctgc    2280
tggggtgcag ctggaggacc ctgagttcca ggccagcaac atcatgcaca gcatcaatgg    2340
ctatgtgttt gacagcctgc agctgtctgt gtgcctgcat gaggtggcct actggtacat    2400
cctgagcatt ggggcсccaga ctgacttcct gtctgtgttc ttctctggct acaccttcaa    2460
gcacaagatg gtgtatgagg acaccсctgac cctgttcccc ttctctgggg agactgtgtt    2520
catgagcatg gagaaccctg gcctgtggat tctgggctgc cacaactctg acttcaggaa    2580
caggggcatg actgccсctgc tgaaagtctc cagctgtgac aagaacactg ggactacta    2640 tgaggacagc tatgaggaca tctctgccta cctgctgagc aagaacaatg ccattgagcc    2700
caggagcttc agccagaacc ccccagtgct gaagaggcac cagagggaga tcaccaggac    2760 caccсctgcag tctgaccagg aggagattga ctatgatgac accatctctg tggagatgaa    2820
gaaggaggac tttgacatct acgacgagga cgagaaccag agccccagga gcttccagaa    2880
gaagaccagg cactacttca ttgctgctgt ggagaggctg tgggactatg catgagcag    2940 cagcccccat gtgctgagga cagggccca gtctggctct gtgccсccagt tcaagaaggt    3000 ggtgttccag gagttcactg atggcagctt cacccagccc ctgtacagag gggagctgaa    3060
tgagcacctg gcctgctgg gccсcctacat cagggctgag gtgaggaccacacatcatggt    3120 gaccttcagg aaccaggcca gcaggсссcta cagcttctac agcagcctga tcagctatga    3180
ggaggaccag aggcaggggg ctgagcccag gaagaacttt gtgaagccca atgaaaccaa    3240
gacctacttc tggaaggtgc agcaccacat ggcсccсccacc aaggatgagt ttgactgcaa    3300
ggcctgggcc tacttctctg atgtggacct ggagaaggat gtgcactctg gcctgattgg    3360 ccсccctgctg gtgtgccaca ccaacaccсct gaaccсctgcc catggcaggc aggtgactgt    3420
gcaggagttt gccctgttct tcaccatctt tgatgaaacc aagagctggt acttcactga    3480
```

```
gaacatggag aggaactgca gggcccctg caacatccag atggaggacc ccaccttcaa    3540
ggagaactac aggttccatg ccatcaatgg ctacatcatg acaccctgc ctggcctggt    3600
gatggcccag gaccagagga tcaggtggta cctgctgagc atgggcagca atgagaacat    3660
ccacagcatc cacttctctg ccatgtgtt cactgtgagg aagaaggagg agtacaagat    3720
ggccctgtac aacctgtacc ctggggtgtt tgagactgtg agatgctgc ccagcaaggc    3780
tggcatctgg agggtggagt gcctgattgg ggagcacctg catgctggca tgagcaccct    3840
gttcctggtg tacagcaaca agtgccagac cccctgggc atggcctctg ccacatcag    3900
ggacttccag atcactgcct ctggccagta tggccagtgg gccccaagc tggccaggct    3960
gcactactct ggcagcatca atgcctggag caccaaggag cccttcagct ggatcaaggt    4020
ggacctgctg gcccccatga tcatccatgg catcaagacc caggggggcca ggcagaagtt    4080
cagcagcctg tacatcagcc agttcatcat catgtacagc ctggatggca agaagtggca    4140
gacctacagg ggcaacagca ctggcaccct gatggtgttc tttggcaatg tggacagctc    4200
tggcatcaag cacaacatct tcaaccccc catcattgcc agatacatca ggctgcaccc    4260
cacccactac agcatcagga gcaccctgag gatggagctg atgggctgtg acctgaacag    4320
ctgcagcatg ccctgggca tggagagcaa ggccatctct gatgcccaga tcactgccag    4380
cagctacttc accaacatgt tgccacctg gagcccagc aaggccagc tgcacctgca    4440
gggcaggagc aatgcctgga ggccccaggt caacaacccc aaggagtggc tgcaggtgga    4500
cttccagaag accatgaagg tgactggggt gaccacccag ggggtgaaga gcctgctgac    4560
cagcatgtat gtgaaggagt tcctgatcag cagcagccag gatggccacc agtggaccct    4620
gttcttccag aatggcaagg tgaaggtgtt ccagggcaac aggacagct tcaccctgt    4680
ggtgaacagc ctggaccccc ccctgctgac cagatacctg aggattcacc ccagagctg    4740
ggtgcaccag attgccctga ggatggaggt gctgggctgt gaggcccagg acctgtacta    4800
ataaaagatc tttattttca ttagatctgt gtgttggttt tttgtgtgag tgatggagtt    4860
ggccactccc tctctgcgcg ctcgctcgct cactgaggcc gggcgaccaa aggtcgcccg    4920
acgcccgggc tttgcccggg cggcctcagt gagcgagcga gcgcgcagag agggagtggc    4980
caa                                                                 4983

<210> SEQ ID NO 4
<211> LENGTH: 4984
<212> TYPE: DNA
<213> ORGANISM: Adeno-Associated Virus

<400> SEQUENCE: 4
ttggccactc cctctctgcg cgctcgctcg ctcactgagg ccgccgggc aaagcccggg      60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctcccccgt tgcccctctg    240
gatccactgc ttaaatacgg acgaggacag ggccctgtct cctcagcttc aggcaccacc    300
actgacctgg acagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac accctaaaat gggcaaacat tgcaagcagc    540
aaacattcta attttcctt tcttcacgca gatttcctcc tagagtgcca aatctttc       600
```

```
cattcaacac ctcagtcgtg tacaaaaaga ctctgtttgt agaattcacg gatcacctt     660 tcaacatcgc taagcccagg ccccctgga tgggcctgct gggccccacc atccaggctg     720
aggtgtatga cactgtggtg atcaccctga agaacatggc cagccaccct gtgagcctgc    780
atgctgtggg ggtgagctac tggaaggcct ctgaggggc tgagtatgat gaccagacca     840
gccagaggga aaggaggat gacaaggtgt ccctgggggg cagccacacc tatgtgtggc     900
aggtgctgaa ggagaatggc cccatggcct ctgacccct gtgcctgacc tacagctacc     960
tgagccatgt ggacctggtg aaggacctga actctggcct gattggggcc ctgctggtgt   1020
gcagggaggc cagcctggcc aaggagaaga cccagaccct gcacaagttc atcctgctgt   1080
ttgctgtgtt tgatgagggc aagagctggc actctgaaac caagaacagc ctgatgcagg   1140
acagggatgc tgcctctgcc agggcctggc ccaagatgca cactgtgaat ggctatgtga   1200
acaggagcct gcctggcctg attggctgcc acaggaagtc tgtgtactgg catgtgattg   1260
gcatgggcac caccctgag gtgcacagca tcttcctgga gggccacacc ttcctggtca   1320
ggaaccacag gcaggccagc ctggagatca gccccatcac cttcctgact gcccagaccc   1380
tgctgatgga cctgggccag ttcctgctgt tctgccacat cagcagccac cagcatgatg   1440
gcatggaggc ctatgtgaag gtggacagct gccctgagga gccccagctg aggatgaaga   1500
acaatgagga ggctgaggac tatgatgatg acctgactga ctctgagatg gatgtggtga   1560
ggtttgatga tgacaacagc cccagcttca tccagatcag gtctgtggcc aagaagcacc   1620
ccaagacctg ggtgcactac attgctgctg aggaggagga ctgggactat gccccccctgg  1680 tgctggcccc tgatgacagg agctacaaga gccagtacct gaacaatggc cccagagga   1740 ttggcaggaa gtacaagaag gtcaggttca tggcctacac tgatgaaacc ttcaagacca   1800
gggaggccat ccagcatgag tctggcatcc tgggcccct gctgtatggg gaggtggggg   1860
acaccctgct gatcatcttc aagaaccagg ccagcaggcc ctacaacatc taccccccatg  1920 gcatcactga tgtgaggccc ctgtacagca ggaggctgcc aagggggtg aagcacctga   1980 aggacttccc catcctgcct ggggagatct tcaagtacaa gtggactgtg actgtggagg   2040
atggccccac caagtctgac cccaggtgcc tgaccagata ctacagcagc tttgtgaaca   2100
tggagaggga cctggcctct ggcctgattg gccccctgct gatctgctac aaggagtctg   2160
tggaccagag gggcaaccag atcatgtctg acaagaggaa tgtgatcctg ttctctgtgt   2220
ttgatgagaa caggagctgg tacctgactg agaacatcca gaggttcctg cccaaccctg   2280
ctggggtgca gctggaggac cctgagttcc aggccagcaa catcatgcac agcatcaatg   2340
gctatgtgtt tgacagcctg cagctgtctg tgtgcctgca tgaggtggcc tactggtaca   2400
tcctgagcat tggggcccag actgacttcc tgtctgtgtt cttctctggc tacaccttca   2460
agcacaagat ggtgtatgag gacaccctga ccctgttccc cttctctggg gagactgtgt   2520
tcatgagcat ggagaaccct ggcctgtgga ttctgggctg ccacaactct gacttcagga   2580
acagggccat gactgccctg ctgaaagtct ccagctgtga caagaacact ggggactact   2640
atgaggacag ctatgaggac atctctgcct acctgctgag caagaacaat gccattgagc   2700
ccaggagctt cagccagaac cccccagtgc tgaagaggca ccagaggga atcaccagga   2760 ccacccctgca gtctgaccag gaggagattg actatgatga caccatctct gtggagatga   2820
agaaggagga ctttgacatc tacgacgagg acgagaacca gagcccccagg agcttccaga   2880 agaagaccag gcactacttc attgctgctg tggagaggct gtgggactat ggcatgagca   2940
```

```
gcagccccca tgtgctgagg aacagggccc agtctggctc tgtgcccag ttcaagaagg      3000
tggtgttcca ggagttcact gatggcagct caccagcc cctgtacaga ggggagctga       3060
atgagcacct gggcctgctg gcccctaca tcagggctga ggtggaggac aacatcatgg     3120
tgaccttcag gaaccaggcc agcaggccct acagcttcta cagcagcctg atcagctatg    3180
aggaggacca gaggcagggg gctgagccca ggaagaactt tgtgaagccc aatgaaacca    3240
agacctactt ctggaaggtg cagcaccaca tggcccccac caaggatgag tttgactgca    3300
aggcctgggc ctacttctct gatgtggacc tggagaagga tgtgcactct ggcctgattg    3360
gccccctgct ggtgtgccac accaacaccc tgaaccctgc ccatggcagg caggtgactg    3420
tgcaggagtt tgccctgttc ttcaccatct ttgatgaaac caagagctgg tacttcactg    3480
agaacatgga gaggaactgc agggcccct gcaacatcca gatggaggac cccaccttca     3540
aggagaacta caggttccat gccatcaatg ctacatcat ggacaccctg cctggcctgg    3600
tgatggccca ggaccagagg atcaggtggt acctgctgag catgggcagc aatgagaaca    3660
tccacagcat ccacttctct ggccatgtgt tcactgtgag gaagaaggag gagtacaaga    3720
tggccctgta caacctgtac cctggggtgt tgagactgt ggagatgctg cccagcaagg    3780
ctggcatctg gagggtggag tgcctgattg gggagcacct gcatgctggc atgagcaccc    3840
tgttcctggt gtacagcaac aagtgccaga ccccctggg catggcctct ggccacatca    3900
gggacttcca gatcactgcc tctggccagt atggccagtg ggccccaag ctggccaggc    3960
tgcactactc tggcagcatc aatgcctgga gcaccaagga gcccttcagc tggatcaagg    4020
tggacctgct ggcccccatg atcatccatg gcatcaagac caggggccgc aggcagaagt    4080
tcagcagcct gtacatcagc cagttcatca tcatgtacag cctggatggc aagaagtggc    4140
agacctacag gggcaacagc actggcaccc tgatggtgtt ctttggcaat gtggacagct    4200
ctggcatcaa gcacaacatc ttcaacccc ccatcatgc cagatacatc aggctgcacc    4260
ccaccccacta cagcatcagg agcacctga ggatggagct gatgggctgt gacctgaaca    4320
gctgcagcat gccctgggc atggagagca aggccatctc tgatgccag atcactgcca    4380
gcagctactt caccaacatg tttgccacct ggagccccag caaggccagg ctgcacctgc    4440
agggcaggag caatgcctgg aggccccagg tcaacaaccc caaggagtgg ctgcaggtgg    4500
acttccagaa gaccatgaag gtgactgggg tgacccccca ggggtgaag agcctgctga    4560
ccagcatgta tgtgaaggag ttcctgatca gcagcagcca ggatggccac cagtggaccc    4620
tgttcttcca gaatggcaag gtgaaggtgt tccaggggcaa ccaggacagc ttcacccctg    4680
tggtgaacag cctggacccc cccctgctga ccagatacct gaggattcac cccagagct    4740
gggtgcacca gattgccctg aggatggagg tgctgggctg tgaggcccag gacctgtact    4800
aataaaagat ctttattttc attagatctg tgtgttggtt ttttgtgtga gtgatggagt    4860
tggccactcc ctctctgcgc gctcgctcgc tcactgaggc cgggcgacca aaggtcgccc    4920
gacgcccggg ctttgcccgg gcggcctcag tgagcgagcg agcgcgcaga gagggagtgg    4980
ccaa                                                                 4984
```

<210> SEQ ID NO 5
<211> LENGTH: 4805
<212> TYPE: DNA
<213> ORGANISM: Adeno-Associated Virus

<400> SEQUENCE: 5

```
ttggccactc cctctctgcg cgctcgctcg ctcactgagg ccgcccgggc aaagcccggg       60
```

```
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgaggttc tgcttctctg ccaccaggag atactacctg    480
ggggctgtgg agctgagctg ggactacatg cagtctgacc tggggagct gcctgtggat    540 gccaggttcc cccccagagt gcccaagagc ttccccttca cacctctgt ggtgtacaag    600 aagaccctgt tgtggagtt cactgaccac ctgttcaaca ttgccaagcc caggccccc    660 tggatgggcc tgctgggccc caccatccag gctgaggtgt atgacactgt ggtgatcacc    720
ctgaagaaca tggccagcca ccctgtgagc ctgcatgctg tgggggtgag ctactggaag    780
gcctctgagg gggctgagta tgatgaccag accagccaga gggagaagga ggatgacaag    840
gtgttccctg ggggcagcca cacctatgtg tggcaggtgc tgaaggagaa tggcccccatg    900 gcctctgacc ccctgtgcct gacctacagc tacctgagcc atgtggacct ggtgaaggac    960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga gtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggatg aagaacaatg aggaggctga ggactatgat    1500
gatgacctga ctgactctga gatggatgtg gtgaggtttg atgatgacaa cagccccagc    1560
ttcatccaga tcaggtctgt ggccaagaag caccccaaga cctgggtgca ctacattgct    1620
gctgaggagg aggactggga ctatgccccc ctggtgctgg cccctgatga caggagctac    1680
aagagccagt acctgaacaa tggcccccag aggattggca ggaagtacaa gaaggtcagg    1740
ttcatggcct acactgatga aaccttcaag accaggggagg ccatccagca tgagtctggc    1800
atcctgggcc cctgctgta tggggaggtg ggggacaccc tgctgatcat cttcaagaac    1860
caggccagca ggccctacaa catctacccc catggcatca ctgatgtgag gcccctgtac    1920
agcaggaggc tgcccaaggg ggtgaagcac ctgaaggact tccccatcct gcctggggag    1980
atcttcaagt acaagtggac tgtgactgtg gaggatggcc ccaccaagtc tgaccccagg    2040
tgcctgacca gatactacag cagctttgtg aacatggaga gggacctggc ctctggcctg    2100
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
actgagaaca tccagaggtt cctgcccaac cctgctgggg tgcagctgga ggaccctgag    2280
ttccaggcca gcaacatcat gcacagcatc aatggctatg tgtttgacag cctgcagctg    2340
tctgtgtgcc tgcatgaggt ggcctactgg tacatcctga gcattgggc ccagactgac    2400
```

```
ttcctgtctg tgttcttctc tggctacacc ttcaagcaca agatggtgta tgaggacacc    2460
ctgaccctgt tccccttctc tggggagact gtgttcatga gcatggagaa ccctggcctg    2520
tggattctgg gctgccacaa ctctgacttc aggaacaggg gcatgactgc cctgctgaaa    2580
gtctccagct gtgacaagaa cactgggggac tactatgagg acagctatga ggacatctct    2640
gcctacctgc tgagcaagaa caatgccatt gagcccagga gcttccagaa gaagaccagg    2700
cactacttca ttgctgctgt ggagaggctg tgggactatg gcatgagcag cagcccccat    2760
gtgctgagga acagggccca gtctggctct gtgccccagt tcaagaaggt ggtgttccag    2820
gagttcactg atggcagctt cacccagccc ctgtacagag gggagctgaa tgagcacctg    2880
ggcctgctgg gcccctacat cagggctgag gtggaggaca acatcatggt gaccttcagg    2940
aaccaggcca gcaggcccta cagcttctac agcagcctga tcagctatga ggaggaccag    3000
aggcaggggg ctgagcccag gaagaacttt gtgaagccca tgaaaccaa gacctacttc    3060
tggaaggtgc agcaccacat ggccccccacc aaggatgagt ttgactgcaa ggcctgggcc    3120
tacttctctg atgtggacct ggagaaggat gtgcactctg gcctgattgg ccccctgctg    3180
gtgtgccaca ccaacaccct gaaccctgcc catggcaggc aggtgactgt gcaggagttt    3240
gccctgttct tcaccatctt tgatgaaacc aagagctggt acttcactga gaacatggag    3300
aggaactgca gggccccctg caacatccag atggaggacc ccaccttcaa ggagaactac    3360
aggttccatg ccatcaatgg ctacatcatg gacacccctgc ctggcctggt gatggcccag    3420
gaccagagga tcaggtggta cctgctgagc atgggcagca atgagaacat ccacagcatc    3480
cacttctctg gccatgtgtt cactgtgagg aagaaggagg agtacaagat ggccctgtac    3540
aacctgtacc ctgggggtgtt tgagactgtg agatgctgc ccagcaaggc tggcatctgg    3600
agggtggagt gcctgattgg ggagcacctg catgctggca tgagcaccct gttcctggtg    3660
tacagcaaca agtgccagac ccccctgggc atggcctctg ccacatcag ggacttccag    3720
atcactgcct ctggccagta tggccagtgg gcccccaagc tggccaggct gcactactct    3780
ggcagcatca atgcctggag caccaaggag cccttcagct ggatcaaggt ggacctgctg    3840
gcccccatga tcatccatgg catcaagacc aggggggcca ggcagaagtt cagcagcctg    3900
tacatcagcc agttcatcat catgtacagc ctggatggca agaagtggca gacctacagg    3960
ggcaacagca ctggcacccct gatggtgttc tttggcaatg tggacagctc tggcatcaag    4020
cacaacatct tcaacccccc catcattgcc agatacatca ggctgcaccc cacccactac    4080
agcatcagga gcaccctgag gatggagctg atgggctgtg acctgaacag ctgcagcatg    4140
cccctgggca tggagagcaa ggccatctct gatgcccaga tcactgccag cagctacttc    4200
accaacatgt ttgccacctg gagccccagc aaggccaggc tgcacctgca gggcaggagc    4260
aatgcctgga ggccccaggt caacaacccc aaggagtggc tgcaggtgga cttccagaag    4320
accatgaagg tgactggggt gaccacccag ggggtgaaga gcctgctgac cagcatgtat    4380
gtgaaggagt tcctgatcag cagcagccag gatggccacc agtggacccct gttcttccag    4440
aatggcaagg tgaaggtgtt ccagggcaac caggacagct tcacccctgt ggtgaacagc    4500
ctggaccccc cctgctgac cagatacctg aggattcacc cccagagctg ggtgcaccag    4560
attgccctga ggatggaggt gctgggctgt gaggcccagg acctgtactg aaataaaaga    4620
tcttttatttt cattagatct gtgtgttggt tttttgtgtg aggaacccct agtgatggag    4680
ttggccactc cctctctgcg cgctcgctcg ctcactgagg ccgggcgacc aaaggtcgcc    4740
cgacgcccgg gctttgcccg ggcggcctca gtgagcgagc gagcgcgcag agagggagtg    4800
``` gccaa                                                                         4805

<210> SEQ ID NO 6
<211> LENGTH: 4934
<212> TYPE: DNA
<213> ORGANISM: Adeno-Associated Virus

<400> SEQUENCE: 6

```
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcctgtttg ctgcttgcaa tgtttgccca ttttagggtg   180
gacacaggac gctgtggttt ctgagccagg gggcgactca gatcccagcc agtggactta   240 gccctgtt tgctcctccga taactggggt gaccttggtt aatattcacc agcagcctcc   300
cccgttgccc ctctggatcc actgcttaaa tacggacgag gacagggccc tgtctcctca   360
gcttcaggca ccaccactga cctgggacag tgaatcgcca ccatgcagat tgagctgagc   420
acctgcttct tcctgtgcct gctgagattc tgctttagtg ccaccagaag atactacctg   480
ggtgcagtgg aactgtcatg ggactatatg caaagtgatc tcggtgagct gcctgtggac   540
gcaaggtaaa ggcatgtcct gtagggtctg atcggggcca ggattgtggg gatgtaagtc   600
tgcttggagg aaggtgcaga catcgggtta ggatggttgt gatgctattc tgactttttc   660
ctttcttcac gcagatttcc tcctagagtg ccaaaatctt ttccattcaa cacctcagtc   720
gtgtacaaaa agactctgtt tgtagaattc acggatcacc ttttcaacat cgctaagccc   780 aggccccct ggatgggcct gctgggcccc accatccagg ctgaggtgta tgacactgtg   840
gtgatcaccc tgaagaacat ggccagccac cctgtgagcc tgcatgctgt gggggtgagc   900
tactggaagg cctctgaggg ggctgagtat gatgaccaga ccagccagag ggagaaggag   960
gatgacaagg tgttccctgg gggcagccac acctatgtgt ggcaggtgct gaaggagaat  1020
ggccccatgg cctctgaccc cctgtgcctg acctacagct acctgagcca tgtggacctg  1080
gtgaaggacc tgaactctgg cctgattggg ccctgctgg tgtgcaggga gggcagcctg  1140
gccaaggaga gacccagac cctgcacaag ttcatcctgc tgtttgctgt gtttgatgag  1200
ggcaagagct ggcactctga aaccaagaac agcctgatgc aggacaggga tgctgcctct  1260
gccagggcct ggcccaagat gcacactgtg aatggctatg tgaacaggag cctgcctggc  1320
ctgattggct gccacaggaa gtctgtgtac tggcatgtga ttggcatggg caccacccct  1380
gaggtgcaca gcatcttcct ggagggccac accttcctgg tcaggaacca caggcaggcc  1440
agcctggaga tcagccccat caccttcctg actgcccaga ccctgctgat ggacctgggc  1500
cagttcctgc tgttctgcca catcagcagc caccagcatg atggcatgga ggcctatgtg  1560
aaggtggaca gctgccctga ggagcccag ctgaggatga gaacaatga ggaggctgag  1620 gactatgatg atgacctgac tgactctgag atggatgtgg tgaggtttga tgatgacaac  1680
agccccagct tcatccagat caggtctgtg gccaagaagc accccaagac ctgggtgcac  1740
tacattgctg ctgaggagga ggactgggac tatgcccccc tggtgctggc ccctgatgac  1800
aggagctaca agagccagta cctgaacaat ggcccccaga ggattggcag gaagtacaag  1860
aaggtcaggt tcatggccta cactgatgaa accttcaaga ccaggggagc catccagcat  1920
gagtctggca tcctgggccc cctgctgtat ggggaggtgg gggacaccct gctgatcatc  1980
ttcaagaacc aggccagcag gccctacaac atctacccc atggcatcac tgatgtgagg  2040
```

```
cccctgtaca gcaggaggct gcccaagggg gtgaagcacc tgaaggactt ccccatcctg    2100
cctggggaga tcttcaagta caagtggact gtgactgtgg aggatgggcc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga acaggagc     2340
tggtacctga ctgagaacat ccagaggttc ctgcccaacc ctgctggggt gcagctggag    2400
gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg gagaggctgt gggactatgg catgagcagc    2880
agcccccatg tgctgaggaa cagggcccag tctggctctg tgcccagtt caagaaggtg    2940
gtgttccagg agttcactga tggcagcttc acccagcccc tgtacagagg ggagctgaat    3000
gagcacctgg gcctgctggg ccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg agaaggatg tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta cttcactgag    3420
aacatggaga ggaactgcag ggccccctgc aacatccaga tggaggaccc caccttcaag    3480
gagaactaca ggttccatgc catcaatggc tacatcatgg acacctgcc tggcctggtg    3540
atggcccagg accagaggat caggtggtac ctgctgagca tgggcagcaa tgagaacatc    3600
cacagcatcc acttctctgg ccatgtgttc actgtgagga gaaggagga gtacaagatg    3660
gccctgtaca acctgtaccc tgggggtgttt gagactgtgg agatgctgcc cagcaaggct    3720
ggcatctgga gggtggagtg cctgattggg gagcacctgc atgctggcat gagcacccctg   3780
ttcctggtgt acagcaacaa gtgccagacc cccctgggca tggcctctgg ccacatcagg    3840
gacttccaga tcactgcctc tggccagtat ggccagtggg cccccaagct ggccaggctg    3900
cactactctg gcagcatcaa tgcctggagc accaaggagc ccttcagctg gatcaaggtg    3960
gacctgctgg cccccatgat catccatggc atcaagaccc aggggccag gcagaagttc    4020
agcagcctgt acatcagcca gttcatcatc atgtacagcc tggatggcaa gaagtggcag    4080
acctacaggg gcaacagcac tggcacccctg atggtgttct ttggcaatgt ggacagctct    4140
ggcatcaagc acaacatctt caaccccccc atcattgcca gatacatcag gctgcaccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca ggccaggct gcacctgcag    4380
ggcaggagca atgcctggag gccccaggtc aacaaccccca aggagtggct gcaggtggac    4440
```

```
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccctgtg     4620 gtgaacagcc tggacccccc cctgctgacc agatacctga ggattcaccc ccagagctgg    4680
gtgcaccaga ttgccctgag gatggaggtg ctgggctgtg aggcccagga cctgtactga    4740
aataaaagat ctttattttc attagatctg tgtgttggtt ttttgtgtga ggaacccta    4800 gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934

<210> SEQ ID NO 7
<211> LENGTH: 4934
<212> TYPE: DNA
<213> ORGANISM: Adeno-Associated Virus

<400> SEQUENCE: 7
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttaggggtg    180 gacacaggac gctgtggttt ctgagccagg gggcgactca gatcccagcc agtggactta    240
gccctgtttt gctcctccga taactggggt gaccttggtt aatattcacc agcagcctcc    300
cccgttgccc ctctggatcc actgcttaaa tacgacgag acagggccc tgtctcctca     360 gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggctgtttgc tgcttgcaat gtttgcccat tttaggggg gatgtaagtc    600 tgcttggagg aaggtgcaga catcgggtta ggatggttgt gatgctattc tgactttttc    660 cttttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg ggcagccac acctatgtgt ggcaggtgct gaaggagaat   1020
ggccccatgg cctctgaccc cctgtgcctg acctacagct acctgagcca tgtggacctg   1080
gtgaaggacc tgaactctgg cctgattggg gccctgctgg tgtgcaggga gggcagcctg   1140
gccaaggaga gacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccaccccct   1380 gaggtgcaca gcatcttcct ggagggccac accttcctgg tcaggaacca caggcaggcc   1440
agcctggaga tcagccccat caccttcctg actgcccaga cctgctgat ggacctgggc   1500 cagttcctgc tgttctgcca catcagcagc caccagcatg atggcatgga ggcctatgtg   1560
```

```
aaggtggaca gctgccctga ggagccccag ctgaggatga agaacaatga ggaggctgag    1620
gactatgatg atgacctgac tgactctgag atggatgtgg tgaggtttga tgatgacaac    1680
agccccagct tcatccagat caggtctgtg gccaagaagc accccaagac ctgggtgcac    1740
tacattgctg ctgaggagga ggactgggac tatgccccc  tggtgctggc ccctgatgac    1800
aggagctaca agagccagta cctgaacaat ggcccccaga ggattggcag aagtacaag     1860 aaggtcaggt tcatggccta cactgatgaa accttcaaga ccaggaggc  catccagcat    1920 gagtctggca tcctgggccc cctgctgtat ggggaggtgg gggacaccct gctgatcatc    1980
ttcaagaacc aggccagcag gccctacaac atctacccc  atggcatcac tgatgtgagg    2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga acaggagc     2340 tggtacctga ctgagaacat ccagaggttc ctgcccaacc tgctggggt  gcagctggag    2400 gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg agaggctgt  gggactatgg catgagcagc    2880
agcccccatg tgctgaggaa cagggcccag tctggctctg tgcccagtt  caagaaggtg    2940 gtgttccagg agttcactga tggcagcttc acccagcccc tgtacagagg ggagctgaat    3000
gagcacctgg gcctgctggg cccctacatc agggctgagg tggaggacaa catcatggtg    3060
accttcagga accaggccag caggccctac agcttctaca gcagcctgat cagctatgag    3120
gaggaccaga ggcaggggc  tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg agaaggatg  tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta  cttcactgag    3420 aacatggaga ggaactgcag ggccccctgc aacatccaga tggaggaccc caccttcaag    3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc cccctgggca tggcctctgg ccacatcagg    3840
gacttccaga tcactgcctc tggccagtat ggccagtggg cccccaagct ggccaggctg    3900
cactactctg gcagcatcaa tgcctggagc accaaggagc ccttcagctg gatcaaggtg    3960
```

```
gacctgctgg cccccatgat catccatggc atcaagaccc aggggggccag gcagaagttc    4020 agcagcctgt acatcagcca gttcatcatc atgtacagcc tggatggcaa gaagtggcag    4080
acctacaggg gcaacagcac tggcacccctg atggtgttct ttggcaatgt ggacagctct    4140
ggcatcaagc acaacatctt caacccccccc atcattgcca gatacatcag gctgcacccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca aggccaggct gcacctgcag    4380
ggcaggagca atgcctggag gccccaggtc aacaacccca aggagtggct gcaggtggac    4440
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccccctgtg    4620 gtgaacagcc tggaccccccc cctgctgacc agatacctga ggattcaccc ccagagctgg    4680
gtgcaccaga ttgccctgag gatggaggtg ctgggctgtg aggcccagga cctgtactga    4740
aataaaagat cttttattttc attagatctg tgtgttggtt ttttgtgtga ggaaccccta    4800
gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934

<210> SEQ ID NO 8
<211> LENGTH: 4934
<212> TYPE: DNA
<213> ORGANISM: Adeno-Associated Virus

<400> SEQUENCE: 8
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta    240 gccccctgttt gctcctccga taactggggt gaccttggtt aatattcacc agcagcctcc    300
cccgttgccc ctctggatcc actgcttaaa tacgacgag gacagggccc tgtctcctca     360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa gcatgtcct gtagggtctg atcggggcca ggattgtggg gatgtaagtc    600
tgcttggagg aagccctaaa atgggcaaac attgcaagca gcaaacattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat    1020 ggcccccatgg cctctgaccc cctgtgcctg acctacagct acctgagcca tgtggacctg    1080
```

```
gtgaaggacc tgaactctgg cctgattggg gccctgctgg tgtgcaggga gggcagcctg    1140
gccaaggaga agacccagac cctgcacaag ttcatcctgc tgtttgctgt gtttgatgag    1200
ggcaagagct ggcactctga aaccaagaac agcctgatgc aggacaggga tgctgcctct    1260
gccagggcct ggcccaagat gcacactgtg aatggctatg tgaacaggag cctgcctggc    1320
ctgattggct gccacaggaa gtctgtgtac tggcatgtga ttggcatggg caccacccct    1380
gaggtgcaca gcatcttcct ggagggccac accttcctgg tcaggaacca caggcaggcc    1440
agcctggaga tcagccccat caccttcctg actgcccaga ccctgctgat ggacctgggc    1500
cagttcctgc tgttctgcca catcagcagc caccagcatg atggcatgga ggcctatgtg    1560
aaggtggaca gctgccctga ggagccccag ctgaggatga agaacaatga ggaggctgag    1620
gactatgatg atgacctgac tgactctgag atggatgtgg tgaggtttga tgatgacaac    1680
agccccagct tcatccagat caggtctgtg gccaagaagc accccaagac ctgggtgcac    1740
tacattgctg ctgaggagga ggactgggac tatgccccccc tggtgctggc ccctgatgac    1800
aggagctaca gagccagta cctgaacaat ggccccccaga ggattggcag gaagtacaag    1860
aaggtcaggt tcatgcccta cactgatgaa accttcaaga ccagggaggc catccagcat    1920
gagtctggca tcctgggccc cctgctgtat ggggaggtgg gggacaccct gctgatcatc    1980
ttcaagaacc aggccagcag gccctacaac atctacccccc atggcatcac tgatgtgagg    2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga aacaggagc    2340 tggtacctga ctgagaacat ccagaggttc ctgcccaacc tgctgggggt gcagctggag    2400
gaccctgagt ccaggccag caacatcatg cacagcatca tggctatgt gtttgacagc    2460 ctgcagctgt ctgtgtgcct gcatgaggtg gcctactggt acatcctgag cattgggcc    2520 cagactgact tcctgtctgt gttcttctct ggctacacct tcaagcacaa gatggtgtat    2580 gaggacacccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actgggggact actatgagga cagctatgag    2760
gacatctctg cctacctgct gagcaagaac aatgccattg agcccaggag cttccagaag    2820
aagaccaggc actacttcat tgctgctgtg agaggctgt gggactatgg catgagcagc    2880
agcccccatg tgctgaggaa cagggcccag tctggctctg tgcccccagtt caagaaggtg    2940 gtgttccagg agttcactga tggcagcttc acccagcccc tgtacagagg ggagctgaat    3000
gagcacctgg gcctgctggg ccccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gccccccacca aggatgagtt tgactgcaag    3240
gcctgggcct acttctctga tgtggacctg agaaggatg tgcactctgg cctgattggc    3300
cccctgctgg tgtgccacac caacacccctg aaccctgccc atggcaggca ggtgactgtg    3360
caggagtttg ccctgttctt caccatcttt gatgaaacca agagctggta cttcactgag    3420
aacatggaga ggaactgcag ggccccctgc aacatccaga tggaggaccc caccttcaag    3480
```

-continued

| | |
|---|---|
| gagaactaca ggttccatgc catcaatggc tacatcatgg acaccctgcc tggcctggtg | 3540 |
| atggcccagg accagaggat caggtggtac ctgctgagca tgggcagcaa tgagaacatc | 3600 |
| cacagcatcc acttctctgg ccatgtgttc actgtgagga agaaggagga gtacaagatg | 3660 |
| gccctgtaca acctgtaccc tggggtgttt gagactgtgg agatgctgcc cagcaaggct | 3720 |
| ggcatctgga gggtggagtg cctgattggg gagcacctgc atgctggcat gagcaccctg | 3780 |
| ttcctggtgt acagcaacaa gtgccagacc cccctgggca tggcctctgg ccacatcagg | 3840 |
| gacttccaga tcactgcctc tggccagtat ggccagtggg cccccaagct ggccaggctg | 3900 |
| cactactctg gcagcatcaa tgcctggagc accaaggagc cttcagctg gatcaaggtg | 3960 |
| gacctgctgg cccccatgat catccatggc atcaagaccc agggggccag gcagaagttc | 4020 |
| agcagcctgt acatcagcca gttcatcatc atgtacagcc tggatggcaa gaagtggcag | 4080 |
| acctacaggg gcaacagcac tggcacccctg atggtgttct ttggcaatgt ggacagctct | 4140 |
| ggcatcaagc acaacatctt caaccccccc atcattgcca gatacatcag gctgcacccc | 4200 |
| acccactaca gcatcaggag cacccctgagg atggagctga tgggctgtga cctgaacagc | 4260 |
| tgcagcatgc ccctgggcat ggagagcaag gccatctctg atgcccagat cactgccagc | 4320 |
| agctacttca ccaacatgtt tgccacctgg agccccagca aggccaggct gcacctgcag | 4380 |
| ggcaggagca atgcctggag gccccaggtc aacaacccca aggagtggct gcaggtggac | 4440 |
| ttccagaaga ccatgaaggt gactggggtg accacccagg gggtgaagag cctgctgacc | 4500 |
| agcatgtatg tgaaggagtt cctgatcagc agcagccagg atggccacca gtggacctg | 4560 |
| ttcttccaga atggcaaggt gaaggtgttc cagggcaacc aggacagctt caccctgtg | 4620 |
| gtgaacagcc tggaccccccc cctgctgacc agatacctga ggattcaccc ccagagctgg | 4680 |
| gtgcaccaga ttgccctgag gatggaggtg ctgggctgtg aggcccagga cctgtactga | 4740 |
| aataaaagat ctttattttc attagatctg tgtgttggtt ttttgtgtga ggaacccta | 4800 |
| gtgatggagt tggccactcc ctctctgcgc gctcgctcgc tcactgaggc cgggcgacca | 4860 |
| aaggtcgccc gacgcccggg ctttgcccgg gcggcctcag tgagcgagcg agcgcgcaga | 4920 |
| gagggagtgg ccaa | 4934 |

<210> SEQ ID NO 9
<211> LENGTH: 5511
<212> TYPE: DNA
<213> ORGANISM: Adeno-Associated Virus 2

<400> SEQUENCE: 9

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaacca cgccaggaca acctctgctc ctctccaccg aaattccaag ggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |
| ggaggatggg aactgagggg ttggaagggg gcagggtgag cccagaaact cctgtgtgcc | 480 |
| tctgagcctg cagacgcgaa acgtcgactg gacacaggac gctgtggttt ctgagccagg | 540 |
| gggcgactca gatcccagcc agtggactta gcccctgttt gctcctccga taactgggt | 600 |

```
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggccctttt gctaatcatg ttcataccto    840
ttatcttcct cccacagctc ctgggcaacg tgctggtctg tgtgctggcc atcactttg     900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt     1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg ggctgagta    1320
tgatgaccag accagccaga gggagaagga ggatgacaag gtgttccctg ggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt    1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg tcaggaacc acaggcaggc cagcctggag atcagcccca tcaccttcct    1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg tgaggttg atgatgacaa cagccccagc ttcatccaga tcaggtctgt    2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gccctgtac agcaggaggc tgcccaaggg    2460
ggtgaagcac ctgaaggact ccccatcct gcctgggag atcttcaagt acaagtggac     2520
tgtgactgtg gaggatggcc ccaccaagtc tgacccagg tgcctgacca gatactacag    2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgacccttgt tccccttctc   3000
```

```
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga actttgtgaa    3720
gcccaatgaa accaagacct acttctggaa ggtgcagcac acatggccc ccaccaagga    3780 tgagtttgac tgcaaggcct gggcctactt ctctgatgtg gacctggaga aggatgtgca    3840
ctctggcctg attggccccc tgctggtgtg ccacaccaac ccctgaacc ctgcccatgg    3900 caggcaggtg actgtgcagg agtttgccct gttcttcacc atctttgatg aaaccaagag    3960
ctggtacttc actgagaaca tggagaggaa ctgcagggcc cctgcaaca tccagatgga    4020 ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260 gctgccagc aaggctggca tctggagggt ggagtgcctg attggggagc acctgcatgc    4320
tggcatgagc accctgttcc tggtgtacag caacaagtgc cagaccccc tgggcatggc    4380 ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac ccccccatca ttgccagata    4740
catcaggctg caccccaccc actacagcat caggagcacc ctgaggatgg agctgatggg    4800
ctgtgacctg aacagctgca gcatgccct gggcatggag agcaaggcca tctctgatgc    4860
ccagatcact gccagcagct acttccaccaa catgtttgcc acctggagcc ccagcaaggc    4920
caggctgcac ctgcagggca ggagcaatgc ctggaggccc caggtcaaca cccccaagga    4980
gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160 cagcttcacc cctgtggtga acagcctgga cccccccctg ctgaccagat acctgaggat    5220
tcacccccag agctgggtgc accagattgc cctgaggatg gaggtgctgg gctgtgaggc    5280
ccaggacctg tactgacctc gaggaataaa ggaaatttat tttcattgca atagtgtgtt    5340
```

```
ggttttttgt gtcacgtggc ggccgcagga accoctagtg atggagttgg ccactccctc    5400
tctgcgcgct cgctcgctca ctgaggccgg gcgaccaaag gtcgcccgac gcccgggctt    5460
tgcccgggcg gcctcagtga gcgagcgagc gcgcagagag ggagtggcca a             5511

<210> SEQ ID NO 10
<211> LENGTH: 5688
<212> TYPE: DNA
<213> ORGANISM: Adeno-Associated Virus 2

<400> SEQUENCE: 10
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180 acctaaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc ccgttgccc ctctggatcc actgcttaaa     660 tacgacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggcccttt  gctaatcatg ttcatacctc     840
ttatcttcct cccacagctc tgggcaacg tgctggtctg tgtgctggcc catcactttg     900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat ccaggttcc  cccccagagt   1080 gcccaagagc ttccccttca cacctctgt ggtgtacaag aagacccgtt ttgtggagtt    1140
cactgaccac ctgttcaaca ttgccaagcc caggccccc tggatgggcc tgctgggccc   1200
caccatccag gctgaggtgt atgacactgt ggtgatcacc ctgaagaaca tggccagcca    1260
ccctgtgagc ctgcatgctg tggggtgag ctactggaag gcctctgagg gggctgagta    1320
tgatgaccag accagccaga gggagaagga ggatgacaag gtgttccctg ggggcagcca    1380
cacctatgtg tggcaggtgc tgaaggagaa tggccccatg gcctctgacc cctgtgcct    1440 gacctacagc tacctgagcc atgtggacct ggtgaaggac ctgaactctg gcctgattgg    1500
ggccctgctg gtgtgcaggg agggcagcct ggccaaggag aagacccaga ccctgcacaa    1560
gttcatcctg ctgtttgctg tgtttgatga gggcaagagc tggcactctg aaaccaagaa    1620
cagcctgatg caggacaggg atgctgcctc tgccagggcc tggccaaga tgcacactgt    1680 gaatggctat gtgaacagga gcctgcctgg cctgattggc tgccacagga agtctgtgta    1740
ctggcatgtg attggcatgg gcaccacccc tgaggtgcac agcatcttcc tggagggcca    1800
caccttcctg gtcaggaacc acaggcaggc cagcctggag atcagcccca tcaccttcct    1860
gactgcccag accctgctga tggacctggg ccagttcctg ctgttctgcc acatcagcag    1920
ccaccagcat gatggcatgg aggcctatgt gaaggtggac agctgccctg aggagcccca    1980
```

```
gctgaggatg aagaacaatg aggaggctga ggactatgat gatgacctga ctgactctga    2040
gatggatgtg gtgaggtttg atgatgacaa cagccccagc ttcatccaga tcaggtctgt    2100
ggccaagaag cacccccaaga cctgggtgca ctacattgct gctgaggagg aggactggga    2160
ctatgccccc ctggtgctgg cccctgatga caggagctac aagagccagt acctgaacaa    2220
tggcccccag aggattggca ggaagtacaa gaaggtcagg ttcatggcct acactgatga    2280
aaccttcaag accagggagg ccatccagca tgagtctggc atcctgggcc ccctgctgta    2340
tggggaggtg ggggacaccc tgctgatcat cttcaagaac caggccagca ggccctacaa    2400
catctacccc catggcatca ctgatgtgag gcccctgtac agcaggaggc tgcccaaggg    2460
ggtgaagcac ctgaaggact tccccatcct gcctgggag atcttcaagt acaagtggac    2520
tgtgactgtg gaggatggcc ccaccaagtc tgacccagg tgcctgacca gatactacag    2580
cagctttgtg aacatggaga gggacctggc ctctggcctg attggccccc tgctgatctg    2640
ctacaaggag tctgtggacc agaggggcaa ccagatcatg tctgacaaga ggaatgtgat    2700
cctgttctct gtgtttgatg agaacaggag ctggtacctg actgagaaca tccagaggtt    2760
cctgcccaac cctgctgggg tgcagctgga ggaccctgag ttccaggcca gcaacatcat    2820
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca gatggtgta tgaggacacc ctgaccctgt tcccccttctc    3000 tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac acccctgaacc ctgcccatgg    3900 caggcaggtg actgtgcagg agtttgccct gttcttcacc atctttgatg aaaccaagag    3960
ctggtacttc actgagaaca tggagaggaa ctgcagggcc cctgcaaca tccagatgga    4020 ggacccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggaggt ggagtgcctg attggggagc acctgcatgc    4320
```

```
tggcatgagc acccctgttcc tggtgtacag caacaagtgc cagaccccc tgggcatggc     4380 ctctggccac atcagggact tccagatcac tgcctctggc cagtatggcc agtgggcccc     4440
caagctggcc aggctgcact actctggcag catcaatgcc tggagcacca aggagccctt     4500
cagctggatc aaggtggacc tgctggcccc catgatcatc catggcatca agacccaggg     4560
ggccaggcag aagttcagca gcctgtacat cagccagttc atcatcatgt acagcctgga     4620
tggcaagaag tggcagacct acaggggcaa cagcactggc accctgatgg tgttctttgg     4680
caatgtggac agctctggca tcaagcacaa catcttcaac ccccccatca ttgccagata     4740
catcaggctg cacccacccc actacagcat caggagcacc ctgaggatgg agctgatggg     4800
ctgtgacctg aacagctgca gcatgccct gggcatggag agcaaggcca tctctgatgc     4860
ccagatcact gccagcagct acttcaccaa catgtttgcc acctggagcc ccagcaaggc     4920
caggctgcac ctgcagggca ggagcaatgc ctggaggccc caggtcaaca acccccaagga     4980 gtggctgcag gtggacttcc agaagaccat gaaggtgact ggggtgacca cccagggggt     5040
gaagagcctg ctgaccagca tgtatgtgaa ggagttcctg atcagcagca gccaggatgg     5100
ccaccagtgg acctgttct ccagaatgg caaggtgaag gtgttccagg caaccagga     5160 cagcttcacc cctgtggtga acagcctgga ccccccctg ctgaccagat acctgaggat     5220 tcaccccag agctgggtgc accagattgc cctgaggatg aggtgctgg gctgtgaggc     5280 ccaggacctg tactgacctc gaggtgtgcc ttctagttgc cagccatctg ttgtttgccc     5340
ctcccccgtg ccttccttga cctggaagg tgccactccc actgtccttt cctaataaaa     5400
tgaggaaatt gcatcgcatt gtctgagtag gtgtcattct attctggggg gtggggtggg     5460
gcaggacagc aaggggggagg attgggaaga caatagcagg catgctgggg atgcggtggg     5520 ctctatggc acgtggcggc cgcaggaacc cctagtgatg gagttggcca ctccctctct     5580
gcgcgctcgc tcgctcactg aggccgggcg accaaaggtc gcccgacgcc cgggctttgc     5640
ccgggcggcc tcagtgagcg agcgagcgcg cagagaggga gtggccaa                  5688

<210> SEQ ID NO 11
<211> LENGTH: 5613
<212> TYPE: DNA
<213> ORGANISM: Adeno-Associated Virus 2

<400> SEQUENCE: 11
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag ggtcgagtg      240 gatgttggag gtggcatggg cccagagagg tctctgacct ctgccccagc tccaaggtca     300
gcaggcaggg agggctgtgt gtttgctgtt tgctgcttgc aatgtttgcc catttaggg      360 acatgagtag gctgaagttt gttcagtgtg gacttcagag gcagcacaca aacagctgct     420
ggaggatggg aactgagggg ttggaagggg gcagggtgag cccagaaact cctgtgtgcc     480
tctgagcctg cagacgcgaa acgtcgactg acacaggac gctgtggttt ctgagccagg     540
gggcgactca gatcccagcc agtggactta gcccctgttt gctcctccga taactggggt     600
gaccttggtt aatattcacc agcagcctcc ccgttgccc ctctggatcc actgcttaaa     660 tacgacgag acagggccc tgtctcctca gcttcaggca ccaccactga cctgggacag     720
tgaatcgtaa gtactagcag ctacaatcca gctaccattc tgcttttatt ttatggttgg     780
```

```
gataaggctg gattattctg agtccaagct aggccctttt gctaatcatg ttcatacctc      840
ttatcttcct cccacagctc ctgggcaacg tgctggtctg tgtgctggcc catcactttg      900
gcaaagaatt gcgatcgcca ccatgcagat tgagctgagc acctgcttct tcctgtgcct      960
gctgaggttc tgcttctctg ccaccaggag atactacctg ggggctgtgg agctgagctg     1020
ggactacatg cagtctgacc tgggggagct gcctgtggat gccaggttcc cccccagagt     1080
gcccaagagc ttccccttca acacctctgt ggtgtacaag aagaccctgt tgtggagtt      1140 cactgaccac ctgttcaaca ttgccaagcc caggccccc  tggatgggcc tgctgggccc     1200
caccatccag gctgaggtgt atgacactgt ggtgatcacc ctgaagaaca tggccagcca     1260
ccctgtgagc ctgcatgctg tgggggtgag ctactggaag gcctctgagg gggctgagta     1320
tgatgaccaa accagccaga gggagaagga ggatgacaag gtgttccctg ggggcagcca     1380
cacctatgtg tggcaggtgc tgaaggagaa tggccccatg gcctctgacc ccctgtgcct     1440
gacctacagc tacctgagcc atgtggacct ggtgaaggac ctgaactctg gcctgattgg     1500
ggccctgctg gtgtgcaggg agggcagcct ggccaaggag aagacccaga ccctgcacaa     1560
gttcatcctg ctgtttgctg tgtttgatga gggcaagagc tggcactctg aaaccaagaa     1620
cagcctgatg caggacaggg atgctgcctc tgccagggcc tggcccaaga tgcacactgt     1680
gaatggctat gtgaacagga gcctgcctgg cctgattggc tgccacagga gtctgtgta      1740 ctggcatgtg attggcatgg gcaccacccc tgaggtgcac agcatcttcc tggagggcca     1800
caccttcctg gtcaggaacc acaggcaggc cagcctggag atcagcccca tcaccttcct     1860
gactgcccag accctgctga tggacctggg ccagttcctg ctgttctgcc acatcagcag     1920
ccaccagcat gatggcatgg aggcctatgt gaaggtggac agctgccctg aggagcccca     1980
gctgaggatg aagaacaatg aggaggctga ggactatgat gatgacctga ctgactctga     2040
gatggatgtg gtgaggtttg atgatgacaa cagccccagc ttcatccaga tcaggtctgt     2100
ggccaagaag cacccaaga  cctgggtgca ctacattgct gctgaggagg aggactggga     2160
ctatgccccc ctggtgctgg cccctgatga caggagctac aagagccagt acctgaacaa     2220
tggcccccag aggattggca ggaagtacaa gaaggtcagg ttcatggcct acactgatga     2280
aaccttcaag accagggagg ccatccagca tgagtctggc atcctgggcc ccctgctgta     2340
tgggagggtg ggggacaccc tgctgatcat cttcaagaac caggccagca ggccctacaa     2400
catctacccc catggcatca ctgatgtgag gcccctgtac agcaggaggc tgcccaaggg     2460
ggtgaagcac ctgaaggact tccccatcct gcctggggga tcttcaagt  acaagtggac     2520 tgtgactgtg gaggatggcc ccaccaagtc tgaccccagg tgcctgacca gatactacag     2580
cagctttgtg aacatggaga gggacctggc ctctggcctg attggccccc tgctgatctg     2640
ctacaaggag tctgtggacc agaggggcaa ccagatcatg tctgacaaga ggaatgtgat     2700
cctgttctct gtgtttgatg agaacaggag ctggtacctg actgagaaca tccagaggtt     2760
cctgcccaac cctgctgggg tgcagctgga ggaccctgag ttccaggcca gcaacatcat     2820
gcacagcatc aatggctatg tgtttgacag cctgcagctg tctgtgtgcc tgcatgaggt     2880
ggcctactgg tacatcctga gcattggggc ccagactgac ttcctgtctg tgttcttctc     2940
tggctacacc ttcaagcaca agatggtgta tgaggacacc ctgacccgt  tcccttctc     3000 tggggagact gtgttcatga gcatggagaa ccctggcctg tggattctgg gctgccacaa     3060
ctctgacttc aggaacaggg gcatgactgc cctgctgaaa gtctccagct gtgacaagaa     3120
```

```
cactggggac tactatgagg acagctatga ggacatctct gcctacctgc tgagcaagaa    3180
caatgccatt gagcccagga gcttcagcca gaaccccca gtgctgaaga ggcaccagag     3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga actttgtgaa     3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc ccctgcaaca tccagatgga    4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc     4380 ctctggccac atcagggact tccagatcac tgcctctggc cagtatggcc agtgggcccc    4440
caagctggcc aggctgcact actctggcag catcaatgcc tggagcacca aggagcccttt   4500 cagctggatc aaggtggacc tgctggcccc catgatcatc catggcatca gacccaggg    4560 ggccaggcag aagttcagca gcctgtacat cagccagttc atcatcatgt acagcctgga    4620
tggcaagaag tggcagacct acaggggcaa cagcactggc acccctgatgg tgttctttgg   4680 caatgtggac agctctggca tcaagcacaa catcttcaac cccccatca ttgccagata    4740 catcaggctg cacccaccc actacagcat caggagcacc ctgaggatgg agctgatggg    4800
ctgtgacctg aacagctgca gcatgccct gggcatggag agcaaggcca tctctgatgc    4860
ccagatcact gccagcagct acttcaccaa catgtttgcc acctggagcc ccagcaaggc    4920
caggctgcac ctgcagggca ggagcaatgc ctggaggccc caggtcaaca cccccaagga    4980
gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg accctgttct tccagaatgg caaggtgaag gtgttccagg caaccagga    5160 cagcttcacc cctgtggtga acagcctgga cccccccctg ctgaccagat acctgaggat    5220
tcacccccag agctgggtgc accagattgc cctgaggatg aggtgctgg gctgtgaggc    5280 ccaggacctg tactgacctc gaggcactgt cctttcctaa taaaatgagg aaattgcatc    5340
gcattgtctg agtaggtgtc attctattct gggggtggg gtgggcagg acagcaaggg     5400 ggaggattgg gaagacaata gcaggcatgc tggggatgcg gtgggctcta tgggcacgtg    5460
gcggccgcag gaacccctag tgatggagtt ggccactccc tctctgcgcg ctcgctcgct   5520
```

```
cactgaggcc gggcgaccaa aggtcgcccg acgcccgggc tttgcccggg cggcctcagt    5580
gagcgagcga gcgcgcagag agggagtggc caa                                 5613

<210> SEQ ID NO 12
<211> LENGTH: 5362
<212> TYPE: DNA
<213> ORGANISM: Adeno-Associated Virus 2

<400> SEQUENCE: 12
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc attttaggga catgtttgct gtttgctgct tgcaatgttt     240
gcccatttta gggacatgtt tgctgtttgc tgcttgcaat gtttgcccat tttagggaca     300
tgtttgctgt tgctgcttg caatgtttgc ccattttagg acaacgcga aacgtcgact       360 ggacacagga cgctgtggtt tctgagccag ggggcgactc agatcccagc cagtggactt     420 agccctgtt tgctcctccg ataactgggg tgaccttggt taatattcac cagcagcctc      480
ccccgttgcc cctctggatc cactgcttaa atacggacga ggacagggcc ctgtctcctc     540
agcttcaggc accaccactg acctgggaca gtgaatcgta agtactagca gctacaatcc     600
agctaccatt ctgcttttat tttatggttg ggataaggct ggattattct gagtccaagc     660
taggcccttt tgctaatcat gttcatacct cttatcttcc tcccacagct cctgggcaac     720
gtgctggtct gtgtgctggc ccatcacttt ggcaaagaat tgcgatcgcc accatgcaga     780
ttgagctgag cacctgcttc ttcctgtgcc tgctgaggtt ctgcttctct gccaccagga     840
gatactacct gggggctgtg agctgagct gggactacat gcagtctgac ctgggggagc     900
tgcctgtgga tgccaggttc ccccccagag tgcccaagag cttccccttc aacacctctg     960
tggtgtacaa gaagaccctg tttgtggagt tcactgacca cctgttcaac attgccaagc    1020
ccaggccccc ctggatgggc ctgctgggcc ccaccatcca ggctgaggtg tatgacactg    1080
tggtgatcac cctgaagaac atggccagcc acccctgtga gcctgcatgct gtggggtga    1140 gctactggaa ggcctctgag ggggctgagt atgatgacca gaccagccag agggagaagg    1200
aggatgacaa ggtgttccct ggggggcagcc acacctatgt gtggcaggtg ctgaaggaga    1260
atggccccat ggcctctgac ccctgtgcc tgacctacag ctacctgagc catgtggacc    1320
tggtgaagga ccctgaactct ggcctgattg ggccctgct ggtgtgcagg gagggcagcc    1380
tggccaagga agacccag accctgcaca agttcatcct gctgtttgct gtgtttgatg    1440
agggcaagag ctggcactct gaaaccaaga cagcctgat gcaggacagg gatgctgcct    1500
ctgccagggc ctggccaag atgcacactg tgaatggcta tgtgaacagg agcctgcctg    1560
gcctgattgg ctgccacagg aagtctgtgt actggcatgt gattggcatg ggcaccaccc    1620
ctgaggtgca cagcatcttc ctggagggcc acaccttcct ggtcaggaac acaggcagg    1680 ccagcctgga gatcagcccc atcaccttcc tgactgccca gaccctgctg atggaccgg    1740 gccagttcct gctgttctgc cacatcagca gccaccagca tgatggcatg gaggcctatg    1800
tgaaggtgga cagctgccct gaggagccc agctgaggat gaagaacaat gaggaggctg    1860
aggactatga tgatgacctg actgactctg agatggatgt ggtgaggttt gatgatgaca    1920
acagccccag cttcatccag atcaggtctg tggccaagaa gcaccccaag acctgggtgc    1980
```

-continued

```
actacattgc tgctgaggag gaggactggg actatgcccc cctggtgctg gcccctgatg      2040
acaggagcta caagagccag tacctgaaca atggccccca gaggattggc aggaagtaca      2100
agaaggtcag gttcatggcc tacactgatg aaaccttcaa gaccagggag gccatccagc      2160
atgagtctgg catcctgggc cccctgctgt atggggaggt gggggacacc ctgctgatca      2220
tcttcaagaa ccaggccagc aggccctaca acatctaccc ccatggcatc actgatgtga      2280
ggcccctgta cagcaggagg ctgcccaagg gggtgaagca cctgaaggac ttccccatcc      2340
tgcctgggga gatcttcaag tacaagtgga ctgtgactgt ggaggatggc cccaccaagt      2400
ctgaccccag gtgcctgacc agatactaca gcagctttgt gaacatggag agggacctgg      2460
cctctggcct gattggcccc ctgctgatct gctacaagga gtctgtggac cagaggggca      2520
accagatcat gtctgacaag aggaatgtga tcctgttctc tgtgtttgat gagaacagga      2580
gctggtacct gactgagaac atccagaggt tcctgcccaa ccctgctggg gtgcagctgg      2640
aggaccctga gttccaggcc agcaacatca tgcacagcat caatggctat gtgtttgaca      2700
gcctgcagct gtctgtgtgc ctgcatgagg tggcctactg gtacatcctg agcattgggg      2760
cccagactga cttcctgtct gtgttcttct ctggctacac cttcaagcac aagatggtgt      2820
atgaggacac cctgacccct gttccccttct ctggggagac tgtgttcatg agcatggaga      2880
accctggcct gtggattctg gctgccaca actctgactt caggaacagg ggcatgactg      2940
ccctgctgaa agtctccagc tgtgacaaga acactgggga ctactatgag acagctatg      3000 aggacatctc tgcctacctg ctgagcaaga caatgccat tgagcccagg agcttcagcc      3060 agaaccccc agtgctgaag aggcaccaga gggagatcac caggaccacc ctgcagtctg      3120
accaggagga gattgactat gatgacacca tctctgtgga gatgaagaag gaggactttg      3180
acatctacga cgaggacgag aaccagagcc caggagctt ccagaagaag accaggcact      3240
acttcattgc tgctgtggag aggctgtggg actatggcat gagcagcagc ccccatgtgc      3300
tgaggaacag ggcccagtct ggctctgtgc cccagttcaa gaaggtggtg ttccaggagt      3360
tcactgatgg cagcttcacc cagcccctgt acagagggga gctgaatgag cacctgggcc      3420
tgctgggccc ctacatcagg gctgaggtgg aggacaacat catggtgacc ttcaggaacc      3480
aggccagcag gccctacagc ttctacagca gcctgatcag ctatgaggag gaccagaggc      3540 aggggggctga gcccaggaag aactttgtga gcccaatga aaccaagacc tacttctgga      3600
aggtgcagca ccacatggcc cccaccaagg atgagtttga ctgcaaggcc tgggcctact      3660
tctctgatgt ggacctggag aaggatgtgc actctggcct gattggcccc ctgctggtgt      3720
gccacaccaa caccctgaac cctgcccatg gcaggcaggt gactgtgcag gagtttgccc      3780
tgttcttcac catcttttgat gaaaccaaga gctggtactt cactgagaac atggagagga      3840
actgcagggc ccctgcaac atccagatgg aggaccccac cttcaaggag aactacaggt      3900
tccatgccat caatggctac atcatggaca ccctgcctgg cctggtgatg gcccaggacc      3960
agaggatcag gtggtacctg ctgagcatgg gcagcaatga aacatccac agcatccact      4020 tctctggcca tgtgttcact gtgaggaaga aggaggagta caagatggcc ctgtacaacc      4080
tgtaccctgg ggtgtttgag actgtggaga tgctgcccag caaggctggc atctggaggg      4140
tggagtgcct gattggggag cacctgcatg ctggcatgag caccctgttc ctggtgtaca      4200
gcaacaagtg ccagacccccc ctgggcatgg cctctggcca catcaggac ttccagatca      4260 ctgcctctgg ccagtatggc cagtgggccc caagctggc caggctgcac tactctggca      4320
gcatcaatgc ctggagcacc aaggagccct tcagctggat caaggtggac ctgctggccc      4380
```

```
ccatgatcat ccatggcatc aagacccagg gggccaggca gaagttcagc agcctgtaca    4440
tcagccagtt catcatcatg tacagcctgg atggcaagaa gtggcagacc tacagggca    4500 acagcactgg caccctgatg gtgttctttg gcaatgtgga cagctctggc atcaagcaca    4560
acatcttcaa ccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttccacca   4740 acatgtttgc cacctggagc cccagcaagg ccaggctgca cctgcagggc aggagcaatg    4800
cctggaggcc ccaggtcaac aaccccaagg agtggctgca ggtggacttc cagaagacca    4860
tgaaggtgac tggggtgacc acccagggg tgaagagcct gctgaccagc atgtatgtga    4920
aggagttcct gatcagcagc agccaggatg ccaccagtg gaccctgttc ttccagaatg     4980
gcaaggtgaa ggtgttccag ggcaaccagg acagcttcac ccctgtggtg aacagcctgg    5040
acccccccct gctgaccaga tacctgagga ttcaccccca gagctgggtg caccagattg    5100
ccctgaggat ggaggtgctg ggctgtgagg cccaggacct gtactgacct cgaggaataa    5160
aggaaattta ttttcattgc aatagtgtgt tggttttttg tgtcacgtgg cggccgcagg    5220
aacccctagt gatggagttg gccactccct ctctgcgcgc tcgctcgctc actgaggccg    5280
ggcgaccaaa ggtcgcccga cgcccgggct tgcccgggc ggcctcagtg agcgagcgag    5340
cgcgcagaga gggagtggcc aa                                            5362
```

<210> SEQ ID NO 13
<211> LENGTH: 5464
<212> TYPE: DNA
<213> ORGANISM: Adeno-Associated Virus 2

<400> SEQUENCE: 13

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc atttaggga catgtttgct gtttgctgct tgcaatgttt      240
gcccatttta gggacatgtt tgctgtttgc tgcttgcaat gtttgcccat tttaggaca     300 tgtttgctgt tgctgcttg caatgtttgc ccatttagg acaacgcga aacgtcgact       360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtactagca gctacaatcc    600
agctaccatt ctgctttat tttatggttg ggataaggct ggattattct gagtccaagc    660
taggcccttt tgctaatcat gttcatacct cttatcttcc tcccacagct cctgggcaac    720
gtgctggtct gtgtgctggc ccatcacttt ggcaaagaat tgcgatcgcc accatgcaga    780
ttgagctgag cacctgcttc ttcctgtgcc tgctgaggtt ctgcttctct gccaccagga    840
gatactacct gggggctgtg agctgagct gggactacat gcagtctgac ctggggagc     900 tgcctgtgga tgccaggttc ccccccagag tgcccaagag cttcccctttc aacacctctg    960 tggtgtacaa gaagacc ctg tttgtggagt tcactgacca cctgttcaac attgccaagc   1020
ccaggccccc ctggatgggc ctgctgggcc ccaccatcca ggctgaggtg tatgacactg    1080
```

```
tggtgatcac cctgaagaac atggccagcc accctgtgag cctgcatgct gtggggtga    1140 gctactggaa ggcctctgag ggggctgagt atgatgacca gaccagccag agggagaagg   1200
aggatgacaa ggtgttccct gggggcagcc acacctatgt gtggcaggtg ctgaaggaga   1260
atggccccat ggcctctgac cccctgtgcc tgacctacag ctacctgagc catgtggacc   1320
tggtgaagga cctgaactct ggcctgattg gggccctgct ggtgtgcagg gagggcagcc   1380
tggccaagga gaagacccag accctgcaca agttcatcct gctgtttgct gtgtttgatg   1440
agggcaagag ctggcactct gaaaccaaga acagcctgat gcaggacagg gatgctgcct   1500
ctgccagggc ctggcccaag atgcacactg tgaatggcta tgtgaacagg agcctgcctg   1560
gcctgattgg ctgccacagg aagtctgtgt actggcatgt gattggcatg ggcaccaccc   1620
ctgaggtgca cagcatcttc ctggagggcc acaccttcct ggtcaggaac acaggcagg   1680 ccagcctgga gatcagcccc atcaccttcc tgactgccca gaccctgctg atggacctgg   1740
gccagttcct gctgttctgc cacatcagca gccaccagca tgatggcatg gaggcctatg   1800
tgaaggtgga cagctgccct gaggagcccc agctgaggat gaagaacaat gaggaggctg   1860
aggactatga tgatgacctg actgactctg agatggatgt ggtgaggttt gatgatgaca   1920
acagccccag cttcatccag atcaggtctg tggccaagaa gcaccccaag acctgggtgc   1980
actacattgc tgctgaggag gaggactggg actatgcccc cctggtgctg gcccctgatg   2040
acaggagcta caagagccag tacctgaaca atggccccca gaggattggc aggaagtaca   2100
agaaggtcag gttcatggcc tacactgatg aaaccttcaa gaccagggag gccatccagc   2160
atgagtctgg catcctgggc cccctgctgt atggggaggt gggggacacc ctgctgatca   2220
tcttcaagaa ccaggccagc aggccctaca acatctaccc ccatggcatc actgatgtga   2280 ggccctgta cagcaggagg ctgcccaagg gggtgaagca cctgaaggac ttccccatcc   2340
tgcctgggga gatcttcaag tacaagtgga ctgtgactgt ggaggatggc cccaccaagt   2400
ctgaccccag gtgcctgacc agatactaca gcagctttgt gaacatggag agggacctgg   2460
cctctggcct gattggcccc ctgctgatct gctacaagga gtctgtggac cagaggggca   2520
accagatcat gtctgacaag aggaatgtga tcctgttctc tgtgtttgat gagaacagga   2580
gctggtacct gactgagaac atccagaggt tcctgcccaa ccctgctggg gtgcagctgg   2640
aggaccctga gttccaggcc agcaacatca tgcacagcat caatggctat gtgtttgaca   2700
gcctgcagct gtctgtgtgc ctgcatgagg tggcctactg gtacatcctg agcattgggg   2760
cccagactga cttcctgtct gtgttcttct ctggctacac cttcaagcac aagatggtgt   2820
atgaggacac cctgaccctg ttccccttct ctggggagac tgtgttcatg agcatggaga   2880
accctggcct gtggattctg gctgccaca actctgactt caggaacagg gcatgactg    2940 ccctgctgaa agtctccagc tgtgacaaga acactgggga ctactatgag acagctatg   3000 aggacatctc tgcctacctg ctgagcaaga acaatgccat tgagcccagg agcttcagcc   3060 agaaccccc agtgctgaag aggcaccaga gggagatcac caggaccacc ctgcagtctg   3120
accaggagga gattgactat gatgacacca tctctgtgga gatgaagaag gaggactttg   3180
acatctacga cgaggacgag aaccagagcc caggagctt ccagaagaag accaggcact   3240
acttcattgc tgctgtggag aggctgtggg actatggcat gagcagcagc ccccatgtgc   3300
tgaggaacag ggcccagtct ggctctgtgc cccagttcaa gaaggtggtg ttccaggagt   3360
tcactgatgg tcagcttcacc cagccccctgt acagagggga gctgaatgag cacctgggcc   3420
tgctgggccc ctacatcagg gctgaggtgg aggacaacat catggtgacc ttcaggaacc   3480
```

```
aggccagcag gccctacagc ttctacagca gcctgatcag ctatgaggag gaccagaggc    3540
agggggctga gcccaggaag aactttgtga agcccaatga aaccaagacc tacttctgga    3600
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg caggcaggt  gactgtgcag gagtttgccc    3780
tgttcttcac catctttgat gaaaccaaga gctggtactt cactgagaac atggagagga    3840
actgcagggc ccctgcaac  atccagatgg aggaccccac cttcaaggag aactacaggt    3900
tccatgccat caatggctac atcatggaca ccctgcctgg cctggtgatg gcccaggacc    3960
agaggatcag gtggtacctg ctgagcatgg gcagcaatga aacatccac  agcatccact    4020 tctctggcca tgtgttcact gtgaggaaga aggaggagta caagatgcc  ctgtacaacc    4080 tgtaccctgg ggtgtttgag actgtggaga tgctgcccag caaggctggc atctggaggg    4140
tggagtgcct gattggggag cacctgcatg ctggcatgag cacccctgttc ctggtgtaca    4200 gcaacaagtg ccagaccccc ctgggcatgg cctctggcca catcagggac ttccagatca    4260
ctgcctctgg ccagtatggc cagtgggccc caagctggc  caggctgcac tactctggca    4320
gcatcaatgc ctggagcacc aaggagccct tcagctggat caaggtggac ctgctggccc    4380
ccatgatcat ccatggcatc aagacccagg gggccaggca gaagttcagc agcctgtaca    4440
tcagccagtt catcatcatg tacagcctgg atggcaagaa gtggcagacc tacaggggca    4500
acagcactgg caccctgatg gtgttctttg gcaatgtgga cagctctggc atcaagcaca    4560
acatcttcaa cccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttcacca    4740
acatgtttgc cacctggagc cccagcaagg ccaggctgca cctgcagggc aggagcaatg    4800
cctggaggcc ccaggtcaac aaccccaagg agtggctgca ggtggacttc cagaagacca    4860
tgaaggtgac tgggggtgacc acccagggg  tgaagagcct gctgaccagc atgtatgtga    4920
aggagttcct gatcagcagc agccaggatg gccaccagtg gacccctgttc ttccagaatg    4980 gcaaggtgaa ggtgttccag ggcaaccagg acagcttcac ccctgtggtg aacagcctgg    5040 accccccccct gctgaccaga tacctgagga ttcacccccca gagctgggtg caccagattg    5100
ccctgaggat ggaggtgctg ggctgtgagg cccaggacct gtactgacct cgaggcactg    5160
tcctttccta taaaatgag  gaaattgcat cgcattgtct gagtaggtgt cattctattc    5220
tggggggtgg ggtggggcag gacagcaagg gggaggattg ggaagacaat agcaggcatg    5280
ctggggatgc ggtgggctct atgggcacgt ggcggccgca ggaaccccta gtgatggagt    5340
tggccactcc ctctctgcgc gctcgctcgc tcactgaggc cgggcgacca aggtcgccc    5400 gacgcccggg ctttgcccgg gcggcctcag tgagcgagcg agcgcgcaga gagggagtgg    5460
ccaa                                                                5464
```

<210> SEQ ID NO 14
<211> LENGTH: 6354
<212> TYPE: DNA
<213> ORGANISM: Adeno-Associated Virus 2

<400> SEQUENCE: 14

```
ttggccactc cctctctgcg cgctcgctcg ctcactgagg ccgcccgggc aaagcccggg      60
```

```
cgtcgggcga cctttggtcg cccggcctca gtgagcgagc gagcgcgcag agagggagtg      120
gccaactcca tcactagggg ttcctgcggc cgcacgcgtg tttaaacgtc gacaggttaa      180 ttttaaaaa gcagtcaaaa gtccaagtgg cccttggcag catttactct ctctgtttgc       240
tctggttaat aatctcagga gcacaaacat tcctggaggc aggagaagaa atcaacatcc      300
tggacttatc ctctgggcct ctccccaccc ccaggagagg ctcaggttaa ttttaaaaa      360 gcagtcaaaa gtccaagtgg cccttggcag catttactct ctctgtttgc tctggttaat     420
aatctcagga gcacaaacat tcctggaggc aggagaagaa atcaacatcc tggacttatc     480
ctctgggcct ctccccaccc ccaggagagg ctgtcgactg gacacaggac gctgtggttt     540
ctgagccagg gggcgactca gatcccagcc agtggactta gccctgtttt gctcctccga     600 taactgggt gaccttggtt aatattcacc agcagcctcc cccgttgccc ctctggatcc       660
actgcttaaa tacggacgag gacagggccc tgtctcctca gcttcaggca ccaccactga     720
cctgggacag tgaatcgtaa gtactagcag ctacaatcca gctaccattc tgcttttatt     780
ttatggttgg gataaggctg gattattctg agtccaagct aggcccttt gctaatcatg      840 ttcatacctc ttatcttcct cccacagctc ctgggcaacg tgctggtctg tgtgctggcc     900
catcactttg gcaaagaatt gcgatcgcca ccatgcagat tgagctgagc acctgcttct     960
tcctgtgcct gctgaggttc tgcttctctg ccaccaggag atactacctg ggggctgtgg    1020
agctgagctg gactacatg cagtctgacc tgggggagct gcctgtggat gccaggttcc     1080
cccccagagt gcccaagagc ttccccttca cacctctgt ggtgtacaag aagaccctgt     1140
ttgtggagtt cactgaccac ctgttcaaca ttgccaagcc caggccccc tggatgggcc     1200 tgctgggccc caccatccag gctgaggtgt atgacactgt ggtgatcacc ctgaagaaca    1260
tggccagcca ccctgtgagc ctgcatgctg tgggggtgag ctactggaag gcctctgagg    1320
gggctgagta tgatgaccag accagccaga gggagaagga ggatgacaag gtgttccctg    1380
ggggcagcca cacctatgtg tggcaggtgc tgaaggagaa tggcccatg gcctctgacc     1440 ccctgtgcct gacctacagc tacctgagcc atgtggacct ggtgaaggac ctgaactctg    1500
gcctgattgg ggccctgctg gtgtgcaggg agggcagcct ggccaaggag aagacccaga    1560
ccctgcacaa gttcatcctg ctgtttgctg tgtttgatga gggcaagagc tggcactctg    1620
aaaccaagaa cagcctgatg caggacaggg atgctgcctc tgccagggcc tggcccaaga    1680
tgcacactgt gaatggctat gtgaacagga gcctgcctgg cctgattggc tgccacagga    1740
agtctgtgta ctggcatgtg attggcatgg gcaccacccc tgaggtgcac agcatcttcc    1800
tggagggcca caccttcctg gtcaggaacc acaggcaggc cagcctggag atcagcccca    1860
tcaccttcct gactgcccag accctgctga tggacctggg ccagttcctg ctgttctgcc    1920
acatcagcag ccaccagcat gatggcatgg aggcctatgt gaaggtggac agctgccctg    1980 aggagccca gctgaggatg aagaacaatg aggaggctga ggactatgat gatgacctga     2040
ctgactctga gatggatgtg gtgaggttg atgatgacaa cagccccagc ttcatccaga    2100
tcaggtctgt ggccaagaag caccccaaga cctgggtgca ctacattgct gctgaggagg    2160
aggactggga ctatgccccc ctggtgctgg cccctgatga caggagctac aagagccagt    2220
acctgaacaa tggcccccag aggattggca ggaagtacaa gaaggtcagg ttcatggcct    2280
acactgatga aaccttcaag accagggagg ccatccagca tgagtctggc atcctgggcc    2340
ccctgctgta tggggaggtg ggggacaccc tgctgatcat cttcaagaac caggccagca    2400
ggccctacaa catctacccc catggcatca ctgatgtgag gccctgtac agcaggaggc     2460
```

```
tgcccaaggg ggtgaagcac ctgaaggact tccccatcct gcctggggag atcttcaagt   2520
acaagtggac tgtgactgtg gaggatggcc ccaccaagtc tgaccccagg tgcctgacca   2580
gatactacag cagctttgtg aacatggaga gggacctggc ctctggcctg attggccccc   2640
tgctgatctg ctacaaggag tctgtggacc agaggggcaa ccagatcatg tctgacaaga   2700
ggaatgtgat cctgttctct gtgtttgatg agaacaggag ctggtacctg actgagaaca   2760
tccagaggtt cctgcccaac cctgctgggg tgcagctgga ggaccctgag ttccaggcca   2820
gcaacatcat gcacagcatc aatggctatg tgtttgacag cctgcagctg tctgtgtgcc   2880
tgcatgaggt ggcctactgg tacatcctga gcattgggc ccagactgac ttcctgtctg   2940
tgttcttctc tggctacacc ttcaagcaca agatggtgta tgaggacacc ctgaccctgt   3000
tccccttctc tggggagact gtgttcatga gcatggagaa ccctggcctg tggattctgg   3060
gctgccacaa ctctgacttc aggaacaggg gcatgactgc cctgctgaaa gtctccagct   3120
gtgacaagaa cactggggac tactatgagg acagctatga ggacatctct gcctacctgc   3180
tgagcaagaa caatgccatt gagcccagga gcttcagcca gaaccccca gtgctgaaga   3240 ggcaccagag ggagatcacc aggaccaccc tgcagtctga ccaggaggag attgactatg   3300
atgacaccat ctctgtggag atgaagaagg aggactttga catctacgac gaggacgaga   3360
accagagccc caggagcttc cagaagaaga ccaggcacta cttcattgct gctgtggaga   3420
ggctgtggga ctatggcatg agcagcagcc cccatgtgct gaggaacagg gcccagtctg   3480
gctctgtgcc ccagttcaag aaggtggtgt tccaggagtt cactgatggc agcttcaccc   3540 agccccctgta cagaggggag ctgaatgagc acctgggcct gctgggcccc tacatcaggg   3600
ctgaggtgga ggacaacatc atggtgacct tcaggaacca ggccagcagg ccctacagct   3660
tctacagcag cctgatcagc tatgaggagg accagaggca gggggctgag cccaggaaga   3720
actttgtgaa gcccaatgaa accaagacct acttctggaa ggtgcagcac cacatggccc   3780
ccaccaagga tgagttttgac tgcaaggcct gggcctactt ctctgatgtg gacctggaga   3840
aggatgtgca ctctggcctg attggccccc tgctggtgtg ccacaccaac ccctgaacc   3900 ctgcccatgg caggcaggtg actgtgcagg agtttgccct gttcttcacc atctttgatg   3960
aaaccaagag ctggtacttc actgagaaca tggagaggaa ctgcagggcc ccctgcaaca   4020
tccagatgga ggaccccacc ttcaaggaga actacaggtt ccatgccatc aatggctaca   4080
tcatggacac cctgcctggc ctggtgatgg cccaggacca gaggatcagg tggtacctgc   4140
tgagcatggg cagcaatgag aacatccaca gcatccactt ctctggccat gtgttcactg   4200
tgaggaagaa ggaggagtac aagatggccc tgtacaacct gtaccctggg gtgtttgaga   4260
ctgtggagat gctgcccagc aaggctgca tctggagggt ggagtgcctg attggggagc   4320
acctgcatgc tggcatgagc acccctgttcc tggtgtacag caacaagtgc cagacccccc   4380
tgggcatggc ctctggccac atcagggact tccagatcac tgcctctggc cagtatggcc   4440
agtgggcccc caagctggcc aggctgcact actctggcag catcaatgcc tggagcacca   4500
aggagccctt cagctggatc aaggtggacc tgctggcccc catgatcatc catggcatca   4560
agacccaggg ggccaggcag aagttcagca gcctgtacat cagccagttc atcatcatgt   4620
acagcctgga tggcaagaag tggcagacct acaggggcaa cagcactggc accctgatgg   4680
tgttctttgg caatgtggac agctctggca tcaagcacaa catcttcaac ccccccatca   4740
ttgccagata catcaggctg cacccccacc actacagcat caggagcacc ctgaggatgg   4800
```

```
agctgatggg ctgtgacctg aacagctgca gcatgcccct gggcatggag agcaaggcca   4860
tctctgatgc ccagatcact gccagcagct acttcaccaa catgtttgcc acctggagcc   4920
ccagcaaggc caggctgcac ctgcagggca ggagcaatgc ctggaggccc aggtcaaca    4980
accccaagga gtggctgcag gtggacttcc agaagaccat gaaggtgact gggggtgacca  5040
cccaggggg gaagagcctg ctgaccagca tgtatgtgaa ggagttcctg atcagcagca   5100
gccaggatgg ccaccagtgg accctgttct tccagaatgg caaggtgaag gtgttccagg   5160
gcaaccagga cagcttcacc cctgtggtga acagcctgga ccccccctg ctgaccagat    5220
acctgaggat tcaccccag agctgggtgc accagattgc cctgaggatg gaggtgctgg    5280
gctgtgaggc ccaggacctg tactgacctc gaggtgtgcc ttctagttgc cagccatctg   5340
ttgtttgccc ctccccgtg ccttccttga ccctggaagg tgccactccc actgtccttt    5400
cctaataaaa tgaggaaatt gcatcgcatt gtctgagtag gtgtcattct attctggggg   5460
gtggggtggg gcaggacagc aaggggagg attgggaaga caatagcagg catgctgggg   5520
atgcggtggg ctctatgggc acgtgccctc tcacactacc taaaccacgc caggacaacc   5580
tctgctcctc tccaccgaaa ttccaagggg tcgagtggat gttggaggtg catgggccc    5640
agagaggtct ctgacctctg ccccagctcc aaggtcagca ggcagggagg gctgtgtgtt   5700
tgctgtttgc tgcttgcaat gttgcccat tttagggaca tgagtaggct gaagtttgtt    5760
cagtgtggac ttcagaggca gcacacaaac agctgctgga ggatgggaac tgaggggttg   5820
gaaggggca gggtgagccc agaaactcct gtgtgcctct gagcctgcag ccctctcaca    5880
ctacctaaac cacgccagga caacctctgc tcctctccac cgaaattcca aggggtcgag   5940
tggatgttgg agtgcatg ggcccagaga ggtctctgac ctctgcccca gctccaaggt    6000
cagcaggcag ggaggctgt gtgtttgctg tttgctgctt gcaatgtttg cccattttag   6060
ggacatgagt aggctgaagt tgttcagtg tggacttcag aggcagcaca caaacagctg   6120
ctggaggatg ggaactgagg ggttggaagg gggcagggtg agcccagaaa ctcctgtgtg   6180
cctctgagcc tgcagcacgt ggcggccgca ggaaccccta gtgatggagt tggccactcc   6240
ctctctgcgc gctcgctcgc tcactgaggc cgggcgacca aggtcgccc gacgcccggg   6300
ctttgcccgg gcggcctcag tgagcgagcg agcgcgcaga gagggagtgg ccaa         6354

<210> SEQ ID NO 15
<211> LENGTH: 6308
<212> TYPE: DNA
<213> ORGANISM: Adeno-Associated Virus 2

<400> SEQUENCE: 15
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttaattttta aaaagcagtc   180
aaaagtccaa gtggcccttg gcagcattta ctctctctgt ttgctctggt taataatctc   240
aggagcacaa acattcctgg aggcaggaga agaaatcaac atcctggact tatcctctgg   300
gcctgttaat ttttaaaaag cagtcaaaag tccagtggc ccttggcagc atttactctc    360
tctgtttgct ctggttaata atctcaggag cacaaacatt cctggaggca ggagaagaaa   420
tcaacatcct ggacttatcc tctgggccta ggcctgaggc tggtcaaaat tgaacctcct   480
cctgctctga gcagctgggg gggcagacta agcagaggc tgtgcagacc cacataaaga    540
gcctactgtg tgccaggcac ttcacccgag gcacttcaca agcatgcttg ggaatgaaac   600
```

```
ttccaactct ttgggatgca ggtgaaacag ttcctggttc agagaggtga agcggcctgc    660
ctgaggcagc acagctcttc tttacagatg tgcttcccca cctctaccct gtctcacggc    720
cccccatgcc agcctgacgg ttgtgtctgc ctcagtcatg ctccattttt ccatcgggac    780
catcaagagg gtgtttgtgt ctaaggctga ctgggtaact ttggatgagc ggtctctccg    840
ctctgagcct gtttcctcat ctgtcaaatg gctctaacc cactctgatc tcccagggcg     900
gcagtaagtc ttcagcatca ggcattttgg ggtgactcag taaatggtag atcttgctac    960
cagtggaaca gccactaagg attctgcagt gagagcagag ggccagctaa gtggtactct   1020
cccagagact gtctgactca cgccacccc tccaccttgg acacaggacg ctgtggtttc    1080
tgagccaggt acaatgactc ctttcggtaa gtgcagtgga agctgtacac tgcccaggca   1140
aagcgtccgg gcagcgtagg cgggcgactc agatcccagc cagtggactt agcccctgtt   1200
tgctcctccg ataactgggg tgaccttggt taatattcac cagcagcctc cccgttgcc    1260 cctctggatc cactgcttaa atacggacga ggacagggcc ctgtctcctc agcttcaggc   1320
accaccactg acctgggaca gtgaatcgta agtactagca gctacaatcc agctaccatt   1380
ctgcttttat tttatggttg ggataaggct ggattattct gagtccaagc taggcccttt   1440
tgctaatcat gttcatacct cttatcttcc tcccacagct cctgggcaac gtgctggtct   1500
gtgtgctggc ccatcacttt ggcaaagaat tgcgatcgcc accatgcaga ttgagctgag   1560
cacctgcttc ttcctgtgcc tgctgaggtt ctgcttctct gccaccagga gatactacct   1620 ggggggctgtg gagctgagct gggactacat gcagtctgac ctgggggagc tgcctgtgga   1680
tgccaggttc ccccccagag tgcccaagag cttccccttc aacacctctg tggtgtacaa   1740
gaagaccctg tttgtggagt tcactgacca cctgttcaac attgccaagc ccaggccccc   1800
ctggatgggc ctgctgggcc ccaccatcca ggctgaggtg tatgacactg tggtgatcac   1860
cctgaagaac atggccagcc accctgtgag cctgcatgct gtgggggtga gctactggaa   1920
ggcctctgag ggggctgagt atgatgacca gaccagccag agggagaagg aggatgacaa   1980
ggtgttccct gggggcagcc acacctatgt gtggcaggtg ctgaaggaga atggcccat    2040 ggcctctgac cccctgtgcc tgacctacag ctacctgagc catgtggacc tggtgaagga   2100
cctgaactct ggcctgattg gggcctgct ggtgtgcagg gagggcagcc tggccaagga    2160
gaagacccag accctgcaca gttcatcct gctgtttgct gtgtttgatg agggcaagag    2220
ctggcactct gaaaccaaga acagcctgat gcaggacagg gatgctgcct ctgccagggc   2280
ctggcccaag atgcacactg tgaatggcta tgtgaacagg agcctgcctg gcctgattgg   2340
ctgccacagg aagtctgtgt actggcatgt gattggcatg ggcaccaccc tgaggtgca   2400 cagcatcttc ctggagggcc acaccttcct ggtcaggaac cacaggcagg ccagcctgga   2460
gatcagcccc atcaccttcc tgactgccca gaccctgctg atggacctgg gccagttcct   2520
gctgttctgc cacatcagca gccaccagca tgatggcatg gaggcctatg tgaaggtgga   2580
cagctgccct gaggagcccc agctgaggat gaagaacaat gaggaggctg aggactatga   2640
tgatgacctg actgactctg agatggatgt ggtgaggttt gatgatgaca acagccccag   2700
cttcatccag atcaggtctg tggccaagaa gcaccccaag acctgggtgc actacattgc   2760
tgctgaggag gaggactggg actatgcccc cctggtgctg gcccctgatg acaggagcta   2820
caagagccaa tacctgaaca atggccccca gaggattggc aggaagtaca agaaggtcag   2880
gttcatggcc tacactgatg aaaccttcaa gaccaggggag gccatccagc atgagtctgg   2940
```

-continued

| | |
|---|---|
| catcctgggc ccccctgctgt atggggaggt gggggacacc ctgctgatca tcttcaagaa | 3000 |
| ccaggccagc aggccctaca acatctaccc ccatggcatc actgatgtga ggccctgta | 3060 |
| cagcaggagg ctgcccaagg gggtgaagca cctgaaggac ttccccatcc tgcctggga | 3120 |
| gatcttcaag tacaagtgga ctgtgactgt ggaggatggc cccaccaagt ctgaccccag | 3180 |
| gtgcctgacc agatactaca gcagctttgt gaacatggag agggacctgg cctctggcct | 3240 |
| gattggcccc ctgctgatct gctacaagga gtctgtggac cagaggggca accagatcat | 3300 |
| gtctgacaag aggaatgtga tcctgttctc tgtgtttgat gagaacagga gctggtacct | 3360 |
| gactgagaac atccagaggt tcctgcccaa ccctgctggg gtgcagctgg aggaccctga | 3420 |
| gttccaggcc agcaacatca tgcacagcat caatggctat gtgtttgaca gcctgcagct | 3480 |
| gtctgtgtgc ctgcatgagg tggcctactg gtacatcctg agcattgggg cccagactga | 3540 |
| cttcctgtct gtgttcttct ctggctacac cttcaagcac aagatggtgt atgaggacac | 3600 |
| cctgaccctg ttccccttct ctggggagac tgtgttcatg agcatggaga ccctggcct | 3660 |
| gtggattctg ggctgccaca actctgactt caggaacagg gcatgactg ccctgctgaa | 3720 |
| agtctccagc tgtgacaaga acactgggga ctactatgag acagctatg aggacatctc | 3780 |
| tgcctacctg ctgagcaaga acaatgccat tgagcccagg agcttcagcc agaaccccc | 3840 |
| agtgctgaag aggcaccaga gggagatcac caggaccacc ctgcagtctg accaggagga | 3900 |
| gattgactat gatgacacca tctctgtgga gatgaagaag gaggactttg acatctacga | 3960 |
| cgaggacgag aaccagagcc caggagctt ccagaagaag accaggcact acttcattgc | 4020 |
| tgctgtggag aggctgtggg actatggcat gagcagcagc ccccatgtgc tgaggaacag | 4080 |
| ggcccagtct ggctctgtgc cccagttcaa gaaggtggtg ttccaggagt tcactgatgg | 4140 |
| cagcttcacc cagcccctgt acagagggga gctgaatgag cacctgggcc tgctgggccc | 4200 |
| ctacatcagg gctgaggtgg aggacaacat catggtgacc ttcaggaacc aggccagcag | 4260 |
| gccctacagc ttctacagca gcctgatcag ctatgaggag gaccagaggc aggggctga | 4320 |
| gcccaggaag aactttgtga agcccaatga aaccaagacc tacttctgga aggtgcagca | 4380 |
| ccacatggcc cccaccaagg atgagtttga ctgcaaggcc tggcctact ctctgatgt | 4440 |
| ggacctggag aaggatgtgc actctggcct gattggcccc ctgctggtgt gccacaccaa | 4500 |
| caccctgaac cctgcccatg gcaggcaggt gactgtgcag gagtttgccc tgttcttcac | 4560 |
| catctttgat gaaaccaaga gctggtactt cactgagaac atggagagga actgcagggc | 4620 |
| cccctgcaac atccagatgg aggacccac cttcaaggag aactacaggt tccatgccat | 4680 |
| caatggctac atcatggaca ccctgcctgg cctggtgatg gcccaggacc agaggatcag | 4740 |
| gtggtacctg ctgagcatgg gcagcaatga gaacatccac agcatccact tctctggcca | 4800 |
| tgtgttcact gtgaggaaga aggaggagta caagatggcc ctgtacaacc tgtaccctgg | 4860 |
| ggtgtttgag actgtggaga tgctgcccag caaggctggc atctggaggg tggagtgcct | 4920 |
| gattggggag cacctgcatg ctggcatgag cacccctgttc ctggtgtaca gcaacaagtg | 4980 |
| ccagaccccc ctgggcatgg cctctggcca catcagggac ttccagatca ctgcctctgg | 5040 |
| ccagtatggc cagtgggccc ccaagctggc caggctgcac tactctggca gcatcaatgc | 5100 |
| ctggagcacc aaggagccct tcagctggat caaggtggac ctgctggccc ccatgatcat | 5160 |
| ccatggcatc aagacccagg gggcaggca gaagttcagc agcctgtaca tcagccagtt | 5220 |
| catcatcatg tacagcctgg atggcaagaa gtggcagacc tacaggggca acagcactgg | 5280 |
| caccctgatg gtgttctttg gcaatgtgga cagctctggc atcaagcaca acatcttcaa | 5340 |

```
cccccccatc attgccagat acatcaggct gcaccccacc cactacagca tcaggagcac    5400
cctgaggatg gagctgatgg gctgtgacct gaacagctgc agcatgcccc tgggcatgga    5460
gagcaaggcc atctctgatg cccagatcac tgccagcagc tacttcacca acatgtttgc    5520
cacctggagc cccagcaagg ccaggctgca cctgcagggc aggagcaatg cctggaggcc    5580
ccaggtcaac aaccccaagg agtggctgca ggtggacttc agaagacca tgaaggtgac     5640 tggggtgacc acccagggg tgaagagcct gctgaccagc atgtatgtga aggagttcct    5700
gatcagcagc agccaggatg gccaccagtg gaccctgttc ttccagaatg caaggtgaa    5760 ggtgttccag gcaaccagg acagcttcac ccctgtggtg aacagcctgg acccccccct    5820
gctgaccaga tacctgagga ttcaccccca gagctgggtg caccagattg ccctgaggat    5880
ggaggtgctg ggctgtgagg cccaggacct gtactgacct cgagctgtgc cttctagttg    5940
ccagccatct gttgtttgcc cctcccccgt gccttccttg accctggaag gtgccactcc    6000
cactgtcctt tcctaataaa atgaggaaat tgcatcgcat tgtctgagta ggtgtcattc    6060
tattctgggg ggtggggtgg ggcaggacag caaggggag gattgggaag acaatagcag    6120
gcatgctggg gatgcggtgg gctctatgga ccggtgcggc cgcaggaacc cctagtgatg    6180
gagttggcca ctccctctct gcgcgctcgc tcgctcactg aggccgggcg accaaaggtc    6240
gcccgacgcc cgggctttgc ccgggcggcc tcagtgagcg agcgagcgcg cagagaggga    6300
gtggccaa                                                            6308

<210> SEQ ID NO 16
<211> LENGTH: 5635
<212> TYPE: DNA
<213> ORGANISM: Adeno-Associate Virus 2

<400> SEQUENCE: 16
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttaattttta aaaagcagtc     180
aaaagtccaa gtggcccttg gcagcattta ctctctctgt ttgctctggt taataatctc     240
aggagcacaa acattcctgg aggcaggaga agaaatcaac atcctggact tatcctctgg     300
gcctgttaat ttttaaaaag cagtcaaaag tccaagtggc ccttggcagc atttactctc     360
tctgtttgct ctggttaata atctcaggag cacaaacatt cctggaggca ggagaagaaa     420
tcaacatcct ggacttatcc tctgggccta gtcgactgga cacaggacgc tgtggtttct     480
gagccagggg gcgactcaga tcccagccag tggacttagc ccctgtttgc tcctccgata     540
actggggtga ccttggttaa tattcaccag cagcctcccc cgttgcccct ctggatccac     600
tgcttaaata cggacgagga cagggccctg tctcctcagc ttcaggcacc accactgacc     660
tgggacagta atcgtaagt actagcagct acaatccagc taccattctg ctttttatttt     720 atggttggga taaggctgga ttattctgag tccaagctag gccttttgc taatcatgtt      780 catacctctt atcttcctcc cacagctcct gggcaacgtg ctggtctgtg tgctggccca    840
tcactttggc aaagaattgc gatcgccacc atgcagatta gctgagcac ctgcttcttc     900 ctgtgcctgc tgaggttctg cttctctgcc accaggagat actacctggg ggctgtggag    960
ctgagctggg actacatgca gtctgacctg ggggagctgc ctgtggatgc aggttcccc    1020 cccagagtgc ccaagagctt ccccttcaac acctctgtgg tgtacaagaa gaccctgttt    1080
```

```
gtggagttca ctgaccacct gttcaacatt gccaagccca ggccccctg datgggcctg    1140 ctgggcccca ccatccaggc tgaggtgtat gacactgtgg tgatcaccct gaagaacatg    1200
gccagccacc ctgtgagcct gcatgctgtg ggggtgagct actggaaggc ctctgagggg    1260
gctgagtatg atgaccagac cagccagagg gagaaggagg atgacaaggt gttccctggg    1320
ggcagccaca cctatgtgtg gcaggtgctg aaggagaatg gccccatggc ctctgacccc    1380
ctgtgcctga cctacagcta cctgagccat gtggacctgg tgaaggacct gaactctggc    1440
ctgattgggg ccctgctggt gtgcagggag ggcagcctgg ccaaggagaa gacccagacc    1500
ctgcacaagt tcatcctgct gtttgctgtg tttgatgagg gcaagagctg gcactctgaa    1560
accaagaaca gcctgatgca ggacagggat gctgcctctg ccagggcctg gcccaagatg    1620
cacactgtga atggctatgt gaacaggagc ctgcctggcc tgattggctg ccacaggaag    1680
tctgtgtact ggcatgtgat tggcatgggc accacccctg aggtgcacag catcttcctg    1740
gagggccaca ccttcctggt caggaaccac aggcaggcca gcctggagat cagccccatc    1800
accttcctga ctgcccagac cctgctgatg gacctgggcc agttcctgct gttctgccac    1860
atcagcagcc accagcatga tggcatggag gcctatgtga aggtggacag ctgccctgag    1920
gagccccagc tgaggatgaa gaacaatgag gaggctgagg actatgatga tgacctgact    1980
gactctgaga tggatgtggt gaggtttgat gatgacaaca gccccagctt catccagatc    2040
aggtctgtgg ccaagaagca ccccaagacc tgggtgcact acattgctgc tgaggaggag    2100
gactgggact atgccccct ggtgctggcc cctgatgaca ggagctacaa gagccagtac    2160
ctgaacaatg gccccagag gattggcagg aagtacaaga aggtcaggtt catggcctac    2220
actgatgaaa ccttcaagac cagggaggcc atccagcatg agtctggcat cctgggcccc    2280
ctgctgtatg gggaggtggg ggacaccctg ctgatcatct tcaagaacca ggccagcagg    2340
ccctacaaca tctaccccca tggcatcact gatgtgaggc ccctgtacag caggaggctg    2400
cccaaggggg tgaagcacct gaaggacttc cccatcctgc ctggggagat cttcaagtac    2460
aagtggactg tgactgtgga ggatggcccc accaagtctg accccaggtg cctgaccaga    2520
tactacagca gctttgtgaa catggagagg gacctggcct ctggcctgat ggcccctg    2580 ctgatctgct acaaggagtc tgtggaccag aggggcaacc agatcatgtc tgacaagagg    2640
aatgtgatcc tgttctctgt gtttgatgag aacaggagc ggtacctgac tgagaacatc    2700
cagaggttcc tgcccaaccc tgctggggtg cagctggagg accctgagtt ccaggccagc    2760
aacatcatgc acagcatcaa tggctatgtg tttgacagcc tgcagctgtc tgtgtgcctg    2820
catgaggtgg cctactggta tcctgagac attggggccc agactgactt cctgtctgtg    2880
ttcttctctg gctacacctt caagcacaag atggtgtatg aggacaccct gaccctgttc    2940
cccttctctg gggagactgt gttcatgagc atggagaacc ctggcctgtg gattctgggc    3000
tgccacaact ctgacttcag gaacaggggc atgactgccc tgctgaaagt ctccagctgt    3060
gacaagaaca ctgggactac tatgaggac agctatgagg acatctctgc ctacctgctg    3120
agcaagaaca atgccattga gccaggagc ttcagccaga acccccagt gctgaagagg    3180 caccagaggg agatcaccag gaccaccctg cagtctgacc aggaggagat tgactatgat    3240
gacaccatct ctgtggagat gaagaaggag gactttgaca tctacgacga ggacgagaac    3300
cagagcccca ggagcttcca gaagaagacc aggcactact tcattgctgc tgtggagagg    3360
ctgtgggact atggcatgag cagcagcccc catgtgctga ggaacagggc ccagtctggc    3420
tctgtgcccc agttcaagaa ggtggtgttc caggagttca ctgatggcag cttcacccag    3480
```

```
ccctgtaca gaggggagct gaatgagcac ctgggcctgc tgggccccta catcagggct    3540
gaggtggagg acaacatcat ggtgaccttc aggaaccagg ccagcaggcc ctacagcttc    3600
tacagcagcc tgatcagcta tgaggaggac cagaggcagg gggctgagcc caggaagaac    3660
tttgtgaagc ccaatgaaac caagacctac ttctggaagg tgcagcacca catggccccc    3720
accaaggatg agtttgactg caaggcctgg gcctacttct ctgatgtgga cctggagaag    3780
gatgtgcact ctggcctgat tgcccccctg ctggtgtgcc acaccaacac cctgaaccct    3840
gcccatggca ggcaggtgac tgtgcaggag tttgccctgt tcttcaccat ctttgatgaa    3900
accaagagct ggtacttcac tgagaacatg gagaggaact gcagggcccc ctgcaacatc    3960
cagatggagg accccacctt caaggagaac tacaggttcc atgccatcaa tggctacatc    4020
atggacaccc tgcctggcct ggtgatggcc caggaccaga ggatcaggtg gtacctgctg    4080
agcatgggca gcaatgagaa catccacagc atccacttct ctggccatgt gttcactgtg    4140
aggaagaagg aggagtacaa gatggccctg tacaacctgt accctggggt gtttgagact    4200
gtggagatgc tgcccagcaa ggctggcatc tggaggg tgg agtgcctgat tggggagcac    4260
ctgcatgctg gcatgagcac cctgttcctg gtgtacagca acaagtgcca gacccccctg    4320
ggcatggcct ctggccacat cagggacttc cagatcactg cctctggcca gtatggccag    4380
tgggccccca gctggccag gctgcactac tctggcagca tcaatgcctg gagcaccaag    4440
gagcccttca gctggatcaa ggtggacctg ctggccccca tgatcatcca tggcatcaag    4500
acccagggg gccaggcagaa gttcagcagc ctgtacatca gccagttcat catcatgtac    4560
agcctggatg gcaagaagtg gcagacctac aggggcaaca gcactggcac cctgatggtg    4620
ttctttggca atgtggacag ctctggcatc aagcacaaca tcttcaaccc ccccatcatt    4680
gccagataca tcaggctgca ccccacccac tacagcatca ggagcaccct gaggatggag    4740
ctgatgggct gtgacctgaa cagctgcagc atgcccctgg gcatggagag caaggccatc    4800
tctgatgccc agatcactgc cagcagctac ttcaccaaca tgtttgccac ctggagcccc    4860
agcaaggcca ggctgcacct gcagggcagg agcaatgcct ggaggccca ggtcaacaac    4920
cccaaggagt ggctgcaggt ggacttccag aagaccatga aggtgactgg ggtgaccacc    4980
caggggtga gagcctgct gaccagcatg tatgtgaagg agttcctgat cagcagcagc    5040
caggatggcc accagtggac cctgttcttc cagaatggca aggtgaaggt gttccagggc    5100
aaccaggaca gcttcacccc tgtggtgaac agcctggacc ccccctgct gaccagatac    5160
ctgaggattc accccagag ctgggtgcac cagattgccc tgaggatgga ggtgctgggc    5220
tgtgaggccc aggacctgta ctgacctcga gctgtgcctt ctagttgcca gccatctgtt    5280
gtttgcccct cccccgtgcc ttccttgacc ctggaaggtg ccactcccac tgtcctttcc    5340
taataaaatg aggaaattgc atcgcattgt ctgagtaggt gtcattctat tctggggggt    5400
ggggtggggc aggacagcaa gggggaggat tggaagaca atagcaggca tgctgggat    5460
gcggtgggct ctatggaccg gtgcggccgc aggaaccct agtgatggag ttggccactc    5520
cctctctgcg cgctcgctcg ctcactgagg ccgggcgacc aaaggtcgcc cgacgcccgg    5580
gctttgcccg gcggcctcca gtgagcgagc gagcgcgcag agagggagtg gccaa         5635
```

<210> SEQ ID NO 17
<211> LENGTH: 6962
<212> TYPE: DNA
<213> ORGANISM: Adeno-Associated Virus 2

<400> SEQUENCE: 17

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgta ggctcagagg cacacaggag     180
tttctgggct caccctgccc ccttccaacc cctcagttcc catcctccag cagctgtttg     240
tgtgctgcct ctgaagtcca cactgaacaa acttcagcct actcatgtcc ctaaaatggg     300
caaacattgc aagcagcaaa cagcaaacac acagccctcc ctgcctgctg accttggagc     360
tggggcagag gtcagagacc tctctgggcc catgccacct ccaacatcca ctcgacccct     420
tggaatttcg gtggagagga gcagaggttg tcctggcgtg gtttaggtag tgtgagaggg     480
gtcgacaggc tcagaggcac acaggagttt ctgggctcac cctgccccct tccaacccct     540
cagttcccat cctccagcag ctgtttgtgt gctgcctctg aagtccacac tgaacaaact     600
tcagcctact catgtcccta aaatgggcaa acattgcaag cagcaaacag caaacacaca     660
gccctccctg cctgctgacc ttggagctgg ggcagaggtc agagacctct ctgggcccat     720
gccacctcca acatccactc gaccccttgg aatttcggtg gagaggagca gaggttgtcc     780
tggcgtggtt taggtagtgt gagaggggtc gacgttaatt tttaaaaagc agtcaaaagt     840
ccaagtggcc cttggcagca tttactctct ctgtttgctc tggttaataa tctcaggagc     900
acaaacattc ctggaggcag gagaagaaat caacatcctg gacttatcct ctgggcctgt     960
taatttttaa aaagcagtca aaagtccaag tggcccttgg cagcatttac tctctctgtt    1020
tgctctggtt aataatctca ggagcacaaa cattcctgga ggcaggagaa gaaatcaaca    1080
tcctggactt atcctctggg cctaggcctg aggctggtca aaattgaacc tcctcctgct    1140
ctgagcagcc tgggggggcag actaagcaga gggctgtgca gacccacata agagcctac    1200
tgtgtgccag gcacttcacc cgaggcactt cacaagcatg cttgggaatg aaacttccaa    1260
ctctttggga tgcaggtgaa acagttcctg gttcagagag gtgaagcggc ctgcctgagg    1320
cagcacagct cttctttaca gatgtgcttc cccacctcta ccctgtctca cggcccccca    1380
tgccagcctg acgttgtgt ctgcctcagt catgctccat ttttccatcg ggaccatcaa    1440
gagggtgttt gtgtctaagg ctgactgggt aactttggat gagcggtctc tccgctctga    1500
gcctgtttcc tcatctgtca aatgggctct aacccactct gatctcccag ggcggcagta    1560
agtcttcagc atcaggcatt tggggtgac tcagtaaatg gtagatcttg ctaccagtgg     1620
aacagccact aaggattctg cagtgagagc agagggccag ctaagtggta ctctcccaga    1680
gactgtctga ctcacgccac ccctccacc ttggacacag gacgctgtgg tttctgagcc     1740
aggtacaatg actcctttcg gtaagtgcag tggaagctgt acactgccca ggcaaagcgt    1800
ccgggcagcg taggcgggcg actcagatcc cagccagtgg acttagcccc tgtttgctcc    1860
tccgataact ggggtgacct tggttaatat tcaccagcag cctccccgt tgcccctctg     1920
gatccactgc ttaaatacgg acgaggacag ggccctgtct cctcagcttc aggcaccacc    1980
actgacctgg gacagtgaat cgtaagtact agcagctaca atccagctac cattctgctt    2040
ttatttatg gttgggataa ggctggatta ttctgagtcc aagctaggcc ttttgctaa     2100
tcatgttcat acctcttatc ttcctcccac agctcctggg caacgtgctg gtctgtgtgc    2160
tggcccatca ctttggcaaa gaattgcgat cgccaccatg cagattgagc tgagcacctg    2220
cttcttcctt tgcctgctga ggttctgctt ctctgccacc aggagatact acctgggggc    2280
tgtggagctg agctgggact acatgcagtc tgacctgggg gagctgcctg tggatgccag    2340
```

```
gttccccccc agagtgccca agagcttccc cttcaacacc tctgtggtgt acaagaagac   2400
cctgtttgtg gagttcactg accacctgtt caacattgcc aagcccaggc cccctggat   2460 gggcctgctg gccccacca tccaggctga ggtgtatgac actgtggtga tcacctgaa    2520 gaacatggcc agccaccctg tgagcctgca tgctgtgggg gtgagctact ggaaggcctc   2580
tgagggggct gagtatgatg accagaccag ccagagggag aaggaggatg caaggtgtt   2640 ccctgggggc agccacacct atgtgtggca ggtgctgaag gagaatggcc ccatggcctc   2700
tgaccccctg tgcctgacct acagctacct gagccatgtg gacctggtga aggacctgaa   2760
ctctggcctg attggggccc tgctggtgtg cagggagggc agcctggcca aggagaagac   2820
ccagaccctg cacaagttca tcctgctgtt tgctgtgttt gatgagggca gagctggca   2880 ctctgaaacc aagaacagcc tgatgcagga caggatgct gcctctgcca gggcctggcc   2940
caagatgcac actgtgaatg ctatgtgaa caggagcctg cctggcctga ttggctgcca   3000
caggaagtct gtgtactggc atgtgattgg catgggcacc accctgagg tgcacagcat   3060 cttcctggag ggccacacct tcctggtcag gaaccacagg caggccagcc tggagatcag   3120
ccccatcacc ttcctgactg cccagaccct gctgatggac ctgggccagt tcctgctgtt   3180
ctgccacatc agcagccacc agcatgatgg catggaggcc tatgtgaagg tggacagctg   3240
ccctgaggag ccccagctga ggatgaagaa caatgaggag gctgaggact atgatgatga   3300
cctgactgac tctgagatgg atgtggtgag gtttgatgat gacaacagcc ccagcttcat   3360
ccagatcagg tctgtggcca agaagcaccc caagacctgg gtgcactaca ttgctgctga   3420
ggaggaggac tgggactatg cccccctggt gctggcccct gatgacagga gctacaagag   3480
ccagtacctg aacaatggcc cccagaggat tggcaggaag tacaagaagg tcaggttcat   3540
ggcctacact gatgaaacct tcaagaccag ggaggccatc cagcatgagt ctggcatcct   3600 gggcccctg ctgtatgggg aggtgggga caccctgctg atcatcttca agaaccaggc   3660
cagcaggccc tacaacatct accccatgg catcactgat gtgaggcccc tgtacagcag   3720
gaggctgccc aaggggtga agcacctgaa ggacttcccc atcctgcctg gggagatctt   3780
caagtacaag tggactgtga ctgtggagga tggcccacc aagtctgacc ccaggtgcct   3840
gaccagatac tacagcagct tgtgaacat ggagagggac ctggcctctg gcctgattgg   3900 cccctgctg atctgctaca aggagtctgt ggaccagagg ggcaaccaga tcatgtctga   3960
caagaggaat gtgatcctgt tctctgtgtt tgatgagaac aggagctggt acctgactga   4020
gaacatccag aggttcctgc ccaaccctgc tggggtgcag ctggaggacc ctgagttcca   4080
ggccagcaac atcatgcaca gcatcaatgg ctatgtgttt gacagcctgc agctgtctgt   4140
gtgcctgcat gaggtggcct actggtacat cctgagcatt ggggccaga ctgacttcct   4200 gtctgtgttc ttctctggct acaccttcaa gcacaagatg gtgtatgagg acccctgac    4260 cctgttcccc ttctctgggg agactgtgtt catgagcatg gagaaccctg cctgtggat    4320 tctgggctgc acaactctg acttcaggaa caggggcatg actgccctgc tgaaagtctc   4380
cagctgtgac aagaacactg gggactacta tgaggacagc tatgaggaca tctctgccta   4440
cctgctgagc aagaacaatg ccattgagcc caggagcttc agccagaacc ccccagtgct   4500
gaagaggcac cagagggaga tcaccaggac cacccctgcag tctgaccagg aggagattga   4560
ctatgatgac accatctctg tggagatgaa gaaggaggac tttgacatct acgacgagga   4620
cgagaaccag agcccagga gcttccagaa gaagaccagg cactacttca ttgctgctgt   4680
```

```
ggagaggctg tgggactatg gcatgagcag cagcccccat gtgctgagga acagggccca    4740
gtctggctct gtgccccagt tcaagaaggt ggtgttccag gagttcactg atggcagctt    4800
cacccagccc ctgtacagag gggagctgaa tgagcacctg ggcctgctgg cccctacat     4860
cagggctgag gtgaggaca acatcatggt gaccttcagg aaccaggcca gcaggccta     4920
cagcttctac agcagcctga tcagctatga ggaggaccag aggcagggg ctgagcccag    4980
gaagaacttt gtgaagccca atgaaaccaa gacctacttc tggaaggtgc agcaccacat   5040
ggccccacc aaggatgagt ttgactgcaa ggcctgggcc tacttctctg atgtggacct    5100
ggagaaggat gtgcactctg gcctgattgg ccccctgctg gtgtgccaca ccaacaccct   5160
gaaccctgcc catggcaggc aggtgactgt gcaggagttt gccctgttct tcaccatctt   5220
tgatgaaacc aagagctggt acttcactga gaacatggag aggaactgca gggcccctg    5280
caacatccag atggaggacc ccaccttcaa ggagaactac aggttccatg ccatcaatgg   5340
ctacatcatg gacaccctgc ctggcctggt gatggcccag gaccagagga tcaggtggta   5400
cctgctgagc atgggcagca atgagaacat ccacagcatc cacttctctg gccatgtgtt   5460
cactgtgagg aagaaggagg agtacaagat ggcctgtac aacctgtacc tggggtgtt    5520
tgagactgtg gagatgctgc ccagcaaggc tggcatctgg agggtggagt gcctgattgg   5580
ggagcacctg catgctggca tgagcaccct gttcctggtg tacagcaaca agtgccagac   5640
cccctgggc atggcctctg gccacatcag ggacttccag atcactgcct ctggccagta   5700
tggccagtgg gcccccaagc tggccaggct gcactactct ggcagcatca atgcctggag   5760
caccaaggag cccttcagct ggatcaaggt ggacctgctg gcccccatga tcatccatgg   5820
catcaagacc cagggggcca ggcagaagtt cagcagcctg tacatcagcc agttcatcat   5880
catgtacagc ctgatggca agaagtggca gacctacagg ggcaacagca ctggcaccct   5940
gatggtgttc tttggcaatg tggacagctc tggcatcaag cacaacatct tcaaccccc    6000
catcattgcc agatacatca ggctgcaccc caccactac agcatcagga gcaccctgag   6060
gatggagctg atgggctgtg acctgaacag ctgcagcatg ccctgggca tggagagcaa   6120
ggccatctct gatgcccaga tcactgccag cagctacttc accaacatgt ttgccacctg   6180
gagccccagc aaggccaggc tgcacctgca gggcaggagc aatgcctgga ggccccaggt   6240
caacaacccc aaggagtggc tgcaggtgga cttccagaag accatgaagg tgactggggt   6300
gaccacccag ggggtgaaga gcctgctgac cagcatgtat gtgaaggagt tcctgatcag   6360
cagcagccag gatggccacc agtggaccct gttcttccag aatggcaagg tgaaggtgtt   6420
ccagggcaac caggacagct tcaccctgt ggtgaacagc ctggaccccc ccctgctgac    6480
cagatacctg aggattcacc cccagagctg ggtgcaccag attgccctga ggatggaggt   6540
gctgggctgt gaggcccagg acctgtactg aacctcgagct gtgccttcta gttgccagcc   6600
atctgttgtt tgcccctccc ccgtgccttc cttgaccctg gaaggtgcca ctcccactgt   6660
ccttttcctaa taaaatgagg aaattgcatc gcattgtctg agtaggtgtc attctattct   6720
gggggtggg gtgggcagg acagcaaggg ggaggattgg gaagacaata gcaggcatgc     6780
tggggatgcg gtgggctcta tggaccggt cggccgcagg aaccccctagt gatggagttg    6840
gccactccct ctctgcgcgc tcgctcgctc actgaggccg gcgaccaaa ggtcgcccga    6900
cgcccgggct ttgcccgggc ggcctcagtg agcgagcgag cgcgcagaga gggagtggcc   6960
aa                                                                  6962
```

<210> SEQ ID NO 18
<211> LENGTH: 6289
<212> TYPE: DNA
<213> ORGANISM: Adeno-Associated Virus 2

<400> SEQUENCE: 18

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgta ggctcagagg cacacaggag     180
tttctgggct caccctgccc ccttccaacc cctcagttcc catcctccag cagctgtttg     240
tgtgctgcct ctgaagtcca cactgaacaa acttcagcct actcatgtcc ctaaaatggg     300
caaacattgc aagcagcaaa cagcaaacac acagccctcc ctgcctgctg accttggagc     360
tggggcagag gtcagagacc tctctgggcc catgccacct ccaacatcca ctcgacccct     420
tggaatttcg gtggagagga gcagaggttg tcctggcgtg gtttaggtag tgtgagaggg     480
gtcgacaggt tcagaggcac acaggagttt ctgggctcac cctgcccct tccaacccct     540 cagttcccat cctccagcag ctgtttgtgt gctgcctctg aagtccacac tgaacaaact     600
tcagcctact catgtcccta aaatgggcaa acattgcaag cagcaaacag caaacacaca     660
gccctccctg cctgctgacc ttggagctgg ggcagaggtc agagacctct ctgggcccat     720
gccacctcca acatccactc gaccccttgg aatttcggtg gagaggagca gaggttgtcc     780
tggcgtggtt aggtagtgt gagaggggtc gacgttaatt tttaaaaagc agtcaaaagt     840
ccaagtggcc cttggcagca tttactctct ctgtttgctc tggttaataa tctcaggagc     900
acaaacattc ctggaggcag gagaagaaat caacatcctg gacttatcct ctgggcctgt     960 taattttaa aaagcagtca aaagtccaag tggcccttgg cagcatttac tctctctgtt    1020
tgctctggtt aataatctca ggagcacaaa cattcctgga ggcaggagaa gaaatcaaca    1080
tcctggactt atcctctggg cctagtcgac tggacacagg acgctgtggt ttctgagcca    1140
gggggcgact cagatcccag ccagtggact tagcccctgt tgctcctcc gataactggg    1200 gtgaccttgg ttaatattca ccagcagcct ccccgttgc ccctctggat ccactgctta    1260
aatacggacg aggacagggc cctgtctcct cagcttcagg caccaccact gacctgggac    1320
agtgaatcgt aagtactagc agctacaatc cagctaccat tctgcttta ttttatggtt    1380 gggataaggc tggattattc tgagtccaag ctaggcccttt tgctaatca tgttcatacc    1440 tcttatcttc ctcccacagc tcctgggcaa cgtgctggtc tgtgtgctgg cccatcactt    1500
tggcaaagaa ttgcgatcgc caccatgcag attgagctga gcacctgctt cttcctgtgc    1560
ctgctgaggt tctgcttctc tgccaccagg agatactacc tggggctgt ggagctgagc    1620 tgggactaca tgcagtctga cctggggag ctgcctgtgg atgccaggtt ccccccagag    1680
gtgcccaaga gcttcccctt caacacctct gtggtgtaca agaagaccct gtttgtggag    1740
ttcactgacc acctgttcaa cattgccaag cccaggcccc ctggatggg cctgctgggc    1800 cccaccatcc aggctgaggt gtatgacact gtggtgatca ccctgaagaa catggccagc    1860
caccctgtga gctgcatgc tgtgggggtg agctactgga aggcctctga ggggctgag    1920 tatgatgacc agaccagcca gagggagaag gaggatgaca aggtgttccc tggggcagc    1980 cacacctatg tgtggcaggt gctgaaggag aatggcccca tggcctctga ccccctgtgc    2040
ctgacctaca gctacctgag ccatgtggac ctggtgaagg acctgaactc tggcctgatt    2100
ggggccctgc tggtgtgcag ggaggggcagc ctggccaagg agaagaccca gaccctgcac    2160
```

```
aagttcatcc tgctgtttgc tgtgtttgat gagggcaaga gctggcactc tgaaaccaag    2220
aacagcctga tgcaggacag ggatgctgcc tctgccaggg cctggcccaa gatgcacact    2280
gtgaatggct atgtgaacag gagcctgcct ggcctgattg gctgccacag gaagtctgtg    2340
tactggcatg tgattggcat gggcaccacc cctgaggtgc acagcatctt cctggagggc    2400
cacaccttcc tggtcaggaa ccacaggcag gccagcctgg agatcagccc catcaccttc    2460
ctgactgccc agaccctgct gatggacctg ggccagttcc tgctgttctg ccacatcagc    2520
agccaccagc atgatggcat ggaggcctat gtgaaggtgg acagctgccc tgaggagccc    2580
cagctgagga tgaagaacaa tgaggaggct gaggactatg atgatgacct gactgactct    2640
gagatggatg tggtgaggtt tgatgatgac aacagcccca gcttcatcca gatcaggtct    2700
gtggccaaga agcaccccaa gacctgggtg cactacattg ctgctgagga ggaggactgg    2760
gactatgccc ccctggtgct ggcccctgat gacaggagct acaagagcca gtacctgaac    2820
aatggccccc agaggattgg caggaagtac aagaaggtca ggttcatggc ctacactgat    2880
gaaaccttca gaccagggga ggccatccag catgagtctg gcatcctggg ccccctgctg    2940
tatggggagg tgggggacac cctgctgatc atcttcaaga accaggccag caggccctac    3000
aacatctacc cccatggcat cactgatgtg aggcccctgt acagcaggag gctgcccaag    3060
ggggtgaagc acctgaagga cttccccatc ctgcctgggg agatcttcaa gtacaagtgg    3120
actgtgactg tggaggatgg ccccaccaag tctgaccccca ggtgcctgac cagatactac    3180
agcagctttg tgaacatgga gagggacctg gcctctggcc tgattggccc cctgctgatc    3240
tgctacaagg agtctgtgga ccagaggggc aaccagatca tgtctgacaa gaggaatgtg    3300
atcctgttct ctgtgtttga tgagaacagg agctggtacc tgactgagaa catccagagg    3360
ttcctgccca accctgctgg ggtgcagctg gaggaccctg agttccaggc cagcaacatc    3420
atgcacagca tcaatggcta tgtgtttgac agcctgcagc tgtctgtgtg cctgcatgag    3480
gtggcctact ggtacatcct gagcattggg gcccagactg acttcctgtc tgtgttcttc    3540
tctggctaca ccttcaagca caagatggtg tatgaggaca ccctgaccct gttcccctt    3600 tctggggaga ctgtgttcat gagcatggag aaccctggcc tgtggattct gggctgccac    3660
aactctgact tcaggaacag gggcatgact gccctgctga aagtctccag ctgtgacaag    3720
aacactgggg actactatga ggacagctat gaggacatct ctgcctacct gctgagcaag    3780
aacaatgcca ttgagcccag gagcttcagc cagaacccccc cagtgctgaa gaggcaccag    3840
agggagatca ccaggaccac cctgcagtct gaccaggagg agattgacta tgatgacacc    3900
atctctgtgg agatgaagaa ggaggacttt gacatctacg acgaggacga gaaccagagc    3960
cccaggagct tccagaagaa gaccaggcac tacttcattg ctgctgtgga gaggctgtgg    4020
gactatggca tgagcagcag ccccccatgtg ctgaggaaca gggcccagtc tggctctgtg    4080
ccccagttca agaaggtggt gttccaggag ttcactgatg gcagcttcac ccagcccctg    4140
tacagagggg agctgaatga gcacctgggc ctgctgggcc cctacatcag ggctgaggtg    4200
gaggacaaca tcatggtgac cttcaggaac caggccagca ggccctacag cttctacagc    4260
agcctgatca gctatgagga ggaccagagg caggggctg agcccaggaa gaactttgtg    4320
aagcccaatg aaaccaagac ctacttctgg aaggtgcagc accacatggc ccccaccaag    4380
gatgagtttg actgcaaggc ctgggcctac ttctctgatg tggacctgga aaggatgtg    4440 cactctggcc tgattggccc cctgctggtg tgccacacca cacccctgaa ccctgccat    4500 ggcaggcagg tgactgtgca ggagtttgcc ctgttcttca ccatctttga tgaaaccaag    4560
```

-continued

```
agctggtact tcactgagaa catggagagg aactgcaggg cccctgcaa catccagatg    4620 gaggacccca ccttcaagga gaactacagg ttccatgcca tcaatggcta catcatggac    4680
accctgcctg gcctggtgat ggcccaggac cagaggatca ggtggtacct gctgagcatg    4740
ggcagcaatg agaacatcca cagcatccac ttctctggcc atgtgttcac tgtgaggaag    4800
aaggaggagt acaagatggc cctgtacaac ctgtaccctg gggtgtttga ctgtggag      4860 atgctgccca gcaaggctgg catctggagg gtggagtgcc tgattgggga gcacctgcat    4920
gctggcatga gcaccctgtt cctggtgtac agcaacaagt gccagacccc cctgggcatg    4980
gcctctggcc acatcaggga cttccagatc actgcctctg ccagtatgg ccagtgggcc     5040 cccaagctgg ccaggctgca ctactctggc agcatcaatg cctggagcac aaggagccc    5100 ttcagctgga tcaaggtgga cctgctggcc ccatgatca tccatggcat caagacccag    5160
ggggccaggc agaagttcag cagcctgtac atcagccagt tcatcatcat gtacagcctg    5220
gatggcaaga gtggcagac ctacaggggc aacagcactg gcaccctgat ggtgttcttt    5280
ggcaatgtgg acagctctgg catcaagcac aacatcttca accccccat cattgccaga    5340 tacatcaggc tgcaccccac ccactacagc atcaggagca ccctgaggat ggagctgatg    5400
ggctgtgacc tgaacagctg cagcatgccc ctgggcatgg agagcaaggc catctctgat    5460
gcccagatca ctgccagcag ctacttcacc aacatgtttg ccacctggag ccccagcaag    5520
gccaggctgc acctgcaggg caggagcaat gcctggaggc ccaggtcaa caaccccaag    5580 gagtggctgc aggtggactt ccagaagacc atgaaggtga ctggggtgac cacccagggg    5640
gtgaagagcc tgctgaccag catgtatgtg aaggagttcc tgatcagcag cagccaggat    5700
ggccaccagt ggaccctgtt cttccagaat ggcaaggtga aggtgttcca gggcaaccag    5760
gacagcttca cccctgtggt gaacagcctg gaccccccc tgctgaccag atacctgagg    5820
attcaccccc agagctgggt gcaccagatt gccctgagga tggaggtgct gggctgtgag    5880
gcccaggacc tgtactgacc tcgagctgtg ccttctagtt gccagccatc tgttgtttgc    5940
ccctcccccg tgccttcctt gaccctggaa ggtgccactc ccactgtcct ttcctaataa    6000
aatgaggaaa ttgcatcgca ttgtctgagt aggtgtcatt ctattctggg gggtggggtg    6060
gggcaggaca gcaaggggga ggattgggaa gacaatagca ggcatgctgg gatgcggtg    6120 ggctctatgg accggtgcgg ccgcaggaac ccctagtgat ggagttggcc actccctctc    6180
tgcgcgctcg ctcgctcact gaggccgggc gaccaaaggt cgcccgacgc ccgggctttg    6240
cccgggcggc ctcagtgagc gagcgagcgc gcagagaggg agtggccaa               6289
```

<210> SEQ ID NO 19
<211> LENGTH: 5430
<212> TYPE: DNA
<213> ORGANISM: Adeno-Associated Virus 2

<400> SEQUENCE: 19

```
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg    120
gccaactcca tcactagggg ttcctgcggc cgcacgcgtg ttttcgacgt ggacttagcc    180
cctgtttgct cctccgataa ctggggtgac cttggttaat attcaccagc agcctcccg    240 tggacttagc cctgtttgc tcctccgata actggggtga ccttggttaa tattcaccag    300
cagcctcccc acgcgaaacg tcgactggac acaggacgct gtggtttctg agccaggggg    360
```

```
cgactcagat cccagccagt ggacttagcc cctgtttgct cctccgataa ctggggtgac   420
cttggttaat attcaccagc agcctccccc gttgcccctc tggatccact gcttaaatac   480
ggacgaggac agggccctgt ctcctcagct tcaggcacca ccactgacct gggacagtga   540
atcgtaagta ctagcagcta caatccagct accattctgc ttttatttta tggttgggat   600
aaggctggat tattctgagt ccaagctagg ccctttttgct aatcatgttc atacctctta   660
tcttcctccc acagctcctg gcaacgtgc tggtctgtgt gctggcccat cactttggca   720
aagaattgcg atcgccacca tgcagattga gctgagcacc tgcttcttcc tgtgcctgct   780
gaggttctgc ttctctgcca ccaggagata ctacctgggg gctgtggagc tgagctggga   840
ctacatgcag tctgacctgg gggagctgcc tgtggatgcc aggttccccc ccagagtgcc   900
caagagcttc cccttcaaca cctctgtggt gtacaagaag accctgtttg tggagttcac   960
tgaccacctg ttcaacattg ccaagcccag gccccctgg atgggcctgc tgggcccac   1020
catccaggct gaggtgtatg acactgtggt gatcaccctg aagaacatgg ccagccaccc   1080
tgtgagcctg catgctgtgg gggtgagcta ctggaaggcc tctgagggg ctgagtatga   1140
tgaccagacc agccagaggg agaaggagga tgacaaggtg ttccctgggg gcagccacac   1200
ctatgtgtgg caggtgctga aggagaatgg ccccatggcc tctgacccc tgtgcctgac   1260
ctacagctac ctgagccatg tggacctggt gaaggacctg aactctggcc tgattggggc   1320
cctgctggtg tgcagggagg gcagcctggc caaggagaag acccagaccc tgcacaagtt   1380
catcctgctg tttgctgtgt tgatgaggg caagagctgg cactctgaaa ccaagaacag   1440
cctgatgcag acagggatg ctgcctctgc cagggcctgg cccaagatgc acactgtgaa   1500
tggctatgtg aacaggagcc tgcctggcct gattggctgc acaggaagt ctgtgtactg   1560
gcatgtgatt ggcatgggca ccaccctga ggtgcacagc atcttcctgg agggccacac   1620
cttcctggtc aggaaccaca ggcaggccag cctggagatc agccccatca ccttcctgac   1680
tgcccagacc ctgctgatgg acctgggcca gttcctgctg ttctgccaca tcagcagcca   1740
ccagcatgat ggcatggagg cctatgtgaa ggtggacagc tgccctgagg agccccagct   1800
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgccccctg gtgctggccc ctgatgacag gagctacaag agccagtacc tgaacaatgg   2040
ccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc caaggggggt   2280
gaagcacctg aaggacttcc ccatcctgcc tggggagatc ttcaagtaca gtgtggactgt   2340
gactgtggag gatggcccca ccaagtctga ccccaggtgc ctgaccagat actacagcag   2400
ctttgtgaac atggagaggg acctggcctc tggcctgatt ggcccctgc tgatctgcta   2460
caaggagtct gtgaccagag gggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
```

```
ctacaccttc aagcacaaga tggtgtatga ggacaccctg accctgttcc ccttctctgg   2820
ggagactgtg ttcatgagca tggagaaccc tggcctgtgg attctgggct gccacaactc   2880
tgacttcagg aacaggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact tgtgaagcc   3540 caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggccccctgc tggtgtgcca caccaacacc ctgaaccctg ccatgcgcag   3720
gcaggtgact gtgcaggagt tgccctgtt cttcaccatc tttgatgaaa ccaagagctg   3780
gtacttcact gagaacatgg agaggaactg cagggccccc tgcaacatcc agatggagga   3840
ccccaccttc aaggagaact acaggttcca tgccatcaat ggctacatca tggacaccct   3900
gcctggcctg gtgatggccc aggaccagag gatcaggtgg tacctgctga gcatgggcag   3960
caatgagaac atccacagca tccacttctc tggccatgtg ttcactgtga ggaagaagga   4020
ggagtacaag atggccctgt acaacctgta ccctgggtg tttgagactg tggagatgct   4080
gcccagcaag gctggcatct ggaggtgga gtgcctgatt ggggagcacc tgcatgctgg   4140
catgagcacc ctgttcctgg tgtacagcaa caagtgccag acccccctgg gcatggcctc   4200
tggccacatc agggacttcc agatcactgc ctctggccca tatggccagt gggcccccaa   4260
gctggccagg ctgcactact ctggcagcat caatgcctgg agcaccaagg agcccttcag   4320
ctggatcaag gtgaccctgc tggccccat gatcatccat ggcatcaaga cccagggggc   4380
caggcagaag ttcagcagcc tgtacatcag ccagttcatc atcatgtaca gcctggatgg   4440
caagaagtgg cagacctaca ggggcaacag cactggcacc ctgatggtgt tctttggcaa   4500
tgtggacagc tctggcatca gcacaacat cttcaacccc ccatcattg ccagatacat   4560 caggctgcac cccacccact acagcatcag gagcaccctg aggatggagc tgatgggctg   4620
tgacctgaac agctgcagca tgccctggg catggagagc aaggccatct ctgatgccca   4680
gatcactgcc agcagctact tcaccaacat gtttgccacc tggagcccca gcaaggccag   4740
gctgcacctg cagggcagga gcaatgcctg gaggcccag gtcaacaacc caaggagtg   4800 gctgcaggtg gacttccaga agaccatgaa ggtgactggg gtgaccaccc aggggtgaa   4860 gagcctgcta ccagcatgt atgtgaagga gttcctgatc agcagcagcc aggatggcca   4920
ccagtggacc ctgttcttcc agaatggcaa ggtgaaggtg ttccagggca ccaggacag   4980 cttcaccccct gtggtgaaca gcctggaccc cccctgctg accagatacc tgaggattca   5040
cccccagagc tgggtgcacc agattgccct gaggatggag gtgctgggct gtgaggccca   5100
```

| | |
|---|---:|
| ggacctgtac tgacctcgag gcactgtcct ttcctaataa aatgaggaaa ttgcatcgca | 5160 |
| ttgtctgagt aggtgtcatt ctattctggg gggtggggtg gggcaggaca gcaaggggga | 5220 |
| ggattgggaa gacaatagca ggcatgctgg ggatgcggtg ggctctatgg gcacgtggcg | 5280 |
| gccgcaggaa ccccctagtga tggagttggc cactccctct ctgcgcgctc gctcgctcac | 5340 |
| tgaggccggg cgaccaaagg tcgcccgacg cccgggcttt gcccgggcgg cctcagtgag | 5400 |
| cgagcgagcg cgcagagagg gagtggccaa | 5430 |

```
<210> SEQ ID NO 20
<211> LENGTH: 5779
<212> TYPE: DNA
<213> ORGANISM: Adeno-Associated Virus 2

<400> SEQUENCE: 20
```

| | |
|---|---:|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgacgt ggacttagcc | 180 |
| cctgtttgct cctccgataa ctggggtgac cttggttaat attcaccagc agcctccccg | 240 |
| tggacttagc ccctgtttgc tcctccgata actggggtga ccttggttaa tattcaccag | 300 |
| cagcctcccc acgcgaaacg tcgactggac acaggacgct gtggtttctg agccaggggg | 360 |
| cgactcagat cccagccagt ggacttagcc cctgtttgct cctccgataa ctggggtgac | 420 |
| cttggttaat attcaccagc agcctccccg gttgcccctc tggatccact gcttaaatac | 480 |
| ggacgaggac agggccctgt ctcctcagct tcaggcacca ccactgacct gggacagtga | 540 |
| atcgtaagta ctagcagcta caatccagct accattctgc ttttattta tggttgggat | 600 |
| aaggctggat tattctgagt ccaagctagg ccctttgct aatcatgttc atacctctta | 660 |
| tcttcctccc acagctcctg ggcaacgtgc tggtctgtgt gctggcccat cactttggca | 720 |
| aagaattgcg atcgccacca tgcagattga gctgagcacc tgcttcttcc tgtgcctgct | 780 |
| gaggttctgc ttctctgcca caggagata ctacctgggg gctgtggagc tgagctggga | 840 |
| ctacatgcag tctgacctgg gggagctgcc tgtggatgcc aggttccccc ccagagtgcc | 900 |
| caagagcttc ccccttcaaca cctctgtggt gtacaagaag accctgtttg tggagttcac | 960 |
| tgaccacctg ttcaacattg ccaagcccag gcccccctgg atgggcctgc tgggccccac | 1020 |
| catccaggct gaggtgtatg acactgtggt gatcaccctg aagaacatgg ccagccaccc | 1080 |
| tgtgagcctg catgctgtgg gggtgagcta ctggaaggcc tctgagggg ctgagtatga | 1140 |
| tgaccagacc agccagaggg agaaggagga tgacaaggtg ttccctgggg gcagccacac | 1200 |
| ctatgtgtgg caggtgctga aggagaatgg ccccatggcc tctgaccccc tgtgcctgac | 1260 |
| ctacagctac ctgagccatg tggacctggt gaaggacctg aactctggcc tgattggggc | 1320 |
| cctgctggtg tgcagggagg gcagcctggc caaggagaag acccagaccc tgcacaagtt | 1380 |
| catcctgctg tttgctgtgt tgatgagggg caagagctgg cactctgaaa ccaagaacag | 1440 |
| cctgatgcag gacagggatg ctgcctctgc cagggcctgg cccaagatgc acactgtgaa | 1500 |
| tggctatgtg aacaggagcc tgcctggcct gattggctgc cacaggaagt ctgtgtactg | 1560 |
| gcatgtgatt ggcatgggca ccaccccttga ggtgcacagc atcttcctgg agggccacac | 1620 |
| cttcctggtc aggaaccaca ggcaggccag cctggagatc agccccatca ccttcctgac | 1680 |
| tgcccagacc ctgctgatgg acctgggcca gttcctgctg ttctgccaca tcagcagcca | 1740 |
| ccagcatgat ggcatggagg cctatgtgaa ggtggacagc tgccctgagg agccccagct | 1800 |

```
gaggatgaag aacaatgagg aggctgagga ctatgatgat gacctgactg actctgagat    1860
ggatgtggtg aggtttgatg atgacaacag ccccagcttc atccagatca ggtctgtggc    1920
caagaagcac cccaagacct gggtgcacta cattgctgct gaggaggagg actgggacta    1980
tgcccccctg gtgctggccc ctgatgcaga gagctacaag agccagtacc tgaacaatgg    2040
cccccagagg attggcagga agtacaagaa ggtcaggttc atggcctaca ctgatgaaac    2100
cttcaagacc agggaggcca tccagcatga gtctggcatc ctgggccccc tgctgtatgg    2160
ggaggtgggg gacaccctgc tgatcatctt caagaaccag gccagcaggc cctacaacat    2220 ctaccccat ggcatcactg atgtgaggcc cctgtacagc aggaggctgc ccaagggggt    2280
gaagcacctg aaggacttcc ccatcctgcc tggggagatc ttcaagtaca gtggactgt    2340 gactgtggag gatggcccca ccaagtctga ccccaggtgc ctgaccagat actacagcag    2400
ctttgtgaac atggagaggg acctggcctc tggcctgatt ggccccctgc tgatctgcta    2460
caaggagtct gtggaccaga ggggcaacca gatcatgtct gacaaggagga atgtgatcct    2520 gttctctgtg tttgatgaga acaggagctg gtacctgact gagaacatcc agaggttcct    2580
gcccaaccct gctggggtgc agctggagga ccctgagttc caggccagca acatcatgca    2640
cagcatcaat ggctatgtgt tgacagcct gcagctgtct gtgtgcctgc atgaggtggc    2700
ctactggtac atcctgagca ttggggccca gactgacttc ctgtctgtgt tcttctctgg    2760
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
tgacttcagg aacaggggca tgactgccct gctgaaagtc tccagctgtg acaagaacac    2940
tggggactac tatgaggaca gctatgagga catctctgcc tacctgctga gcaagaacaa    3000
tgccattgag cccaggagct tcagccagaa ccccccagtg ctgaagaggc accagaggga    3060
gatcaccagg accaccctgc agtctgacca ggaggagatt gactatgatg acaccatctc    3120
tgtggagatg aagaaggagg actttgacat ctacgacgag gacgagaacc agagccccag    3180
gagcttccag aagaagacca ggcactactt cattgctgct gtggagaggc tgtgggacta    3240
tggcatgagc agcagccccc atgtgctgag gaacagggcc cagtctggct ctgtgcccca    3300
gttcaagaag gtggtgttcc aggagttcac tgatggcagc ttcacccagc ccctgtacag    3360
aggggagctg aatgagcacc tgggcctgct gggcccctac atcagggctg aggtggagga    3420
caacatcatg gtgaccttca ggaaccaggc cagcaggccc tacagcttct acagcagcct    3480
gatcagctat gaggaggacc agaggcaggg ggctgagccc aggaagaact tgtgaagcc    3540 caatgaaacc aagacctact tctggaaggt gcagcaccac atggccccca ccaaggatga    3600
gtttgactgc aaggcctggg cctacttctc tgatgtggac ctggagaagg atgtgcactc    3660
tggcctgatt ggccccctgc tggtgtgcca caccaacacc ctgaaccctg cccatggcag    3720
gcaggtgact gtgcaggagt ttgccctgtt cttcaccatc tttgatgaaa ccaagagctg    3780
gtacttcact gagaacatgg agaggaactg cagggccccc tgcaacatcc agatggagga    3840
ccccaccttc aaggagaact acaggttcca tgccatcaat ggctacatca tggacaccct    3900
gcctggcctg tgtgatggcc aggaccagag gatcaggtgg tacctgctga gcatgggcag    3960
caatgagaac atccacagca tccacttctc tggccatgtg ttcactgtga ggaagaagga    4020
ggagtacaag atgccctgt acaacctgta ccctggggtg tttgagactg tggagatgct    4080
gcccagcaag gctggcatct ggaggtgga gtgcctgatt ggggagcacc tgcatgctgg    4140
```

```
catgagcacc ctgttcctgg tgtacagcaa caagtgccag accccctgg gcatggcctc      4200 tggccacatc agggacttcc agatcactgc ctctggccag tatggccagt gggcccccaa    4260
gctggccagg ctgcactact ctggcagcat caatgcctgg agcaccaagg agcccttcag    4320
ctggatcaag gtggacctgc tggcccccat gatcatccat ggcatcaaga cccagggggc    4380
caggcagaag ttcagcagcc tgtacatcag ccagttcatc atcatgtaca gcctggatgg    4440
caagaagtgg cagacctaca ggggcaacag cactggcacc ctgatggtgt tctttggcaa    4500
tgtggacagc tctggcatca agcacaacat cttcaacccc ccatcattg ccagatacat    4560 caggctgcac cccaccccact acagcatcag gagcaccctg aggatggagc tgatgggctg    4620
tgacctgaac agctgcagca tgcccctggg catggagagc aaggccatct ctgatgccca    4680
gatcactgcc agcagctact tcaccaacat gtttgccacc tggagcccca gcaaggccag    4740
gctgcacctg cagggcagga gcaatgcctg gaggccccag gtcaacaacc ccaaggagtg    4800
gctgcaggtg gacttccaga gaccatgaa ggtgactggg gtgaccaccc agggggtgaa     4860
gagcctgctg accagcatgt atgtgaagga gttcctgatc agcagcagcc aggatggcca    4920
ccagtggacc ctgttcttcc agaatggcaa ggtgaaggtg ttccagggca accaggacag    4980
cttcacccct gtggtgaaca gcctggaccc ccccctgctg accagatacc tgaggattca    5040
cccccagagc tgggtgcacc agattgccct gaggatggag gtgctgggct gtgaggccca    5100
ggacctgtac tgacctcgag gcactgtcct ttcctaataa aatgaggaaa ttgcatcgca    5160
ttgtctgagt aggtgtcatt ctattctggg gggtgggtg gggcaggaca gcaaggggga    5220
ggattgggaa gacaatagca ggcatgctgg ggatgcggtg ggctctatgg gcactcgaca    5280
ggttaatttt taaaaagcag tcaaaagtcc aagtggccct tggcagcatt tactctctct    5340
gtttgctctg gttaataatc tcaggagcac aaacattcct ggaggcagga gaagaaatca    5400
acatcctgga cttatcctct gggcctctcc caccccag gagaggctca ggttaatttt     5460
taaaaagcag tcaaaagtcc aagtggccct tggcagcatt tactctctct gtttgctctg    5520
gttaataatc tcaggagcac aaacattcct ggaggcagga gaagaaatca acatcctgga    5580
cttatcctct gggcctctcc caccccag gagaggctgt cgagtggcgg ccgcaggaac      5640
ccctagtgat ggagttggcc actccctctc tgcgcgctcg ctcgctcact gaggccgggc    5700
gaccaaaggt cgcccgacgc ccgggctttg cccgggcggc ctcagtgagc gagcgagcgc    5760
gcagagaggg agtggccaa                                                 5779
```

<210> SEQ ID NO 21
<211> LENGTH: 5962
<212> TYPE: DNA
<213> ORGANISM: Adeno-Associated Virus 2

<400> SEQUENCE: 21

```
ttggccactc cctctctgcg cgctcgctcg ctcactgagg ccgccgggc aaagcccggg       60 cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg acttcagag gcagcacaca aacagctgct    420
ggaggatggg aactgagggg ttggaagggg gcagggtgag cccagaaact cctgtgtgcc    480
```

```
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggccctttt gctaatcatg ttcatacctc    840
ttatcttcct cccacagctc tgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt    1140 cactgaccac ctgttcaaca ttgccaagcc caggccccc tggatgggcc tgctgggccc   1200
caccatccag gctgaggtgt atgacactgt ggtgatcacc ctgaagaaca tggccagcca   1260
ccctgtgagc ctgcatgctg tggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggcccccatg gcctctgacc cctgtgcct   1440 gacctacagc tacctgagcc atgtggacct ggtgaaggac ctgaactctg gcctgattgg   1500
ggccctgctg gtgtgcaggg agggcagcct ggccaaggaa aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaagaa tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc cctgctgta   2340 tgggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact cccccatcct gcctgggag atcttcaagt acaagtggac   2520
tgtgactgtg gaggatggcc ccaccaagtc tgacccagg tgcctgacca gatactacag   2580
cagctttgtg aacatggaga gggacctggc ctctggcctg attggccccc tgctgatctg   2640
ctacaaggag tctgtggacc agagggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
```

```
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca agatggtgta tgaggacacc ctgaccctgt tccccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatgggcatg agcagcagcc cccatgtgct gaggaacagg gcccagtctg ctctgtgcc    3480
ccagttcaag aaggtggtgt tccaggagtt cactgatggc agcttcaccc agcccctgta    3540
cagagggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga ctttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggcccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagacccccc tgggcatggc    4380
ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac cccccatca ttgccagata    4740
catcaggctg caccccaccc actacagcat caggagcacc ctgaggatgg agctgatggg    4800
ctgtgacctg aacagctgca gcatgccct gggcatggag agcaaggcca tctctgatgc    4860
ccagatcact gccagcagct acttccacca catgtttgcc acctggagcc ccagcaaggc    4920
caggctgcac ctgcagggca ggagcaatgc ctggaggccc caggtcaaca ccccaagga    4980
gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160
cagcttcacc cctgtggtga acagcctgga ccccccctg ctgaccagat acctgaggat    5220
```

```
tcaccccag   agctgggtgc   accagattgc   cctgaggatg   gaggtgctgg   gctgtgaggc     5280
ccaggacctg   tactgacctc   gaggcactgt   cctttcctaa   taaaatgagg   aaattgcatc     5340
gcattgtctg   agtaggtgtc   attctattct   gggggtggg    gtggggcagg   acagcaaggg     5400
ggaggattgg   gaagacaata   gcaggcatgc   tggggatgcg   gtgggctcta   tgggcactcg     5460
acaggttaat   ttttaaaaag   cagtcaaaag   tccaagtggc   ccttggcagc   atttactctc     5520
tctgtttgct   ctggttaata   atctcaggag   cacaaacatt   cctggaggca   ggagaagaaa     5580
tcaacatcct   ggacttatcc   tctgggcctc   tccccacccc   caggagaggc   tcaggttaat     5640
ttttaaaaag   cagtcaaaag   tccaagtggc   ccttggcagc   atttactctc   tctgtttgct     5700
ctggttaata   atctcaggag   cacaaacatt   cctggaggca   ggagaagaaa   tcaacatcct     5760
ggacttatcc   tctgggcctc   tccccacccc   caggagaggc   tgtcgagtgg   cggccgcagg     5820
aacccctagt   gatggagttg   gccactccct   ctctgcgcgc   tcgctcgctc   actgaggccg     5880
ggcgaccaaa   ggtcgcccga   cgcccgggct   ttgcccgggc   ggcctcagtg   agcgagcgag     5940
cgcgcagaga   gggagtggcc   aa                                                   5962
```

<210> SEQ ID NO 22
<211> LENGTH: 5919
<212> TYPE: DNA
<213> ORGANISM: Adeno-Associated Virus 2

<400> SEQUENCE: 22

```
ttggccactc   cctctctgcg   cgctcgctcg   ctcactgagg   ccgccgggc    aaagcccggg       60 cgtcgggcga   cctttggtcg   cccggcctca   gtgagcgagc   gagcgcgcag   agagggagtg     120
gccaactcca   tcactagggg   ttcctgcggc   cgcacgcgta   ggctcagagg   cacacaggag     180
tttctgggct   caccctgccc   ccttccaacc   cctcagttcc   catcctccag   cagctgtttg     240
tgtgctgcct   ctgaagtcca   cactgaacaa   acttcagcct   actcatgtcc   ctaaaatggg     300
caaacattgc   aagcagcaaa   cagcaaacac   acagccctcc   ctgcctgctg   accttggagc     360
tggggcagag   gtcagagacc   tctctggcc   catgccacct   ccaacatcca   ctcgacccct     420
tggaatttcg   gtggagagga   gcagaggttg   tcctggcgtg   gtttaggtag   tgtgagaggg     480
gtcgacgatc   ttgctaccag   tggaacagcc   actaaggatt   ctgcagtgag   agcagagggc     540
cagctaagtg   gtactctccc   agagactgtc   tgactcacgc   cacccctcc    accttggaca     600 caggacgctg   tggtttctga   gccaggtaca   atgactcctt   tcggtaagtg   cagtggaagc     660
tgtacactgc   ccaggcaaag   cgtccgggca   gcgtaggcgg   gcgactcaga   tcccagccag     720
tggacttagc   ccctgtttgc   tcctccgata   actgggtga    ccttggttaa   tattcaccag     780
cagcctcccc   cgttgcccct   ctggatccac   tgcttaaata   cggacgagga   cagggccctg     840
tctcctcagc   ttcaggcacc   accactgacc   tgggacagtg   aatcgtaagt   atgcctttca     900
ctgcgagagt   ttctggagag   gcttctgagc   tccccatggc   ccaggcaggc   agcaggtctg     960
gggcaggagg   ggggttgtgg   agtgggtatc   cgcctgctga   ggtgcagggc   agatcatcat    1020
gtgccttgac   tcggggcctg   gccccccat   ctctgtcttg   caggacaatt   gccgtcttct    1080
gtctcgtggg   gcatcctcct   gctggcaggc   ctgtgctgcc   tggtccctgt   ctccctggct    1140
gaggaccggc   accatgcag   attgagctga   gcacctgctt   cttcctgtgc   tgctgaggt     1200 tctgcttctc   tgccaccagg   agatactacc   tgggggctgt   ggagctgagc   tgggactaca    1260
tgcagtctga   cctgggggag   ctgcctgtgg   atgccaggtt   cccccccaga   gtgcccaaga    1320
```

```
gcttcccctt caacacctct gtggtgtaca agaagaccct gtttgtggag ttcactgacc    1380
acctgttcaa cattgccaag cccaggcccc cctggatggg cctgctgggc ccaccatcc    1440
aggctgaggt gtatgacact gtggtgatca ccctgaagaa catggccagc cacctgtga    1500
gcctgcatgc tgtgggggtg agctactgga aggcctctga gggggctgag tatgatgacc    1560
agaccagcca gagggagaag gaggatgaca aggtgttccc tgggggcagc cacacctatg    1620
tgtggcaggt gctgaaggag aatggcccca tggcctctga cccctgtgc ctgacctaca    1680
gctacctgag ccatgtggac ctggtgaagg acctgaactc tggcctgatt ggggccctgc    1740
tggtgtgcag ggagggcagc ctggccaagg agaagaccca gaccctgcac aagttcatcc    1800
tgctgtttgc tgtgtttgat gagggcaaga gctggcactc tgaaaccaag aacagcctga    1860
tgcaggacag ggatgctgcc tctgccaggg cctggcccaa gatgcacact gtgaatggct    1920
atgtgaacag gagcctgcct ggcctgattg ctgccacag gaagtctgtg tactggcatg    1980
tgattggcat gggcaccacc cctgaggtgc acagcatctt cctggagggc acaccttcc    2040
tggtcaggaa ccacaggcag gccagcctgg agatcagccc catcaccttc ctgactgccc    2100
agaccctgct gatggacctg gccagttcc tgctgttctg ccacatcagc agccaccagc    2160
atgatggcat ggaggcctat gtgaaggtgg acagctgccc tgaggagccc agctgagga    2220
tgaagaacaa tgaggaggct gaggactatg atgatgacct gactgactct gagatggatg    2280
tggtgaggtt tgatgatgac aacagcccca gcttcatcca gatcaggtct gtggccaaga    2340
agcaccccaa gacctgggtg cactacattg ctgctgagga ggaggactgg gactatgccc    2400
ccctggtgct ggcccctgat gacaggagct acaagagcca gtacctgaac aatggccccc    2460
agaggattgg caggaagtac aagaaggtca ggttcatggc ctacactgat gaaaccttca    2520
agaccaggga ggccatccag catgagtctg gcatcctggg ccccctgctg tatgggagg    2580
tggggacac cctgctgatc atcttcaaga accaggccag caggccctac aacatctacc    2640
ccatggcat cactgatgtg aggccctgt acagcaggag gctgcccaag ggggtgaagc    2700
acctgaagga cttccccatc ctgcctgggg agatcttcaa gtacaagtgg actgtgactg    2760
tggaggatgg ccccaccaag tctgaccca ggtgcctgac cagatactac agcagctttg    2820
tgaacatgga gagggacctg gcctctggcc tgattggccc cctgctgatc tgctacaagg    2880
agtctgtgga ccagagggc aaccagatca tgtctgacaa gaggaatgtg atcctgttct    2940
ctgtgtttga tgagaacagg agctggtacc tgactgagaa catccagagg ttcctgccca    3000
accctgctgg ggtgcagctg gaggaccctg agttccaggc cagcaacatc atgcacagca    3060
tcaatggcta tgtgtttgac agcctgcagc tgtctgtgtg cctgcatgag gtggcctact    3120
ggtacatcct gagcattggg gcccagactg acttcctgtc tgtgttcttc tctggctaca    3180
ccttcaagca caagatggtg tatgaggaca ccctgacct gttcccttc tctggggaga    3240
ctgtgttcat gagcatggag aaccctggcc tgtggattct gggctgccac aactctgact    3300
tcaggaacag gggcatgact gccctgctga aagtctccag ctgtgacaag aacactgggg    3360
actactatga ggacagctat gaggacatct ctgcctacct gctgagcaag aacaatgcca    3420
ttgagcccag gagcttcagc cagaaccccc cagtgctgaa aggcaccag agggagatca    3480
ccaggaccac cctgcagtct gaccaggagg agattgacta tgatgacacc atctctgtgg    3540
agatgaagaa ggaggacttt gacatctacg acgaggacga gaaccagagc ccaggagct    3600
tccagaagaa gaccaggcac tacttcattg ctgctgtgga ggctgtgg gactatggca    3660
tgagcagcag ccccccatgtg ctgaggaaca gggcccagtc tggctctgtg ccccagttca    3720
```

```
agaaggtggt gttccaggag ttcactgatg gcagcttcac ccagcccctg tacagagggg    3780
agctgaatga gcacctgggc ctgctgggcc cctacatcag ggctgaggtg gaggacaaca    3840
tcatggtgac cttcaggaac caggccagca ggccctacag cttctacagc agcctgatca    3900
gctatgagga ggaccagagg caggggctg agcccaggaa gaactttgtg aagcccaatg     3960
aaaccaagac ctacttctgg aaggtgcagc accacatggc ccccaccaag gatgagtttg    4020
actgcaaggc ctgggcctac ttctctgatg tggacctgga gaaggatgtg cactctggcc    4080
tgattggccc cctgctggtg tgccacacca cacccctgaa ccctgcccat ggcaggcagg    4140
tgactgtgca ggagtttgcc ctgttcttca ccatctttga tgaaaccaag agctggtact    4200
tcactgagaa catggagagg aactgcaggg cccctgcaa catccagatg gaggacccca    4260
ccttcaagga gaactacagg ttccatgcca tcaatggcta catcatggac accctgcctg    4320
gcctggtgat ggcccaggac cagaggatca ggtggtacct gctgagcatg ggcagcaatg    4380
agaacatcca cagcatccac ttctctggcc atgtgttcac tgtgaggaag aaggaggagt    4440
acaagatggc cctgtacaac ctgtaccctg gggtgtttga ctgtggag atgctgccca     4500 gcaaggctgg catctggagg gtggagtgcc tgattgggga gcacctgcat gctggcatga    4560
gcaccctgtt cctggtgtac agcaacaagt gccagacccc cctgggcatg gcctctggcc    4620
acatcaggga cttccagatc actgcctctg ccagtatgg ccagtgggcc ccaagctgg     4680 ccaggctgca ctactctggc agcatcaatg cctggagcac caaggagccc ttcagctgga    4740
tcaaggtgga cctgctggcc cccatgatca tccatggcat caagacccag ggggccaggc    4800
agaagttcag cagcctgtac atcagccagt tcatcatcat gtacagcctg gatggcaaga    4860
agtggcagac ctacaggggc aacagcactg gcaccctgat ggtgttcttt ggcaatgtgg    4920
acagctctgg catcaagcac aacatcttca acccccccat cattgccaga tacatcaggc    4980
tgcaccccac ccactacagc atcaggagca ccctgaggat ggagctgatg ggctgtgacc    5040
tgaacagctg cagcatgccc ctgggcatgg agagcaaggc catctctgat gcccagatca    5100
ctgccagcag ctacttcacc aacatgtttg ccacctggag cccccagaag gccaggctgc    5160
acctgcaggg caggagcaat gcctggaggc cccaggtcaa caaccccaag gagtggctgc    5220
aggtggactt ccagaagacc atgaaggtga ctgggtgac cacccagggg gtgaagagcc     5280
tgctgaccag catgtatgtg aaggagttcc tgatcagcag cagccaggat ggccaccagt    5340
ggaccctgtt cttccagaat ggcaaggtga aggtgttcca gggcaaccag gacagcttca    5400
cccctgtggt gaacagcctg gaccccccc tgctgaccag atacctgagg attcaccccc    5460
agagctgggt gcaccagatt gccctgagga tggaggtgct gggctgtgag gcccaggacc    5520
tgtactgagc tcgagctgtg ccttctagtt gccagccatc tgttgtttgc cctcccccg    5580 tgccttcctt gaccctggaa ggtgccactc ccactgtcct ttcctaataa aatgaggaaa    5640
ttgcatcgca ttgtctgagt aggtgtcatt ctattctggg gggtggggtg gggcaggaca    5700
gcaaggggga ggattgggaa gacaatagca ggcatgctgg ggatgcggtg ggctctatgg    5760
accggtgcgg ccgcaggaac ccctagtgat ggagttggcc actccctctc tgcgcgctcg    5820
ctcgctcact gaggccgggc gaccaaaggt cgcccgacgc ccgggctttg cccgggcggc    5880
ctcagtgagc gagcgagcgc gcagagaggg agtggccaa                          5919
```

<210> SEQ ID NO 23
<211> LENGTH: 5306
<212> TYPE: DNA

<213> ORGANISM: Adeno-Associated Virus 2

<400> SEQUENCE: 23

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttaaacgt cgaccctaaa     180
atgggcaaac attgcaagca gcaaacagca aactgacctt ggagctgggg cagaggtcag     240
agacctctct gggcactcga ccccttggaa tttcggtgga gaggagcaga ggtacacagc     300
cctccctgcc tgcccatgc cacctccaac atctgtcctg gcgtggttta ggtagtgtga     360
gaggggaatg actcctttcg gtaagtgcag tggaagctgt acactgccca ggcaaagcgt     420
ccgggcagcg taggcgggcg actcagatcc cagccagtgg acttagcccc tgtttgctcc     480
tccgataact ggggtgacct tggttaatat tcaccagcag cctcccccgt tgcccctctg     540
gatccactgc ttaaatacgg acgaggacag ggccctgtct cctcagcttc aggcaccacc     600
actgacctgg gacagtgaat cgcgatcgca ctgcttaaat acggacgagg acagggccct     660
gtctcctcag cttcaggcac caccactgac ctgggacagt gaatcgcgat cgccaccatg     720
cagattgagc tgagcacctg cttcttcctg tgcctgctga ggttctgctt ctctgccacc     780
aggagatact acctgggggc tgtggagctg agctgggact acatgcagtc tgacctgggg     840
gagctgcctg tggatgccag gttcccccc agagtgccca gagcttccc cttcaacacc     900
tctgtggtgt acaagaagac cctgtttgtg gagttcactg accacctgtt caacattgcc     960
aagcccaggc cccctggat gggcctgctg gccccacca tccaggctga ggtgtatgac    1020
actgtggtga tcaccctgaa gaacatggcc agccaccctg tgagcctgca tgctgtgggg    1080
gtgagctact ggaaggcctc tgagggggct gagtatgatg accagaccag ccagaggag    1140
aaggaggatg acaaggtgtt ccctggggc agccacacct atgtgtggca ggtgctgaag    1200
gagaatggcc ccatggcctc tgaccccctg tgcctgacct acagctacct gagccatgtg    1260
gacctggtga aggacctgaa ctctggcctg attggggccc tgctggtgtg cagggagggc    1320
agcctggcca aggagaagac ccagaccctg cacaagttca tcctgctgtt tgctgtgttt    1380
gatgagggca gagctggca ctctgaaacc aagaacagcc tgatgcagga cagggatgct    1440
gcctctgcca gggcctggcc caagatgcac actgtgaatg ctatgtgaa caggagcctg    1500
cctggcctga ttggctgcca caggaagtct gtgtactggc atgtgattgg catgggcacc    1560
accccctgagg tgcacagcat cttcctggag ggccacacct tcctggtcag gaaccacagg    1620
caggccagcc tggagatcag ccccatcacc ttcctgactg cccagaccct gctgatggac    1680
ctgggccagt cctgctgtt ctgccacatc agcagccacc agcatgatgg catggaggcc    1740
tatgtgaagg tggacagctg ccctgaggag cccagctga ggatgaagaa caatgaggag    1800
gctgaggact atgatgatga cctgactgac tctgagatgg atgtggtgag gtttgatgat    1860
gacaacagcc ccagcttcat ccagatcagg tctgtggcca agaagcaccc caagacctgg    1920
gtgcactaca ttgctgctga ggaggaggac tgggactatg cccccctggt gctggcccct    1980
gatgacagga gctacaagag ccagtacctg aacaatggcc cccagaggat ggcaggaag    2040
tacaagaagg tcaggttcat ggcctacact gatgaaacct tcaagaccag ggaggccatc    2100
cagcatgagt ctggcatcct gggcccctg ctgtatgggg aggtgggga caccctgctg    2160
atcatcttca gaaccaggc cagcaggccc tacaacatct accccatgg catcactgat    2220
gtgaggcccc tgtacagcag gaggctgccc aagggggtga agcacctgaa ggacttcccc    2280
```

```
atcctgcctg gggagatctt caagtacaag tggactgtga ctgtggagga tggccccacc    2340
aagtctgacc ccaggtgcct gaccagatac tacagcagct ttgtgaacat ggagagggac    2400
ctggcctctg gcctgattgg cccctgctg atctgctaca aggagtctgt ggaccagagg     2460
ggcaaccaga tcatgtctga caagaggaat gtgatcctgt tctctgtgtt tgatgagaac    2520
aggagctggt acctgactga gaacatccag aggttcctgc ccaaccctgc tggggtgcag    2580
ctggaggacc ctgagttcca ggccagcaac atcatgcaca gcatcaatgg ctatgtgttt    2640
gacagcctgc agctgtctgt gtgcctgcat gaggtggcct actggtacat cctgagcatt    2700
ggggcccaga ctgacttcct gtctgtgttc ttctctggct acaccttcaa gcacaagatg    2760
gtgtatgagg acaccctgac cctgttcccc ttctctgggg agactgtgtt catgagcatg    2820
gagaaccctg gctgtggat tctgggctgc acaactctg acttcaggaa caggggcatg      2880
actgccctgc tgaaagtctc cagctgtgac aagaacactg gggactacta tgaggacagc    2940
tatgaggaca tctctgccta cctgctgagc aagaacaatg ccattgagcc caggagcttc    3000
agccagaacc ccccagtgct gaagaggcac cagagggaga tcaccaggac caccctgcag    3060
tctgaccagg aggagattga ctatgatgac accatctctg tggagatgaa gaaggaggac    3120
tttgacatct acgacgagga cgagaaccag agccccagga gcttccagaa gaagaccagg    3180
cactacttca ttgctgctgt ggagaggctg tgggactatg gcatgagcag cagcccccat    3240
gtgctgagga caggggccca gtctggctct gtgccccagt tcaagaaggt ggtgttccag    3300
gagttcactg atggcagctt cacccagccc ctgtacagag gggagctgaa tgagcacctg    3360
ggcctgctgg gcccctacat cagggctgag gtggaggaca acatcatggt gaccttcagg    3420
aaccaggcca gcaggcccta cagcttctac agcagcctga tcagctatga ggaggaccag    3480
aggcaggggg ctgagcccag gaagaacttt gtgaagccca tgaaaccaag acctacttc      3540
tggaaggtgc cagcaccaca tggcccccacc aaggatgagt ttgactgcaa ggcctgggcc   3600
tacttctctg atgtggacct ggagaaggat gtgcactctg gcctgattgg cccctgctg      3660
gtgtgccaca ccaacaccct gaaccctgcc catggcaggc aggtgactgt gcaggagttt    3720
gccctgttct tcaccatctt tgatgaaacc aagagctggt acttcactga gaacatggag    3780
aggaactgca gggcccctg caacatccag atggaggacc ccaccttcaa ggagaactac    3840
aggttccatg ccatcaatgg ctacatcatg gacaccctgc ctggcctggt gatggcccag    3900
gaccagagga tcaggtggta cctgctgagc atgggcagca atgagaacat ccacagcatc    3960
cacttctctg ccatgtgttt cactgtgagg aagaaggagg agtacaagat ggccctgtac    4020
aacctgtacc ctgggtgtt tgagactgtg agatgctgc ccagcaaggc tggcatctgg       4080
agggtggagt gcctgattgg ggagcacctg catgctggca tgagcaccct gttcctggtg    4140
tacagcaaca agtgccagac ccccctgggc atggcctctg ccacatcag ggacttccag      4200
atcactgcct ctggccagta tggccagtgg gcccccaagc tggccaggct gcactactct    4260
ggcagcatca atgcctggag caccaaggag ccttcagct ggatcaaggt ggacctgctg       4320
gcccccatga tcatccatgg catcaagacc caggggggcca ggcagaagtt cagcagcctg    4380
tacatcagcc agttcatcat catgtacagc ctggatggca gaagtggca gacctacagg      4440
ggcaacagca ctggcaccct gatggtgttc tttggcaatg tggacagctc tggcatcaag    4500
cacaacatct tcaaccccccc catcattgcc agatacatca ggctgcaccc cacccactac    4560
agcatcagga gcacccctgag gatggagctg atgggctgtg acctgaacag ctgcagcatg    4620
```

```
cccctgggca tggagagcaa ggccatctct gatgcccaga tcactgccag cagctacttc    4680
accaacatgt ttgccacctg gagccccagc aaggccaggc tgcacctgca gggcaggagc    4740
aatgcctgga ggccccaggt caacaacccc aaggagtggc tgcaggtgga cttccagaag    4800
accatgaagg tgactggggt gaccacccag ggggtgaaga gcctgctgac cagcatgtat    4860
gtgaaggagt tcctgatcag cagcagccag gatggccacc agtggaccct gttcttccag    4920
aatggcaagt gaaggtgtt ccagggcaac caggacagct tcacccctgt ggtgaacagc    4980
ctggaccccc ccctgctgac cagatacctg aggattcacc cccagagctg ggtgcaccag    5040
attgccctga ggatggaggt gctgggctgt gaggcccagg acctgtactg acctcgagga    5100
ataaaggaaa tttattttca ttgcaatagt gtgttggttt tttgtgtcac gtggcggccg    5160
caggaacccc tagtgatgga gttggccact ccctctctgc gcgctcgctc gctcactgag    5220
gccgggcgac caaaggtcgc ccgacgcccg ggctttgccc gggcggcctc agtgagcgag    5280
cgagcgcgca gagagggagt ggccaa    5306

<210> SEQ ID NO 24
<211> LENGTH: 5461
<212> TYPE: DNA
<213> ORGANISM: Adeno-Associated Virus 2

<400> SEQUENCE: 24
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactt tatttgccac     180
aaaaacccta tcagatgggc gtctttatca tttccattgt acagatgggg aaacaggctt     240
cggggtcggg gcatagccac ttactgacga ctccccaccc agcaagtggt tttgaacccg     300
gaccctctca cactacctaa accacgccag acaacctct gctcctctcc accgaaattc     360
caaggggtcg agtggatgtt ggaggtggca tgggcccaga gaggtctctg acctctgccc     420
cagctccaag gtcagcaggc agggagggct gtgtgtttgc tgtttgctgc ttgcaatgtt     480
tgcccatttt agggacatga gtaggctgaa gtttgttcag tgtggacttc agaggcagca     540
cacaaacagc tgctggagga tgggaactga ggggttggaa gggggcaggg tgagcccaga     600
aactcctgtg tgcctctgag cctgcagacg cgaaacgtcg actggacaca ggacgctgtg     660
gtttctgagc caggggggcga ctcagatccc agccagtgga cttagcccct gtttgctcct     720
ccgataactg gggtgacctt ggttaatatt caccagcagc ctccccgtt gcccctctgg     780 atccactgct taaatacgga cgaggacagg gccctgtctc ctcagcttca ggcaccacca     840
ctgacctggg acagtgaatc gcgatcgcca ccatgcagat tgagctgagc acctgcttct     900
tcctgtgcct gctgaggttc tgcttctctg ccaccaggag atactacctg ggggctgtgg     960
agctgagctg ggactacatg cagtctgacc tgggggagct gcctgtggat gccaggttcc    1020
cccccagagt gcccaagagc ttcccctcca cacctctgt ggtgtacaag aagacctgt    1080 ttgtggagtt cactgaccac ctgttcaaca ttgccaagcc caggcccccc tggatgggcc    1140
tgctgggccc caccatccag gctgaggtgt atgacactgt ggtgatcacc ctgaagaaca    1200
tggccagcca ccctgtgagc ctgcatgctg tgggggtgag ctactggaag gcctctgagg    1260
gggctgagta tgatgaccag accagccaga gggagaagga ggatgacaag gtgttccctg    1320
ggggcagcca cacctatgtg tggcaggtgc tgaaggagaa tggccccatg gcctctgacc    1380
ccctgtgcct gacctacagc tacctgagcc atgtggacct ggtgaaggac ctgaactctg    1440
```

```
gcctgattgg ggccctgctg gtgtgcaggg agggcagcct ggccaaggag aagacccaga    1500
ccctgcacaa gttcatcctg ctgtttgctg tgtttgatga gggcaagagc tggcactctg    1560
aaaccaagaa cagcctgatg caggacaggg atgctgcctc tgccagggcc tggcccaaga    1620
tgcacactgt gaatggctat gtgaacagga gcctgcctgg cctgattggc tgccacagga    1680
agtctgtgta ctggcatgtg attggcatgg gcaccacccc tgaggtgcac agcatcttcc    1740
tggagggcca caccttcctg gtcaggaacc acaggcaggc cagcctggag atcagcccca    1800
tcaccttcct gactgcccag accctgctga tggacctggg ccagttcctg ctgttctgcc    1860
acatcagcag ccaccagcat gatggcatgg aggcctatgt gaaggtggac agctgccctg    1920
aggagcccca gctgaggatg aagaacaatg aggaggctga ggactatgat gatgacctga    1980
ctgactctga gatggatgtg gtgaggtttg atgatgacaa cagccccagc ttcatccaga    2040
tcaggtctgt ggccaagaag caccccaaga cctgggtgca ctacattgct gctgaggagg    2100
aggactggga ctatgccccc ctggtgctgg cccctgatga caggagctac aagagccagt    2160
acctgaacaa tggcccccag aggattggca ggaagtacaa gaaggtcagg ttcatggcct    2220
acactgatga aaccttcaag accagggagg ccatccagca tgagtctggc atcctgggcc    2280
ccctgctgta tggggaggtg ggggacaccc tgctgatcat cttcaagaac caggccagca    2340
ggccctacaa catctacccc catggcatca ctgatgtgag gcccctgtac agcaggaggc    2400
tgcccaaggg ggtgaagcac ctgaaggact cccccatcct gcctggggag atcttcaagt    2460
acaagtggac tgtgactgtg gaggatggcc ccaccaagtc tgaccccagg tgcctgacca    2520
gatactacag cagctttgtg aacatggaga gggacctggc ctctggcctg attggccccc    2580
tgctgatctg ctacaaggag tctgtggacc agagggggcaa ccagatcatg tctgacaaga    2640
ggaatgtgat cctgttctct gtgtttgatg agaacaggag ctggtacctg actgagaaca    2700
tccagaggtt cctgcccaac cctgctgggg tgcagctgga ggaccctgag ttccaggcca    2760
gcaacatcat gcacagcatc aatggctatg tgtttgacag cctgcagctg tctgtgtgcc    2820
tgcatgaggt ggcctactgg tacatcctga gcattgggggc ccagactgac ttcctgtctg    2880
tgttcttctc tggctacacc ttcaagcaca agatggtgta tgaggacacc ctgacccctgt    2940 tccccttctc tggggagact gtgttcatga gcatggagaa ccctggcctg tggattctgg    3000
gctgccacaa ctctgacttc aggaacaggg gcatgactgc cctgctgaaa gtctccagct    3060
gtgacaagaa cactggggac tactatgagg acagctatga ggacatctct gcctacctgc    3120
tgagcaagaa caatgccatt gagcccagga gcttcagcca gaaccccca gtgctgaaga    3180 ggcaccagag ggagatcacc aggaccaccc tgcagtctga ccaggaggag attgactatg    3240
atgacaccat ctctgtggag atgaagaagg aggactttga catctacgac gaggacgaga    3300
accagagccc caggagcttc cagaagaaga ccaggcacta cttcattgct gctgtggaga    3360
ggctgtggga ctatgcatg agcagcagcc ccatgtgct gaggaacagg cccagtctg    3420 gctctgtgcc ccagttcaag aaggtggtgt tccaggagtt cactgatggc agcttcaccc    3480 agccccctgta cagaggggag ctgaatgagc acctgggcct gctgggcccc tacatcaggg    3540
ctgaggtgga ggacaacatc atggtgacct tcaggaacca ggccagcagg ccctacagct    3600
tctacagcag cctgatcagc tatgaggagg accagaggca gggggctgag cccaggaaga    3660
actttgtgaa gccaatgaa accaagacct acttctggaa ggtgcagcac cacatggccc    3720
ccaccaagga tgagtttgac tgcaaggcct gggcctactt ctctgatgtg gacctggaga    3780
```

```
aggatgtgca ctctggcctg attggccccc tgctggtgtg ccacaccaac ccctgaacc    3840 ctgcccatgg caggcaggtg actgtgcagg agtttgccct gttcttcacc atctttgatg    3900
aaaccaagag ctggtacttc actgagaaca tggagaggaa ctgcagggcc ccctgcaaca    3960
tccagatgga ggaccccacc ttcaaggaga actacaggtt ccatgccatc aatggctaca    4020
tcatggacac cctgcctggc ctggtgatgg cccaggacca gaggatcagg tggtacctgc    4080
tgagcatggg cagcaatgag aacatccaca gcatccactt ctctggccat gtgttcactg    4140
tgaggaagaa ggaggagtac aagatggccc tgtacaacct gtaccctggg gtgtttgaga    4200
ctgtggagat gctgcccagc aaggctgcca tctggagggt ggagtgcctg attggggagc    4260
acctgcatgc tggcatgagc accctgttcc tggtgtacag caacaagtgc cagaccccc    4320 tgggcatggc ctctgccac atcagggact ccagatcac tgcctctggc cagtatggcc    4380
agtgggcccc caagctggcc aggctgcact actctggcag catcaatgcc tggagcacca    4440
aggagccctt cagctggatc aaggtggacc tgctggcccc catgatcatc catggcatca    4500
agacccaggg ggccaggcag aagttcagca gcctgtacat cagccagttc atcatcatgt    4560
acagcctgga tggcaagaag tggcagacct acaggggcaa cagcactggc accctgatgg    4620
tgttctttgg caatgtggac agctctggca tcaagcacaa catcttcaac ccccccatca    4680
ttgccagata catcaggctg caccccaccc actacagcat caggagcacc ctgaggatgg    4740
agctgatggg ctgtgacctg aacagctgca gcatgccct gggcatggag agcaaggcca    4800
tctctgatgc ccagatcact gccagcagct acttcaccaa catgtttgcc acctggagcc    4860
ccagcaaggc caggctgcac ctgcaggca ggagcaatgc ctggaggccc caggtcaaca    4920
accccaagga gtggctgcag gtggacttcc agaagaccat gaaggtgact ggggtgacca    4980
cccagggggt gaagagcctg ctgaccagca tgtatgtgaa ggagttcctg atcagcagca    5040
gccaggatgg ccaccagtgg acctgttct tccagaatgg caaggtgaag gtgttccagg    5100
gcaaccagga cagcttcacc cctgtggtga acagcctgga ccccccctg ctgaccagat    5160 acctgaggat tcacccccag agctgggtgc accagattgc cctgaggatg gaggtgctgg    5220
gctgtgaggc ccaggacctg tactgacctc gaggaataaa ggaaatttat tttcattgca    5280
atagtgtgtt ggttttttgt gtcacgtggc ggccgcagga ccccctagtg atggagttgg    5340
ccactccctc tctgcgcgct cgctcgctca ctgaggccgg gcgaccaaag gtcgcccgac    5400
gcccgggctt tgcccgggcg gcctcagtga gcgagcgagc gcgcagagag ggagtggcca    5460
a                                                                   5461
```

<210> SEQ ID NO 25
<211> LENGTH: 5327
<212> TYPE: DNA
<213> ORGANISM: Adeno-Associated Virus 2

<400> SEQUENCE: 25

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
```

```
ggaggatggg aactgagggg ttggaagggg gcagggtgag cccagaaact cctgtgtgcc      480
tctgagcctg cagacgcgaa acgtcgactg gacacaggac gctgtggttt ctgagccagg      540
gggcgactca gatcccagcc agtggactta gcccctgttt gctcctccga taactggggt      600
gaccttggtt aatattcacc agcagcctcc cccgttgccc ctctggatcc actgcttaaa      660
tacggacgag gacagggccc tgtctcctca gcttcaggca ccaccactga cctgggacag      720
tgaatcgcga tcgccaccat gcagattgag ctgagcacct gcttcttcct gtgcctgctg      780
aggttctgct tctctgccac caggagatac tacctggggg ctgtggagct gagctgggac      840
tacatgcagt ctgacctggg ggagctgcct gtggatgcca ggttccccccc cagagtgccc      900
aagagcttcc ccttcaacac ctctgtggtg tacaagaaga ccctgtttgt ggagttcact      960
gaccacctgt tcaacattgc caagcccagg ccccctgga tgggcctgct gggccccacc      1020
atccaggctg aggtgtatga cactgtggtg atcaccctga agaacatggc cagccaccct      1080
gtgagcctgc atgctgtggg ggtgagctac tggaaggcct ctgagggggc tgagtatgat      1140
gaccagacca gccagaggga aaggaggat gacaaggtgt ccctgggggg cagccacacc      1200
tatgtgtggc aggtgctgaa ggagaatggc cccatgcct ctgaccccct gtgcctgacc      1260
tacagctacc tgagccatgt ggacctggtg aaggacctga actctggcct gattggggcc      1320
ctgctggtgt gcagggaggg cagcctggcc aaggagaaga cccagaccct gcacaagttc      1380
atcctgctgt ttgctgtgtt tgatgagggc aagagctggc actctgaaac caagaacagc      1440
ctgatgcagg acagggatgc tgcctctgcc agggcctggc caagatgca cactgtgaat      1500
ggctatgtga acaggagcct gcctggcctg attggctgcc acaggaagtc tgtgtactgg      1560
catgtgattg gcatgggcac caccctgag gtgcacagca tcttcctgga gggccacacc      1620
ttcctggtca ggaaccacag gcaggccagc ctggagatca gccccatcac cttcctgact      1680
gcccagaccc tgctgatgga cctgggccag ttcctgctgt tctgccacat cagcagccac      1740
cagcatgatg gcatggaggc ctatgtgaag gtggacagct gccctgagga gccccagctg      1800
aggatgaaga acaatgagga ggctgaggac tatgatgatg acctgactga ctctgagatg      1860
gatgtggtga ggtttgatga tgacaacagc cccagcttca tccagatcag gtctgtggcc      1920
aagaagcacc ccaagacctg ggtgcactac attgctgctg aggaggagga ctgggactat      1980
gcccccctgg tgctggcccc tgatgacagg agctacaaga ccagtacct gaacaatggc      2040
ccccagagga ttggcaggaa gtacaagaag gtcaggttca tggcctacac tgatgaaacc      2100
ttcaagacca gggaggccat ccagcatgag tctggcatcc tgggcccct gctgtatggg      2160
gaggtggggg acaccctgct gatcatcttc aagaaccagg ccagcaggcc ctacaacatc      2220
taccccatg gcatcactga tgtgaggccc ctgtacagca ggaggctgcc caaggggtg      2280
aagcacctga aggacttccc catcctgcct ggggagatct tcaagtacaa gtggactgtg      2340
actgtggagg atggcccac caagtctgac cccaggtgcc tgaccagata ctacagcagc      2400
tttgtgaaca tggagaggga cctggcctct ggcctgattg gcccctgct gatctgctac      2460
aaggagtctg tggaccagag gggcaaccag atcatgtctg acaagaggaa tgtgatcctg      2520
ttctctgtgt ttgatgagaa caggagctgg tacctgactg agaacatcca gaggttcctg      2580
cccaaccctg ctggggtgca gctggaggac cctgagttcc aggccagcaa catcatgcac      2640
agcatcaatg gctatgtgtt tgacagcctg cagctgtctg tgtgcctgca tgaggtggcc      2700
tactggtaca tcctgagcat tggggcccag actgacttcc tgtctgtgtt cttctctggc      2760
```

```
tacaccttca agcacaagat ggtgtatgag gacaccctga ccctgttccc cttctctggg    2820
gagactgtgt tcatgagcat ggagaaccct ggcctgtgga ttctgggctg ccacaactct    2880
gacttcagga acagggcat gactgccctg ctgaaagtct ccagctgtga caagaacact     2940
ggggactact atgaggacag ctatgaggac atctctgcct acctgctgag caagaacaat    3000
gccattgagc ccaggagctt cagccagaac cccccagtgc tgaagaggca ccagagggag    3060
atcaccagga ccaccctgca gtctgaccag gaggagattg actatgatga ccatctctct    3120
gtggagatga agaaggagga ctttgacatc tacgacgagg acgagaacca gagccccagg    3180
agcttccaga agaagaccag gcactacttc attgctgctg tggagaggct gtgggactat    3240
ggcatgagca gcagcccca tgtgctgagg aacagggccc agtctggctc tgtgccccag    3300
ttcaagaagg tggtgttcca ggagttcact gatggcagct tcacccagcc cctgtacaga    3360
ggggagctga atgagcacct gggcctgctg gcccctaca tcagggctga ggtggaggac     3420
aacatcatgg tgaccttcag gaaccaggcc agcaggccct acagcttcta cagcagcctg    3480
atcagctatg aggaggacca gaggcagggg gctgagccca gaagaacttt tgtgaagccc     3540
aatgaaacca gacctacttt ctggaaggtg cagcaccaca tggccccccac caaggatgag    3600 tttgactgca aggcctgggc ctacttctct gatgtggacc tggagaagga tgtgcactct    3660
ggcctgattg gccccctgct ggtgtgccac accaacaccc tgaaccctgc ccatggcagg    3720
caggtgactg tgcaggagtt tgccctgttc ttcaccatct tgatgaaac caagagctgg    3780 tacttcactg agaacatgga gaggactgc agggcccct gcaacatcca gatggaggac     3840
cccaccttca aggagaacta caggttccat gccatcaatg ctacatcat ggacaccctg    3900 cctggcctgg tgatggccca ggaccagagg atcaggtggt acctgctgag catgggcagc    3960
aatgagaaca tccacagcat ccacttctct ggccatgtgt tcactgtgag gaagaaggag    4020
gagtacaaga tggccctgta caacctgtac cctggggtgt tgagactgt ggagatgctg     4080 cccagcaagg ctggcatctg gagggtggag tgcctgattg gggagcacct gcatgctggc    4140
atgagcaccc tgttcctggt gtacagcaac aagtgccaga ccccctgggg catggcctct    4200
ggccacatca gggacttcca gatcactgcc tctggccagt atggccagtg ggcccccaag    4260
ctggccaggc tgcactactc tggcagcatc aatgcctgga gcaccaagga gcccttcagc    4320
tggatcaagg tggacctgct ggcccccatg atcatccatg gcatcaagac caggggggcc    4380
aggcagaagt tcagcagcct gtacatcagc cagttcatca tcatgtacag cctggatggc    4440
aagaagtggc agacctacag gggcaacagc actggcaccc tgatggtgtt ctttggcaat    4500
gtggacagct ctggcatcaa gcacaacatc ttcaacccc ccatcattgc cagatacatc     4560
aggctgcacc ccacccacta cagcatcagg agcaccctga ggatggagct gatgggctgt    4620
gacctgaaca gctgcagcat gcccctgggc atggagagca aggccatctc tgatgcccag    4680
atcactgcca gcagctactt caccaacatg tttgccacct ggagcccag caaggccagg     4740 ctgcacctgc agggcaggag caatgcctgg aggcccagg tcaacaaccc caaggagtgg    4800
ctgcaggtgg acttccagaa gaccatgaag gtgactgggg tgaccaccca gggggtgaag    4860
agcctgctga ccagcatgta tgtgaaggag ttcctgatca gcagcagcca ggatggccac    4920
cagtggaccc tgttcttcca gaatggcaag gtgaaggtgt tccagggcaa ccaggacagc    4980
ttcacccctg tggtgaacag cctggaccc cccctgctga ccagataccc tgaggattcac     5040 ccccagagct gggtgcacca gattgccctg aggatggagg tgctgggctg tgaggcccag    5100
gacctgtact gacctcgagg aataaaggaa atttattttc attgcaatag tgtgttggtt    5160
```

| | |
|---|---|
| ttttgtgtca cgtggcggcc gcaggaaccc ctagtgatgg agttggccac tccctctctg | 5220 |
| cgcgctcgct cgctcactga ggccgggcga ccaaaggtcg cccgacgccc gggctttgcc | 5280 |
| cgggcggcct cagtgagcga gcgagcgcgc agagagggag tggccaa | 5327 |

<210> SEQ ID NO 26
<211> LENGTH: 5309
<212> TYPE: DNA
<213> ORGANISM: Adeno-Associated Virus 2

<400> SEQUENCE: 26

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtc tgcaggctca gaggcacaca | 180 |
| ggagtttctg ggctcaccct gccccttcc aaccctcag ttcccatcct ccagcagctg | 240 |
| tttgtgtgct gcctctgaag tccacactga acaaacttca gcctactcat gtccctaaaa | 300 |
| tgggcaaaca ttgcaagcag caaacagcaa acacacagcc ctccctgcct gctgaccttg | 360 |
| gagctggggc agaggtcaga gacctctctg ggcccatgcc acctccaaca tccactcgac | 420 |
| cccttggaat tcggtggag aggagcagag gttgtcctgg cgtggtttag gtagtgtgag | 480 |
| aggggtcgac tggacacagg acgctgtggt ttctgagcca gggggcgact cagatcccag | 540 |
| ccagtggact tagcccctgt tgctcctcc gataactggg gtgaccttgg ttaatattca | 600 |
| ccagcagcct ccccgttgc ccctctggat ccactgctta atacggacg aggacagggc | 660 |
| cctgtctcct cagcttcagg caccaccact gacctgggac agtgaatcgc gatcgccacc | 720 |
| atgcagattg agctgagcac ctgcttcttc ctgtgcctgc tgaggttctg cttctctgcc | 780 |
| accaggagat actacctggg ggctgtggag ctgagctgga ctacatgca gtctgacctg | 840 |
| ggggagctgc ctgtggatgc caggttcccc ccagagtgc caagagctt ccccttcaac | 900 |
| acctctgtgg tgtacaagaa gaccctgttt gtggagttca ctgaccacct gttcaacatt | 960 |
| gccaagccca ggccccctg gatgggcctg ctgggcccca ccatccaggc tgaggtgtat | 1020 |
| gacactgtgg tgatcaccct gaagaacatg gccagccacc ctgtgagcct gcatgctgtg | 1080 |
| ggggtgagct actggaaggc ctctgagggg gctgagtatg atgaccagac cagccagagg | 1140 |
| gagaaggagg atgacaaggt gttccctggg gcagccaca cctatgtgtg gcaggtgctg | 1200 |
| aaggagaatg cccccatggc ctctgacccc ctgtgcctga cctacagcta cctgagccat | 1260 |
| gtggacctgg tgaaggacct gaactctggc ctgattgggg ccctgctggt gtgcaggag | 1320 |
| ggcagcctgg ccaaggagaa gacccagacc ctgcacaagt tcatcctgct gtttgctgtg | 1380 |
| tttgatgagg gcaagagctg gcactctgaa accaagaaca gcctgatgca ggacagggat | 1440 |
| gctgcctctg ccagggcctg gcccaagatg cacactgtga atggctatgt gaacaggagc | 1500 |
| ctgcctggcc tgattggctg ccacaggaag tctgtgtact ggcatgtgat tggcatgggc | 1560 |
| accaccctg aggtgcacag catcttcctg gagggccaca ccttcctggt caggaaccac | 1620 |
| aggcaggcca gctgagat cagccccatc accttcctga ctgccagac cctgctgatg | 1680 |
| gacctgggcc agttcctgct gttctgccac atcagcagcc accagcatga tggcatggag | 1740 |
| gcctatgtga aggtggacag ctgccctgag agccccagc tgaggatgaa gaacaatgag | 1800 |
| gaggctgagg actatgatga tgacctgact gactctgaga tggatgtggt gaggtttgat | 1860 |
| gatgacaaca gccccagctt catccagatc aggtctgtgg ccaagaagca ccccaagacc | 1920 |

-continued

```
tgggtgcact acattgctgc tgaggaggag gactgggact atgcccccct ggtgctggcc    1980
cctgatgaca ggagctacaa gagccagtac ctgaacaatg ccccagag gattggcagg       2040 aagtacaaga aggtcaggtt catggcctac actgatgaaa ccttcaagac cagggaggcc    2100
atccagcatg agtctggcat cctgggcccc ctgctgtatg gggaggtggg ggacaccctg    2160
ctgatcatct tcaagaacca ggccagcagg ccctacaaca tctaccccca tggcatcact    2220
gatgtgaggc ccctgtacag caggaggctg cccaagggg tgaagcacct gaaggacttc     2280
cccatcctgc tggggagat cttcaagtac aagtggactg tgactgtgga ggatggcccc     2340
accaagtctg accccaggtg cctgaccaga tactacagca gctttgtgaa catggagagg    2400
gacctggcct ctggcctgat ggcccctg ctgatctgct acaaggagtc tgtggaccag      2460
aggggcaacc agatcatgtc tgacaagagg aatgtgatcc tgttctctgt gtttgatgag    2520
aacaggagct ggtacctgac tgagaacatc cagaggttcc tgcccaaccc tgctggggtg    2580
cagctggagg accctgagtt ccaggccagc aacatcatgc acagcatcaa tggctatgtg    2640
tttgacagcc tgcagctgtc tgtgtgcctg catgaggtgg cctactggta catcctgagc    2700
attggggccc agactgactt cctgtctgtg ttcttctctg gctacacctt caagcacaag    2760
atggtgtatg aggacaccct gaccctgttc cccttctctg gggagactgt gttcatgagc    2820
atggagaacc ctggcctgtg gattctgggc tgccacaact ctgacttcag aacaggggc    2880 atgactgccc tgctgaaagt ctccagctgt gacaagaaca ctggggacta ctatgaggac    2940
agctatgagg acatctctgc ctacctgctg agcaagaaca atgccattga gcccaggagc    3000
ttcagccaga ccccccagt gctgaagagg caccagaggg agatcaccag gaccaccctg     3060
cagtctgacc aggaggagat tgactatgat gacaccatct ctgtggagat gaagaaggag    3120
gactttgaca tctacgacga ggacgagaac cagagcccca ggagcttcca agaagagacc    3180
aggcactact tcattgctgc tgtggagagg ctgtgggact atggcatgag cagcagcccc    3240
catgtgctga ggaacagggc ccagtctggc tctgtgcccc agttcaagaa ggtggtgttc    3300
caggagttca ctgatggcag cttcacccag cccctgtaca gggggagct gaatgagcac     3360 ctgggcctgc tgggcccta catcagggct gaggtggagg acaacatcat ggtgaccttc    3420
aggaaccagg ccagcaggcc ctacagcttc tacagcagcc tgatcagcta tgaggaggac    3480
cagaggcagg ggctgagcc caggaagaac tttgtgaagc ccaatgaaac caagacctac    3540
ttctggaagg tgcagcacca catggccccc accaaggatg agtttgactg caaggcctgg    3600
gcctacttct ctgatgtgga cctggagaag gatgtgcact ctggcctgat ggccccctg     3660 ctggtgtgcc acaccaacac cctgaaccct gccatggca ggcaggtgac tgtgcaggag     3720
tttgccctgt tcttcaccat ctttgatgaa accaagagct ggtacttcac tgagaacatg    3780
gagaggaact gcagggcccc ctgcaacatc cagatggagg accccacctt caaggagaac    3840
tacaggttcc atgccatcaa tggctacatc atggacaccc tgcctggcct ggtgatggcc    3900
caggaccaga ggatcaggtg gtacctgctg agcatgggca caatgagaa catccacagc    3960 atccacttct ctggccatgt gttcactgtg aggaagaagg aggagtacaa gatggccctg    4020
tacaacctgt accctggggt gtttgagact gtggagatgc tgcccagcaa ggctggcatc    4080
tggagggtgg agtgcctgat tggggagcac ctgcatgctg gcatgagcac cctgttcctg    4140
gtgtacagca caagtgcca gacccccctg gcatggcct ctggccacat cagggacttc      4200
cagatcactg cctctggcca gtatggccag tgggccccca gctggccag gctgcactac    4260 tctggcagca tcaatgcctg gagcaccaag gagcccttca gctggatcaa ggtggacctg    4320
```

-continued

```
ctggccccca tgatcatcca tggcatcaag acccagggggg ccaggcagaa gttcagcagc    4380
ctgtacatca gccagttcat catcatgtac agcctggatg caagaagtg gcagacctac     4440 aggggcaaca gcactggcac cctgatggtg ttctttggca atgtggacag ctctggcatc    4500
aagcacaaca tcttcaaccc ccccatcatt gccagataca tcaggctgca ccccacccac    4560
tacagcatca ggagcaccct gaggatggag ctgatgggct gtgacctgaa cagctgcagc    4620
atgcccctgg gcatggagag caaggccatc tctgatgccc agatcactgc cagcagctac    4680
ttcaccaaca tgtttgccac ctggagcccc agcaaggcca ggctgcacct gcagggcagg    4740
agcaatgcct ggaggcccca ggtcaacaac cccaaggagt ggctgcaggt ggacttccag    4800
aagaccatga aggtgactgg ggtgaccacc caggggggtga agagcctgct gaccagcatg    4860
tatgtgaagg agttcctgat cagcagcagc caggatggcc accagtggac cctgttcttc    4920
cagaatggca aggtgaaggt gttccagggc aaccaggaca gcttcacccc tgtggtgaac    4980
agcctggacc ccccctgct gaccagatac ctgaggattc accccagag ctgggtgcac     5040 cagattgccc tgaggatgga ggtgctgggc tgtgaggccc aggacctgta ctgacctcga    5100
ggaataaagg aaatttattt tcattgcaat agtgtgttgg tttttttgtgt cacgtggcgg   5160 ccgcaggaac ccctagtgat ggagttggcc actccctctc tgcgcgctcg ctcgctcact    5220
gaggccgggc gaccaaaggt cgcccgacgc ccgggctttg cccgggcggc ctcagtgagc    5280
gagcgagcgc gcagagaggg agtggccaa                                     5309
```

<210> SEQ ID NO 27
<211> LENGTH: 5532
<212> TYPE: DNA
<213> ORGANISM: Adeno-Associated Virus 2

<400> SEQUENCE: 27

```
ttggccactc cctctctgcg cgctcgctcg ctcactgagg ccgccgggc aaagcccggg      60 cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag acagggccc tgtctcctca gcttcaggca ccaccactga cctgggacag     720
tgaatcgtaa gtatgccttt cactgcgaga ggttctggag aggcttctga gctccccatg    780
gcccaggcag gcagcaggtc tggggcagga gggggttgt ggagtgcctt gactcggggc    840 ctggccccc catctctgtc ttgcaggaca attgccgtct tctgtctcgt ggggcatcct    900
cctgctggca ggcctgtgct gcctggtccc tgcgatcgcc accatgcaga ttgagctgag    960
cacctgcttc ttcctgtgcc tgctgaggtt ctgcttctct gccaccagga gatactacct   1020
gggggctgtg gagctgagct gggactacat gcagtctgac ctgggggagc tgcctgtgga   1080
```

-continued

```
tgccaggttc cccccagag tgcccaagag cttcccctcc aacacctctg tggtgtacaa    1140
gaagaccctg tttgtggagt tcactgacca cctgttcaac attgccaagc ccaggccccc    1200
ctggatgggc ctgctgggcc ccaccatcca ggctgaggtg tatgacactg tggtgatcac    1260
cctgaagaac atggccagcc accctgtgag cctgcatgct gtgggggtga gctactggaa    1320
ggcctctgag ggggctgagt atgatgacca gaccagccag agggagaagg aggatgacaa    1380
ggtgttccct gggggcagcc acacctatgt gtggcaggtg ctgaaggaga atggcccat     1440
ggcctctgac cccctgtgcc tgacctacag ctacctgagc catgtggacc tggtgaagga    1500
cctgaactct ggcctgattg gggccctgct ggtgtgcagg gagggcagcc tggccaagga    1560
gaagacccag accctgcaca agttcatcct gctgtttgct gtgtttgatg agggcaagag    1620
ctggcactct gaaaccaaga acagcctgat gcaggacagg gatgctgcct ctgccagggc    1680
ctggcccaag atgcacactg tgaatggcta tgtgaacagg agcctgcctg gcctgattgg    1740
ctgccacagg aagtctgtgt actggcatgt gattggcatg ggcaccaccc ctgaggtgca    1800
cagcatcttc ctggagggcc acaccttcct ggtcaggaac acaggcagg ccagcctgga     1860
gatcagcccc atcaccttcc tgactgccca gaccctgctg atggacctgg gccagttcct    1920
gctgttctgc cacatcagca gccaccagca tgatggcatg gaggcctatg tgaaggtgga    1980
cagctgccct gaggagcccc agctgaggat gaagaacaat gaggaggctg aggactatga    2040
tgatgacctg actgactctg agatggatgt ggtgagggtt tgatgatgaca acagccccag    2100
cttcatccag atcaggtctg tggccaagaa gcaccccaag acctgggtgc actacattgc    2160
tgctgaggag gaggactggg actatgcccc cctggtgctg gcccctgatg acaggagcta    2220
caagagccag tacctgaaca atggcccca gaggattggc aggaagtaca gaaggtcag     2280
gttcatggcc tacactgatg aaaccttcaa gaccagggag gccatccagc atgagtctgg    2340
catcctgggc cccctgctgt atggggaggt ggggggacacc ctgctgatca tcttcaagaa    2400
ccaggccagc aggccctaca acatctaccc ccatggcatc actgatgtga ggcccctgta    2460
cagcaggagg ctgcccaagg gggtgaagca cctgaaggac ttccccatcc tgcctgggga    2520
gatcttcaag tacaagtgga ctgtgactgt ggaggatggc cccaccaagt ctgaccccag    2580
gtgcctgacc agatactaca gcagctttgt gaacatggag agggacctgg cctctggcct    2640
gattggcccc ctgctgatct gctacaagga gtctgtggac cagaggggca accagatcat    2700
gtctgacaag aggaatgtga tcctgttctc tgtgtttgat gagaacagga gctggtacct    2760
gactgagaac atccagaggt tcctgcccaa ccctgctggg gtgcagctgg aggaccctga    2820
gttccaggcc agcaacatca tgcacagcat caatggctat gtgtttgaca gcctgcagct    2880
gtctgtgtgc ctgcatgagg tggcctactg gtacatcctg agcattgggg cccagactga    2940
cttcctgtct gtgttcttct ctggctacac cttcaagcac aagatggtgt atgaggacac    3000
cctgaccctg ttccccttct ctggggagac tgtgttcatg agcatggaga acctggcct     3060
gtggattctg gctgccaca actctgactt caggaacagg gcatgactg ccctgctgaa     3120
agtctccagc tgtgacaaga acactgggga ctactatgag gacagctatg aggacatctc    3180
tgcctacctg ctgagcaaga caatgccat tgagccccag gcttcagcc agaaccccc      3240
agtgctgaag aggcaccaga gggagatcac caggaccacc ctgcagtctg accaggagga    3300
gattgactat gatgacacca tctctgtgga gatgaagaag gaggactttg acatctacga    3360
cgaggacgag aaccagagcc ccaggagctt ccagaagaag accaggcact acttcattgc    3420
tgctgtggag aggctgtggg actatggcat gagcagcagc ccccatgtgc tgaggaacag    3480
```

```
ggcccagtct ggctctgtgc cccagttcaa gaaggtggtg ttccaggagt tcactgatgg   3540
cagcttcacc cagcccctgt acagagggga gctgaatgag cacctgggcc tgctgggccc   3600
ctacatcagg gctgaggtgg aggacaacat catggtgacc ttcaggaacc aggccagcag   3660
gccctacagc ttctacagca gcctgatcag ctatgaggag gaccagaggc aggggggctga  3720 gcccaggaag aactttgtga agcccaatga aaccaagacc tacttctgga aggtgcagca   3780
ccacatggcc cccaccaagg atgagtttga ctgcaaggcc tgggcctact tctctgatgt   3840
ggacctggag aaggatgtgc actctggcct gattggcccc ctgctggtgt gccacaccaa   3900
caccctgaac cctgcccatg caggcaggt gactgtgcag gagtttgccc tgttcttcac    3960
catctttgat gaaaccaaga gctggtactt cactgagaac atggagagga actgcagggc   4020
cccctgcaac atccagatgg aggacccac cttcaaggag aactacaggt tccatgccat    4080
caatggctac atcatggaca ccctgcctgg cctggtgatg gcccaggacc agaggatcag   4140
gtggtacctg ctgagcatgg gcagcaatga aacatccac agcatccact tctctggcca    4200
tgtgttcact gtgaggaaga aggaggagta caagatggcc ctgtacaacc tgtaccctgg   4260
ggtgtttgag actgtggaga tgctgcccag caaggctggc atctggaggg tggagtgcct   4320
gattggggag cacctgcatg ctggcatgag caccctgttc ctggtgtaca gcaacaagtg   4380
ccagaccccc ctgggcatgg cctctggcca catcagggac ttccagatca ctgcctctgg   4440
ccagtatggc cagtgggccc ccaagctggc caggctgcac tactctggca gcatcaatgc   4500
ctggagcacc aaggagccct tcagctggat caaggtggac ctgctggccc ccatgatcat   4560
ccatggcatc aagacccagg gggccaggca gaagttcagc agcctgtaca tcagccagtt   4620
catcatcatg tacagcctgg atggcaagaa gtggcagacc tacaggggca acagcactgg   4680
caccctgatg gtgttctttg gcaatgtgga cagctctggc atcaagcaca acatcttcaa   4740 ccccccatc attgccagat acatcaggct gcacccacc cactacagca tcaggagcac    4800
cctgaggatg gagctgatgg gctgtgacct gaacagctgc agcatgcccc tgggcatgga   4860
gagcaaggcc atctctgatg cccagatcac tgccagcagc tacttcacca acatgtttgc   4920
cacctggagc cccagcaagg ccaggctgca cctgcagggc aggagcaatg cctggaggcc   4980
ccaggtcaac aaccccaagg agtggctgca ggtggacttc cagaagacca tgaaggtgac   5040 tgggggtgacc acccagggg tgaagagcct gctgaccagc atgtatgtga aggagttcct   5100
gatcagcagc agccaggatg gccaccagtg gaccctgttc ttccagaatg gcaaggtgaa   5160
ggtgttccag ggcaaccagg acagcttcac ccctgtggtg aacagcctgg acccccccct   5220
gctgaccaga tacctgagga ttcacccca gagctgggtg caccagattg ccctgaggat   5280
ggaggtgctg ggctgtgagg cccaggacct gtactgacct cgaggaataa ggaaatttta  5340
ttttcattgc aatagtgtgt tggttttttg tgtcacgtgg cggccgcagg aacccctagt   5400
gatggagttg gccactccct ctctgcgcgc tcgctcgctc actgaggccg ggcgaccaaa   5460
ggtcgcccga cgcccgggct ttgcccgggc ggcctcagtg agcgagcgag cgcgcagaga   5520
gggagtggcc aa                                                      5532
```

<210> SEQ ID NO 28
<211> LENGTH: 5877
<212> TYPE: DNA
<213> ORGANISM: Adeno-Associated Virus 2

<400> SEQUENCE: 28

-continued

```
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgaccc ctctcacact       180
acctaaacca cgccaggaca acctctgctc ctctccaccg aaattccaag ggtcgagtg        240 gatgttggag gtggcatggg cccagagagg tctctgacct ctgcccagc tccaaggtca       300 gcaggcaggg agggctgtgt gtttgctgtt tgctgcttgc aatgtttgcc cattttaggg       360
acatgagtag gctgaagttt gttcagtgtg gacttcagag gcagcacaca aacagctgct       420
ggaggatggg aactgagggg ttggaagggg gcagggtgag cccagaaact cctgtgtgcc       480
tctgagcctg cagacgcgaa acgtcgacag gttaattttt aaaaagcagt caaaagtcca       540
agtggccctt ggcagcattt actctctctg tttgctctgg ttaataatct caggagcaca       600
aacattcctg gaggcaggag aagaaatcaa catcctggac ttatcctctg ggcctctccc       660
cacccccagg agaggctcag gttaattttt aaaaagcagt caaaagtcca agtggccctt       720
ggcagcattt actctctctg tttgctctgg ttaataatct caggagcaca aacattcctg       780
gaggcaggag aagaaatcaa catcctggac ttatcctctg ggcctctccc cacccccagg       840
agaggctgtc gactggacac aggacgctgt ggtttctgag ccaggggcg actcagatcc       900 cagccagtgg acttagcccc tgtttgctcc tccgataact ggggtgacct tggttaatat       960
tcaccagcag cctcccccgt tgcccctctg gatccactgc ttaaatacgg acgaggacag      1020
ggccctgtct cctcagcttc aggcaccacc actgacctgg gacagtgaat cgtaagtatg      1080
cctttcactg cgagaggttc tggagaggct tctgagctcc ccatggccca ggcaggcagc      1140
aggtctgggg caggagggg gttgtggagt gccttgactc ggggcctggc cccccatct       1200 ctgtcttgca ggacaattgc cgtcttctgt ctcgtggggc atcctcctgc tggcaggcct      1260
gtgctgcctg gtccctgcga tcgccaccat gcagattgag ctgagcacct gcttcttcct      1320
gtgcctgctg aggttctgct tctctgccac caggagatac tacctggggg ctgtggagct      1380
gagctgggac tacatgcagt ctgacctggg ggagctgcct gtggatgcca ggttcccccc      1440
cagagtgccc aagagcttcc ccttcaacac ctctgtggtg tacaagaaga ccctgtttgt      1500
ggagttcact gaccacctgt tcaacattgc caagcccagg cccccctgga tgggcctgct      1560
gggccccacc atccaggctg aggtgtatga cactgtggtg atcacccctga gaacatggc      1620 cagccaccct gtgagcctgc atgctgtggg ggtgagctac tggaaggcct ctgagggggc      1680
tgagtatgat gaccagacca gccagaggga aaggaggat gacaaggtgt tccctggggg      1740
cagccacacc tatgtgtggc aggtgctgaa ggagaatggc cccatggcct ctgaccccct      1800
gtgcctgacc tacagctacc tgagccatgt ggacctggtg aaggacctga actctggcct      1860
gattggggcc ctgctggtgt gcagggaggg cagcctggcc aaggagaaga cccagaccct      1920
gcacaagttc atcctgctgt ttgctgtgtt tgatgagggc aagagctggc actctgaaac      1980
caagaacagc ctgatgcagg acaggggatgc tgcctctgcc agggcctggc ccaagatgca      2040
cactgtgaat ggctatgtga acaggagcct gcctggcctg attggctgcc acaggaagtc      2100
tgtgtactgg catgtgattg gcatgggcac caccccctgag gtgcacagca tcttcctgga      2160
gggccacacc ttcctggtca ggaaccacag gcaggccagc ctggagatca gccccatcac      2220
cttcctgact gcccagaccc tgctgatgga cctgggccag ttcctgctgt tctgccacat      2280
cagcagccac cagcatgatg gcatggaggc ctatgtgaag gtggacagct gccctgagga      2340
gccccagctg aggatgaaga acaatgagga ggctgaggac tatgatgatg acctgactga      2400
```

-continued

```
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gccccctgg tgctggcccc tgatgacagg agctacaaga gccagtacct     2580
gaacaatggc cccagagga ttggcaggaa gtacaagaag gtcaggttca tggcctacac     2640
tgatgaaacc ttcaagacca gggaggccat ccagcatgag tctggcatcc tgggcccct    2700 gctgtatggg gaggtggggg acaccctgct gatcatcttc aagaaccagg ccagcaggcc    2760
ctacaacatc taccccatg gcatcactga tgtgaggccc ctgtacagca ggaggctgcc    2820 caaggggtg aagcacctga aggacttccc catcctgcct ggggagatct tcaagtacaa     2880
gtggactgtg actgtggagg atggccccac caagtctgac cccaggtgcc tgaccagata    2940
ctacagcagc tttgtgaaca tggagaggga cctggcctct ggcctgattg ccccctgct    3000 gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctggggtgca gctggaggac cctgagttcc aggccagcaa    3180
catcatgcac agcatcaatg gctatgtgtt tgacagcctg cagctgtctg tgtgcctgca    3240
tgaggtggcc tactggtaca tcctgagcat tggggcccag actgacttcc tgtctgtgtt    3300
cttctctggc tacaccttca gcacaagat ggtgtatgag gacaccctga ccctgttccc     3360
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840 tgtgcccag ttcaagaagg tggtgttcca ggagttcact gatggcagct tcacccagcc     3900
cctgtacaga ggggagctga atgagcacct gggcctgctg ggcccctaca tcagggctga    3960
ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggccccac     4140 caaggatgag tttgactgca aggcctgggc ctacttctct gatgtggacc tggagaagga    4200
tgtgcactct ggcctgattg ccccctgct ggtgtgccac accaacccc tgaaccctgc     4260 ccatggcagg caggtgactg tgcaggagtt tgccctgttc ttcaccatct ttgatgaaac    4320
caagagctgg tacttcactg agaacatgga gaggaactgc agggccccct gcaacatcca    4380
gatggaggac cccaccttca aggagaacta caggttccat gccatcaatg gctacatcat    4440
ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggcctgta caacctgtac cctgggtgt ttgagactgt     4620 ggagatgctg cccagcaagg ctggcatctg gagggtggga tgcctgattg gggagcacct    4680
gcatgctggc atgagcaccc tgttcctggt gtacagcaac aagtgccaga ccccctggg    4740
```

| | |
|---|---:|
| catggcctct ggccacatca gggacttcca gatcactgcc tctggccagt atggccagtg | 4800 |
| ggcccccaag ctggccaggc tgcactactc tggcagcatc aatgcctgga gcaccaagga | 4860 |
| gcccttcagc tggatcaagg tggacctgct ggcccccatg atcatccatg gcatcaagac | 4920 |
| ccagggggcc aggcagaagt tcagcagcct gtacatcagc cagttcatca tcatgtacag | 4980 |
| cctggatggc aagaagtggc agacctacag gggcaacagc actggcaccc tgatggtgtt | 5040 |
| ctttggcaat gtggacagct ctggcatcaa gcacaacatc ttcaaccccc ccatcattgc | 5100 |
| cagatacatc aggctgcacc ccacccacta cagcatcagg agcaccctga ggatggagct | 5160 |
| gatgggctgt gacctgaaca gctgcagcat gcccctgggc atggagagca aggccatctc | 5220 |
| tgatgcccag atcactgcca gcagctactt caccaacatg tttgccacct ggagccccag | 5280 |
| caaggccagg ctgcacctgc agggcaggag caatgcctgg aggcccccag tcaacaaccc | 5340 |
| caaggagtgg ctgcaggtgg acttccagaa gaccatgaag gtgactgggg tgaccaccca | 5400 |
| gggggtgaag agcctgctga ccagcatgta tgtgaaggag ttcctgatca gcagcagcca | 5460 |
| ggatggccac cagtggaccc tgttcttcca gaatggcaag gtgaaggtgt tccagggcaa | 5520 |
| ccaggacagc ttcacccctg tggtgaacag cctggacccc cccctgctga ccagatacct | 5580 |
| gaggattcac ccccagagct gggtgcacca gattgccctg aggatggagg tgctgggctg | 5640 |
| tgaggcccag acctgtact gacctcgagg aataaaggaa atttattttc attgcaatag | 5700 |
| tgtgttggtt ttttgtgtca cgtggcggcc gcaggaaccc ctagtgatgg agttggccac | 5760 |
| tccctctctg cgcgctcgct cgctcactga ggccgggcga ccaaaggtcg cccgacgccc | 5820 |
| gggctttgcc cgggcggcct cagtgagcga gcgagcgcgc agagagggag tggccaa | 5877 |

<210> SEQ ID NO 29
<211> LENGTH: 6054
<212> TYPE: DNA
<213> ORGANISM: Adeno-Associated Virus 2

<400> SEQUENCE: 29

| | |
|---|---:|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaacca cgccaggaca acctctgctc ctctccaccg aaattccaag ggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |
| ggaggatggg aactgagggg ttggaagggg cagggtgag cccagaaact cctgtgtgcc | 480 |
| tctgagcctg cagacgcgaa acgtcgacag gttaattttt aaaaagcagt caaaagtcca | 540 |
| agtggccctt ggcagcattt actctctctg tttgctctgg ttaataatct caggagcaca | 600 |
| acattcctg gaggcaggag aagaaatcaa catcctggac ttatcctctg ggcctctccc | 660 |
| cacccccagg agaggctcag gttaattttt aaaaagcagt caaaagtcca agtggccctt | 720 |
| ggcagcattt actctctctg tttgctctgg ttaataatct caggagcaca acattcctg | 780 |
| gaggcaggag aagaaatcaa catcctggac ttatcctctg ggcctctccc cacccccagg | 840 |
| agaggctgtc gactgacac aggacgctgt ggtttctgag ccagggggcg actcagatcc | 900 |
| cagccagtga acttagcccc tgtttgctcc tccgataact ggggtgacct tggttaatat | 960 |
| tcaccagcag cctcccccgt tgcccctctg gatccactgc ttaaatacgg acgaggacag | 1020 |

```
ggccctgtct cctcagcttc aggcaccacc actgacctgg gacagtgaat cgtaagtatg    1080
cctttcactg cgagaggttc tggagaggct tctgagctcc ccatggccca ggcaggcagc    1140
aggtctgggg caggagggggg gttgtggagt gccttgactc ggggcctggc cccccatct    1200 ctgtcttgca ggacaattgc cgtcttctgt ctcgtggggc atcctcctgc tggcaggcct    1260
gtgctgcctg gtccctgcga tcgccaccat gcagattgag ctgagcacct gcttcttcct    1320
gtgcctgctg aggttctgct tctctgccac caggagatac tacctggggg ctgtggagct    1380
gagctgggac tacatgcagt ctgacctggg ggagctgcct gtggatgcca ggttcccccc    1440
cagagtgccc aagagcttcc ccttcaacac ctctgtggtg tacaagaaga ccctgtttgt    1500
ggagttcact gaccacctgt tcaacattgc caagcccagg ccccctggga tgggcctgct    1560 gggcccacc atccaggctg aggtgtatga cactgtggtg atcaccctga gaacatggc    1620 cagccaccct gtgagcctgc atgctgtggg ggtgagctac tggaaggcct ctgaggggc    1680 tgagtatgat gaccagacca gccagaggga aaggaggat gacaaggtgt ccctgggggg    1740
cagccacacc tatgtgtggc aggtgctgaa ggagaatggc cccatggcct ctgaccccct    1800
gtgcctgacc tacagctacc tgagccatgt ggacctggtg aaggacctga actctggcct    1860
gattggggcc ctgctggtgt gcagggaggg cagcctggcc aaggagaaga cccagaccct    1920
gcacaagttc atcctgctgt tgctgtgtt tgatgagggc aagagctggc actctgaaac    1980
caagaacagc ctgatgcagg acagggatgc tgcctctgcc agggcctggc ccaagatgca    2040
cactgtgaat ggctatgtga acaggagcct gcctggcctg attggctgcc acaggaagtc    2100
tgtgtactgg catgtgattg gcatgggcac cacccctgag gtgcacagca tcttcctgga    2160
gggccacacc ttcctggtca ggaaccacag gcaggccagc ctggagatca gccccatcac    2220
cttcctgact gcccagaccc tgctgatgga cctgggccag ttcctgctgt tctgccacat    2280
cagcagccac cagcatgatg gcatggaggc ctatgtgaag gtggacagct gccctgagga    2340
gccccagctg aggatgaaga caatgagga ggctgaggac tatgatgatg acctgactga    2400
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gccccctgg tgctggcccc tgatgacagg agctacaaga gccagtacct    2580
gaacaatggc ccccagagga ttggcaggaa gtacaagaag gtcaggttca tggcctacac    2640
tgatgaaacc ttcaagacca gggaggccat ccagcatgag tctggcatcc tgggccccct    2700
gctgtatggg gaggtggggg acaccctgct gatcatcttc aagaaccagg ccagcaggcc    2760
ctacaacatc taccccatg gcatcactga tgtgaggccc ctgtacagca ggaggctgcc    2820
caagggggtg aagcacctga aggacttccc catcctgcct gggagatct tcaagtacaa    2880 gtggactgtg actgtggagg atggccccac caagtctgac cccaggtgcc tgaccagata    2940
ctacagcagc tttgtgaaca tggagaggga cctggcctct ggcctgattg ccccctgct    3000 gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctgggtgca gctggaggac cctgagttcc aggccagcaa    3180
catcatgcac agcatcaatg gctatgtgtt tgacagcctg cagctgtctg tgtgcctgca    3240
tgaggtggcc tactgtgaca tcctgagcat tggggcccag actgacttcc tgtctgtgtt    3300
cttctctggc tacaccttca gcacaagat ggtgtatgag gacaccctga ccctgttccc    3360
```

```
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga atgagcacct gggcctgctg gcccctaca tcagggctga    3960 ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggccccac     4140 caaggatgag tttgactgca aggcctgggc ctacttctct gatgtggacc tggagaagga    4200
tgtgcactct ggcctgattg gccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga aggaactgc agggcccct gcaacatcca     4380 gatggaggac cccaccttca aggagaacta caggttccat gccatcaatg ctacatcat    4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctggc atgagcaccc tgttcctggt gtacagcaac aagtgccaga ccccctggg     4740 catggcctct ggccacatca gggacttcca gatcactgcc tctggccagt atggccagtg    4800 ggccccaag ctggccaggc tgcactactc tggcagcatc aatgcctgga gcaccaagga    4860
gcccttcagc tggatcaagg tggacctgct ggcccccatg atcatccatg catcaagac     4920 ccagggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaacccc ccatcattgc     5100 cagatacatc aggctgcacc ccaccacta cagcatcagg agcaccctga ggatggagct    5160
gatgggctgt gacctgaaca gctgcagcat gccctgggc atggagagca aggccatctc     5220
tgatgcccag atcactgcca gcagctactt caccaacatg tttgccacct ggagcccag     5280 caaggccagc tgcacctgc agggcaggag caatgcctgg aggcccccag tcaacaaccc    5340
caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcacccctg tggtgaacag cctggaccc ccctgctga ccagatacct    5580 gaggattcac ccccagagct gggtgcacca gattgccctg aggatggagg tgctgggctg    5640
tgaggcccag gacctgtact gacctcgagg tgtgccttct agttgccagc catctgttgt    5700
ttgcccctcc cccgtgcctt ccttgaccct ggaaggtgcc actcccactg tcctttccta    5760
```

| | | |
|---|---|---|
| ataaaatgag gaaattgcat cgcattgtct gagtaggtgt cattctattc tgggggtgg | 5820 | |
| ggtggggcag dacagcaagg gggaggattg ggaagacaat agcaggcatg ctggggatgc | 5880 | |
| ggtgggctct atgggcacgt ggcggccgca ggaaccccta gtgatggagt tggccactcc | 5940 | |
| ctctctgcgc gctcgctcgc tcactgaggc cgggcgacca aaggtcgccc gacgcccggg | 6000 | |
| cttttgcccgg gcggcctcag tgagcgagcg agcgcgcaga gagggagtgg ccaa | 6054 | |

<210> SEQ ID NO 30
<211> LENGTH: 6054
<212> TYPE: DNA
<213> ORGANISM: Adeno-Associated Virus 2

<400> SEQUENCE: 30

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaaacca cgccaggaca acctctgctc ctctccaccg aaattccaag gggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |
| ggaggatggg aactgagggg ttggaagggg gcagggtgag cccagaaact cctgtgtgcc | 480 |
| tctgagcctg cagacgcgaa acgtcgaagc ctctcctggg ggtggggaga ggcccagagg | 540 |
| ataagtccag gatgttgatt tcttctcctg cctccaggaa tgtttgtgct cctgagatta | 600 |
| ttaaccagag caaacagaga gagtaaatgc tgccaagggc cacttggact tttgactgct | 660 |
| tttaaaaat taacctgagc ctctcctggg ggtggggaga ggcccagagg ataagtccag | 720 |
| gatgttgatt tcttctcctg cctccaggaa tgtttgtgct cctgagatta ttaaccagag | 780 |
| caaacagaga gagtaaatgc tgccaagggc cacttggact tttgactgct ttttaaaaat | 840 |
| taacctggtc gactggacac aggacgctgt ggtttctgag ccaggggggcg actcagatcc | 900 |
| cagccagtgg acttagcccc tgtttgctcc tccgataact ggggtgacct tggttaatat | 960 |
| tcaccagcag cctccccgt tgcccctctg gatccactgc ttaaatacgg acgaggacag | 1020 |
| ggccctgtct cctcagcttc aggcaccacc actgacctgg dacagtgaat cgtaagtatg | 1080 |
| cctttcactg cgagaggttc tggagaggct tctgagctcc ccatggccca ggcaggcagc | 1140 |
| aggtctgggg caggaggggg gttgtggagt gccttgactc ggggcctggc cccccatct | 1200 |
| ctgtcttgca ggacaattgc cgtcttctgt ctcgtggggc atcctcctgc tggcaggcct | 1260 |
| gtgctgcctg gtccctgcga tcgccaccat gcagattgag ctgagcacct gcttcttcct | 1320 |
| gtgcctgctg aggttctgct tctctgccac caggagatac tacctggggg ctgtggagct | 1380 |
| gagctgggac tacatgcagt ctgacctggg ggagctgcct gtggatgcca ggttcccccc | 1440 |
| cagagtgccc aagagcttcc ccttcaacac ctctgtggtg tacaagaaga ccctgttgt | 1500 |
| ggagttcact gaccacctgt tcaacattgc caagcccagg cccccctgga tgggcctgct | 1560 |
| gggccccacc atccaggctg aggtgtatga cactgtggtg atcaccctga agaacatggc | 1620 |
| cagccaccct gtgagcctgc atgctgtggg ggtgagctac tggaaggcct ctgaggggc | 1680 |
| tgagtatgat gaccagacca gccagggga aggaggat gacaaggtgt ccctggggg | 1740 |
| cagccacacc tatgtgtggc aggtgctgaa ggagaatggc cccatggcct ctgaccccct | 1800 |

```
gtgcctgacc tacagctacc tgagccatgt ggacctggtg aaggacctga actctggcct    1860
gattggggcc ctgctggtgt gcagggaggg cagcctggcc aaggagaaga cccagaccct    1920
gcacaagttc atcctgctgt ttgctgtgtt tgatgagggc aagagctggc actctgaaac    1980
caagaacagc ctgatgcagg cagggatgc tgcctctgcc agggcctggc caagatgca     2040 cactgtgaat ggctatgtga acaggagcct gcctggcctg attggctgcc acaggaagtc    2100
tgtgtactgg catgtgattg gcatgggcac caccctgag gtgcacagca tcttcctgga    2160
gggccacacc ttcctggtca ggaaccacag gcaggccagc ctggagatca gccccatcac    2220
cttcctgact gcccagaccc tgctgatgga cctgggccag ttcctgctgt tctgccacat    2280
cagcagccac cagcatgatg gcatggaggc ctatgtgaag gtgacagct gccctgagga    2340 gccccagctg aggatgaaga acaatgagga ggctgaggac tatgatgatg acctgactga    2400
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gcccccctgg tgctggcccc tgatgacagg agctacaaga gccagtacct    2580
gaacaatggc ccccagagga ttggcaggaa gtacaagaag gtcaggttca tggcctacac    2640
tgatgaaacc ttcaagacca gggaggcat ccagcatgag tctggcatcc tgggccccct    2700
gctgtatggg gaggtggggg acaccctgct gatcatcttc aagaaccagg ccagcaggcc    2760
ctacaacatc taccccatg gcatcactga tgtgaggccc ctgtacagca ggaggctgcc    2820
caagggggtg aagcacctga aggacttccc catcctgcct ggggagatct tcaagtacaa    2880
gtggactgtg actgtggagg atggccccac caagtctgac cccaggtgcc tgaccagata    2940
ctacagcagc tttgtgaaca tggagaggga cctggcctct ggcctgattg ccccctgct    3000 gatctgctac aaggagtctg tggaccagag gggcaaccag atcatgtctg acaagaggaa    3060
tgtgatcctg ttctctgtgt tgatgagaa caggagctgg tacctgactg agaacatcca    3120
gaggttcctg cccaaccctg ctggggtgca gctggaggac cctgagttcc aggccagcaa    3180
catcatgcac agcatcaatg gctatgtgtt tgacagcctg cagctgtctg tgtgcctgca    3240
tgaggtggcc tactgtgtaca tcctgagcat tggggcccag actgacttcc tgtctgtgtt    3300
cttctctggc tacaccttca gcacaagat ggtgtatgag gacaccctga ccctgttccc    3360
cttctctggg gagactgtgt tcatgagcat ggagaaccct ggcctgtgga ttctgggctg    3420
ccacaactct gacttcagga caggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga tgagcacct gggcctgctg gcccctaca tcagggctga    3960 ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca gacctactt ctggaaggtg cagcaccaca tggccccac     4140 caaggatgag tttgactgca aggcctgggc ctacttctct gatgtggacc tggagaagga    4200
```

-continued

```
tgtgcactct ggcctgattg gccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga gaggaactgc agggcccct gcaacatcca     4380 gatggaggac cccaccttca aggagaacta caggttccat gccatcaatg ctacatcat    4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt tgagactgt     4620 ggagatgctg cccagcaagg ctggcatctg gagggtggag tgcctgattg gggagcacct    4680
gcatgctggc atgagcaccc tgttcctggt gtacagcaac aagtgccaga ccccctggg     4740 catggcctct ggccacatca gggacttcca gatcactgcc tctggccagt atggccagtg    4800 ggccccaag ctggccaggc tgcactactc tggcagcatc aatgcctgga gcaccaagga    4860
gcccttcagc tggatcaagg tggacctgct ggccccatg atcatccatg catcaagac     4920 ccagggggcc aggcagaagt tcagcagcct gtacatcagc cagttcatca tcatgtacag    4980
cctggatggc aagaagtggc agacctacag gggcaacagc actggcaccc tgatggtgtt    5040 cttttggcaat gtggacagct ctggcatcaa gcacaacatc ttcaacccc ccatcattgc    5100 cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggccccagg tcaacaaccc    5340
caaggagtgg ctgcaggtgg acttccagaa gaccatgaag gtgactgggg tgaccaccca    5400 ggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcaccctg tggtgaacag cctggacccc cccctgctga ccagatacct    5580
gaggattcac cccagagct gggtgcacca gattgccctg aggatggagg tgctgggctg    5640
tgaggcccag gacctgtact gacctcgagg tgtgccttct agttgccagc catctgttgt    5700
ttgcccctcc cccgtgcctt ccttgaccct ggaaggtgcc actcccactg tcctttccta    5760
ataaaatgag gaaattgcat cgcattgtct gagtaggtgt cattctattc tggggggtgg    5820
ggtggggcag gacagcaagg gggaggattg ggaagacaat agcaggcatg ctggggatgc    5880
ggtgggctct atgggcacgt ggcggccgca ggaaccccta gtgatggagt tggccactcc    5940
ctctctgcgc gctcgctcgc tcactgaggc cgggcgacca aaggtcgccc gacgcccggg    6000
ctttgcccgg gcggcctcag tgagcgagcg agcgcgcaga gagggagtgg ccaa          6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag gggtcgagtg     240
```

```
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactgggt     600 gaccttggtt aatattcacc agcagcctcc cccgttgccc ctctggatcc actgcttaaa    660 tacgacgag gacagggccc tgtctcctca gcttcaggca ccaccactga cctgggacag     720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttccccccc cagagtgccc    900 aagagcttcc ccttcaacac ctctgtggtg tacaagaaga ccctgtttgt ggagttcact    960
gaccacctgt tcaacattgc caagcccagg cccccctgga tgggcctgct gggccccacc   1020
atccaggctg aggtgtatga cactgtggtg atcaccctga gaacatggc cagccaccct    1080 gtgagcctgc atgctgtggg ggtgagctac tggaaggcct ctgaggggc tgagtatgat    1140 gaccagacca gccagaggga aaggaggat gacaaggtgt ccctgggggg cagccacacc    1200
tatgtgtggc aggtgctgaa ggagaatggc cccatgcct ctgacccct gtgcctgacc     1260 tacagctacc tgagccatgt ggacctggtg aaggacctga actctggcct gattggggcc   1320
ctgctggtgt gcagggaggg cagcctggcc aaggagaaga cccagaccct gcacaagttc    1380
atcctgctgt ttgctgtgtt tgatgagggc aagagctggc actctgaaac caagaacagc    1440
ctgatgcagg acagggatgc tgcctctgcc agggcctggc caagatgca cactgtgaat     1500 ggctatgtga acaggagcct gcctggcctg attggctgcc acaggaagtc tgtgtactgg   1560
catgtgattg gcatgggcac cacccctgag gtgcacagca tcttcctgga gggccacacc    1620
ttcctggtca ggaaccacag gcaggccagc ctggagatca gccccatcac cttcctgact    1680
gcccagaccc tgctgatgga cctggggcag ttcctgctgt tctgccacat cagcagccac    1740
cagcatgatg gcatggaggc ctatgtgaag gtggacagct ccctgagga gccccagctg    1800 aggatgaaga acaatgagga ggctgaggac tatgatgatg acctgactga ctctgagatg    1860
gatgtggtga ggtttgatga tgacaacagc cccagcttca tccagatcag gtctgtggcc    1920
aagaagcacc ccaagacctg ggtgcactac attgctgctg aggaggagga ctgggactat    1980
gcccccctgg tgctggcccc tgatgacagg agctacaaga gccagtacct gaacaatggc    2040
ccccagagga ttggcaggaa gtacaagaag gtcaggttca tggcctacac tgatgaaacc    2100
ttcaagacca gggaggccat ccagcatgag tctggcatcc tgggccccct gctgtatggg    2160
gaggtggggg acaccctgct gatcatcttc aagaaccagg ccagcaggcc ctacaacatc    2220 taccccatg gcatcactga tgtgaggccc ctgtacagca ggaggctgcc aagggggtg     2280 aagcacctga aggacttccc catcctgcct ggggagatct caagtacaa gtggactgtg    2340 actgtggagg atgcccccac caagtctgac cccaggtgcc tgaccagata ctacagcagc    2400
tttgtgaaca tggagaggga cctggcctct ggcctgattg gcccctgct gatctgctac    2460 aaggagtctg tggaccagag gggcaaccag atcatgtctg acaagaggaa tgtgatcctg    2520
ttctctgtgt ttgatgagaa caggagctgg tacctgactg agaacatcca gaggttcctg    2580
cccaaccctg ctggggtgca gctggaggac cctgagttcc aggccagcaa catcatgcac    2640
```

```
agcatcaatg gctatgtgtt tgacagcctg cagctgtctg tgtgcctgca tgaggtggcc    2700
tactggtaca tcctgagcat tggggcccag actgacttcc tgtctgtgtt cttctctggc    2760
tacaccttca agcacaagat ggtgtatgag acaccctga ccctgttccc cttctctggg     2820
gagactgtgt tcatgagcat ggagaaccct ggcctgtgga ttctgggctg ccacaactct    2880
gacttcagga acaggggcat gactgccctg ctgaaagtct ccagctgtga caagaacact    2940
ggggactact atgaggacag ctatgaggac atctctgcct acctgctgag caagaacaat    3000
gccattgagc ccaggagctt cagccagaac cccccagtgc tgaagaggca ccagagggag    3060
atcaccagga ccaccctgca gtctgaccag gaggagattg actatgatga ccatctctct    3120
gtggagatga agaaggagga ctttgacatc tacgacgagg acgagaacca gagccccagg    3180
agcttccaga agaagaccag gcactacttc attgctgctg tggagaggct gtgggactat    3240
ggcatgagca gcagccccca tgtgctgagg aacagggccc agtctggctc tgtgccccag    3300
ttcaagaagg tggtgttcca ggagttcact gatggcagct tcacccagcc cctgtacaga    3360
ggggagctga atgagcacct gggcctgctg gcccctaca tcagggctga ggtggaggac     3420
aacatcatgg tgaccttcag gaaccaggcc agcaggccct acagcttcta cagcagcctg    3480
atcagctatg aggaggacca gaggcagggg gctgagccca ggaagaactt tgtgaagccc    3540
aatgaaacca agacctactt ctggaaggtg cagcaccaca tggcccccac caaggatgag    3600
tttgactgca aggcctgggc ctacttctct gatgtggacc tggagaagga tgtgcactct    3660
ggcctgattg cccccctgct ggtgtgccac accaacaccc tgaaccctgc ccatggcagg    3720
caggtgactg tgcaggagtt tgccctgttc ttcaccatct ttgatgaaac caagagctgg    3780
tacttcactg agaacatgga gaggaactgc agggcccct gcaacatcca gatggaggac     3840
cccaccttca aggagaacta caggttccat gccatcaatg ctacatcat ggacaccctg     3900
cctggcctgg tgatggccca ggaccagagg atcaggtggt acctgctgag catgggcagc    3960
aatgagaaca tccacagcat ccacttctct ggccatgtgt tcactgtgag gaagaaggag    4020
gagtacaaga tggcccctgt caacctgtac cctggggtgt ttgagactgt ggagatgctg    4080
cccagcaagg ctggcatctg gagggtggag tgcctgattg gggagcacct gcatgctggc    4140
atgagcaccc tgttcctggt gtacagcaac aagtgccaga ccccctggg catggcctct     4200
ggccacatca gggacttcca gatcactgcc tctggccagt atggccagtg ggcccccaag    4260
ctggccaggc tgcactactc tggcagcatc aatgcctgga gcaccaagga gcccttcagc    4320
tggatcaagg tggacctgct ggccccatg atcatccatg gcatcaagac ccaggggcc      4380
aggcagaagt tcagcagcct gtacatcagc cagttcatca tcatgtacag cctggatggc    4440
aagaagtgga gacctacag gggcaacagc actggcaccc tgatggtgtt ctttggcaat    4500
gtggacagct ctggcatcaa gcacaacatc ttcaacccc ccatcattgc cagatacatc     4560
aggctgcacc ccaccacta cagcatcagg agcaccctga ggatggagct gatgggctgt    4620
gacctgaaca gctgcagcat gccctgggc atggagagca aggccatctc tgatgcccag     4680
atcactgcca gcagctactt caccaacatg tttgccacct ggagcccag caaggccagg     4740
ctgcacctgc agggcaggag caatgcctgg aggccccagg tcaacaaccc caaggagtgg    4800
ctgcaggtgg acttccagaa gaccatgaag gtgactgggg tgaccaccca ggggtgaag     4860
agcctgctga ccagcatgta tgtgaaggag ttcctgatca gcagcagcca ggatggccac    4920
cagtggaccc tgttcttcca gaatggcaag gtgaaggtgt tccagggcaa ccaggacagc    4980
```

```
ttcacccctg tggtgaacag cctggacccc ccctgctga ccagatacct gaggattcac    5040
ccccagagct gggtgcacca gattgccctg aggatggagg tgctgggctg tgaggcccag    5100
gacctgtact gacctcgagg tgtgccttct agttgccagc catctgttgt ttgcccctcc    5160
cccgtgcctt ccttgaccct ggaaggtgcc actccactg tcctttccta ataaaatgag    5220
gaaattgcat cgcattgtct gagtaggtgt cattctattc tggggggtgg ggtggggcag    5280
gacagcaagg gggaggattg gaagacaat agcaggcatg ctggggatgc ggtgggctct    5340
atgggcacgt ggcggccgca ggaaccccta gtgatggagt tggccactcc ctctctgcgc    5400
gctcgctcgc tcactgaggc cgggcgacca aggtcgccc gacgcccggg ctttgcccgg    5460
gcggcctcag tgagcgagcg agcgcgcaga gagggagtgg ccaa                    5504
```

<210> SEQ ID NO 32
<211> LENGTH: 5507
<212> TYPE: DNA
<213> ORGANISM: Adeno-Associated Virus 2

<400> SEQUENCE: 32

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacga tcttgctacc agtggaacag ccactaagga    540
ttctgcagtg agagcagagg gccagctaag tggtactctc ccagagactg tctgactcac    600
gccaccccct ccaccttgga cacaggacgc tgtggtttct gagccaggta caatgactcc    660
tttcggtaag tgcagtggaa gctgtacact gcccaggcaa agcgtccggg cagcgtaggc    720
gggcgactca gatcccagcc agtggactta gcccctgttt gctcctccga taactggggt    780
gaccttggtt aatattcacc agcagcctcc ccgttgccc ctctggatcc actgcttaaa    840
tacggacgag gacagggccc tgtctcctca gcttcaggca ccaccactga cctgggacag    900
tgaatcgcga tcgccaccat gcagattgag ctgagcacct gcttcttcct gtgcctgctg    960
aggttctgct tctctgccac caggagatac tacctggggg ctgtggagct gagctgggac    1020
tacatgcagt ctgacctggg ggagctgcct gtggatgcca ggttccccc cagagtgccc    1080 aagagcttcc ccttcaacac ctctgtggtg tacaagaaga cctgtttgt ggagttcact    1140 gaccacctgt tcaacattgc caagcccagg ccccctgga tgggcctgct gggccccacc    1200
atccaggctg aggtgtatga cactgtggtg atcaccctga gaacatggc cagccaccct    1260 gtgagcctgc atgctgtggg ggtgagctac tggaaggcct ctgaggggc tgagtatgat    1320 gaccagacca gccagggga aaggaggat acaaggtgt ccctgggggg cagccacacc    1380
tatgtgtggc aggtgctgaa ggagaatggc cccatggcct ctgacccct gtgcctgacc    1440 tacagctacc tgagccatgt ggacctggtg aaggacctga actctggcct gattggggcc    1500
ctgctggtgt gcagggaggg cagcctgacc aaggagaaga cccagaccct gcacaagttc    1560
atcctgctgt ttgctgtgtt tgatgagggc aagagctggc actctgaaac caagaacagc    1620
```

```
ctgatgcagg acagggatgc tgcctctgcc agggcctggc ccaagatgca cactgtgaat      1680
ggctatgtga acaggagcct gcctggcctg attggctgcc acaggaagtc tgtgtactgg      1740
catgtgattg gcatgggcac caccectgag gtgcacagca tcttcctgga gggccacacc      1800
ttcctggtca ggaaccacag gcaggccagc ctggagatca gccccatcac cttcctgact      1860
gcccagaccc tgctgatgga cctgggccag ttcctgctgt tctgccacat cagcagccac      1920
cagcatgatg gcatggaggc ctatgtgaag gtggacagct gccctgagga gccccagctg      1980
aggatgaaga acaatgagga ggctgaggac tatgatgatg acctgactga ctctgagatg      2040
gatgtggtga ggtttgatga tgacaacagc cccagcttca tccagatcag gtctgtggcc      2100
aagaagcacc ccaagacctg ggtgcactac attgctgctg aggaggagga ctgggactat      2160
gccccctgg tgctggcccc tgatgacagg agctacaaga ccagtacct gaacaatggc       2220
ccccagagga ttggcaggaa gtacaagaag gtcaggttca tggcctacac tgatgaaacc      2280
ttcaagacca gggaggccat ccagcatgag tctggcatcc tgggcccect gctgtatggg      2340
gaggtggggg acaccctgct gatcatcttc aagaaccagg ccagcaggcc ctacaacatc      2400
taccccatg gcatcactga tgtgaggccc ctgtacagca ggaggctgcc caaggggtg        2460
aagcacctga aggacttccc catcctgcct ggggagatct tcaagtacaa gtggactgtg      2520
actgtggagg atggccccac caagtctgac cccaggtgcc tgaccagata ctacagcagc      2580
tttgtgaaca tggagaggga cctggcctct ggcctgattg ccccctgct gatctgctac       2640
aaggagtctg tggaccagag gggcaaccag atcatgtctg acaagaggaa tgtgatcctg      2700
ttctctgtgt ttgatgagaa caggagctgg tacctgactg agaacatcca gaggttcctg      2760
cccaaccctg ctggggtgca gctggaggac cctgagttcc aggccagcaa catcatgcac      2820
agcatcaatg gctatgtgtt tgacagcctg cagctgtctg tgtgcctgca tgaggtggcc      2880
tactggtaca tcctgagcat tggggcccag actgacttcc tgtctgtgtt cttctctggc      2940
tacaccttca agcacaagat ggtgtatgag gacaccctga ccctgttccc cttctctggg      3000
gagactgtgt tcatgagcat ggagaaccct ggcctgtgga ttctgggctg ccacaactct      3060
gacttcagga cagggcat gactgccctg ctgaaagtct ccagctgtga caagaacact       3120
ggggactact atgaggacag ctatgaggac atctctgcct acctgctgag caagaacaat      3180
gccattgagc ccaggagctt cagccagaac cccccagtgc tgaagaggca ccagagggag     3240
atcaccagga ccaccctgca gtctgaccag gaggagattg actatgatga ccacatctct      3300
gtggagatga agaggagga ctttgacatc tacgacgagg acgagaacca gagccccagg       3360
agcttccaga agaaaccag gcactacttc attgctgctg tggagaggct gtgggactat      3420
ggcatgagca gcagccccca tgtgctgagg aacagggccc agtctggctc tgtgccccag      3480
ttcaagaagg tggtgttcca ggagttcact gatggcagct tcacccagcc cctgtacaga      3540
ggggagctga atgagcacct gggcctgctg ggccctaca tcagggctga ggtggaggac      3600
aacatcatgg tgaccttcag gaaccaggcc agcaggccct acagcttcta cagcagcctg      3660
atcagctatg aggaggacca gaggcagggg gctgagccca ggaagaactt tgtgaagccc      3720
aatgaaacca gacctactt ctggaaggtg cagcaccaca tggcccccac caaggatgag       3780
tttgactgca aggcctgggc ctacttctct gatgtggacc tggagaagga tgtgcactct      3840
ggcctgattg gcccectgct ggtgtgccac accaacaccc tgaaccctgc ccatggcagg      3900
caggtgactg tgcaggagtt tgccctgttc ttcaccatct ttgatgaaac caagagctgg      3960
```

```
tacttcactg agaacatgga gaggaactgc agggcccct gcaacatcca gatggaggac      4020
cccaccttca aggagaacta caggttccat gccatcaatg ctacatcat ggacaccctg      4080
cctggcctgg tgatggccca ggaccagagg atcaggtggt acctgctgag catgggcagc    4140
aatgagaaca tccacagcat ccacttctct ggccatgtgt tcactgtgag gaagaaggag    4200
gagtacaaga tggccctgta caacctgtac cctggggtgt ttgagactgt ggagatgctg    4260
cccagcaagg ctggcatctg gagggtggag tgcctgattg gggagcacct gcatgctggc   4320
atgagcaccc tgttcctggt gtacagcaac aagtgccaga ccccctgggg catggcctct    4380
ggccacatca gggacttcca gatcactgcc tctggccagt atggccagtg ggcccccaag   4440
ctggccaggc tgcactactc tggcagcatc aatgcctgga gcaccaagga gcccttcagc   4500
tggatcaagg tggacctgct ggcccccatg atcatccatg gcatcaagac ccagggggcc   4560
aggcagaagt tcagcagcct gtacatcagc cagttcatca tcatgtacag cctggatggc   4620
aagaagtggc agacctacag gggcaacagc actggcaccc tgatggtgtt ctttggcaat   4680
gtggacagct ctggcatcaa gcacaacatc ttcaacccc ccatcattgc cagatacatc     4740
aggctgcacc ccacccacta cagcatcagg agcaccctga ggatggagct gatgggctgt   4800
gacctgaaca gctgcagcat gccctgggc atggagagca aggccatctc tgatgcccag   4860
atcactgcca gcagctactt caccaacatg tttgccacct ggagcccag caaggccagg    4920
ctgcacctgc agggcaggag caatgcctgg aggcccagg tcaacaaccc caaggagtgg    4980
ctgcaggtgg acttccagaa gaccatgaag gtgactgggg tgaccaccca gggggtgaag   5040
agcctgctga ccagcatgta tgtgaaggag ttcctgatca gcagcagcca ggatggccac   5100
cagtggaccc tgttcttcca gaatggcaag gtgaaggtgt tccagggcaa ccaggacagc   5160
ttcacccctg tggtgaacag cctggacccc ccctgctga ccagatacct gaggattcac     5220
ccccagagct gggtgcacca gattgccctg aggatggagg tgctgggctg tgaggcccag    5280
gacctgtact gacctcgagg aataaaggaa atttattttc attgcaatag tgtgttggtt    5340
ttttgtgtca cgtggcggcc gcaggaaccc ctagtgatgg agttggccac tccctctctg    5400
cgcgctcgct cgctcactga ggccgggcga ccaaaggtcg cccgacgccc gggctttgcc    5460
cgggcggcct cagtgagcga gcgagcgcgc agagagggag tggccaa                  5507

<210> SEQ ID NO 33
<211> LENGTH: 5311
<212> TYPE: DNA
<213> ORGANISM: Adeno-Associated Virus 2

<400> SEQUENCE: 33
ttggccactc cctctctgcg cgctcgctcg ctcactgagg ccgccgggc aaagcccggg        60
cgtcgggcga cctttggtcg cccggcctca gtgagcgagc gagcgcgcag agagggagtg     120
gccaactcca tcactagggg ttcctgcggc cgcacgcgtg ttttcgacgc agagaggtct    180
ctgacctctg ccccagctcc aaggtcagca ggcagggagg gctgtgtgtt tgctgtttgc    240
tgcttgcaat gttttgcccat tttagggaca tgagtaggct gaagtttgtt cagtgtggac   300
ttcagaggca gcacacaaac agccagagag gtctctgacc tctgccccag ctccaaggtc   360
agcaggcagg gagggctgtg tgtttgctgt ttgctgcttg caatgtttgc ccattttagg    420
gacatgagta ggctgaagtt tgttcagtgt ggacttcaga ggcagcacac aaacagcacg   480
cgaaacgtcg actggacaca ggacgctgtg gtttctgagc caggggggcga ctcagatccc   540
agccagtgga cttagcccct gtttgctcct ccgataactg gggtgacctt ggttaatatt   600
```

```
caccagcagc ctcccccgtt gcccctctgg atccactgct taaatacgga cgaggacagg    660
gccctgtctc ctcagcttca ggcaccacca ctgacctggg acagtgaatc gcgatcgcca    720
ccatgcagat tgagctgagc acctgcttct tcctgtgcct gctgaggttc tgcttctctg    780
ccaccaggag atactacctg ggggctgtgg agctgagctg ggactacatg cagtctgacc    840
tgggggagct gcctgtggat gccaggttcc cccccagagt gcccaagagc ttccccttca    900
acacctctgt ggtgtacaag aagaccctgt ttgtggagtt cactgaccac ctgttcaaca    960
ttgccaagcc caggcccccc tggatgggcc tgctgggccc caccatccag gctgaggtgt   1020
atgacactgt ggtgatcacc ctgaagaaca tggccagcca ccctgtgagc ctgcatgctg   1080
tgggggtgag ctactggaag gcctctgagg gggctgagta tgatgaccag accagccaga   1140
gggagaagga ggatgacaag gtgttccctg ggggcagcca cacctatgtg tggcaggtgc   1200
tgaaggagaa tggccccatg gcctctgacc ccctgtgcct gacctacagc tacctgagcc   1260
atgtggacct ggtgaaggac ctgaactctg gcctgattgg ggccctgctg gtgtgcaggg   1320
agggcagcct ggccaaggag aagacccaga ccctgcacaa gttcatcctg ctgtttgctg   1380
tgtttgatga gggcaagagc tggcactctg aaaccaagaa cagcctgatg caggacaggg   1440
atgctgcctc tgccagggcc tggcccaaga tgcacactgt gaatggctat gtgaacagga   1500
gcctgcctgg cctgattggc tgccacagga agtctgtgta ctggcatgtg attggcatgg   1560
gcaccacccc tgaggtgcac agcatcttcc tggagggcca caccttcctg gtcaggaacc   1620
acaggcaggc cagcctggag atcagcccca tcaccttcct gactgcccag accctgctga   1680
tggacctggg ccagttcctg ctgttctgcc acatcagcag ccaccagcat gatggcatgg   1740
aggcctatgt gaaggtggac agctgccctg aggagcccca gctgaggatg aagaacaatg   1800
aggaggctga ggactatgat gatgacctga ctgactctga gatggatgtg gtgaggtttg   1860
atgatgacaa cagcccccag cttcatccaga tcaggtctgt ggccaagaag cacccccaaga   1920 cctgggtgca ctacattgct gctgaggagg aggactggga ctatgccccc ctggtgctgg   1980
cccctgatga caggagctac aagagccagt acctgaacaa tggcccccag aggattggca   2040
ggaagtacaa gaaggtcagg ttcatggcct acactgatga aaccttcaag accagggagg   2100
ccatccagca tgagtctggc atcctgggcc ccctgctgta tggggaggtg ggggacaccc   2160
tgctgatcat cttcaagaac caggccagca ggccctacaa catctacccc catggcatca   2220
ctgatgtgag gcccctgtac agcaggaggc tgcccaaggg ggtgaagcac ctgaaggact   2280
tccccatcct gcctggggag atcttcaagt acaagtggac tgtgactgtg gaggatggcc   2340
ccaccaagtc tgaccccagg tgcctgacca gatactacag cagctttgtg aacatggaga   2400
gggacctggc ctctggcctg attggccccc tgctgatctg ctacaaggag tctgtggacc   2460 agagggggcaa ccagatcatg tctgacaaga ggaatgtgat cctgttctct gtgtttgatg   2520
agaacaggag ctggtacctg actgagaaca tccagaggtt cctgcccaac cctgctgggg   2580
tgcagctgga ggaccctgag ttccaggcca gcaacatcat gcacagcatc aatggctatg   2640
tgtttgacag cctgcagctg tctgtgtgcc tgcatgaggt ggcctactgg tacatcctga   2700
gcattggggc ccagactgac ttcctgtctg tgttcttctc tggctacacc ttcaagcaca   2760
agatggtgta tgaggacacc ctgaccctgt tccccttctc tggggagact gtgttcatga   2820
gcatggagaa ccctggcctg tggattctgg gctgccacaa ctctgacttc aggaacaggg   2880
gcatgactgc cctgctgaaa gtctccagct gtgacaagaa cactggggac tactatgagg   2940
```

-continued

```
acagctatga ggacatctct gcctacctgc tgagcaagaa caatgccatt gagcccagga    3000
gcttcagcca gaaccccca gtgctgaaga ggcaccagag ggagatcacc aggaccaccc     3060
tgcagtctga ccaggaggag attgactatg atgacaccat ctctgtggag atgaagaagg    3120
aggactttga catctacgac gaggacgaga accagagccc caggagcttc agaagaaga    3180
ccaggcacta cttcattgct gctgtggaga ggctgtggga ctatggcatg agcagcagcc    3240
cccatgtgct gaggaacagg gcccagtctg gctctgtgcc ccagttcaag aaggtggtgt    3300
tccaggagtt cactgatggc agcttcaccc agcccctgta cagaggggag ctgaatgagc    3360
acctgggcct gctgggcccc tacatcaggg ctgaggtgga ggacaacatc atggtgacct    3420
tcaggaacca ggccagcagg ccctacagct tctacagcag cctgatcagc tatgaggagg    3480
accagaggca gggggctgag cccaggaaga actttgtgaa gcccaatgaa accaagacct    3540
acttctggaa ggtgcagcac cacatggccc ccaccaagga tgagtttgac tgcaaggcct    3600
gggcctactt ctctgatgtg gacctggaga aggatgtgca ctctggcctg attggccccc    3660
tgctggtgtg ccacaccaac accctgaacc ctgcccatgg caggcaggtg actgtgcagg    3720
agtttgccct gttcttcacc atctttgatg aaaccaagag ctggtacttc actgagaaca    3780
tggagaggaa ctgcagggcc ccctgcaaca tccagatgga ggaccccacc ttcaaggaga    3840
actacaggtt ccatgccatc aatggctaca tcatggacac cctgcctggc ctggtgatgg    3900
cccaggacca gaggatcagg tggtacctgc tgagcatggg cagcaatgag aacatccaca    3960
gcatccactt ctctggccat gtgttcactg tgaggaagaa ggaggagtac aagatggccc    4020
tgtacaacct gtaccctggg gtgtttgaga ctgtggagat gctgcccagc aaggctggca    4080
tctggagggt ggagtgcctg attggggagc acctgcatgc tggcatgagc accctgttcc    4140
tggtgtacag caacaagtgc cagacccccc tgggcatggc ctctggccac atcagggact    4200
tccagatcac tgcctctggc cagtatggcc agtgggcccc caagctggcc aggctgcact    4260
actctggcag catcaatgcc tggagcacca aggagccctt cagctggatc aaggtggacc    4320
tgctggcccc catgatcatc catggcatca agacccaggg ggccaggcag aagttcagca    4380
gcctgtacat cagccagttc atcatcatgt acagcctgga tggcaagaag tggcagacct    4440
acaggggcaa cagcactggc accctgatgg tgttctttgg caatgtggac agctctggca    4500
tcaagcacaa catcttcaac ccccccatca ttgccagata catcaggctg cacccccacc    4560
actacagcat caggagcacc ctgaggatgg agctgatggg ctgtgacctg aacagctgca    4620
gcatgccccg gggcatggag agcaaggcca tctctgatgc ccagatcact gccagcagct    4680
acttcaccaa catgtttgcc acctggagcc ccagcaaggc caggctgcac ctgcagggca    4740
ggagcaatgc ctggaggccc caggtcaaca accccaagga gtggctgcag gtggacttcc    4800
agaagaccat gaaggtgact ggggtgacca cccagggggt gaagagcctg ctgaccagca    4860
tgtatgtgaa ggagttcctg atcagcagca gccaggatgg ccaccagtgg acccctgttct   4920
tccagaatgg caaggtgaag gtgttccagg caaccagga cagcttcacc cctgtggtga     4980
acagcctgga ccccccctg ctgaccagat acctgaggat tcaccccag agctgggtgc      5040
accagattgc cctgaggatg gaggtgctgg gctgtgaggc ccaggacctg tactgacctc    5100
gaggaataaa ggaaatttat tttcattgca atagtgtgtt ggttttttgt gtcacgtggc    5160
ggccgcagga accctagtg atggagttgg ccactccctc tctgcgcgct cgctcgctca     5220
ctgaggccgg gcgaccaaag gtcgcccgac gcccgggctt tgcccgggcg gcctcagtga    5280
gcgagcgagc gcgcagagag ggagtggcca a                                   5311
```

<210> SEQ ID NO 34
<211> LENGTH: 5156
<212> TYPE: DNA
<213> ORGANISM: Adeno-Associated Virus 2

<400> SEQUENCE: 34

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgcggc | cgcacgcgtg | ttttcgacca | gagaggtctc | 180 |
| tgacctctgc | cccagctcca | aggtcagcag | gcagggaggg | ctgtgtgttt | gctgtttgct | 240 |
| gcttgcaatg | tttgcccatt | ttagggacat | gagtaggctg | aagtttgttc | agtgtggact | 300 |
| tcagaggcag | cacacaaaca | gcacgcgaaa | cgtcgactgg | acacaggacg | ctgtggtttc | 360 |
| tgagccaggg | ggcgactcag | atcccagcca | gtggacttag | cccctgtttg | ctcctccgat | 420 |
| aactggggtg | accttggtta | atattcacca | gcagcctccc | ccgttgcccc | tctggatcca | 480 |
| ctgcttaaat | acggacgagg | acagggccct | gtctcctcag | cttcaggcac | caccactgac | 540 |
| ctgggacagt | gaatcgcgat | cgccaccatg | cagattgagc | tgagcaccctg | cttcttcctg | 600 |
| tgcctgctga | ggttctgctt | ctctgccacc | aggagatact | acctgggggc | tgtggagctg | 660 |
| agctgggact | acatgcagtc | tgacctgggg | gagctgcctg | tggatgccag | gttccccccc | 720 |
| agagtgccca | agagcttccc | cttcaacacc | tctgtggtgt | acaagaagac | cctgtttgtg | 780 |
| gagttcactg | accacctgtt | caacattgcc | aagcccaggc | cccctggat | gggcctgctg | 840 |
| ggccccacca | tccaggctga | ggtgtatgac | actgtggtga | tcaccctgaa | gaacatggcc | 900 |
| agccaccctg | tgagcctgca | tgctgtgggg | gtgagctact | ggaaggcctc | tgagggggct | 960 |
| gagtatgatg | accagaccag | ccagagggag | aaggaggatg | acaaggtgtt | ccctgggggc | 1020 |
| agccacacct | atgtgtggca | ggtgctgaag | gagaatggcc | ccatggcctc | tgacccctg | 1080 |
| tgcctgacct | acagctacct | gagccatgtg | gacctggtga | aggacctgaa | ctctggcctg | 1140 |
| attggggccc | tgctggtgtg | cagggaggc | agcctggcca | aggagaagac | ccagaccctg | 1200 |
| cacaagttca | tcctgctgtt | tgctgtgttt | gatgaggca | agagctggca | ctctgaaacc | 1260 |
| aagaacagcc | tgatgcagga | cagggatgct | gcctctgcca | gggcctggcc | caagatgcac | 1320 |
| actgtgaatg | gctatgtgaa | caggagcctg | cctggcctga | ttggctgcca | caggaagtct | 1380 |
| gtgtactggc | atgtgattgg | catgggcacc | acccctgagg | tgcacagcat | cttcctggag | 1440 |
| ggccacacct | tcctggtcag | gaaccacagg | caggccagcc | tggagatcag | ccccatcacc | 1500 |
| ttcctgactg | cccagaccct | gctgatggac | ctgggccagt | tcctgctgtt | ctgccacatc | 1560 |
| agcagccacc | agcatgatgg | catggaggcc | tatgtgaagg | tggacagctg | ccctgaggag | 1620 |
| ccccagctga | ggatgaagaa | caatgaggag | gctgaggact | atgatgatga | cctgactgac | 1680 |
| tctgagatgg | atgtggtgag | gtttgatgat | gacaacagcc | cagcttcat | ccagatcagg | 1740 |
| tctgtggcca | agaagcaccc | caagacctgg | gtgcactaca | ttgctgctga | ggaggagac | 1800 |
| tgggactatg | cccccctggt | gctggccccct | gatgacagga | gctacaagag | ccagtacctg | 1860 |
| aacaatggcc | cccagaggat | tggcaggaag | tacaagaagg | tcaggttcat | ggcctacact | 1920 |
| gatgaaacct | tcaagaccag | ggaggccatc | cagcatgagt | ctggcatcct | gggccccctg | 1980 |
| ctgtatgggg | aggtggggga | caccctgctg | atcatcttca | agaaccaggc | cagcaggccc | 2040 |
| tacaacatct | acccccatgg | catcactgat | gtgaggcccc | tgtacagcag | gaggctgccc | 2100 |

```
aaggggggtga agcacctgaa ggacttcccc atcctgcctg ggagatcttc aagtacaag    2160
tggactgtga ctgtggagga tggccccacc aagtctgacc caggtgcct gaccagatac     2220
tacagcagct tgtgaacat ggagagggac ctggcctctg gcctgattgg cccctgctg      2280
atctgctaca aggagtctgt ggaccagagg ggcaaccaga tcatgtctga caagaggaat    2340
gtgatcctgt tctctgtgtt tgatgagaac aggagctggt acctgactga gaacatccag   2400
aggttcctgc ccaaccctgc tggggtgcag ctggaggacc ctgagttcca ggccagcaac    2460
atcatgcaca gcatcaatgg ctatgtgttt gacagcctgc agctgtctgt gtgcctgcat   2520
gaggtggcct actggtacat cctgagcatt gggcccaga ctgacttcct gtctgtgttc     2580
ttctctggct acaccttcaa gcacaagatg gtgtatgagg acaccctgac cctgttcccc   2640
ttctctgggg agactgtgtt catgagcatg agaaccctg gcctgtggat ctgggctgc      2700
cacaactctg acttcaggaa cagggcatg actgccctgc tgaaagtctc cagctgtgac    2760
aagaacactg gggactacta tgaggacagc tatgaggaca tctctgccta cctgctgagc   2820
aagaacaatg ccattgagcc caggagcttc agccagaacc ccagtgct gaagaggcac     2880
cagagggaga tcaccaggac cacctgcag tctgaccagg aggagattga ctatgatgac    2940
accatctctg tggagatgaa gaaggaggac tttgacatct acgacgagga cgagaaccag   3000
agccccagga gcttccagaa gaagaccagg cactacttca ttgctgctgt ggagaggctg   3060
tgggactatg gcatgagcag cagcccccat gtgctgagga acagggccca gtctggctct  3120
gtgccccagt tcaagaaggt ggtgttccag gagttcactg atggcagctt cacccagccc    3180
ctgtacagag gggagctgaa tgagcacctg ggcctgctgg gcccctacat cagggctgag   3240
gtggaggaca acatcatggt gaccttcagg aaccaggcca gcaggcccta cagcttctac    3300
agcagcctga tcagctatga ggaggaccag aggcagggg ctgagcccag gaagaacttt    3360
gtgaagccca atgaaaccaa gacctacttc tggaaggtgc agcaccacat ggcccccacc    3420
aaggatgagt ttgactgcaa ggcctgggcc tacttctctg atgtggacct ggagaaggat   3480
gtgcactctg gcctgattgg cccctgctg gtgtgccaca ccaacaccct gaaccctgcc    3540
catggcaggc aggtgactgt gcaggagttt gccctgtct tcaccatctt tgatgaaacc    3600
aagagctggt acttcactga gaacatggag aggaactgca gggccccctg caacatccag   3660
atggaggacc ccaccttcaa ggagaactac aggttccatg ccatcaatgg ctacatcatg    3720
gacaccctgc ctggcctggt gatggcccag gaccagagga tcaggtggta cctgctgagc   3780
atgggcagca atgagaacat ccacagcatc cacttctctg gccatgtgtt cactgtgagg   3840
aagaaggagg agtacaagat ggcctgtac aacctgtacc ctgggtgtt tgagactgtg     3900
gagatgctgc ccagcaaggc tggcatctgg agggtggagt gcctgattgg ggagcacctg  3960
catgctggca tgagcacct gttcctggtg tacagcaaca agtgccagac ccccctgggc    4020
atggcctctg ccacatcag ggacttccag atcactgcct ctggccagta tggccagtgg   4080
gcccccaagc tggccaggct gcactactct ggcagcatca atgcctggag caccaaggag   4140
cccttcagct ggatcaaggt ggacctgctg gcccccatga tcatccatgg catcaagacc   4200
caggggccca ggcagaagtt cagcagcctg tacatcagcc agttcatcat catgtacagc   4260
ctggatggca gaagtggca gacctacagg ggcaacagca ctggcaccct gatggtgttc   4320
tttggcaatg tggacagctc tggcatcaag cacaacatct tcaacccccc catcattgcc   4380
agatacatca ggctgcaccc cacccactac agcatcagga gcccctgag gatggagctg   4440
atgggctgtg acctgaacag ctgcagcatg cccctgggca tggagagcaa ggccatctct    4500
```

```
gatgcccaga tcactgccag cagctacttc accaacatgt ttgccacctg gagcccagc    4560 aaggccaggc tgcacctgca gggcaggagc aatgcctgga ggcccaggt caacaacccc    4620 aaggagtggc tgcaggtgga cttccagaag accatgaagg tgactggggt gaccacccag    4680
ggggtgaaga gcctgctgac cagcatgtat gtgaaggagt tcctgatcag cagcagccag    4740
gatggccacc agtggaccct gttcttccag aatggcaagg tgaaggtgtt ccagggcaac    4800
caggacagct tcacccctgt ggtgaacagc ctggaccccc ccctgctgac cagatacctg    4860
aggattcacc cccagagctg ggtgcaccag attgccctga ggatggaggt gctgggctgt    4920
gaggcccagg acctgtactg acctcgagga ataaaggaaa tttattttca ttgcaatagt    4980
gtgttggttt tttgtgtcac gtggcggccg caggaacccc tagtgatgga gttggccact    5040
ccctctctgc gcgctcgctc gctcactgag gccgggcgac caaaggtcgc ccgacgcccg    5100
ggctttgccc gggcggcctc agtgagcgag cgagcgcgca gagagggagt ggccaa       5156
```

<210> SEQ ID NO 35
<211> LENGTH: 5178
<212> TYPE: DNA
<213> ORGANISM: Adeno-Associated Virus 2

<400> SEQUENCE: 35

```
ttggccactc cctctctgcg cgctcgctcg ctcactgagg ccgccgggc aaagcccggg     60 cgtcgggcga cctttggtcg cccggcctca gtgagcgagc gagcgcgcag agagggagtg   120
gccaactcca tcactagggg ttcctgcggc cgcacgcgtg ttttcgactg tttgctgttt   180
gctgcttgca atgtttgccc atttagggga catgtttgct gtttgctgct tgcaatgttt   240
gcccatttta gggacatgtt tgctgttttgc tgcttgcaat gtttgcccat tttaggaca   300 tgtttgctgt ttgctgcttg caatgtttgc cccttttagg acaacgcga acgtcgact    360 ggacacagga cgctgtggtt tctgagccag ggggcgactc agatcccagc cagtggactt   420
agcccctgtt tgctcctccg ataactgggg tgaccttggt taatattcac cagcagcctc   480
ccccgttgcc cctctggatc cactgcttaa atacgacga ggacagggcc ctgtctcctc   540
agcttcaggc accaccactg acctgggaca gtgaatcgcg atcgccacca tgcagattga   600
gctgagcacc tgcttcttcc tgtgcctgct gaggttctgc ttctctgcca ccaggagata   660
ctacctgggg gctgtggagc tgagctggga ctacatgcag tctgacctgg gggagctgcc   720
tgtggatgcc aggttccccc ccagagtgcc caagagcttc ccttcaaca cctctgtggt   780 gtacaagaag accctgtttg tggagttcac tgaccacctg ttcaacattg ccaagccag   840 gccccctgg atgggcctgc tgggccccac catccaggct gaggtgtatg acactgtggt   900
gatcaccctg aagaacatgg ccagccaccc tgtgagcctg catgctgtgg gggtgagcta   960
ctggaaggcc tctgagggg ctgagtatga tgaccagacc agccagaggg agaaggagga  1020
tgacaaggtg ttccctgggg gcagccacac ctatgtgtgg caggtgctga aggagaatgg  1080
ccccatggcc tctgaccccc tgtgcctgac ctacagctac ctgagccatg tggacctggt  1140
gaaggacctg aactctggcc tgattggggc cctgctggtg tgcagggagg cagcctggc   1200 caaggagaag acccagaccc tgcacaagtt catcctgctg tttgctgtgt ttgatgaggg  1260
caagagctgg cactctgaaa ccaagaacag cctgatgcag gacagggatg ctgcctctgc  1320
cagggcctgg cccaagatgc acactgtgaa tggctatgtg aacaggagcc tgcctggcct  1380
gattggctgc cacaggaagt ctgtgtactg gcatgtgatt ggcatgggca ccaccccga  1440
```

```
ggtgcacagc atcttcctgg agggccacac cttcctggtc aggaaccaca ggcaggccag    1500
cctggagatc agccccatca ccttcctgac tgcccagacc ctgctgatgg acctgggcca    1560
gttcctgctg ttctgccaca tcagcagcca ccagcatgat ggcatggagg cctatgtgaa    1620
ggtggacagc tgccctgagg agccccagct gaggatgaag aacaatgagg aggctgagga    1680
ctatgatgat gacctgactg actctgagat ggatgtggtg aggtttgatg atgacaacag    1740
ccccagcttc atccagatca ggtctgtggc caagaagcac cccaagacct gggtgcacta    1800
cattgctgct gaggaggagg actgggacta tgccccctg gtgctggccc ctgatgacag     1860
gagctacaag agccagtacc tgaacaatgg ccccagagg attggcagga agtacaagaa     1920
ggtcaggttc atggcctaca ctgatgaaac cttcaagacc agggaggcca tccagcatga    1980
gtctggcatc ctgggccccc tgctgtatgg ggaggtgggg gacaccctgc tgatcatctt    2040
caagaaccag gccagcaggc cctacaacat ctaccccat ggcatcactg atgtgaggcc     2100
cctgtacagc aggaggctgc caagggggt gaagcacctg aaggacttcc ccatcctgcc     2160
tggggagatc ttcaagtaca gtggactgt gactgtggag gatggccca ccaagtctga      2220 ccccaggtgc ctgaccagat actacagcag cttttgtgaac atggagaggg acctggcctc   2280
tggcctgatt ggccccctgc tgatctgcta caaggagtct gtggaccaga ggggcaacca    2340
gatcatgtct gacaagagga atgtgatcct gttctctgtg tttgatgaga acaggagctg    2400
gtacctgact gagaacatcc agaggttcct gcccaaccct gctgggtgc agctggagga    2460 ccctgagttc caggccagca acatcatgca cagcatcaat ggctatgtgt tgacagcct    2520 gcagctgtct gtgtgcctgc atgaggtggc ctactggtac atcctgagca ttggggccca    2580
gactgacttc ctgtctgtgt tcttctctgg ctacaccttc aagcacaaga tggtgtatga    2640
ggacaccctg accctgttcc ccttctctgg ggagactgtg ttcatgagca tggagaaccc    2700
tggcctgtgg attctgggct gccacaactc tgacttcagg aacaggggca tgactgccct    2760
gctgaaagtc tccagctgtg acaagaacac tggggactac tatgaggaca gctatgagga    2820
catctctgcc tacctgctga gcaagaacaa tgccattgag cccaggagct tcagccagaa    2880 cccccccagtg ctgaagaggc accagaggga gatcaccagg accaccctgc agtctgacca   2940
ggaggagatt gactatgatg acaccatctc tgtggagatg aagaaggagg actttgacat    3000
ctacgacgag gacgagaacc agagcccag gagcttccag aagaagacca ggcactactt    3060
cattgctgct gtggagaggc tgtgggacta tggcatgagc agcagccccc atgtgctgag    3120
gaacagggcc cagtctggct ctgtgcccca gttcaagaag gtggtgttcc aggagttcac    3180
tgatggcagc ttcacccagc ccctgtacag aggggagctg aatgagcacc tgggcctgct    3240
gggcccctac atcagggctg aggtggagga acatcatg gtgaccttca ggaaccaggc     3300
cagcaggccc tacagcttct acagcagcct gatcagctat gaggaggacc agaggcaggg    3360
ggctgagccc aggaagaact tgtgaagcc aatgaaacc aagacctact tctgaaggt     3420 gcagcaccac atggccccca ccaaggatga gtttgactgc aaggcctggg cctacttctc    3480
tgatgtggac ctggagaagg atgtgcactc tggcctgatt ggccccctgc tggtgtgcca    3540
caccaacacc ctgaaccctg cccatggcag gcaggtgact gtgcaggagt ttgccctgtt    3600
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tccacttctc    3840
```

-continued

```
tggccatgtg ttcactgtga ggaagaagga ggagtacaag atggccctgt acaacctgta    3900
ccctggggtg tttgagactg tggagatgct gcccagcaag gctggcatct ggagggtgga    3960
gtgcctgatt ggggagcacc tgcatgctgg catgagcacc ctgttcctgg tgtacagcaa    4020
caagtgccag accccctgg gcatggcctc tggccacatc agggacttcc agatcactgc    4080
ctctggccag tatggccagt gggcccccaa gctggccagg ctgcactact ctggcagcat    4140
caatgcctgg agcaccaagg agcccttcag ctggatcaag gtggacctgc tggcccccat    4200
gatcatccat ggcatcaaga cccagggggc caggcagaag ttcagcagcc tgtacatcag    4260
ccagttcatc atcatgtaca gcctggatgg caagaagtgg cagacctaca ggggcaacag    4320
cactggcacc ctgatggtgt tctttggcaa tgtggacagc tctggcatca agcacaacat    4380
cttcaacccc cccatcattg ccagatacat caggctgcac cccacccact acagcatcag    4440
gagcaccctg aggatggagc tgatgggctg tgacctgaac agctgcagca tgcccctggg    4500
catggagagc aaggccatct ctgatgccca gatcactgcc agcagctact tcaccaacat    4560
gtttgccacc tggagcccca gcaaggccag gctgcacctg cagggcagga gcaatgcctg    4620
gaggcccag gtcaacaacc caaggagtg gctgcaggtg gacttccaga gaccatgaa    4680
ggtgactggg gtgaccaccc aggggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca accaggacag cttcacccct gtggtgaaca gcctggaccc    4860
ccccctgctg accagatacc tgaggattca ccccccagagc tgggtgcacc agattgccct    4920
gaggatggag gtgctgggct gtgaggccca ggacctgtac tgacctcgag gaataaagga    4980
aatttattt cattgcaata gtgtgttggt tttttgtgtc acgtggcggc cgcaggaacc    5040
cctagtgatg gagttggcca ctccctctct gcgcgctcgc tcgctcactg aggccgggcg    5100
accaaaggtc gcccgacgcc cgggctttgc ccgggcggcc tcagtgagcg agcgagcgcg    5160
cagagaggga gtggccaa                                                 5178
```

<210> SEQ ID NO 36
<211> LENGTH: 5160
<212> TYPE: DNA
<213> ORGANISM: Adeno-Associated Virus 2

<400> SEQUENCE: 36

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtt gtccctaaaa tgggcaaaca    180
ttgcaagcag caaacagcaa acatgtccct aaaatgggca acattgcaa gcagcaaaca    240
gcaaacatgt ccctaaaatg gcaaacatt gcaagcagca acagcaaac atgtccctaa    300
aatgggcaaa cattgcaagc agcaaacagc aaacagtcga ctggacacag gacgctgtgg    360
tttctgagcc aggggcgac tcagatccca gccagtggac ttagcccctg tttgctcctc    420
cgataactgg ggtgaccttg gttaatattc accagcagcc tccccgttg ccctctgga    480
tccactgctt aaatacggac gaggacaggg ccctgtctcc tcagcttcag gcaccaccac    540
tgacctggga cagtgaatcg cgatcgccac catgcagatt gagctgagca cctgcttctt    600
cctgtgcctg ctgaggttct gcttctctgc caccaggaga tactacctgg gggctgtgga    660
gctgagctgg gactacatgc agtctgacct ggggagctg cctgtggatg ccaggttccc    720
```

-continued

```
ccccagagtg cccaagagct tccccttcaa cacctctgtg gtgtacaaga agaccctgtt    780
tgtggagttc actgaccacc tgttcaacat tgccaagccc aggccccccct ggatgggcct   840
gctgggcccc accatccagg ctgaggtgta tgacactgtg gtgatcaccc tgaagaacat   900
ggccagccac cctgtgagcc tgcatgctgt ggggtgagc tactggaagg cctctgaggg    960
ggctgagtat gatgaccaga ccagccagag ggagaaggag gatgacaagg tgttccctgg   1020
gggcagccac acctatgtgt ggcaggtgct gaaggagaat ggccccatgg cctctgaccc   1080
cctgtgcctg acctacagct acctgagcca tgtggacctg gtgaaggacc tgaactctgg   1140
cctgattggg gccctgctgg tgtgcaggga gggcagcctg gccaaggaga agacccagac   1200
cctgcacaag ttcatcctgc tgtttgctgt gtttgatgag ggcaagagct ggcactctga   1260
aaccaagaac agcctgatgc aggacaggga tgctgcctct gccagggcct ggcccaagat   1320
gcacactgtg aatggctatg tgaacaggag cctgcctggc ctgattggct gccacaggaa   1380
gtctgtgtac tggcatgtga ttggcatggg caccacccct gaggtgcaca gcatcttcct   1440
ggagggccac accttcctgg tcaggaacca caggcaggcc agcctggaga tcagccccat   1500
caccttcctg actgcccaga ccctgctgat ggacctgggc cagttcctgc tgttctgcca   1560
catcagcagc caccagcatg atggcatgga ggcctatgtg aaggtggaca gctgccctga   1620
ggagccccag ctgaggatga agaacaatga ggaggctgag gactatgatg atgacctgac   1680
tgactctgag atggatgtgg tgaggtttga tgatgacaac agcccagct tcatccagat    1740
caggtctgtg gccaagaagc accccaagac ctgggtgcac tacattgctg ctgaggagga   1800
ggactgggac tatgccccccc tggtgctggc ccctgatgac aggagctaca agagccagta   1860
cctgaacaat ggcccccaga ggattggcag gaagtacaag aaggtcaggt tcatggccta   1920
cactgatgaa accttcaaga ccagggaggc catccagcat gagtctggca tcctgggccc   1980
cctgctgtat ggggaggtgg gggacaccct gctgatcatc ttcaagaacc aggccagcag   2040
gccctacaac atctacccccc atggcatcac tgatgtgagg cccctgtaca gcaggaggct   2100
gcccaagggg gtgaagcacc tgaaggactt ccccatcctg cctggggaga tcttcaagta   2160
caagtggact gtgactgtgg aggatggccc caccaagtct gacccccaggt gcctgaccag   2220
atactacagc agctttgtga acatggagag ggacctggcc tctggcctga ttggcccccct   2280
gctgatctgc tacaaggagt ctgtggacca gaggggcaac cagatcatgt ctgacaagag   2340
gaatgtgatc ctgttctctg tgtttgatga aacaggagc tggtacctga ctgagaacat    2400
ccagaggttc ctgcccaacc tgctgggggt gcagctggag gaccctgagt tccaggccag   2460
caacatcatg cacagcatca atggctatgt gtttgacagc ctgcagctgt ctgtgtgcct   2520
gcatgaggtg gcctactggt acatcctgag cattggggcc cagactgact tcctgtctgt   2580
gttcttctct ggctacacct tcaagcacaa gatggtgtat gaggacaccc tgaccctgtt   2640
cccccttctct ggggagactg tgttcatgag catggagaac cctggcctgt ggattctggg   2700
ctgccacaac tctgacttca ggaacagggg catgactgcc ctgctgaaag tctccagctg   2760
tgacaagaac actggggact actatgagga cagctatgag gacatctctg cctacctgct   2820
gagcaagaac aatgccattg agcccaggag cttcagccag aaccccccag tgctgaagag   2880
gcaccagagg gagatcacca ggaccaccct gcagtctgac caggaggaga ttgactatga   2940
tgacaccatc tctgtggaga tgaagaagga ggactttgac atctacgacg aggacgagaa   3000
ccagagcccc aggagcttcc agaagaagac caggcactac ttcattgctg ctgtggagag   3060
gctgtgggac tatggcatga gcagcagccc ccatgtgctg aggaacaggg cccagtctgg   3120
```

```
ctctgtgccc cagttcaaga aggtggtgtt ccaggagttc actgatggca gcttcaccca    3180 gccctgtac agaggggagc tgaatgagca cctgggcctg ctgggcccct acatcagggc    3240
tgaggtggag acaacatca tggtgacctt caggaaccag gccagcaggc cctacagctt    3300
ctacagcagc ctgatcagct atgaggagga ccagaggcag ggggctgagc ccaggaagaa    3360
ctttgtgaag cccaatgaaa ccaagaccta cttctggaag gtgcagcacc acatggcccc    3420
caccaaggat gagtttgact gcaaggcctg ggcctacttc tctgatgtgg acctggagaa    3480
ggatgtgcac tctggcctga ttggcccccct gctggtgtgc acaccaaca ccctgaaccc    3540 tgcccatggc aggcaggtga ctgtgcagga gtttgccctg ttcttcacca tctttgatga    3600
aaccaagagc tggtacttca ctgagaacat ggagaggaac tgcagggccc cctgcaacat    3660
ccagatggag acccccacct tcaaggagaa ctacaggttc catgccatca atggctacat    3720
catggacacc ctgcctggcc tggtgatggc ccaggaccag aggatcaggt ggtacctgct    3780
gagcatgggc agcaatgaga acatccacag catccacttc tctggccatg tgttcactgt    3840
gaggaagaag gaggagtaca agatggccct gtacaacctg taccctgggg tgtttgagac    3900
tgtggagatg ctgcccagca aggctggcat ctggagggtg gagtgcctga ttggggagca    3960
cctgcatgct ggcatgagca ccctgttcct ggtgtacagc aacaagtgcc agaccccct    4020 gggcatggcc tctggccaca tcagggactt ccagatcact gcctctggcc agtatggcca    4080
gtgggccccc aagctggcca ggctgcacta ctctggcagc atcaatgcct ggagcaccaa    4140
ggagcccttc agctggatca aggtggacct gctggccccc atgatcatcc atggcatcaa    4200
gacccagggg gccaggcaga agttcagcag cctgtacatc agccagttca tcatcatgta    4260
cagcctggat ggcaagaagt ggcagaccta caggggcaac agcactgcca ccctgatggt    4320 gttcttggc aatgtggaca gctctggcat caagcacaac atcttcaacc cccccatcat    4380
tgccagatac atcaggctgc accccacca ctacagcatc aggagcaccc tgaggatgga    4440
gctgatgggc tgtgacctga acagctgcag catgcccctg ggcatggaga gcaaggccat    4500
ctctgatgcc cagatcactg ccagcagcta cttcaccaac atgtttgcca cctggagccc    4560
cagcaaggcc aggctgcacc tgcagggcag gagcaatgcc tggaggcccc aggtcaacaa    4620
ccccaaggag tggctgcagg tggacttcca gaagaccatg aaggtgactg gggtgaccac    4680 ccaggggggtg aagagcctgc tgaccagcat gtatgtgaag gagttcctga tcagcagcag    4740
ccaggatggc caccagtgga cctgttctt ccagaatggc aaggtgaagg tgttccaggg    4800
caaccaggac agcttcaccc ctgtggtgaa cagcctggac ccccccctgc tgaccagata    4860
cctgaggatt cacccccaga gctgggtgca ccagattgcc ctgaggatgg aggtgctggg    4920
ctgtgaggcc caggacctgt actgacctcg aggaataaag gaaatttatt ttcattgcaa    4980
tagtgtgttg gttttttgtg tcacgtggcg gccgcaggaa ccctagtga tggagttggc    5040 cactccctct ctgcgcgctc gctcgctcac tgaggccggg cgaccaaagg tcgcccgacg    5100
ccgggctttt gcccgggcgg cctcagtgag cgagcgagcg cgcagagagg gagtggccaa    5160
```

<210> SEQ ID NO 37
<211> LENGTH: 5383
<212> TYPE: DNA
<213> ORGANISM: Adeno-Associated Virus 2

<400> SEQUENCE: 37

```
ttggccactc cctctctgcg cgctcgctcg ctcactgagg ccgcccgggc aaagcccggg      60
```

-continued

```
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc cattttagg dacaacgcga aacgtcgact     360
ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtatgcctt tcactgcgag    600
aggtctggga gaggcttctg agctccccat ggcccaggca ggcagcaggt ctggggcagg    660 agggggttg tggagtgcct tgactcgggg cctggccccc ccatctctgt cttgcaggac     720
aattgccgtc ttctgtctcg tggggcatcc tcctgctggc aggcctgtgc tgcctggtcc    780
ctgcgatcgc caccatgcag attgagctga gcacctgctt cttcctgtgc ctgctgaggt    840
tctgcttctc tgccaccagg agatactacc tgggggctgt ggagctgagc tgggactaca    900
tgcagtctga cctggggggag ctgcctgtgg atgccaggtt ccccccccaga gtgcccaaga    960 gcttccccct caacacctct gtggtgtaca agaagaccct gtttgtggag ttcactgacc    1020
acctgttcaa cattgccaag cccaggcccc cctggatggg cctgctgggc ccaccatcc    1080 aggctgaggt gtatgacact gtggtgatca ccctgaagaa catggccagc caccctgtga    1140
gcctgcatgc tgtgggggtg agctactgga aggcctctga gggggctgag tatgatgacc    1200
agaccagcca gagggagaag gaggatgaca aggtgttccc tgggggcagc cacacctatg    1260
tgtggcaggt gctgaaggag aatggccccca tggcctctga ccccctgtgc ctgacctaca    1320
gctacctgag ccatgtggac ctggtgaagg acctgaactc tggcctgatt ggggccctgc    1380
tggtgtgcag ggagggcagc ctggccaagg agaagaccca gacctgcac aagttcatcc     1440 tgctgtttgc tgtgtttgat gagggcaaga gctggcactc tgaaaccaag aacagcctga    1500
tgcaggacag ggatgctgcc tctgccaggg cctggcccaa gatgcacact gtgaatggct    1560
atgtgaacag gagcctgcct ggcctgattg gctgccacag gaagtctgtg tactggcatg    1620
tgattggcat gggcaccacc cctgaggtgc acagcatctt cctggagggc cacaccttcc    1680
tggtcaggaa ccacaggcag gccagcctgg agatcagccc catcaccttc ctgactgccc    1740 agacctgct gatggacctg gccagttcc tgctgttctg ccacatcagc agccaccagc      1800
atgatggcat ggaggcctat gtgaaggtgg acagctgccc tgaggagccc cagctgagga    1860
tgaagaacaa tgaggaggct gaggactatg atgatgacct gactgactct gagatggatg    1920
tggtgaggtt tgatgatgac aacagcccca gcttcatcca gatcaggtct gtggccaaga    1980
agcaccccaa gacctgggtg cactacattg ctgctgagga ggaggactgg gactatgccc    2040
ccctggtgct ggcccctgat gacaggagct acaagagcca gtacctgaac aatggccccc    2100
agaggattgg caggaagtac aagaaggtca ggttcatggc ctacactgat gaaaccttca    2160
agaccaggga ggccatccag catgagtctg gcatcctggg cccctgctgt atggggagg     2220 tggggacac cctgctgatc atcttcaaga accaggccag caggccctac aacatctacc     2280 ccatggcat cactgatgtg aggccctgt acagcaggag ctgcccaag ggggtgaagc      2340 acctgaagga cttccccatc ctgcctgggg agatcttcaa gtacaagtgg actgtgactg    2400
tggaggatgg ccccaccaag tctgaccccc ggtgcctgac cagatactac agcagctttg    2460
```

```
tgaacatgga gagggacctg gcctctggcc tgattggccc cctgctgatc tgctacaagg    2520
agtctgtgga ccagaggggc aaccagatca tgtctgacaa gaggaatgtg atcctgttct    2580
ctgtgtttga tgagaacagg agctggtacc tgactgagaa catccagagg ttcctgccca    2640
accctgctgg ggtgcagctg gaggaccctg agttccaggc cagcaacatc atgcacagca    2700
tcaatggcta tgtgtttgac agcctgcagc tgtctgtgtg cctgcatgag gtggcctact    2760
ggtacatcct gagcattggg gcccagactg acttcctgtc tgtgttcttc tctggctaca    2820
ccttcaagca aagatggtg tatgaggaca ccctgaccct gttccccttc tctggggaga    2880
ctgtgttcat gagcatggag aaccctgccc tgtggattct gggctgccac aactctgact    2940
tcaggaacag gggcatgact gccctgctga agtctccag ctgtgacaag aacactgggg    3000
actactatga ggacagctat gaggacatct ctgcctacct gctgagcaag aacaatgcca    3060
ttgagcccag gagcttcagc cagaaccccc cagtgctgaa gaggcaccag agggagatca    3120
ccaggaccac cctgcagtct gaccaggagg agattgacta tgatgacacc atctctgtgg    3180
agatgaagaa ggaggacttt gacatctacg acgaggacga gaaccagagc cccaggagct    3240
tccagaagaa gaccaggcac tacttcattg ctgctgtgga gaggctgtgg gactatggca    3300
tgagcagcag cccccatgtg ctgaggaaca gggcccagtc tggctctgtg ccccagttca    3360
agaaggtggt gttccaggag ttcactgatg gcagcttcac ccagcccctg tacagagggg    3420
agctgaatga gcacctgggc ctgctgggcc cctacatcag ggctgaggtg gaggacaaca    3480
tcatggtgac cttcaggaac caggccagca ggccctacag cttctacagc agcctgatca    3540
gctatgagga ggaccagagg caggggctg agcccaggaa gaactttgtg aagcccaatg    3600
aaaccaagac ctacttctgg aaggtgcagc accacatggc cccaccaag gatgagtttg    3660 actgcaaggc ctgggcctac ttctctgatg tggacctgga aaggatgtg cactctggcc    3720 tgattggccc cctgctggtg tgccacacca cacccctgaa ccctgcccat ggcaggcagg    3780
tgactgtgca ggagtttgcc ctgttcttca ccatctttga tgaaaccaag agctggtact    3840
tcactgagaa catggagagg aactgcaggg cccctgcaa catccagatg gaggaccca    3900 ccttcaagga gaactacagg ttccatgcca tcaatggcta catcatggac accctgcctg    3960
gcctggtgat ggcccaggac cagaggatca ggtggtacct gctgagcatg ggcagcaatg    4020
agaacatcca cagcatccac ttctctggcc atgtgttcac tgtgaggaag aaggaggagt    4080
acaagatggc cctgtacaac ctgtaccctg gggtgtttga gactgtggag atgctgccca    4140
gcaaggctgg catctggagg gtggagtgcc tgattgggga gcacctgcat gctggcatga    4200 gcacccctgtt cctggtgtac agcaacaagt gccagacccc cctgggcatg gcctctggcc    4260
acatcaggga cttccagatc actgcctctg ccagtatgg ccagtgggcc ccaagctgg    4320 ccaggctgca ctactctggc agcatcaatg cctggagcac aaggagccc ttcagctgga    4380 tcaaggtgga cctgctggcc cccatgatca tccatggcat caagacccag ggggccaggc    4440
agaagttcag cagcctgtac atcagccagt tcatcatcat gtacagcctg gatggcaaga    4500
agtggcagac ctacaggggc aacagcactg gcaccctgat ggtgttcttt ggcaatgtgg    4560
acagctctgg catcaagcac aacatcttca accccccat cattgccaga tacatcaggc    4620
tgcaccccac ccactacagc atcaggagca cctgaggat ggagctgatg ggctgtgacc    4680
tgaacagctg cagcatgccc ctgggcatgg agagcaaggc catctctgat gcccagatca    4740
ctgccagcag ctacttcacc aacatgtttg ccacctggag ccccagcaag gccaggctgc    4800
```

-continued

```
acctgcaggg caggagcaat gcctggaggc cccaggtcaa caaccccaag gagtggctgc    4860
aggtggactt ccagaagacc atgaaggtga ctggggtgac cacccagggg gtgaagagcc    4920
tgctgaccag catgtatgtg aaggagttcc tgatcagcag cagccaggat ggccaccagt    4980
ggaccctgtt cttccagaat ggcaaggtga aggtgttcca gggcaaccag acagcttca    5040
cccctgtggt gaacagcctg accccccccc tgctgaccag atacctgagg attcacccc    5100
agagctgggt gcaccagatt gccctgagga tggaggtgct gggctgtgag gcccaggacc    5160
tgtactgacc tcgaggaata aggaaatttt attttcattg caatagtgtg ttggtttttt    5220
gtgtcacgtg gcggccgcag gaaccccctag tgatggagtt ggccactccc tctctgcgcg    5280
ctcgctcgct cactgaggcc gggcgaccaa aggtcgcccg acgcccgggc tttgcccggg    5340
cggcctcagt gagcgagcga gcgcgcagag agggagtggc caa                      5383
```

<210> SEQ ID NO 38
<211> LENGTH: 5728
<212> TYPE: DNA
<213> ORGANISM: Adeno-Associated Virus 2

<400> SEQUENCE: 38

```
ttggccactc cctctctgcg cgctcgctcg ctcactgagg ccgcccgggc aaagcccggg     60
cgtcgggcga cctttggtcg cccggcctca gtgagcgagc gagcgcgcag agggagtg    120
gccaactcca tcactagggg ttcctgcggc cgcacgcgtg ttttcgactg tttgctgttt   180
gctgcttgca atgtttgccc attttaggga catgtttgct gtttgctgct tgcaatgttt   240
gcccatttta gggacatgtt tgctgtttgc tgcttgcaat gtttgcccat tttagggaca   300
tgtttgctgt tgctgcttg caatgtttgc ccatttttagg gacaacgcga acgtcgaca    360
ggttaatttt taaaaagcag tcaaaagtcc aagtggccct tggcagcatt tactctctct    420
gtttgctctg gttaataatc tcaggagcac aaacattcct ggaggcagga agaaaatca    480
acatcctgga cttatcctct gggcctctcc ccaccccccag gagaggctca ggttaatttt   540
taaaaagcag tcaaaagtcc aagtggccct tggcagcatt tactctctct gtttgctctg    600
gttaataatc tcaggagcac aaacattcct ggaggcagga agaaaatca acatcctgga    660
cttatcctct gggcctctcc ccaccccccag gagaggctgt cgactggaca caggacgctg    720
tggtttctga gcaggggggc gactcagatc ccagccagtg gacttagccc ctgtttgctc    780
ctccgataac tgggggtgacc ttggttaata ttcaccagca gcctcccccg ttgccctct    840
ggatccactg cttaaatacg gacgaggaca gggccctgtc tcctcagctt caggcaccac    900
cactgacctg ggacagtgaa tcgtaagtat gcctttcact gcgagaggtt ctggagaggc    960
ttctgagctc cccatggccc aggcaggcag caggtctggg gcaggagggg ggttgtggag   1020
tgccttgact cggggcctgg ccccccatc tctgtcttgc aggacaattg ccgtcttctg   1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttg tggagttcac tgaccacctg ttcaacattg   1380
ccaagcccag gccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
```

-continued

```
agaaggagga tgacaaggtg ttccctgggg gcagccacac ctatgtgtgg caggtgctga    1620
aggagaatgg ccccatggcc tctgaccccc tgtgcctgac ctacagctac ctgagccatg    1680
tggacctggt gaaggacctg aactctggcc tgattggggc cctgctggtg tgcagggagg    1740
gcagcctggc caaggagaag acccagaccc tgcacaagtt catcctgctg tttgctgtgt    1800
ttgatgaggg caagagctgg cactctgaaa ccaagaacag cctgatgcag gacagggatg    1860
ctgcctctgc cagggcctgg cccaagatgc acactgtgaa tggctatgtg aacaggagcc    1920
tgcctggcct gattggctgc acaggaagt ctgtgtactg catgtgatt ggcatgggca     1980 ccaccctga ggtgcacagc atcttcctgg agggccacac cttcctggtc aggaaccaca    2040
ggcaggccag cctggagatc agccccatca ccttcctgac tgcccagacc ctgctgatgg    2100
acctgggcca gttcctgctg ttctgccaca tcagcagcca ccagcatgat ggcatggagg    2160
cctatgtgaa ggtggacagc tgccctgagg agccccagct gaggatgaag aacaatgagg    2220
aggctgagga ctatgatgat gacctgactg actctgagat ggatgtggtg aggtttgatg    2280
atgacaacag ccccagcttc atccagatca ggtctgtggc caagaagcac cccaagacct    2340
gggtgcacta cattgctgct gaggaggagg actgggacta tgccccctg gtgctggccc     2400 ctgatgacag gagctacaag agccagtacc tgaacaatgg cccccagagg attggcagga    2460
agtacaagaa ggtcaggttc atggcctaca ctgatgaaac cttcaagacc agggaggcca    2520
tccagcatga gtctggcatc ctgggccccc tgctgtatgg ggaggtgggg gacaccctgc    2580
tgatcatctt caagaaccag gccagcaggc cctacaacat ctaccccat ggcatcactg     2640 atgtgaggcc cctgtacagc aggaggctgc ccaaggggt gaagcacctg aaggacttcc     2700
ccatcctgcc tggggagatc ttcaagtaca gtggactgt gactgtggag gatggcccca    2760
ccaagtctga ccccaggtgc ctgaccagat actacagcag ctttgtgaac atggagaggg    2820
acctggcctc tggcctgatt ggcccccctgc tgatctgcta caaggagtct gtggaccaga    2880
ggggcaacca gatcatgtct gacaagagga atgtgatcct gttctctgtg tttgatgaga    2940
acaggagctg gtacctgact gagaacatcc agaggttcct gcccaaccct gctggggtgc    3000
agctggagga ccctgagttc caggccagca acatcatgca cagcatcaat ggctatgtgt    3060
ttgacagcct gcagctgtct gtgtgcctgc atgaggtggc ctactggtac atcctgagca    3120
ttggggccca gactgacttc ctgtctgtgt cttctctgg ctacaccttc aagcacaaga     3180
tggtgtatga ggacaccctg accctgttcc ccttctctgg ggagactgtg ttcatgagca    3240
tggagaaccc tggcctgtgg attctgggct gccacaactc tgacttcagg aacagggca     3300 tgactgccct gctgaaagtc tccagctgtg acaagaacac tggggactac tatgaggaca    3360
gctatgagga catctctgcc tacctgctga gcaagaacaa tgccattgag cccaggagct    3420
tcagccagaa ccccccagtg ctgaagaggc accagaggga gatcaccagg accaccctgc    3480
agtctgacca ggaggagatt gactatgatg acaccatctc tgtggagatg aagaaggagg    3540
actttgacat ctacgacgag gacgagaacc agagcccag gagcttccag aagaagacca     3600
ggcactactt cattgctgct gtggagaggc tgtgggacta tggcatgagc agcagccccc    3660
atgtgctgag gaacagggcc cagtctggct ctgtgcccca gttcaagaag gtggtgttcc    3720
aggagttcac tgatggcagc ttcacccagc ccctgtacag aggggagctg aatgagcacc    3780
tgggcctgct gggcccctac atcagggctg aggtggagga caacatcatg gtgaccttca    3840
ggaaccaggc cagcaggccc tacagcttct acagcagcct gatcagctat gaggaggacc    3900
```

| | |
|---|---|
| agaggcaggg ggctgagccc aggaagaact ttgtgaagcc caatgaaacc aagacctact | 3960 |
| tctggaaggt gcagcaccac atggccccca ccaaggatga gtttgactgc aaggcctggg | 4020 |
| cctacttctc tgatgtggac ctggagaagg atgtgcactc tggcctgatt ggccccctgc | 4080 |
| tggtgtgcca caccaacacc ctgaaccctg cccatggcag gcaggtgact gtgcaggagt | 4140 |
| ttgccctgtt cttcaccatc tttgatgaaa ccaagagctg gtacttcact gagaacatgg | 4200 |
| agaggaactg cagggccccc tgcaacatcc agatggagga ccccaccttc aaggagaact | 4260 |
| acaggttcca tgccatcaat ggctacatca tggacaccct gcctggcctg gtgatggccc | 4320 |
| aggaccagag gatcaggtgg tacctgctga gcatgggcag caatgagaac atccacagca | 4380 |
| tccacttctc tggccatgtg ttcactgtga ggaagaagga ggagtacaag atggccctgt | 4440 |
| acaacctgta ccctgggtg tttgagactg tggagatgct gcccagcaag gctggcatct | 4500 |
| ggagggtgga gtgcctgatt ggggagcacc tgcatgctgg catgagcacc ctgttcctgg | 4560 |
| tgtacagcaa caagtgccag acccccctgg gcatggcctc tggccacatc agggacttcc | 4620 |
| agatcactgc ctctggccag tatggccagt gggcccccaa gctggccagg ctgcactact | 4680 |
| ctggcagcat caatgcctgg agcaccaagg agcccttcag ctggatcaag gtggacctgc | 4740 |
| tggcccccat gatcatccat ggcatcaaga cccaggggggc caggcagaag ttcagcagcc | 4800 |
| tgtacatcag ccagttcatc atcatgtaca gcctggatgg caagaagtgg cagacctaca | 4860 |
| ggggcaacag cactggcacc ctgatggtgt tctttggcaa tgtggacagc tctggcatca | 4920 |
| agcacaacat cttcaacccc cccatcattg ccagatacat caggctgcac cccacccact | 4980 |
| acagcatcag gagcacactg aggatggagc tgatgggctg tgacctgaac agctgcagca | 5040 |
| tgccctggg catggagagc aaggccatct ctgatgccca gatcactgcc agcagctact | 5100 |
| tcaccaacat gtttgccacc tggagccca gcaaggccag gctgcacctg cagggcagga | 5160 |
| gcaatgcctg gaggccccag gtcaacaacc caaggagtg gctgcaggtg gacttccaga | 5220 |
| agaccatgaa ggtgactggg gtgaccaccc aggggggtgaa gagcctgctg accagcatgt | 5280 |
| atgtgaagga gttcctgatc agcagcagcc aggatggcca ccagtggacc ctgttcttcc | 5340 |
| agaatggcaa ggtgaaggtg ttccagggca accaggacag cttcacccct gtggtgaaca | 5400 |
| gcctggaccc cccctgctg accagatacc tgaggattca cccccagagc tgggtgcacc | 5460 |
| agattgccct gaggatggag gtgctgggct gtgaggccca ggacctgtac tgacctcgag | 5520 |
| gaataaagga aatttattt cattgcaata gtgtgttggt tttttgtgtc acgtggcggc | 5580 |
| cgcaggaacc cctagtgatg gagttggcca ctccctctct gcgcgctcgc tcgctcactg | 5640 |
| aggccgggcg accaaaggtc gcccgacgcc cgggctttgc ccgggcggcc tcagtgagcg | 5700 |
| agcgagcgcg cagagaggga gtggccaa | 5728 |

<210> SEQ ID NO 39
<211> LENGTH: 5905
<212> TYPE: DNA
<213> ORGANISM: Adeno-Associated Virus 2

<400> SEQUENCE: 39

| | |
|---|---|
| ttggccactc cctctctgcg cgctcgctcg ctcactgagg ccgccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgactg tttgctgttt | 180 |
| gctgcttgca atgtttgccc attttaggga catgtttgct gtttgctgct tgcaatgttt | 240 |
| gcccatttta gggacatgtt tgctgtttgc tgcttgcaat gtttgcccat tttagggaca | 300 |

-continued

```
tgtttgctgt tgctgcttg caatgtttgc ccatttagg gacaacgcga aacgtcgaca    360
ggttaatttt taaaaagcag tcaaaagtcc aagtggccct tggcagcatt tactctctct    420
gtttgctctg gttaataatc tcaggagcac aaacattcct ggaggcagga aagaaatca    480
acatcctgga cttatcctct gggcctctcc ccaccccag gagaggctca ggttaatttt    540
taaaaagcag tcaaaagtcc aagtggccct tggcagcatt tactctctct gtttgctctg    600
gttaataatc tcaggagcac aaacattcct ggaggcagga aagaaatca acatcctgga    660
cttatcctct gggcctctcc ccaccccag gagaggctgt cgactggaca caggacgctg    720
tggtttctga gccaggggc gactcagatc ccagccagtg gacttagccc ctgtttgctc    780
ctccgataac tggggtgacc ttggttaata ttcaccagca gcctccccg ttgcccctct    840
ggatccactg cttaaatacg gacgaggaca gggccctgtc tcctcagctt caggcaccac    900
cactgacctg gacagtgaa tcgtaagtat gcctttcact gcgagaggtt ctggagaggc    960
ttctgagctc cccatggccc aggcaggcag caggtctggg gcaggagggg ggttgtggag   1020
tgccttgact cggggcctgg ccccccatc tctgtcttgc aggacaattg ccgtcttctg   1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttg tggagttcac tgaccacctg ttcaacattg   1380
ccaagcccag gccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg cagccacac ctatgtgtgg caggtgctga   1620
aggagaatgg ccccatggcc tctgacccc tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccaccccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgccccccctg gtgctggccc   2400
ctgatgcaca gagctacaag agccagtacc tgaacaatgg cccccagagg attggcagga   2460
agtacaagaa ggtcaggttc atggcctaca ctgatgaaac cttcaagacc agggaggcca   2520
tccagcatga gtctgcatc ctgggccccc tgctgtatgg ggaggtgggg gacaccctgc   2580
tgatcatctt caagaaccag gccagcaggc cctacaacat ctaccccat ggcatcactg   2640
```

| | |
|---|---|
| atgtgaggcc cctgtacagc aggaggctgc ccaagggggt gaagcacctg aaggacttcc | 2700 |
| ccatcctgcc tggggagatc ttcaagtaca agtggactgt gactgtggag gatggcccca | 2760 |
| ccaagtctga ccccaggtgc ctgaccagat actacagcag ctttgtgaac atggagaggg | 2820 |
| acctggcctc tggcctgatt ggccccctgc tgatctgcta caaggagtct gtggaccaga | 2880 |
| ggggcaacca gatcatgtct gacaagagga atgtgatcct gttctctgtg tttgatgaga | 2940 |
| acaggagctg gtacctgact gagaacatcc agaggttcct gcccaacccct gctgggtgc | 3000 |
| agctggagga ccctgagttc caggccagca acatcatgca cagcatcaat ggctatgtgt | 3060 |
| ttgacagcct gcagctgtct gtgtgcctgc atgaggtggc ctactggtac atcctgagca | 3120 |
| ttggggccca gactgacttc ctgtctgtgt tcttctctgg ctacaccttc aagcacaaga | 3180 |
| tggtgtatga ggacaccctg accctgttcc ccttctctgg ggagactgtg ttcatgagca | 3240 |
| tggagaaccc tggcctgtgg attctgggct gccacaactc tgacttcagg aacagggca | 3300 |
| tgactgccct gctgaaagtc tccagctgtg acaagaacac tggggactac tatgaggaca | 3360 |
| gctatgagga catctctgcc tacctgctga gcaagaacaa tgccattgag cccaggagct | 3420 |
| tcagccagaa cccccagtg ctgaagaggc accagaggga gatcaccagg accaccctgc | 3480 |
| agtctgacca ggaggagatt gactatgatg acaccatctc tgtggagatg aagaaggagg | 3540 |
| actttgacat ctacgacgag gacgagaacc agagccccag gagcttccag aagaagacca | 3600 |
| ggcactactt cattgctgct gtggagaggc tgtgggacta tggcatgagc agcagccccc | 3660 |
| atgtgctgag gaacagggcc cagtctggct ctgtgcccca gttcaagaag gtggtgttcc | 3720 |
| aggagttcac tgatggcagc ttcacccagc ccctgtacag aggggagctg aatgagcacc | 3780 |
| tgggcctgct gggcccctac atcagggctg aggtggagga caacatcatg gtgaccttca | 3840 |
| ggaaccaggc cagcaggccc tacagcttct acagcagcct gatcagctat gaggaggacc | 3900 |
| agaggcaggg ggctgagccc aggaagaact tgtgaagcc caatgaaacc aagacctact | 3960 |
| tctgaaggt gcagcaccac atggccccca ccaaggatga gtttgactgc aaggcctggg | 4020 |
| cctacttctc tgatgtggac ctggagaagg atgtgcactc tggcctgatt ggccccctgc | 4080 |
| tggtgtgcca caccaacacc ctgaaccctg cccatggcag gcaggtgact gtgcaggagt | 4140 |
| ttgccctgtt cttcaccatc tttgatgaaa ccaagagctg gtacttcact gagaacatgg | 4200 |
| agaggaactg cagggccccc tgcaacatcc agatggagga ccccaccttc aaggagaact | 4260 |
| acaggttcca tgccatcaat ggctacatca tggacaccct gcctggcctg gtgatggccc | 4320 |
| aggaccagag gatcaggtgg tacctgctga gcatgggcag caatgagaac atccacagca | 4380 |
| tccacttctc tggccatgtg ttcactgtga ggaagaagga ggagtacaag atggcctgt | 4440 |
| acaacctgta ccctgggtg tttgagactg tggagatgct gcccagcaag ctggcatct | 4500 |
| ggagggtgga gtgcctgatt ggggagcacc tgcatgctgg catgagcacc ctgttcctgg | 4560 |
| tgtacagcaa caagtgccag acccccctgg gcatggcctc tggccacatc agggacttcc | 4620 |
| agatcactgc ctctggccag tatggccagt gggccccccaa gctggccagg ctgcactact | 4680 |
| ctggcagcat caatgcctgg agcaccaagg agcccttcag ctggatcaag gtggacctgc | 4740 |
| tggccccccat gatcatccat ggcatcaaga cccagggggc caggcagaag ttcagcagcc | 4800 |
| tgtacatcag ccagttcatc atcatgtaca gcctggatgg caagaagtgg cagacctaca | 4860 |
| ggggcaacag cactggcacc ctgatggtgt tctttggcaa tgtggacagc tctggcatca | 4920 |
| agcacaacat cttcaacccc cccatcattg ccagatacat caggctgcac cccacccact | 4980 |
| acagcatcag gagcacccctg aggatggagc tgatgggctg tgacctgaac agctgcagca | 5040 |

| | |
|---|---|
| tgcccctggg catggagagc aaggccatct ctgatgccca gatcactgcc agcagctact | 5100 |
| tcaccaacat gtttgccacc tggagcccca gcaaggccag gctgcacctg cagggcagga | 5160 |
| gcaatgcctg gaggcccag gtcaacaacc ccaaggagtg gctgcaggtg gacttccaga | 5220 |
| agaccatgaa ggtgactggg gtgaccaccc aggggtgaa gagcctgctg accagcatgt | 5280 |
| atgtgaagga gttcctgatc agcagcagcc aggatggcca ccagtggacc ctgttcttcc | 5340 |
| agaatggcaa ggtgaaggtg ttccagggca accaggacgc cttcacccct gtggtgaaca | 5400 |
| gcctggaccc cccctgctg accagatacc tgaggattca ccccagagc tgggtgcacc | 5460 |
| agattgccct gaggatggag gtgctgggct gtgaggccca ggacctgtac tgacctcgag | 5520 |
| gtgtgccttc tagttgccag ccatctgttg tttgcccctc cccgtgcct tccttgaccc | 5580 |
| tggaaggtgc cactcccact gtcctttcct aataaaatga ggaaattgca tcgcattgtc | 5640 |
| tgagtaggtg tcattctatt ctgggggtg ggtggggca ggacagcaag ggggaggatt | 5700 |
| gggaagacaa tagcaggcat gctggggatg cgtgggctc tatgggcacg tggcggccgc | 5760 |
| aggaacccct agtgatggag ttggccactc cctctctgcg cgctcgctcg ctcactgagg | 5820 |
| ccgggcgacc aaaggtcgcc cgacgcccgg gctttgcccg gcggcctca gtgagcgagc | 5880 |
| gagcgcgcag agagggagtg gccaa | 5905 |

<210> SEQ ID NO 40
<211> LENGTH: 5355
<212> TYPE: DNA
<213> ORGANISM: Adeno-Associated Virus 2

<400> SEQUENCE: 40

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgactg tttgctgttt | 180 |
| gctgcttgca atgtttgccc attttaggga catgtttgct gtttgctgct tgcaatgttt | 240 |
| gcccatttta gggacatgtt tgctgtttgc tgcttgcaat gtttgcccat tttaggaca | 300 |
| tgtttgctgt ttgctgcttg caatgtttgc ccattttagg acaacgcga acgtcgact | 360 |
| ggacacagga cgctgtggtt tctgagccag ggggcgactc agatcccagc cagtggactt | 420 |
| agcccctgtt tgctcctccg ataactggga tgaccttggt taatattcac cagcagcctc | 480 |
| ccccgttgcc cctctggatc cactgcttaa atacggacga ggacagggcc ctgtctcctc | 540 |
| agcttcaggc accaccactg acctgggaca gtgaatcgcg atcgccacca tgcagattga | 600 |
| gctgagcacc tgcttcttcc tgtgcctgct gaggttctgc ttctctgcca ccaggagata | 660 |
| ctacctgggg gctgtggagc tgagctggga ctacatgcag tctgacctgg ggagctgcc | 720 |
| tgtggatgcc aggttccccc ccagagtgcc caagagcttc cccttcaaca cctctgtggt | 780 |
| gtacaagaag accctgtttg tggagttcac tgaccacctg ttcaacattg ccaagcccag | 840 |
| gcccccctgg atgggcctgc tgggccccac catccaggct gaggtgtatg acactgtggt | 900 |
| gatcaccctg aagaacatgg ccagccaccc tgtgagcctg catgctgtgg gggtgagcta | 960 |
| ctggaaggcc tctgaggggg ctgagtatga tgaccagacc agccagaggg agaaggagga | 1020 |
| tgacaaggtg ttccctgggg gcagccacac ctatgtgtgg caggtgctga aggagaatgg | 1080 |
| ccccatggcc tctgaccccc tgtgcctgac ctacagctac ctgagccatg tggacctggt | 1140 |
| gaaggacctg aactctggcc tgattggggc cctgctggtg tgcagggagg gcagcctggc | 1200 |

```
caaggagaag acccagaccc tgcacaagtt catcctgctg tttgctgtgt tgatgaggg      1260
caagagctgg cactctgaaa ccaagaacag cctgatgcag acagggatg ctgcctctgc      1320
cagggcctgg cccaagatgc acactgtgaa tggctatgtg aacaggagcc tgcctggcct     1380
gattggctgc cacaggaagt ctgtgtactg catgtgatt ggcatgggca ccaccctga       1440
ggtgcacagc atcttcctgg agggccacac cttcctggtc aggaaccaca ggcaggccag     1500
cctggagatc agccccatca ccttcctgac tgcccagacc ctgctgatgg acctgggcca     1560
gttcctgctg ttctgccaca tcagcagcca ccagcatgat ggcatggagg cctatgtgaa     1620
ggtggacagc tgccctgagg agccccagct gaggatgaag aacaatgagg aggctgagga     1680
ctatgatgat gacctgactg actctgagat ggatgtggtg aggtttgatg atgacaacag     1740
cccccagcttc atccagatca ggtctgtggc caagaagcac cccaagacct gggtgcacta   1800
cattgctgct gaggaggagg actgggacta tgccccctg gtgctggccc ctgatgacag     1860
gagctacaag agccagtacc tgaacaatgg ccccagagg attggcagga agtacaagaa     1920
ggtcaggttc atgcctaca ctgatgaaac cttcaagacc agggaggcca tccagcatga    1980
gtctggcatc ctgggccccc tgctgtatgg ggaggtgggg gacaccctgc tgatcatctt     2040
caagaaccag gccagcaggc cctacaacat ctacccccat ggcatcactg atgtgaggcc    2100
cctgtacagc aggaggctgc ccaaggggt gaagcacctg aaggacttcc ccatcctgcc    2160
tggggagatc ttcaagtaca gtggactgt gactgtggag gatggcccca ccaagtctga     2220
ccccaggtgc ctgaccagat actacagcag ctttgtgaac atggagaggg acctggcctc    2280
tggcctgatt ggcccctgc tgatctgcta caaggagtct gtggaccaga ggggcaacca    2340
gatcatgtct gacaagagga atgtgatcct gttctctgtg tttgatgaga caggagctg     2400
gtacctgact gagaacatcc agaggttcct gcccaacct gctggggtgc agctggagga    2460
ccctgagttc caggccagca acatcatgca cagcatcaat ggctatgtgt tgacagcct     2520
gcagctgtct gtgtgcctgc atgaggtggc ctactggtac atcctgagca ttggggccca    2580
gactgacttc ctgtctgtgt tcttctctgg ctacaccttc aagcacaaga tggtgtatga    2640
ggacaccctg accctgttcc ccttctctgg ggagactgtg ttcatgagca tggagaaccc    2700
tggcctgtgg attctgggct gccacaactc tgacttcagg aacaggggca tgactgccct    2760
gctgaaagtc tccagctgtg acaagaacac tggggactac tatgaggaca gctatgagga    2820
catctctgcc tacctgctga gcaagaacaa tgccattgag cccaggagct tcagccagaa    2880
cccccagtg ctgaagaggc accagaggga gatcaccagg accaccctgc agtctgacca    2940
ggaggagatt gactatgatg acaccatctc tgtggagatg aagaaggagg actttgacat    3000
ctacgacgag gacgagaacc agagcccag gagcttccag aagaagacca ggcactactt    3060
cattgctgct gtggagaggc tgtgggacta tggcatgagc agcagccccc atgtgctgag    3120
gaacaggggcc cagtctggct ctgtgcccca gttcaagaag gtggtgttcc aggagttcac    3180
tgatggcagc ttcacccagc ccctgtacag aggggagctg aatgagcacc tgggcctgct    3240
gggcccctac atcagggctg aggtggagga caacatcatg gtgaccttca ggaaccaggc    3300
cagcaggcc tacagcttct acagcagcct gatcagctat gaggaggacc agaggcaggg    3360
ggctgagccc aggaagaact tgtgaagcc aatgaaacc aagacctact tctggaaggt    3420
gcagcaccac atggccccca ccaaggatga gtttgactgc aaggcctggg cctacttctc    3480
tgatgtggac ctggagaagg atgtgcactc tggcctgatt ggccccctgc tggtgtgcca    3540
caccaacacc ctgaaccctg cccatggcag gcaggtgact gtgcaggagt tgccctgtt    3600
```

```
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tcccacttctc   3840 tggccatgtg ttcactgtga ggaagaagga ggagtacaag atggccctgt acaacctgta    3900
ccctggggtg tttgagactg tggagatgct gcccagcaag gctggcatct ggagggtgga    3960
gtgcctgatt ggggagcacc tgcatgctgg catgagcacc ctgttcctgg tgtacagcaa    4020
caagtgccag accccctgg gcatggcctc tggccacatc agggacttcc agatcactgc     4080
ctctggccag tatggccagt gggcccccaa gctggccagg ctgcactact ctggcagcat    4140
caatgcctgg agcaccaagg agcccttcag ctggatcaag gtggacctgc tggccccat    4200 gatcatccat ggcatcaaga cccaggggggc caggcagaag ttcagcagcc tgtacatcag   4260
ccagttcatc atcatgtaca gcctggatgg caagaagtgg cagacctaca ggggcaacag   4320
cactggcacc ctgatggtgt tctttggcaa tgtggacagc tctggcatca gcacaacat    4380 cttcaacccc cccatcattg ccagatacat caggctgcac cccacccact acagcatcag   4440
gagcaccctg aggatggagc tgatgggctg tgacctgaac agctgcagca tgccctggg    4500 catggagagc aaggccatct ctgatgccca gatcactgcc agcagctact tcaccaacat   4560
gtttgccacc tggagcccca gcaaggccag gctgcacctg cagggcagga gcaatgcctg   4620 gaggcccag gtcaacaacc ccaaggagtg gctgcaggtg acttccaga agaccatgaa     4680 ggtgactggg gtgaccaccc aggggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca ccaggacag cttccacccct gtggtgaaca gcctggaccc    4860 cccccctgctg accagatacc tgaggattca cccccagagc tgggtgcacc agattgccct   4920
gaggatggag gtgctgggct gtgaggccca ggacctgtac tgacctcgag gtgtgccttc   4980
tagttgccag ccatctgttg tttgcccctc cccgtgcct tccttgaccc tggaaggtgc     5040
cactcccact gtcctttcct aataaaatga ggaaattgca tcgcattgtc tgagtaggtg    5100
tcattctatt ctgggggggtg gggtggggca ggacagcaag gggggaggatt gggaagacaa   5160 tagcaggcat gctggggatg cggtgggctc tatgggcacg tggcggccgc aggaaccccc    5220
agtgatggag ttggccactc cctctctgcg cgctcgctcg ctcactgagg ccgggcgacc    5280
aaaggtcgcc cgacgcccgg gctttgcccg ggcggcctca gtgagcgagc gagcgcgcag    5340
agagggagtg gccaa                                                      5355
```

<210> SEQ ID NO 41
<211> LENGTH: 5618
<212> TYPE: DNA
<213> ORGANISM: Adeno-Associated Virus 2

<400> SEQUENCE: 41

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacca gagaggtctc    180
tgacctctgc cccagctcca aggtcagcag gcagggaggg ctgtgtgttt gctgtttgct    240
gcttgcaatg tttgcccatt ttagggacat gagtaggctg aagtttgttc agtgtggact    300
```

```
tcagaggcag cacacaaaca gccagagagg tctctgacct ctgccccagc tccaaggtca    360
gcaggcaggg agggctgtgt gtttgctgtt tgctgcttgc aatgtttgcc cattttaggg    420
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gccccagctc    660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga aacgtcgact ggacacagga cgctgtggtt tctgagccag ggggcgactc    840
agatcccagc cagtggactt agcccctgtt tgctcctccg ataactgggg tgaccttggt    900
taatattcac cagcagcctc ccccgttgcc cctctggatc cactgcttaa atacggacga    960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gcccccctgg atgggcctgc tgggcccac catccaggct   1320 gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg gcagcctggc caaggagaag acccagaccc tgcacaagtt catcctgctg   1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccacccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agcccagct gaggatgaag   2100 aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgcccccctg   2280
gtgctggccc ctgatgacag gagctacaag agccagtacc tgaacaatgg ccccagagg   2340 attggcagga agtacaagaa ggtcaggttc atggcctaca ctgatgaaac cttcaagacc   2400
agggaggcca tccagcatga gtctggcatc ctgggcccc tgctgtatgg ggaggtgggg   2460
gacaccctgc tgatcatctt caagaaccag gccagcaggc cctacaacat ctaccccat   2520 ggcatcactg atgtgaggcc cctgtacagc aggaggctgc caaggggggt gaagcacctg   2580
aaggacttcc ccatcctgcc tgggagatc ttcaagtaca gtggactgt gactgtggag   2640 gatggccca ccaagtctga ccccaggtgc ctgaccagat actacagcag ctttgtgaac   2700
```

```
atggagaggg acctggcctc tggcctgatt ggcccctgc tgatctgcta caaggagtct      2760
gtggaccaga ggggcaacca gatcatgtct gacaagagga atgtgatcct gttctctgtg      2820
tttgatgaga acaggagctg gtacctgact gagaacatcc agaggttcct gcccaaccct      2880
gctggggtgc agctggagga ccctgagttc caggccagca acatcatgca cagcatcaat      2940
ggctatgtgt ttgacagcct gcagctgtct gtgtgcctgc atgaggtggc ctactggtac      3000
atcctgagca ttggggccca gactgacttc ctgtctgtgt tcttctctgg ctacaccttc      3060
aagcacaaga tggtgtatga ggacaccctg accctgttcc ccttctctgg ggagactgtg      3120
ttcatgagca tggagaaccc tggcctgtgg attctgggct gccacaactc tgacttcagg      3180
aacaggggca tgactgccct gctgaaagtc tccagctgtg acaagaacac tggggactac      3240
tatgaggaca gctatgagga catctctgcc tacctgctga gcaagaacaa tgccattgag      3300
cccaggagct tcagccagaa ccccccagtg ctgaagaggc accagaggga gatcaccagg      3360
accaccctgc agtctgacca ggaggagatt gactatgatg acaccatctc tgtggagatg      3420
aagaaggagg actttgacat ctacgacgag gacgagaacc agagcccag gagcttccag      3480 aagaagacca ggcactactt cattgctgct gtggagaggc tgtgggacta tggcatgagc      3540
agcagccccc atgtgctgag gaacagggcc cagtctggct ctgtgcccca gttcaagaag      3600
gtggtgttcc aggagttcac tgatggcagc ttcacccagc ccctgtacag aggggagctg      3660
aatgagcacc tgggcctgct gggcccctac atcagggctg aggtggagga caacatcatg      3720
gtgaccttca ggaaccaggc cagcaggccc tacagcttct acagcagcct gatcagctat      3780
gaggaggacc agaggcaggg ggctgagccc aggaagaact ttgtgaagcc caatgaaacc      3840
aagacctact tctggaaggt gcagcaccac atggccccca ccaaggatga gtttgactgc      3900
aaggcctggg cctacttctc tgatgtggac ctggagaagg atgtgcactc tggcctgatt      3960 ggcccctgc tggtgtgcca caccaacacc ctgaaccctg cccatggcag gcaggtgact      4020
gtgcaggagt ttgccctgtt cttcaccatc tttgatgaaa ccaagagctg gtacttcact      4080
gagaacatgg agaggaactg cagggccccc tgcaacatcc agatggagga ccccaccttc      4140
aaggagaact acaggttcca tgccatcaat ggctacatca tggacaccct gcctggcctg      4200
gtgatggccc aggaccagag gatcaggtgg tacctgctga gcatgggcag caatgagaac      4260
atccacagca tccacttctc tggccatgtg ttcactgtga gaagaagga ggagtacaag      4320 atggccctgt acaacctgta ccctgggtg tttgagactg tggagatgct gcccagcaag      4380
gctggcatct ggagggtgga gtgcctgatt ggggagcacc tgcatgctgg catgagcacc      4440
ctgttcctgg tgtacagcaa caagtgccag accccctgg gcatggcctc tggccacatc      4500
agggacttcc agatcactgc ctctggccag tatggccagt gggccccaa gctggccagg      4560 ctgcactact ctggcagcat caatgcctgg agcaccaagg agcccttcag ctggatcaag      4620
gtggacctgc tggcccccat gatcatccat ggcatcaaga cccaggggc caggcagaag      4680 ttcagcagcc tgtacatcag ccagttcatc atcatgtaca gcctggatgg caagaagtgg      4740
cagacctaca gggcaacag cactggcacc ctgatggtgt tctttggcaa tgtggacagc      4800
tctggcatca agcacaacat cttcaacccc cccatcattg ccagatacat caggctgcac      4860
cccacccact acagcatcag gagcaccctg aggatggagc tgatgggctg tgacctgaac      4920
agctgcagca tgcccctggg catggagagc aaggccatct ctgatgccca gatcactgcc      4980
agcagctact tcaccaacat gtttgccacc tggagcccca gcaaggccag gctgcacctg      5040
```

| | |
|---|---:|
| cagggcagga gcaatgcctg gaggccccag gtcaacaacc ccaaggagtg gctgcaggtg | 5100 |
| gacttccaga agaccatgaa ggtgactggg gtgaccaccc agggggtgaa gagcctgctg | 5160 |
| accagcatgt atgtgaagga gttcctgatc agcagcagcc aggatggcca ccagtggacc | 5220 |
| ctgttcttcc agaatggcaa ggtgaaggtg ttccagggca accaggacag cttcacccct | 5280 |
| gtggtgaaca gcctggaccc ccccctgctg accagatacc tgaggattca cccccagagc | 5340 |
| tgggtgcacc agattgccct gaggatggag gtgctgggct gtgaggccca ggacctgtac | 5400 |
| tgacctcgag gaataaagga aatttatttt cattgcaata gtgtgttggt tttttgtgtc | 5460 |
| acgtggcggc cgcaggaacc cctagtgatg gagttggcca ctccctctct gcgcgctcgc | 5520 |
| tcgctcactg aggccgggcg accaaaggtc gcccgacgcc cgggctttgc ccgggcggcc | 5580 |
| tcagtgagcg agcgagcgcg cagagaggga gtggccaa | 5618 |

<210> SEQ ID NO 42
<211> LENGTH: 5993
<212> TYPE: DNA
<213> ORGANISM: Adeno-Associated Virus 2

<400> SEQUENCE: 42

| | |
|---|---:|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtt tttaaacgtc gacaggttaa | 180 |
| ttttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa ttttttaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg acacaggac gctgtggttt | 540 |
| ctgagccagg gggcgactca gatcccagcc agtggactta gcccctgttt gctcctccga | 600 |
| taactggggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgcga tcgccaccat gcagattgag ctgagcacct gcttcttcct | 780 |
| gtgcctgctg aggttctgct tctctgccac caggagatac tacctggggg ctgtggagct | 840 |
| gagctgggac tacatgcagt ctgacctggg ggagctgcct gtggatgcca ggttcccccc | 900 |
| cagagtgccc aagagcttcc ccttcaacac ctctgtggtg tacaagaaga ccctgtttgt | 960 |
| ggagttcact gaccacctgt tcaacattgc caagcccagg cccccctgga tgggcctgct | 1020 |
| gggccccacc atccaggctg aggtgtatga cactgtggtg atcaccctga agaacatggc | 1080 |
| cagccaccct gtgagcctgc atgctgtggg ggtgagctac tggaaggcct gagggggc | 1140 |
| tgagtatgat gaccagacca gccagaggga gaaggaggat gacaaggtgt ccctggggggg | 1200 |
| cagccacacc tatgtgtggc aggtgctgaa ggagaatggc cccatggcct ctgaccccct | 1260 |
| gtgcctgacc tacagctacc tgagccatgt ggacctggtg aaggacctga actctggcct | 1320 |
| gattggggcc ctgctggtgt gcaggagggg cagcctggcc aaggagaaga cccagaccct | 1380 |
| gcacaagttc atcctgctgt ttgctgtgtt tgatgagggc aagagctggc actctgaaac | 1440 |
| caagaacagc ctgatgcagg acagggatgc tgcctctgcc agggcctggc caagatgca | 1500 |
| cactgtgaat ggctatgtga acaggagcct gcctggcctg attggctgcc acaggaagtc | 1560 |

```
tgtgtactgg catgtgattg gcatgggcac caccectgag gtgcacagca tcttcctgga    1620
gggccacacc ttcctggtca ggaaccacag gcaggccagc ctggagatca gcccatcac    1680
cttcctgact gcccagaccc tgctgatgga cctgggccag ttcctgctgt tctgccacat    1740
cagcagccac cagcatgatg gcatggaggc ctatgtgaag gtggacagct gccctgagga    1800
gccccagctg aggatgaaga caatgagga ggctgaggac tatgatgatg acctgactga    1860
ctctgagatg gatgtggtga ggtttgatga tgacaacagc cccagcttca tccagatcag    1920
gtctgtggcc aagaagcacc ccaagacctg ggtgcactac attgctgctg aggaggagga    1980
ctgggactat gccccctgg tgctggcccc tgatgacagg agctacaaga gccagtacct    2040
gaacaatggc ccccagagga ttggcaggaa gtacaagaag gtcaggttca tggcctacac    2100
tgatgaaacc ttcaagacca gggaggccat ccagcatgag tctggcatcc tgggccccct    2160
gctgtatggg gaggtggggg acaccctgct gatcatcttc aagaaccagg ccagcaggcc    2220
ctacaacatc tacccccatg gcatcactga tgtgaggccc ctgtacagca ggaggctgcc    2280
caagggggtg aagcacctga aggacttccc catcctgcct ggggagatct tcaagtacaa    2340
gtggactgtg actgtggagg atggccccac caagtctgac cccaggtgcc tgaccagata    2400
ctacagcagc tttgtgaaca tggagaggga cctggcctct ggcctgattg cccccctgct    2460
gatctgctac aaggagtctg tggaccagag gggcaaccag atcatgtctg acaagaggaa    2520
tgtgatcctg ttctctgtgt ttgatgagaa caggagctgg tacctgactg agaacatcca    2580
gaggttcctg cccaaccctg ctgggtgca gctggaggac cctgagttcc aggccagcaa    2640
catcatgcac agcatcaatg gctatgtgtt tgacagcctg cagctgtctg tgtgcctgca    2700
tgaggtggcc tactggtaca tcctgagcat tgggcccag actgacttcc tgtctgtgtt    2760
cttctctggc tacaccttca gcacaagat ggtgtatgag gacacccctga ccctgttccc    2820
cttctctggg gagactgtgt tcatgagcat ggagaaccct ggcctgtgga ttctgggctg    2880
ccacaactct gacttcagga caggggcat gactgccctg ctgaaagtct ccagctgtga    2940
caagaacact ggggactact atgaggacag ctatgaggac atctctgcct acctgctgag    3000
caagaacaat gccattgagc ccaggagctt cagccagaac cccccagtgc tgaagaggca    3060
ccagagggag atcaccagga ccaccctgca gtctgaccag gaggagattg actatgatga    3120
caccatctct gtggagatga agaggagga ctttgacatc tacgacgagg acgagaacca    3180
gagccccagg agcttccaga agaagaccag gcactacttc attgctgctg tggagaggct    3240
gtgggactat ggcatgagca gcagccccca tgtgctgagg aacagggccc agtctggctc    3300
tgtgccccag ttcaagaagg tggtgttcca ggagttcact gatggcagct caccccagcc    3360
cctgtacaga ggggagctga atgagcacct gggcctgctg gcccctaca tcagggctga    3420
ggtggaggac aacatcatgg tgaccttcag gaaccaggcc agcaggccct acagcttcta    3480
cagcagcctg atcagctatg aggaggacca gaggcagggg gctgagccca ggaagaactt    3540
tgtgaagccc aatgaaacca agacctactt ctggaaggtg cagcaccaca tggcccccac    3600
caaggatgag tttgactgca aggcctgggc ctacttctct gatgtggacc tggagaagga    3660
tgtgcactct ggcctgattg cccccctgct ggtgtgccac accaacaccc tgaaccctgc    3720
ccatggcagg caggtgactg tgcaggagtt tgccctgttc ttcaccatct ttgatgaaac    3780
caagagctgg tacttcactg agaacatgga gaggaactgc agggcccct gcaacatcca    3840
gatggaggac cccaccttca ggagaactac aggttccat gccatcaatg gctacatcat    3900
```

-continued

```
ggacaccctg cctggcctgg tgatggccca ggaccagagg atcaggtggt acctgctgag      3960
catgggcagc aatgagaaca tccacagcat ccacttctct ggccatgtgt tcactgtgag      4020
gaagaaggag gagtacaaga tggccctgta caacctgtac cctggggtgt ttgagactgt      4080
ggagatgctg cccagcaagg ctggcatctg gagggtggag tgcctgattg gggagcacct      4140
gcatgctggc atgagcaccc tgttcctggt gtacagcaac aagtgccaga ccccctggg       4200 catgcctct ggccacatca gggacttcca gatcactgcc tctggccagt atggccagtg       4260 ggccccaag ctggccaggc tgcactactc tggcagcatc aatgcctgga gcaccaagga      4320
gcccttcagc tggatcaagg tggacctgct ggcccccatg atcatccatg catcaagac       4380 ccagggggcc aggcagaagt tcagcagcct gtacatcagc cagttcatca tcatgtacag      4440
cctggatggc aagaagtggc agacctacag gggcaacagc actggcaccc tgatggtgtt      4500
ctttggcaat gtggacagct ctggcatcaa gcacaacatc ttcaacccc ccatcattgc       4560 cagatacatc aggctgcacc ccacccacta cagcatcagg agcaccctga ggatggagct      4620
gatgggctgt gacctgaaca gctgcagcat gcccctgggc atggagagca aggccatctc      4680
tgatgcccag atcactgcca gcagctactt caccaacatg tttgccacct ggagccccag      4740
caaggccagg ctgcacctgc agggcaggag caatgcctgg aggccccagg tcaacaaccc      4800
caaggagtgg ctgcaggtgg acttccagaa gaccatgaag gtgactgggg tgaccaccca      4860
gggggtgaag agcctgctga ccagcatgta tgtgaaggag ttcctgatca gcagcagcca      4920
ggatggccac cagtggaccc tgttcttcca gaatggcaag gtgaaggtgt tccagggcaa      4980
ccaggacagc ttcaccctg tggtgaacag cctggacccc cccctgctga ccagatacct      5040
gaggattcac cccagagct gggtgcacca gattgccctg aggatggagg tgctgggctg       5100
tgaggcccag gacctgtact gacctcgagg aataaaggaa attttatttc attgcaatag      5160
tgtgttggtt ttttgtgtca cgtgccctct cacactacct aaaccacgcc aggacaacct      5220
ctgctcctct ccaccgaaat tccaaggggt cgagtggatg ttggaggtgg catgggccca      5280
gagaggtctc tgacctctgc cccagctcca aggtcagcag gcagggaggg ctgtgtgttt      5340
gctgtttgct gcttgcaatg tttgcccatt ttagggacat gagtaggctg aagtttgttc      5400
agtgtggact tcagaggcag cacacaaaca gctgctggag gatgggaact gaggggttgg      5460 aaggggggcag ggtgagccca gaaactcctg tgtgcctctg agcctgcagc cctctcacac      5520
tacctaaacc acgccaggac aacctctgct cctctccacc gaaattccaa ggggtcgagt      5580
ggatgttgga ggtggcatgg gcccagagag gtctctgacc tctgccccag ctccaaggtc      5640
agcaggcagg gagggctgtg tgtttgctgt ttgctgcttg caatgtttgc ccattttagg      5700
gacatgagta ggctgaagtt tgttcagtgt ggacttcaga ggcagcacac aaacagctgc      5760
tggaggatgg gaactgaggg gttggaaggg ggcagggtga gcccagaaac tcctgtgtgc      5820
ctctgagcct gcagcacgtg gcggccgcag gaaccctag tgatggagtt ggccactccc      5880
tctctgcgcg ctcgctcgct cactgaggcc gggcgaccaa aggtcgcccg acgcccgggc      5940
tttgcccggg cggcctcagt gagcgagcga gcgcgcagag agggagtggc caa             5993
```

<210> SEQ ID NO 43
<211> LENGTH: 5337
<212> TYPE: DNA
<213> ORGANISM: Adeno-Associated Virus 2

<400> SEQUENCE: 43

```
ttggccactc cctctctgcg cgctcgctcg ctcactgagg ccgcccgggc aaagcccggg       60
```

```
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180 ttttttaaaaa gcagtcaaaa gtccaagtgg cccttggcag catttactct ctctgtttgc   240
tctggttaat aatctcagga gcacaaacat tcctggaggc aggagaagaa atcaacatcc    300
tggacttatc ctctgggcct ctccccaccc ccaggagagg ctcaggttaa ttttaaaaa     360 gcagtcaaaa gtccaagtgg cccttggcag catttactct ctctgtttgc tctggttaat   420
aatctcagga gcacaaacat tcctggaggc aggagaagaa atcaacatcc tggacttatc   480
ctctgggcct ctccccaccc ccaggagagg ctgtcgactg gacacaggac gctgtggttt   540
ctgagccagg gggcgactca gatcccagcc agtggactta gcccctgttt gctcctccga   600
taactggggt gaccttggtt aatattcacc agcagcctcc cccgttgccc ctctggatcc   660
actgcttaaa tacgacgag acagggccc tgtctcctca gcttcaggca ccaccactga     720
cctgggacag tgaatcgcga tcgccaccat gcagattgag ctgagcacct gcttcttcct   780
gtgcctgctg aggttctgct tctctgccac caggagatac tacctggggg ctgtggagct   840
gagctgggac tacatgcagt ctgacctggg ggagctgcct gtggatgcca ggttcccccc   900
cagagtgccc aagagcttcc ccttcaacac ctctgtggtg tacaagaaga ccctgtttgt   960
ggagttcact gaccacctgt tcaacattgc caagcccagg cccccctgga tgggcctgct  1020 gggcccacc atccaggctg aggtgtatga cactgtggtg atcaccctga agaacatggc  1080
cagccaccct gtgagcctgc atgctgtggg ggtgagctac tggaaggcct ctgaggggc   1140 tgagtatgat gaccagacca gccagaggga aaggaggat gacaaggtgt tccctggggg  1200
cagccacacc tatgtgtggc aggtgctgaa ggagaatggc cccatggcct ctgaccccct  1260
gtgcctgacc tacagctacc tgagccatgt ggacctggtg aaggacctga actctggcct  1320
gattggggcc ctgctggtgt gcagggaggg cagcctggcc aaggagaaga cccagaccct  1380
gcacaagttc atcctgctgt ttgctgtgtt tgatgagggc aagagctggc actctgaaac  1440
caagaacagc ctgatgcagg acagggatgc tgcctctgcc agggcctggc caagatgca   1500 cactgtgaat ggctatgtga acaggagcct gcctggcctg attggctgcc acaggaagtc  1560
tgtgtactgg catgtgattg gcatgggcac caccctgag gtgcacagca tcttcctgga   1620
gggccacacc ttcctggtca ggaaccacag gcaggccagc ctggagatca gccccatcac  1680
cttcctgact gcccagaccc tgctgatgga cctgggccag ttcctgctgt tctgccacat  1740
cagcagccac cagcatgatg gcatggaggc ctatgtgaag gtggacagct gccctgagga  1800
gccccagctg aggatgaaga caatgagga ggctgaggac tatgatgatg acctgactga   1860
ctctgagatg gatgtggtga ggtttgatga tgacaacagc cccagcttca tccagatcag  1920
gtctgtggcc aagaagcacc ccaagacctg ggtgcactac attgctgctg aggaggagga  1980
ctgggactat gccccctgg tgctggcccc tgatgacagg agctacaaga gccagtacct   2040
gaacaatggc ccccagagga ttggcaggaa gtacaagaag gtcaggttca tggcctacac  2100
tgatgaaacc ttcaagacca gggaggccat ccagcatgag tctggcatcc tgggcccct   2160 gctgtatggg gaggtgggg acaccctgct gatcatcttc aagaaccagg ccagcaggcc   2220
ctacaacatc taccccatg gcatcactga tgtgaggcc ctgtacagca ggaggctgcc    2280
caagggggta agcacctga aggacttccc catcctgcct ggggagatct tcaagtacaa    2340
gtggactgtg actgtggagg atggccccac caagtctgac cccaggtgcc tgaccagata  2400
```

```
ctacagcagc tttgtgaaca tggagaggga cctggcctct ggcctgattg gcccctgct     2460
gatctgctac aaggagtctg tggaccagag gggcaaccag atcatgtctg acaagaggaa    2520
tgtgatcctg ttctctgtgt ttgatgagaa caggagctgg tacctgactg agaacatcca    2580
gaggttcctg cccaaccctg ctggggtgca gctggaggac cctgagttcc aggccagcaa    2640
catcatgcac agcatcaatg ctatgtgtt tgacagcctg cagctgtctg tgtgcctgca     2700
tgaggtggcc tactggtaca tcctgagcat tggggcccag actgacttcc tgtctgtgtt    2760
cttctctggc tacaccttca gcacaagat ggtgtatgag dacaccctga ccctgttccc     2820
cttctctggg gagactgtgt tcatgagcat ggagaaccct ggcctgtgga ttctgggctg    2880
ccacaactct gacttcagga cagggggcat gactgccctg ctgaaagtct ccagctgtga    2940
caagaacact ggggactact atgaggacag ctatgaggac atctctgcct acctgctgag    3000
caagaacaat gccattgagc ccaggagctt cagccagaac cccccagtgc tgaagaggca    3060
ccagagggag atcaccagga ccaccctgca gtctgaccag gaggagattg actatgatga    3120
caccatctct gtggagatga agaaggagga ctttgacatc tacgacgagg acgagaacca    3180
gagccccagg agcttccaga agaagaccag gcactacttc attgctgctg tggagaggct    3240
gtgggactat ggcatgagca gcagcccca tgtgctgagg aacagggccc agtctggctc    3300
tgtgccccag ttcaagaagg tggtgttcca ggagttcact gatggcagct tcacccagcc    3360
cctgtacaga ggggagctga atgagcacct gggcctgctg gcccctaca tcagggctga    3420
ggtggaggac aacatcatgg tgaccttcag gaaccaggcc agcaggccct acagcttcta    3480
cagcagcctg atcagctatg aggaggacca gaggcagggg gctgagccca ggaagaactt    3540
tgtgaagccc aatgaaacca agacctactt ctggaaggtg cagcaccaca tggccccac    3600
caaggatgag tttgactgca aggcctgggc ctacttctct gatgtggacc tggagaagga    3660
tgtgcactct ggcctgattg gcccctgct ggtgtgccac accaacaccc tgaaccctgc    3720
ccatggcagg caggtgactg tgcaggagtt tgccctgttc ttcaccatct ttgatgaaac    3780
caagagctgg tacttcactg agaacatgga gaggaactgc agggcccct gcaacatcca    3840
gatggaggac cccaccttca aggagaacta caggttccat gccatcaatg ctacatcat    3900
ggacaccctg cctggcctgg tgatggccca ggaccagagg atcaggtggt acctgctgag    3960
catgggcagc aatgagaaca tccacagcat ccacttctct ggccatgtgt tcactgtgag    4020
gaagaaggag gagtacaaga tggcccctgta caacctgtac cctggggtgt tgagactgt    4080
ggagatgctg cccagcaagg ctggcatctg gagggtggag tgcctgattg gggagcacct    4140
gcatgctggc atgagcaccc tgttcctggt gtacagcaac aagtgccaga ccccctggg    4200
catgccctct ggccacatca gggacttcca gatcactgcc tctggccagt atggccagtg    4260
ggccccccaag ctggccaggc tgcactactc tggcagcatc aatgcctgga gcaccaagga    4320
gcccttcagc tggatcaagg tggacctgct ggccccatg atcatccatg catcaagac     4380
ccaggggggcc aggcagaagt tcagcagcct gtacatcagc cagttcatca tcatgtacag    4440
cctggatggc aagaagtggc agacctacag gggcaacagc actggcaccc tgatggtgtt    4500
ctttggcaat gtggacagct ctggcatcaa gcacaacatc ttcaacccc ccatcattgc     4560
cagatacatc aggctgcacc ccacccacta cagcatcagg agcaccctga ggatggagct    4620
gatggggctgt gacctgaaca gctgcagcat gccctggggc atggagagca aggccatctc    4680
tgatgcccag atcactgcca gcagctactt caccaacatg tttgccacct ggagcccag     4740
caaggccagg ctgcacctgc agggcaggag caatgcctgg aggccccagg tcaacaaccc    4800
```

```
caaggagtgg ctgcaggtgg acttccagaa gaccatgaag gtgactgggg tgaccaccca    4860 ggggggtgaag agcctgctga ccagcatgta tgtgaaggag ttcctgatca gcagcagcca    4920
ggatggccac cagtggaccc tgttcttcca gaatggcaag gtgaaggtgt tccagggcaa    4980
ccaggacagc ttcacccctg tggtgaacag cctggacccc ccctgctga ccagatacct    5040 gaggattcac ccccagagct gggtgcacca gattgccctg aggatggagg tgctgggctg    5100
tgaggcccag gacctgtact gacctcgagg aataaaggaa atttattttc attgcaatag    5160
tgtgttggtt ttttgtgtca cgtggcggcc gcaggaaccc ctagtgatgg agttggccac    5220
tccctctctg cgcgctcgct cgctcactga ggccgggcga ccaaaggtcg cccgacgccc    5280
gggctttgcc cggcggcct cagtgagcga gcgagcgcgc agagagggag tggccaa       5337
```

<210> SEQ ID NO 44
<211> LENGTH: 5542
<212> TYPE: DNA
<213> ORGANISM: Adeno-Associated Virus 2

<400> SEQUENCE: 44

```
ttggccactc cctctctgcg cgctcgctcg ctcactgagg ccgcccgggc aaagcccggg      60
cgtcgggcga ccttttggtcg cccggcctca gtgagcgagc gagcgcgcag agagggagtg    120
gccaactcca tcactagggg ttcctgcggc cgcacgcgtg tttaaacgtc gacaggttaa    180 ttttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgtaa gtatgccttt cactgcgaga ggttctggag aggcttctga    780
gctccccatg gcccaggcag gcagcaggtc tggggcagga ggggggttgt ggagtgcctt    840
gactcggggc ctggccccccc catctctgtc ttgcaggaca attgccgtct tctgtctcgt    900
ggggcatcct cctgctggca ggcctgtgct gcctggtccc tgcgatcgcc accatgcaga    960
ttgagctgag cacctgcttc ttcctgtgcc tgctgaggtt ctgcttctct gccaccagga    1020
gatactacct gggggctgtg gagctgagct gggactacat gcagtctgac ctgggggagc    1080
tgcctgtgga tgccaggttc ccccccagag tgcccaagag cttcccttc aacacctctg    1140 tggtgtacaa gaagacactg tttgtggagt tcactgacca cctgttcaac attgccaagc    1200
ccaggccccc ctggatgggc ctgctgggcc ccaccatcca ggctgaggtg tatgacactg    1260
tggtgatcac cctgaagaac atggccagcc accctgtgag cctgcatgct gtggggggtga    1320 gctactggaa ggcctctgag ggggctgagt atgatgacca gaccagccag agggagaagg    1380
aggatgacaa ggtgttccct gggggcagcc acacctatgt gtggcaggtg ctgaaggaga    1440
atggccccat ggcctctgac ccctgtgcc tgacctacag ctacctgagc catgtggacc    1500
tggtgaagga cctgaactct ggcctgattg ggcccctgct ggtgtgcagg gagggcagcc    1560
```

```
tggccaagga gaagacccag accctgcaca agttcatcct gctgtttgct gtgtttgatg    1620
agggcaagag ctggcactct gaaaccaaga acagcctgat gcaggacagg gatgctgcct    1680
ctgccagggc ctggcccaag atgcacactg tgaatggcta tgtgaacagg agcctgcctg    1740
gcctgattgg ctgccacagg aagtctgtgt actggcatgt gattggcatg ggcaccaccc    1800
ctgaggtgca cagcatcttc ctggagggcc acaccttcct ggtcaggaac acaggcagg    1860
ccagcctgga gatcagcccc atcaccttcc tgactgccca gaccctgctg atggacctgg    1920
gccagttcct gctgttctgc cacatcagca gccaccagca tgatggcatg gaggcctatg    1980
tgaaggtgga cagctgccct gaggagcccc agctgaggat gaagaacaat gaggaggctg    2040
aggactatga tgatgacctg actgactctg agatggatgt ggtgaggttt gatgatgaca    2100
acagccccag cttcatccag atcaggtctg tggccaagaa gcaccccaag acctgggtgc    2160
actacattgc tgctgaggag gaggactggg actatgcccc cctggtgctg gccctgatg    2220
acaggagcta caagagccag tacctgaaca atgcccccca gaggattggc aggaagtaca    2280
agaaggtcag gttcatggcc tacactgatg aaaccttcaa gaccagggag gccatccagc    2340
atgagtctgg catcctgggc cccctgctgt atggggaggt gggggacacc ctgctgatca    2400
tcttcaagaa ccaggccagc aggccctaca acatctaccc catggcatc actgatgtga    2460
ggcccctgta cagcaggagg ctgcccaagg gggtgaagca cctgaaggac ttccccatcc    2520
tgcctgggga gatcttcaag tacaagtgga ctgtgactgt ggaggatggc cccaccaagt    2580
ctgaccccag gtgcctgacc agatactaca gcagctttgt gaacatggag agggacctgg    2640
cctctggcct gattggcccc ctgctgatct gctacaagga gtctgtggac cagaggggca    2700
accagatcat gtctgacaag aggaatgtga tcctgttctc tgtgtttgat gagaacagga    2760
gctggtacct gactgagaac atccagaggt tcctgcccaa ccctgctggg gtgcagctgg    2820
aggaccctga gttccaggcc agcaacatca tgcacagcat caatggctat gtgtttgaca    2880
gcctgcagct gtctgtgtgc ctgcatgagg tggcctactg gtacatcctg agcattgggg    2940
cccagactga cttcctgtct gtgttcttct ctggctacac cttcaagcac aagatggtgt    3000
atgaggacac cctgacctg ttccccttct ctggggagac tgtgttcatg agcatggaga    3060
accctggcct gtggattctg ggctgccaca actctgactt caggaacagg ggcatgactg    3120
ccctgctgaa agtctccagc tgtgacaaga cactgggga ctactatgag acagctatg    3180
aggacatctc tgcctacctg ctgagcaaga acaatgccat tgagcccagg agcttcagcc    3240
agaaccccc agtgctgaag aggcaccaga gggagatcac caggaccacc ctgcagtctg    3300
accaggagga gattgactat gatgacacca tctctgtgga gatgaagaag gaggactttg    3360
acatctacga cgaggacgag aaccagagcc caggagcttc cagaagaag accaggcact    3420
acttcattgc tgctgtggag aggctgtggg actatggcat gagcagcagc ccccatgtgc    3480
tgaggaacag ggcccagtct ggctctgtgc cccagttcaa gaaggtggtg ttccaggagt    3540
tcactgatgg cagcttcacc cagcccctgt acagagggga gctgaatgag cacctgggcc    3600
tgctgggccc ctacatcagg gctgaggtgg aggacaacat catggtgacc ttcaggaacc    3660
aggccagcag gccctacagc ttctacagca gcctgatcag ctatgaggag gaccagaggc    3720
aggggctga gccaggaag aactttgtga gcccaatga aaccaagacc tacttctgga    3780
aggtgcagca ccacatggcc cccaccaagg atgagtttga ctgcaaggcc tgggcctact    3840
tctctgatgt ggacctggag aaggatgtgc actctggcct gattggcccc ctgctggtgt    3900
gccacaccaa caccctgaac cctgcccatg gcaggcaggt gactgtgcag gagtttgccc    3960
```

| | |
|---|---|
| tgttcttcac catctttgat gaaaccaaga gctggtactt cactgagaac atggagagga | 4020 |
| actgcagggc ccctgcaac atccagatgg aggaccccac cttcaaggag aactacaggt | 4080 |
| tccatgccat caatggctac atcatggaca ccctgcctgg cctggtgatg gcccaggacc | 4140 |
| agaggatcag gtggtacctg ctgagcatgg gcagcaatga gaacatccac agcatccact | 4200 |
| tctctggcca tgtgttcact gtgaggaaga aggaggagta caagatggcc ctgtacaacc | 4260 |
| tgtaccctgg ggtgtttgag actgtggaga tgctgcccag caaggctggc atctggaggg | 4320 |
| tggagtgcct gattggggag cacctgcatg ctggcatgag caccctgttc ctggtgtaca | 4380 |
| gcaacaagtg ccagaccccc ctgggcatgg cctctggcca catcagggac ttccagatca | 4440 |
| ctgcctctgg ccagtatggc cagtgggccc caagctggc caggctgcac tactctggca | 4500 |
| gcatcaatgc ctggagcacc aaggagccct cagctggat caaggtggac ctgctggccc | 4560 |
| ccatgatcat ccatggcatc aagacccagg ggccaggca aagttcagc agcctgtaca | 4620 |
| tcagccagtt catcatcatg tacagcctgg atggcaagaa gtggcagacc tacaggggca | 4680 |
| acagcactgg caccctgatg gtgttctttg gcaatgtgga cagctctggc atcaagcaca | 4740 |
| acatcttcaa ccccccatc attgccagat acatcaggct gcaccccacc cactacagca | 4800 |
| tcaggagcac cctgaggatg gagctgatgg gctgtgacct gaacagctgc agcatgcccc | 4860 |
| tgggcatgga gagcaaggcc atctctgatg cccagatcac tgccagcagc tacttccacc | 4920 |
| acatgtttgc cacctggagc cccagcaagg ccaggctgca cctgcagggc aggagcaatg | 4980 |
| cctggaggcc ccaggtcaac aaccccaagg agtggctgca ggtggacttc cagaagacca | 5040 |
| tgaaggtgac tggggtgacc acccagggg tgaagagcct gctgaccagc atgtatgtga | 5100 |
| aggagttcct gatcagcagc agccaggatg ccaccagtg gacccctgttc ttccagaatg | 5160 |
| gcaaggtgaa ggtgttccag ggcaaccagg acagcttcac ccctgtggtg aacagcctgg | 5220 |
| accccccct gctgaccaga tacctgagga ttcaccccca gagctgggtg caccagattg | 5280 |
| ccctgaggat ggaggtgctg gctgtgagg cccaggacct gtactgacct cgaggaataa | 5340 |
| aggaaattta tttcattgc aatagtgtgt tggttttttg tgtcacgtgg cggccgcagg | 5400 |
| aaccctagt gatggagttg gccactccct ctctgcgcgc tcgctcgctc actgaggccg | 5460 |
| ggcgaccaaa ggtcgcccga cgcccgggct tgcccgggc ggcctcagtg agcgagcgag | 5520 |
| cgcgcagaga gggagtggcc aa | 5542 |

<210> SEQ ID NO 45
<211> LENGTH: 5126
<212> TYPE: DNA
<213> ORGANISM: Adeno-Associated Virus 2

<400> SEQUENCE: 45

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ggaggctgct ggtgaatatt | 180 |
| aaccaaggtc accccagtta tcggaggagc aaacaggggc taagtccacg ggaggctgc | 240 |
| tggtgaatat taaccaaggt caccccagtt atcggaggag caaacagggg ctaagtccac | 300 |
| ggtcgactgg acacaggacg ctgtggtttc tgagccaggg ggcgactcag atcccagcca | 360 |
| gtggacttag cccctgtttg ctcctccgat aactggggtg accttggtta atattcacca | 420 |
| gcagcctccc ccgttgcccc tctggatcca ctgcttaaat acgacgagg acagggccct | 480 |

```
gtctcctcag cttcaggcac caccactgac ctgggacagt gaatcgcgat cgccaccatg    540
cagattgagc tgagcacctg cttcttcctg tgcctgctga ggttctgctt ctctgccacc    600
aggagatact acctggggc tgtggagctg agctgggact acatgcagtc tgacctgggg    660
gagctgcctg tggatgccag gttcccccc agagtgccca agagcttccc cttcaacacc    720
tctgtggtgt acaagaagac cctgtttgtg gagttcactg accacctgtt caacattgcc    780
aagcccaggc ccctggat gggcctgctg gccccacca tccaggctga ggtgtatgac    840
actgtggtga tcaccctgaa gaacatggcc agccaccctg tgagcctgca tgctgtgggg    900
gtgagctact ggaaggcctc tgaggggct gagtatgatg accagaccag ccagagggag    960
aaggaggatg acaaggtgtt ccctggggc agccacacct atgtgtggca ggtgctgaag   1020
gagaatggcc ccatggcctc tgaccccctg tgcctgacct acagctacct gagccatgtg   1080
gacctggtga aggacctgaa ctctggcctg attggggccc tgctggtgtg cagggagggc   1140
agcctggcca aggagaagac ccagaccctg cacaagttca tcctgctgtt tgctgtgttt   1200
gatgagggca gagctggca ctctgaaacc aagaacagcc tgatgcagga cagggatgct   1260
gcctctgcca gggcctggcc caagatgcac actgtgaatg ctatgtgaa caggagcctg   1320 cctggcctga ttggctgcca caggaagtct gtgtactggc atgtgattgg catgggcacc   1380 accctgagg tgcacagcat cttcctggag ggccacacct tcctggtcag gaaccacagg   1440
caggccagcc tggagatcag ccccatcacc ttcctgactg cccagaccct gctgatggac   1500
ctgggccagt cctgctgtt ctgccacatc agcagccacc agcatgatgg catggaggcc   1560
tatgtgaagg tggacagctg ccctgaggag ccccagctga ggatgaagaa caatgaggag   1620
gctgaggact atgatgatga cctgactgac tctgagatgg atgtggtgag gtttgatgat   1680
gacaacagcc ccagcttcat ccagatcagg tctgtggcca agaagcaccc caagacctgg   1740
gtgcactaca ttgctgctga ggaggaggac tgggactatg ccccctggt gctggccct   1800 gatgacagga gctacaagag ccagtacctg aacaatggcc cccagaggat tggcaggaag   1860
tacaagaagg tcaggttcat ggcctacact gatgaaacct tcaagaccag ggaggccatc   1920
cagcatgagt ctggcatcct gggccccctg ctgtatgggg aggtggggga cccctgctg   1980 atcatcttca gaaccaggc cagcaggccc tacaacatct accccatgg catcactgat   2040 gtgaggcccc tgtacagcag gaggctgccc aaggggtga agcacctgaa ggacttcccc   2100
atcctgcctg gggagatctt caagtacaag tggactgtga ctgtggagga tggccccacc   2160
aagtctgacc ccaggtgcct gaccagatac tacagcagct ttgtgaacat ggagagggac   2220
ctggcctctg gcctgattgg cccctgctg atctgctaca aggagtctgt ggaccagagg   2280
ggcaaccaga tcatgtctga caagaggaat gtgatcctgt tctctgtgtt tgatgagaac   2340
aggagctggt acctgactga aacatccag aggttcctgc ccaaccctgc tggggtgcag   2400
ctggaggacc ctgagttcca ggccagcaac atcatgcaca gcatcaatgg ctatgtgttt   2460
gacagcctgc agctgtctgt gtgcctgcat gaggtggcct actggtacat cctgagcatt   2520
ggggcccaga ctgacttcct gtctgtgttc ttctctggct acaccttcaa gcacaagatg   2580
gtgtatgagg acacccctgac cctgttcccc ttctctgggg agactgtgtt catgagcatg   2640
gagaaccctg gcctgtggat tctggctgc cacaactctg acttcaggaa caggggcatg   2700
actgccctgc tgaaagtctc cagctgtgac aagaacactg ggactactg tgaggacagc   2760 tatgaggaca tctctgccta cctgctgagc aagaacaatg ccattgagcc caggagcttc   2820
agccagaacc ccccagtgct gaagaggcac cagagggaga tcaccaggac cacccctgcag   2880
```

-continued

```
tctgaccagg aggagattga ctatgatgac accatctctg tggagatgaa gaaggaggac    2940
tttgacatct acgacgagga cgagaaccag agccccagga gcttccagaa gaagaccagg    3000
cactacttca ttgctgctgt ggagaggctg tgggactatg gcatgagcag cagcccccat    3060
gtgctgagga acagggccca gtctggctct gtgccccagt tcaagaaggt ggtgttccag    3120
gagttcactg atggcagctt cacccagccc ctgtacagag ggagctgaa tgagcacctg     3180 ggcctgctgg cccctacat cagggctgag gtggaggaca acatcatggt gaccttcagg     3240
aaccaggcca gcaggcccta cagcttctac agcagcctga tcagctatga ggaggaccag    3300
aggcaggggg ctgagcccag gaagaacttt gtgaagccca atgaaaccaa gacctacttc    3360
tggaaggtgc agcaccacat ggcccccacc aaggatgagt ttgactgcaa ggcctgggcc    3420
tacttctctg atgtggacct ggagaaggat gtgcactctg gcctgattgg cccctgctg    3480 gtgtgccaca ccaacaccct gaaccctgcc catggcaggc aggtgactgt gcaggagttt    3540
gccctgttct tcaccatctt tgatgaaacc aagagctgg acttcactga gaacatggag    3600
aggaactgca gggcccctg caacatccag atggaggacc ccaccttcaa ggagaactac    3660
aggttccatg ccatcaatgg ctacatcatg gacaccctgc ctggcctggt gatggcccag    3720
gaccagagga tcaggtggta cctgctgagc atgggcagca atgagaacat ccacagcatc    3780
cacttctctg ccatgtgtt cactgtgagg aagaaggagg agtacaagat ggccctgtac    3840
aacctgtacc ctggggtgtt tgagactgtg agatgctgc ccagcaaggc tggcatctgg    3900
agggtggagt gcctgattgg ggagcacctg catgctggca tgagcaccct gttcctggtg    3960
tacagcaaca agtgccagac cccctgggc atggcctctg ccacatcag ggacttccag     4020 atcactgcct ctggccagta tggccagtgg gcccccaagc tggccaggct gcactactct    4080
ggcagcatca atgcctggag caccaaggag cccttcagct ggatcaaggt ggacctgctg    4140
gcccccatga tcatccatgg catcaagacc caggggggcca gcagaagtt cagcagcctg    4200 tacatcagcc agttcatcat catgtacagc ctggatggca agaagtggca gacctacagg    4260
ggcaacagca ctggcaccct gatggtgttc tttggcaatg tggacagctc tggcatcaag    4320
cacaacatct tcaacccccc catcattgcc agatacatca ggctgcaccc cacccactac    4380
agcatcagga gcaccctgag gatggagctg atgggctgtg acctgaacag ctgcagcatg    4440
cccctgggca tggagagcaa ggccatctct gatgcccaga tcactgccag cagctacttc    4500
accaacatgt ttgccacctg gagccccagc aaggccaggc tgcacctgca gggcaggagc    4560
aatgcctgga ggccccaggt caacaacccc aaggagtggc tgcaggtgga cttccagaag    4620
accatgaagg tgactggggt gaccacccag ggggtgaaga gcctgctgac cagcatgtat    4680
gtgaaggagt tcctgatcag cagcagccag gatggccacc agtggaccct gttcttccag    4740
aatggcaagg tgaaggtgtt ccagggcaac aggacagct tcaccctgt ggtgaacagc      4800 ctggaccccc ccctgctgac cagatacctg aggattcacc cccagagctg ggtgcaccag    4860
attgccctga ggatggaggt gctgggctgt gaggcccagg acctgtactg acctcgagga    4920 ataaggaaa tttatttca ttgcaatagt gtgttggttt tttgtgtcac gtggcggccg      4980
caggaacccc tagtgatgga gttggccact ccctctctgc gcgctcgctc gctcactgag    5040
gccgggcgac caaaggtcgc ccgacgcccg ggctttgccc gggcggcctc agtgagcgag    5100
cgagcgcgca gagagggagt ggccaa                                         5126
```